US010576237B2

(12) United States Patent
DeVries et al.

(10) Patent No.: US 10,576,237 B2
(45) Date of Patent: Mar. 3, 2020

(54) ACTIVE EXHALATION VALVE

(71) Applicant: Ventec Life Systems, Inc., Bothell, WA (US)

(72) Inventors: Douglas F. DeVries, Kenmore, WA (US); Shan E. Gaw, Seattle, WA (US)

(73) Assignee: Ventec Life Systems, Inc., Bothell, WA (US)

(*) Notice: Subject to any disclaimer, the term of this patent is extended or adjusted under 35 U.S.C. 154(b) by 0 days.

(21) Appl. No.: 16/167,414

(22) Filed: Oct. 22, 2018

(65) Prior Publication Data
US 2019/0054268 A1 Feb. 21, 2019

Related U.S. Application Data

(60) Division of application No. 14/939,789, filed on Nov. 12, 2015, now Pat. No. 10,105,509, which is a (Continued)

(51) Int. Cl.
*B01D 53/02* (2006.01)
*A61M 16/10* (2006.01)
(Continued)

(52) U.S. Cl.
CPC ...... *A61M 16/101* (2014.02); *A61M 16/0051* (2013.01); *A61M 16/0057* (2013.01);
(Continued)

(58) Field of Classification Search
CPC .... A61M 2202/028; A61M 2202/0007; A61M 16/0051; A61M 16/0057; A61M 16/0063;
(Continued)

(56) References Cited

U.S. PATENT DOCUMENTS 3,789,837 A * 2/1974 Philips ................ A61M 16/00
128/202.22
3,875,626 A 4/1975 Tysk et al.
(Continued)

FOREIGN PATENT DOCUMENTS

EP 0937478 B1 8/2003
WO 9908738 A1 2/1999
(Continued)

OTHER PUBLICATIONS

US 8,012,240, 11/2008, Sprinkle (withdrawn).
(Continued)

*Primary Examiner* — Christopher P Jones
(74) *Attorney, Agent, or Firm* — Perkins Coie LLP

(57) ABSTRACT

An active exhalation valve for use with a ventilator to control flow of patient exhaled gases. The valve includes a patient circuit connection port, a patient connection port, an exhaled gas port, a pilot pressure port, and a valve seat. The valve further has a movable poppet with inner and outer bellows members and a bellows poppet face. An activation pressure applied to the pilot pressure port extends the bellows members to move the poppet face into engagement with the valve seat and restrict flow of patient exhaled gases to the exhaled gas port, and the reduction of the activation pressure allows the bellows members to move the poppet face away from the valve seat and out of engagement with the valve seat to permit flow of patient exhaled gases to the exhaled gas port, thereby controlling the flow of patient exhaled gases from the valve.

16 Claims, 61 Drawing Sheets

Related U.S. Application Data continuation of application No. 14/819,165, filed on Aug. 5, 2015, which is a continuation of application No. 14/803,799, filed on Jul. 20, 2015, which is a continuation of application No. 14/749,397, filed on Jun. 24, 2015, now Pat. No. 9,956,371, which is a continuation of application No. 14/695,708, filed on Apr. 24, 2015, now Pat. No. 10,046,134, which is a continuation of application No. 14/667,451, filed on Mar. 24, 2015, now Pat. No. 10,245,406, which is a continuation of application No. 14/667,480, filed on Mar. 24, 2015.

(51) Int. Cl.
  *A61M 16/00* (2006.01)
  *A61M 16/08* (2006.01)
  *A61M 16/20* (2006.01)
  *B01D 53/053* (2006.01)
  *B01D 53/047* (2006.01)

(52) U.S. Cl.
  CPC .... *A61M 16/0063* (2014.02); *A61M 16/0069* (2014.02); *A61M 16/024* (2017.08); *A61M 16/0808* (2013.01); *A61M 16/0816* (2013.01); *A61M 16/0858* (2014.02); *A61M 16/0883* (2014.02); *A61M 16/201* (2014.02); *A61M 16/202* (2014.02); *A61M 16/207* (2014.02); *A61M 16/208* (2013.01); *A61M 16/107* (2014.02); *A61M 16/1055* (2013.01); *A61M 16/20* (2013.01); *A61M 2016/0027* (2013.01); *A61M 2016/0036* (2013.01); *A61M 2016/0039* (2013.01); *A61M 2016/1025* (2013.01); *A61M 2202/0208* (2013.01); *A61M 2205/0272* (2013.01); *A61M 2205/3334* (2013.01); *A61M 2205/3358* (2013.01); *A61M 2205/42* (2013.01); *A61M 2205/502* (2013.01); *A61M 2205/52* (2013.01); *B01D 53/0476* (2013.01); *B01D 53/053* (2013.01); *B01D 2256/12* (2013.01); *B01D 2257/102* (2013.01); *B01D 2259/401* (2013.01); *B01D 2259/40009* (2013.01); *B01D 2259/4533* (2013.01)

(58) Field of Classification Search
  CPC .......... A61M 16/0069; A61M 16/0808; A61M 16/0816; A61M 16/0858; A61M 16/0883; A61M 16/101; A61M 16/1055; A61M 16/107; A61M 16/20; A61M 16/201; A61M 16/202; A61M 16/207; A61M 16/208; A61M 2016/0027; A61M 2016/0036; A61M 2016/0039; A61M 2016/1025; A61M 2205/0272; A61M 2205/3334; A61M 2205/3358; A61M 2205/42; A61M 2205/502; A61M 2205/52; B01D 2256/12; B01D 2257/102; B01D 2259/40009; B01D 2259/401; B01D 2259/4533; B01D 53/0476; B01D 53/053
  See application file for complete search history.

(56) References Cited

U.S. PATENT DOCUMENTS

| | | | |
|---|---|---|---|
| 4,280,399 A | 7/1981 | Cunning | |
| 4,331,455 A | 5/1982 | Sato | |
| 4,357,936 A | 11/1982 | Ellestad et al. | |
| 4,367,767 A | 1/1983 | Hurd | |
| 4,386,945 A | 6/1983 | Gardner | |
| 4,401,116 A | 8/1983 | Fry et al. | |
| 4,417,573 A | 11/1983 | De Vries | |
| 4,425,914 A | 1/1984 | Ray et al. | |
| 4,449,990 A | 5/1984 | Tedford, Jr. | |
| 4,450,838 A | 5/1984 | Miodownik | |
| 4,459,982 A | 7/1984 | Fry | |
| 4,502,873 A | 3/1985 | Mottram et al. | |
| 4,516,424 A | 5/1985 | Rowland | |
| 4,527,557 A | 7/1985 | Devries et al. | |
| 4,545,790 A | 10/1985 | Miller et al. | |
| 4,561,287 A | 12/1985 | Rowland | |
| 4,576,616 A | 3/1986 | Mottram et al. | |
| 4,602,653 A | 7/1986 | Ruiz-vela et al. | |
| 4,621,632 A | 11/1986 | Bartels et al. | |
| 4,627,860 A | 12/1986 | Rowland | |
| 4,637,386 A | 1/1987 | Baum | |
| 4,648,395 A | 3/1987 | Sato et al. | |
| 4,648,888 A | 3/1987 | Rowland | |
| 4,681,099 A | 7/1987 | Sato et al. | |
| 4,702,240 A | 10/1987 | Chaoui | |
| 4,794,922 A | 1/1989 | Devries | |
| 4,813,979 A | 3/1989 | Miller et al. | |
| 4,869,733 A | 9/1989 | Stanford | |
| 4,880,443 A | 11/1989 | Miller et al. | |
| 4,905,685 A | 3/1990 | Olsson et al. | |
| 4,936,297 A | 6/1990 | Greiff et al. | |
| 4,971,609 A | 11/1990 | Pawlos | |
| 4,983,190 A | 1/1991 | Verrando et al. | |
| 4,993,269 A | 2/1991 | Guillaume et al. | |
| 5,002,591 A | 3/1991 | Stanford | |
| 5,014,694 A | 5/1991 | Devries | |
| 5,021,137 A | 6/1991 | Joshi et al. | |
| 5,034,023 A | 7/1991 | Thompson | |
| 5,071,453 A | 12/1991 | Hradek et al. | |
| 5,072,729 A | 12/1991 | Devries | |
| 5,101,656 A | 4/1992 | Miller | |
| 5,107,831 A | 4/1992 | Halpern et al. | |
| 5,127,400 A | 7/1992 | Devries et al. | |
| 5,129,924 A | 7/1992 | Schultz | |
| 5,134,329 A | 7/1992 | Lang | |
| 5,166,563 A | 11/1992 | Bassine | |
| 5,169,506 A | 12/1992 | Michaels | |
| 5,186,793 A | 2/1993 | Michaels | |
| 5,265,594 A | 11/1993 | Olsson et al. | |
| 5,273,031 A | 12/1993 | Olsson et al. | |
| 5,275,642 A | 1/1994 | Bassine | |
| 5,296,110 A | 3/1994 | Tabatabaie-Raissi | |
| 5,331,995 A | 7/1994 | Westfall et al. | |
| 5,335,426 A | 8/1994 | Settlemyer et al. | |
| 5,354,361 A | 10/1994 | Coffield | |
| 5,370,112 A | 12/1994 | Perkins | |
| 5,378,345 A | 1/1995 | Taylor et al. | |
| 5,397,443 A | 3/1995 | Michaels | |
| 5,400,777 A | 3/1995 | Olsson et al. | |
| 5,469,372 A | 11/1995 | Mcbrearty et al. | |
| 5,474,062 A | 12/1995 | Devires et al. | |
| 5,474,595 A | 12/1995 | Mccombs | |
| 5,494,028 A | 2/1996 | Devries et al. | |
| 5,497,767 A | 3/1996 | Olsson et al. | |
| 5,501,212 A | 3/1996 | Psaros | |
| 5,540,220 A | 7/1996 | Gropper et al. | |
| 5,540,233 A | 7/1996 | Larsson et al. | |
| 5,575,283 A | 11/1996 | Sjoestrand | |
| 5,578,115 A | 11/1996 | Cole | |
| 5,694,924 A | 12/1997 | Cewers | |
| 5,694,926 A | 12/1997 | Devries et al. | |
| 5,701,883 A | 12/1997 | Hete et al. | |
| 5,706,801 A | 1/1998 | Remes et al. | |
| 5,720,277 A | 2/1998 | Olsson et al. | |
| 5,740,796 A | 4/1998 | Skog | |
| 5,743,253 A | 4/1998 | Castor et al. | |
| 5,746,806 A | 5/1998 | Aylsworth et al. | |
| 5,765,557 A * | 6/1998 | Warters | A61M 1/0019 128/207.14 |
| 5,765,558 A | 6/1998 | Psaros et al. | |
| 5,766,310 A | 6/1998 | Cramer | |
| 5,810,324 A | 9/1998 | Eriksson et al. | |
| 5,827,358 A | 10/1998 | Kulish et al. | |
| 5,845,633 A | 12/1998 | Psaros | |

(56) References Cited

U.S. PATENT DOCUMENTS

| | | | |
|---|---|---|---|
| 5,849,219 A | 12/1998 | De et al. |
| 5,858,062 A | 1/1999 | Mcculloh et al. |
| 5,858,063 A | 1/1999 | Cao et al. |
| 5,862,802 A | 1/1999 | Bird |
| 5,868,133 A | 2/1999 | Devries et al. |
| 5,871,564 A | 2/1999 | Mccombs |
| 5,875,777 A | 3/1999 | Eriksson |
| 5,878,744 A | 3/1999 | Pfeiffer |
| 5,881,722 A | 3/1999 | Devries et al. |
| 5,893,944 A | 4/1999 | Dong |
| 5,896,857 A | 4/1999 | Hely et al. |
| 5,906,672 A | 5/1999 | Michaels et al. |
| 5,917,135 A | 6/1999 | Michaels et al. |
| 5,931,162 A | 8/1999 | Christian |
| 5,937,853 A | 8/1999 | Strom |
| 5,948,142 A | 9/1999 | Holmes et al. |
| 5,957,130 A | 9/1999 | Krahbichler et al. |
| 5,968,236 A | 10/1999 | Bassine |
| 5,988,165 A | 11/1999 | Richey et al. |
| 5,997,617 A | 12/1999 | Czabala et al. |
| 6,010,555 A | 1/2000 | Smolarek et al. |
| 6,035,851 A | 3/2000 | Wallen |
| 6,062,218 A | 5/2000 | Krahbichler et al. |
| 6,068,680 A | 5/2000 | Kulish et al. |
| 6,073,630 A | 6/2000 | Adahan |
| 6,095,139 A | 8/2000 | Psaros |
| 6,102,038 A | 8/2000 | Devries |
| 6,112,744 A | 9/2000 | Hognelid |
| 6,113,673 A | 9/2000 | Loutfy et al. |
| 6,123,074 A | 9/2000 | Hete et al. |
| 6,152,132 A | 11/2000 | Psaros |
| 6,152,134 A | 11/2000 | Webber et al. |
| 6,152,135 A | 11/2000 | Devries et al. |
| 6,155,252 A * | 12/2000 | Warters ............. A61M 1/0019 128/200.24 |
| 6,156,100 A | 12/2000 | Conrad et al. |
| 6,158,430 A | 12/2000 | Pfeiffer et al. |
| 6,162,283 A | 12/2000 | Conrad et al. |
| 6,176,897 B1 | 1/2001 | Keefer |
| 6,189,532 B1 | 2/2001 | Hely et al. |
| 6,190,441 B1 | 2/2001 | Czabala et al. |
| 6,192,885 B1 | 2/2001 | Jalde |
| 6,217,635 B1 | 4/2001 | Conrad et al. |
| 6,234,170 B1 | 5/2001 | Bergkvist |
| 6,253,767 B1 | 7/2001 | Mantz |
| 6,263,873 B1 | 7/2001 | Hedenberg |
| 6,269,811 B1 | 8/2001 | Duff |
| 6,298,848 B1 | 10/2001 | Skog |
| 6,302,107 B1 | 10/2001 | Richey et al. |
| 6,344,069 B2 | 2/2002 | Smolarek et al. |
| 6,346,139 B1 | 2/2002 | Czabala |
| 6,348,082 B1 | 2/2002 | Murdoch et al. |
| 6,360,740 B1 | 3/2002 | Ward et al. |
| 6,386,235 B1 | 5/2002 | Mcculloh et al. |
| 6,393,802 B1 | 5/2002 | Bowser et al. |
| 6,394,089 B1 | 5/2002 | Cantrill et al. |
| 6,395,065 B1 | 5/2002 | Murdoch et al. |
| 6,412,483 B1 | 7/2002 | Jones et al. |
| 6,446,630 B1 | 9/2002 | Todd, Jr. |
| 6,471,744 B1 | 10/2002 | Hill |
| 6,478,850 B1 | 11/2002 | Warren |
| 6,478,857 B2 | 11/2002 | Czabala |
| 6,497,755 B2 | 12/2002 | Murdoch et al. |
| 6,514,318 B2 | 2/2003 | Keefer |
| 6,514,319 B2 | 2/2003 | Keefer et al. |
| 6,516,798 B1 * | 2/2003 | Davies ............. A61M 16/047 128/201.13 |
| 6,520,176 B1 | 2/2003 | Dubois et al. |
| 6,524,370 B2 | 2/2003 | Maheshwary et al. |
| 6,526,970 B2 | 3/2003 | Devries et al. |
| 6,532,956 B2 | 3/2003 | Hill |
| 6,547,851 B2 | 4/2003 | Warren |
| 6,551,384 B1 | 4/2003 | Ackley et al. |
| 6,553,992 B1 | 4/2003 | Berthon-Jones et al. |
| 6,558,451 B2 | 5/2003 | Mccombs et al. |
| 6,564,798 B1 | 5/2003 | Jalde |
| 6,565,635 B2 | 5/2003 | Keefer et al. |
| 6,595,213 B2 | 7/2003 | Bennarsten |
| 6,601,583 B2 | 8/2003 | Pessala et al. |
| 6,622,726 B1 | 9/2003 | Du |
| 6,626,175 B2 | 9/2003 | Jafari et al. |
| 6,629,525 B2 | 10/2003 | Hill et al. |
| 6,640,807 B2 | 11/2003 | Bennarsten |
| 6,641,644 B2 | 11/2003 | Jagger et al. |
| 6,641,645 B1 | 11/2003 | Lee et al. |
| 6,644,312 B2 | 11/2003 | Berthon-Jones et al. |
| 6,651,652 B1 | 11/2003 | Waard |
| 6,651,658 B1 | 11/2003 | Hill et al. |
| 6,651,692 B2 | 11/2003 | Meckes et al. |
| 6,660,065 B2 | 12/2003 | Byrd et al. |
| 6,679,258 B1 | 1/2004 | Stroem Christer |
| 6,691,702 B2 | 2/2004 | Appel et al. |
| 6,694,978 B1 | 2/2004 | Bennarsten |
| 6,702,880 B2 | 3/2004 | Roberts et al. |
| 6,712,876 B2 | 3/2004 | Cao et al. |
| 6,712,877 B2 | 3/2004 | Cao et al. |
| 6,739,334 B2 | 5/2004 | Valeij |
| 6,740,146 B2 | 5/2004 | Simonds |
| 6,755,193 B2 | 6/2004 | Berthon-Jones et al. |
| 6,758,216 B1 | 7/2004 | Berthon-Jones et al. |
| 6,761,166 B2 | 7/2004 | Ahlmen et al. |
| 6,764,534 B2 | 7/2004 | Mccombs et al. |
| 6,782,888 B1 | 8/2004 | Friberg et al. |
| 6,793,719 B2 | 9/2004 | Kim et al. |
| 6,805,122 B2 | 10/2004 | Richey et al. |
| 6,811,590 B2 | 11/2004 | Lee et al. |
| 6,837,244 B2 | 1/2005 | Yagi et al. |
| 6,845,773 B2 | 1/2005 | Berthon-Jones et al. |
| 6,860,858 B2 | 3/2005 | Green et al. |
| 6,863,068 B2 | 3/2005 | Jamison et al. |
| 6,866,700 B2 | 3/2005 | Amann |
| 6,877,511 B2 | 4/2005 | Devries et al. |
| 6,889,726 B2 | 5/2005 | Richey et al. |
| 6,896,721 B1 | 5/2005 | Lynn |
| 6,908,503 B2 | 6/2005 | Mccombs et al. |
| 6,910,480 B1 | 6/2005 | Berthon-Jones |
| 6,923,180 B2 | 8/2005 | Richey et al. |
| 6,935,460 B2 | 8/2005 | Mccombs et al. |
| 6,949,133 B2 | 9/2005 | Mccombs et al. |
| 6,997,881 B2 | 2/2006 | Green et al. |
| 7,000,610 B2 | 2/2006 | Bennarsten et al. |
| 7,032,592 B2 | 4/2006 | Castor et al. |
| 7,040,318 B2 | 5/2006 | Daescher et al. |
| 7,055,522 B2 | 6/2006 | Berthon-Jones |
| 7,066,985 B2 | 6/2006 | Deane et al. |
| 7,077,133 B2 | 7/2006 | Yagi et al. |
| 7,081,745 B2 | 7/2006 | Haveri |
| 7,089,937 B2 | 8/2006 | Berthon-Jones et al. |
| 7,094,275 B2 | 8/2006 | Keefer et al. |
| 7,100,609 B2 | 9/2006 | Berthon-Jones et al. |
| 7,105,038 B2 | 9/2006 | Lee et al. |
| 7,121,276 B2 | 10/2006 | Jagger et al. |
| 7,121,277 B2 | 10/2006 | Stroem |
| 7,135,059 B2 | 11/2006 | Deane et al. |
| 7,156,903 B2 | 1/2007 | Mccombs |
| 7,171,963 B2 | 2/2007 | Jagger et al. |
| 7,179,326 B2 | 2/2007 | Nakamura et al. |
| 7,188,621 B2 | 3/2007 | DeVries et al. |
| 7,213,468 B2 | 5/2007 | Fujimoto |
| 7,219,666 B2 | 5/2007 | Friberg et al. |
| 7,222,623 B2 | 5/2007 | Devries et al. |
| 7,250,073 B2 | 7/2007 | Keefer et al. |
| 7,255,103 B2 | 8/2007 | Bassin |
| 7,279,029 B2 | 10/2007 | Occhialini et al. |
| 7,294,170 B2 | 11/2007 | Richey et al. |
| 7,329,304 B2 | 2/2008 | Bliss et al. |
| 7,347,207 B2 | 3/2008 | Ahlmen et al. |
| 7,350,521 B2 | 4/2008 | Whitley et al. |
| 7,367,337 B2 | 5/2008 | Berthon-Jones et al. |
| 7,368,005 B2 | 5/2008 | Bliss et al. |
| RE40,402 E | 6/2008 | Leonhardt et al. |
| 7,402,193 B2 | 7/2008 | Bliss et al. |
| 7,427,315 B2 | 9/2008 | Dolensky et al. |
| 7,428,902 B2 | 9/2008 | Du et al. |

(56) References Cited

U.S. PATENT DOCUMENTS

| | | |
|---|---|---|
| 7,429,289 B2 | 9/2008 | Dolensky et al. |
| 7,431,032 B2 | 10/2008 | Jagger et al. |
| 7,438,745 B2 | 10/2008 | Deane et al. |
| 7,445,546 B2 | 11/2008 | Hondmann et al. |
| 7,445,663 B1 | 11/2008 | Hunter et al. |
| 7,455,717 B2 | 11/2008 | Sprinkle |
| 7,473,299 B2 | 1/2009 | Occhialini et al. |
| 7,491,261 B2 | 2/2009 | Warren et al. |
| 7,497,215 B1 | 3/2009 | Nguyen et al. |
| 7,510,601 B2 | 3/2009 | Whitley et al. |
| 7,517,385 B2 | 4/2009 | Winter |
| 7,524,365 B2 | 4/2009 | Lin |
| 7,527,053 B2 | 5/2009 | Devries et al. |
| 7,533,872 B2 | 5/2009 | Lee et al. |
| 7,550,031 B2 | 6/2009 | Hunter et al. |
| 7,550,036 B2 | 6/2009 | Lee et al. |
| 7,556,670 B2 | 7/2009 | Aylsworth et al. |
| 7,559,326 B2 | 7/2009 | Smith et al. |
| 7,585,351 B2 | 9/2009 | Deane et al. |
| 7,590,551 B2 | 9/2009 | Auer |
| 7,604,004 B2 | 10/2009 | Jagger et al. |
| 7,604,005 B2 | 10/2009 | Jagger et al. |
| 7,628,151 B2 | 12/2009 | Bassin |
| 7,637,989 B2 | 12/2009 | Bong |
| 7,655,059 B2 | 2/2010 | Wang et al. |
| 7,655,063 B2 | 2/2010 | Wang et al. |
| 7,682,428 B2 | 3/2010 | Nawata et al. |
| 7,682,429 B2 | 3/2010 | Dolensky et al. |
| 7,686,870 B1 | 3/2010 | Deane et al. |
| 7,704,304 B2 | 4/2010 | Warren et al. |
| 7,708,802 B1 | 5/2010 | Deane et al. |
| 7,708,818 B2 | 5/2010 | Clark |
| 7,717,981 B2 | 5/2010 | Labuda et al. |
| 7,722,700 B2 | 5/2010 | Sprinkle |
| 7,727,160 B2 | 6/2010 | Green et al. |
| 7,730,887 B2 | 6/2010 | Deane et al. |
| 7,753,996 B1 | 7/2010 | Deane et al. |
| 7,758,672 B2 | 7/2010 | Lee et al. |
| 7,763,103 B2 | 7/2010 | Dolensky et al. |
| 7,766,010 B2 | 8/2010 | Jagger et al. |
| 7,771,511 B2 | 8/2010 | Dolensky |
| 7,780,768 B2 | 8/2010 | Taylor et al. |
| 7,780,769 B2 | 8/2010 | Dolensky et al. |
| 7,794,522 B2 | 9/2010 | Bliss et al. |
| 7,828,878 B2 | 11/2010 | Zhong et al. |
| 7,837,761 B2 | 11/2010 | Bliss et al. |
| 7,841,343 B2 | 11/2010 | Deane et al. |
| 7,849,854 B2 | 12/2010 | Devries et al. |
| 7,857,894 B2 | 12/2010 | Taylor et al. |
| 7,861,716 B2 | 1/2011 | Borrello |
| 7,866,315 B2 | 1/2011 | Jagger et al. |
| 7,874,290 B2 | 1/2011 | Chalvignac |
| 7,875,105 B2 | 1/2011 | Chambers et al. |
| 7,892,322 B2 | 2/2011 | Ono et al. |
| 7,909,034 B2 | 3/2011 | Sinderby et al. |
| 7,914,459 B2 | 3/2011 | Green et al. |
| 7,918,925 B2 | 4/2011 | Dolensky et al. |
| 7,922,789 B1 | 4/2011 | Deane et al. |
| 7,934,499 B2 | 5/2011 | Berthon-Jones |
| 7,954,493 B2 | 6/2011 | Nawata |
| 8,006,692 B2 | 8/2011 | Smith et al. |
| 8,016,916 B2 | 9/2011 | Ono et al. |
| 8,016,918 B2 | 9/2011 | Labuda et al. |
| 8,016,925 B2 | 9/2011 | Mccombs et al. |
| 8,020,553 B2 | 9/2011 | Jagger et al. |
| 8,051,852 B2 | 11/2011 | Bassin |
| 8,062,003 B2 | 11/2011 | Goertzen |
| 8,070,853 B2 | 12/2011 | Sprinkle |
| 8,070,864 B2 | 12/2011 | Uchiyama et al. |
| 8,070,922 B2 | 12/2011 | Nelson et al. |
| 8,075,676 B2 | 12/2011 | Thompson et al. |
| 8,100,125 B2 | 1/2012 | Duquette et al. |
| 8,118,024 B2 | 2/2012 | Devries et al. |
| 8,122,885 B2 | 2/2012 | Berthon-Jones et al. |
| 8,123,497 B2 | 2/2012 | Richey et al. |
| 8,142,544 B2 | 3/2012 | Taylor et al. |
| 8,146,596 B2 | 4/2012 | Smith et al. |
| 8,147,597 B2 | 4/2012 | Dolensky et al. |
| 8,156,937 B2 | 4/2012 | Devries et al. |
| 8,167,988 B2 | 5/2012 | Dolensky et al. |
| 8,192,526 B2 | 6/2012 | Zhong et al. |
| 8,210,205 B2 | 7/2012 | Michaels |
| 8,225,789 B2 | 7/2012 | Berthon-Jones |
| 8,226,745 B2 | 7/2012 | Siew-wah et al. |
| 8,236,095 B1 | 8/2012 | Bassine |
| 8,256,419 B2 | 9/2012 | Sinderby et al. |
| 8,257,473 B2 | 9/2012 | Mccombs et al. |
| 8,280,498 B2 | 10/2012 | Jalde |
| 8,282,717 B2 | 10/2012 | Chambers et al. |
| 8,297,279 B2 | 10/2012 | Devries et al. |
| 8,337,599 B2 | 12/2012 | Kiritake |
| 8,343,259 B2 | 1/2013 | Knaebel |
| 8,349,053 B2 | 1/2013 | Lee et al. |
| 8,361,204 B1 | 1/2013 | Bassine |
| 8,366,815 B2 | 2/2013 | Taylor et al. |
| 8,371,298 B2 | 2/2013 | Hallback et al. |
| 8,375,944 B2 | 2/2013 | Kwok |
| 8,377,180 B2 | 2/2013 | Maeda et al. |
| 8,377,181 B2 | 2/2013 | Taylor et al. |
| 8,388,548 B2 | 3/2013 | Green et al. |
| 8,388,745 B1 | 3/2013 | Pelletier et al. |
| 8,400,290 B2 | 3/2013 | Baker, Jr. |
| 8,418,691 B2 | 4/2013 | Jafari et al. |
| 8,418,692 B2 | 4/2013 | Sanchez |
| 8,424,520 B2 | 4/2013 | Thiessen |
| 8,424,521 B2 | 4/2013 | Jafari et al. |
| 8,428,672 B2 | 4/2013 | Sherman et al. |
| 8,434,480 B2 | 5/2013 | Jafari et al. |
| 8,434,482 B2 | 5/2013 | Borrello |
| 8,434,488 B2 | 5/2013 | Li et al. |
| 8,435,013 B2 | 5/2013 | Kondou et al. |
| 8,440,004 B2 | 5/2013 | Taylor et al. |
| 8,443,294 B2 | 5/2013 | Skidmore et al. |
| 8,448,640 B2 | 5/2013 | Bassin |
| 8,448,641 B2 | 5/2013 | Jafari et al. |
| 8,469,026 B2 | 6/2013 | Blomberg et al. |
| 8,522,780 B2 | 9/2013 | Devries et al. |
| 8,539,952 B2 | 9/2013 | Carbone et al. |
| 8,627,819 B2 | 1/2014 | Devries et al. |
| 8,683,997 B2 | 4/2014 | Devries et al. |
| 8,844,530 B2 | 9/2014 | Birnkrant |
| 9,126,002 B2 | 9/2015 | Devries et al. |
| 9,345,851 B2 | 5/2016 | Kim et al. |
| 9,504,799 B2 | 11/2016 | Hardin et al. |
| 9,956,371 B2 | 5/2018 | DeVries |
| 10,046,134 B2 | 8/2018 | DeVries |
| 10,105,509 B2 | 10/2018 | DeVries |
| 10,245,406 B2 | 4/2019 | Devries |
| 10,350,377 B2 | 7/2019 | Fiorenza |
| 2002/0005197 A1 | 1/2002 | DeVries |
| 2002/0053286 A1 | 5/2002 | Czabala |
| 2002/0092420 A1 | 7/2002 | Jagger et al. |
| 2002/0121278 A1 | 9/2002 | Hete |
| 2003/0010208 A1 | 1/2003 | Jagger et al. |
| 2003/0024766 A1 | 2/2003 | Briscoe |
| 2003/0051729 A1* | 3/2003 | Be'eri ............... A61M 16/20 128/204.18 |
| 2003/0111077 A1 | 6/2003 | Hooser |
| 2003/0131848 A1 | 7/2003 | Stenzler |
| 2003/0196550 A1 | 10/2003 | Keefer et al. |
| 2003/0200865 A1 | 10/2003 | Mccombs et al. |
| 2003/0230308 A1 | 12/2003 | Linden |
| 2004/0021108 A1* | 2/2004 | Hallback ............. F16K 31/082 251/65 |
| 2004/0231913 A1 | 11/2004 | Mccombs et al. |
| 2005/0045040 A1 | 3/2005 | Mccombs |
| 2005/0072298 A1 | 4/2005 | Deane et al. |
| 2005/0072306 A1 | 4/2005 | Deane et al. |
| 2005/0072423 A1 | 4/2005 | Deane et al. |
| 2005/0072426 A1 | 4/2005 | Deane et al. |
| 2005/0103341 A1 | 5/2005 | Deane et al. |
| 2005/0112013 A1 | 5/2005 | Devries et al. |
| 2005/0217481 A1 | 10/2005 | Dunne et al. |
| 2005/0257686 A1 | 11/2005 | Occhialini et al. |

(56) References Cited

U.S. PATENT DOCUMENTS

| | | |
|---|---|---|
| 2005/0274815 A1 | 12/2005 | Bergholtz et al. |
| 2006/0011065 A1 | 1/2006 | Hastings |
| 2006/0064802 A1 | 3/2006 | Damrath et al. |
| 2006/0086251 A1 | 4/2006 | Sprinkle |
| 2006/0102181 A1 | 5/2006 | Mccombs et al. |
| 2006/0107947 A1 | 5/2006 | Rist |
| 2006/0117957 A1 | 6/2006 | Mccombs et al. |
| 2006/0137522 A1 | 6/2006 | Nishimura et al. |
| 2006/0174871 A1 | 8/2006 | Jagger et al. |
| 2006/0174875 A1 | 8/2006 | Jagger et al. |
| 2006/0174877 A1 | 8/2006 | Jagger et al. |
| 2006/0230924 A1 | 10/2006 | Deane et al. |
| 2006/0230929 A1 | 10/2006 | Bliss et al. |
| 2006/0230931 A1 | 10/2006 | Bliss et al. |
| 2006/0230939 A1 | 10/2006 | Bliss et al. |
| 2006/0266357 A1 | 11/2006 | Mccombs et al. |
| 2006/0283325 A1 | 12/2006 | Sugano |
| 2007/0031302 A1 | 2/2007 | Wittrup et al. |
| 2007/0056583 A1 | 3/2007 | Jagger et al. |
| 2007/0056584 A1 | 3/2007 | Jagger et al. |
| 2007/0084342 A1 | 4/2007 | Hunter et al. |
| 2007/0084349 A1 | 4/2007 | Calkins et al. |
| 2007/0101999 A1 | 5/2007 | Duquette et al. |
| 2007/0135757 A1 | 6/2007 | Acker |
| 2007/0144521 A1 | 6/2007 | Devries et al. |
| 2007/0148016 A1 | 6/2007 | Crawford et al. |
| 2007/0169623 A1 | 7/2007 | Lee et al. |
| 2007/0199566 A1 | 8/2007 | Be |
| 2007/0214955 A1 | 9/2007 | Aylsworth et al. |
| 2007/0227360 A1 | 10/2007 | Atlas et al. |
| 2007/0227540 A1 | 10/2007 | Ljungberg et al. |
| 2007/0272243 A1 | 11/2007 | Sherman et al. |
| 2007/0289446 A1 | 12/2007 | Occhialini et al. |
| 2008/0028933 A1 | 2/2008 | Ross et al. |
| 2008/0034975 A1 | 2/2008 | Chambers et al. |
| 2008/0053441 A1 | 3/2008 | Gottlib |
| 2008/0066616 A1 | 3/2008 | Sprinkle |
| 2008/0087170 A1 | 4/2008 | Deane et al. |
| 2008/0092892 A1 | 4/2008 | Boyle et al. |
| 2008/0092893 A1 | 4/2008 | Boyle et al. |
| 2008/0110338 A1 | 5/2008 | Taylor et al. |
| 2008/0110461 A1 | 5/2008 | Mulqueeny et al. |
| 2008/0135044 A1 | 6/2008 | Freitag et al. |
| 2008/0185544 A1 | 8/2008 | Yeh |
| 2008/0196580 A1 | 8/2008 | Bliss et al. |
| 2008/0202337 A1 | 8/2008 | Taylor et al. |
| 2008/0202508 A1 | 8/2008 | Mcclain et al. |
| 2008/0251071 A1 | 10/2008 | Armitstead et al. |
| 2008/0257145 A1 | 10/2008 | Sprinkle et al. |
| 2008/0257349 A1 | 10/2008 | Hedner et al. |
| 2008/0282880 A1 | 11/2008 | Bliss et al. |
| 2008/0302362 A1 | 12/2008 | Kwok |
| 2008/0302363 A1 | 12/2008 | Kroupa |
| 2008/0314385 A1 | 12/2008 | Brunner et al. |
| 2008/0315441 A1 | 12/2008 | Lee et al. |
| 2009/0007912 A1 | 1/2009 | Lindell et al. |
| 2009/0025560 A1 | 1/2009 | Takemasa |
| 2009/0025564 A1 | 1/2009 | Kuwabara |
| 2009/0044698 A1 | 2/2009 | Meacham |
| 2009/0065007 A1 | 3/2009 | Wilkinson et al. |
| 2009/0065526 A1 | 3/2009 | Sprinkle |
| 2009/0071333 A1 | 3/2009 | Labuda et al. |
| 2009/0078251 A1 | 3/2009 | Zucchi et al. |
| 2009/0084381 A1 | 4/2009 | Devries et al. |
| 2009/0107500 A1 | 4/2009 | Edwards |
| 2009/0133368 A1 | 5/2009 | Calkins et al. |
| 2009/0133694 A1 | 5/2009 | Solci et al. |
| 2009/0145428 A1 | 6/2009 | Sward et al. |
| 2009/0167698 A1 | 7/2009 | Altas et al. |
| 2009/0188502 A1 | 7/2009 | Tiedje |
| 2009/0211448 A1 | 8/2009 | Mcclain |
| 2009/0229459 A1 | 9/2009 | Warren et al. |
| 2009/0250059 A1 | 10/2009 | Allum et al. |
| 2009/0301477 A1 | 12/2009 | Pierro et al. |
| 2009/0308396 A1 | 12/2009 | Mcclain |
| 2010/0024819 A1 | 2/2010 | Tiedje |
| 2010/0051030 A1 | 3/2010 | Richard et al. |
| 2010/0052293 A1 | 3/2010 | Brooks et al. |
| 2010/0078018 A1 | 4/2010 | Heinonen |
| 2010/0095841 A1 | 4/2010 | Naheiri |
| 2010/0116270 A1 | 5/2010 | Branson Richard D et al. |
| 2010/0122699 A1 | 5/2010 | Birnkrant |
| 2010/0126249 A1 | 5/2010 | Matsuzaki |
| 2010/0229867 A1 | 9/2010 | Bertinetti et al. |
| 2010/0275921 A1 | 11/2010 | Schindhelm et al. |
| 2010/0282084 A1 | 11/2010 | Hansen Peter et al. |
| 2010/0288279 A1 | 11/2010 | Seiver et al. |
| 2010/0294127 A1 | 11/2010 | Dolensky |
| 2011/0000489 A1 | 1/2011 | Laksov et al. |
| 2011/0030684 A1 | 2/2011 | Wilkinson et al. |
| 2011/0030685 A1 | 2/2011 | Wilkinson et al. |
| 2011/0030686 A1 | 2/2011 | Wilkinson et al. |
| 2011/0030687 A1 | 2/2011 | Wilkinson et al. |
| 2011/0030689 A1 | 2/2011 | Wilkinson et al. |
| 2011/0057651 A1 | 3/2011 | Duric et al. |
| 2011/0067699 A1* | 3/2011 | Caruso .............. A61M 16/0463 128/205.29 |
| 2011/0073115 A1* | 3/2011 | Wood .................. A61M 16/04 128/207.15 |
| 2011/0113964 A1 | 5/2011 | Chambers et al. |
| 2011/0154986 A1 | 6/2011 | Lee et al. |
| 2011/0192122 A1 | 8/2011 | Whitesel et al. |
| 2011/0197882 A1 | 8/2011 | Truschel et al. |
| 2011/0197883 A1 | 8/2011 | Mcdaniel et al. |
| 2011/0197884 A1 | 8/2011 | Duff et al. |
| 2011/0197887 A1 | 8/2011 | Truschel et al. |
| 2011/0209706 A1 | 9/2011 | Truschel et al. |
| 2011/0209707 A1 | 9/2011 | Terhark |
| 2011/0220107 A1 | 9/2011 | Kimm et al. |
| 2011/0232483 A1 | 9/2011 | Haberland et al. |
| 2011/0232645 A1 | 9/2011 | Smith |
| 2011/0247616 A1 | 10/2011 | Von et al. |
| 2011/0247620 A1 | 10/2011 | Armstrong et al. |
| 2011/0247621 A1 | 10/2011 | Richard et al. |
| 2011/0247622 A1 | 10/2011 | Schneider et al. |
| 2011/0259334 A1 | 10/2011 | Alfieri et al. |
| 2011/0297153 A1* | 12/2011 | Grimsey ................. B63C 11/24 128/204.18 |
| 2011/0303223 A1 | 12/2011 | Kane et al. |
| 2011/0315140 A1 | 12/2011 | Shuman |
| 2012/0000462 A1 | 1/2012 | Edwards et al. |
| 2012/0006199 A1 | 1/2012 | Mccombs et al. |
| 2012/0006326 A1 | 1/2012 | Ahmad |
| 2012/0012109 A1 | 1/2012 | Chalvignac |
| 2012/0017909 A1 | 1/2012 | Porges et al. |
| 2012/0027628 A1 | 2/2012 | Ogawa |
| 2012/0037159 A1 | 2/2012 | Mulqueeny et al. |
| 2012/0055340 A1 | 3/2012 | Wilkinson et al. |
| 2012/0055474 A1 | 3/2012 | Wilkinson |
| 2012/0055475 A1 | 3/2012 | Wilkinson |
| 2012/0055477 A1 | 3/2012 | Wilkinson |
| 2012/0055480 A1 | 3/2012 | Wilkinson |
| 2012/0055482 A1 | 3/2012 | Wilkinson |
| 2012/0055483 A1 | 3/2012 | Wilkinson et al. |
| 2012/0060840 A1 | 3/2012 | Refsland et al. |
| 2012/0125336 A1 | 5/2012 | Berthon-Jones et al. |
| 2012/0125337 A1 | 5/2012 | Asanoi |
| 2012/0152248 A1 | 6/2012 | Richey et al. |
| 2012/0167883 A1 | 7/2012 | Taylor et al. |
| 2012/0167886 A1 | 7/2012 | Taylor et al. |
| 2012/0167887 A1 | 7/2012 | Taylor et al. |
| 2012/0167888 A1 | 7/2012 | Taylor et al. |
| 2012/0177546 A1 | 7/2012 | Hilbig |
| 2012/0192862 A1 | 8/2012 | Lewis et al. |
| 2012/0192864 A1 | 8/2012 | Galbraith et al. |
| 2012/0192867 A1 | 8/2012 | Lewis et al. |
| 2012/0247329 A1 | 10/2012 | Hilbig |
| 2012/0266883 A1 | 10/2012 | Taylor et al. |
| 2012/0285543 A1 | 11/2012 | Michaels |
| 2012/0291884 A1 | 11/2012 | Yamaura et al. |
| 2012/0304867 A1 | 12/2012 | Watanabe et al. |
| 2012/0308779 A1 | 12/2012 | Klee et al. |
| 2012/0318145 A1 | 12/2012 | Hilbig et al. |
| 2013/0008438 A1 | 1/2013 | Sugawara et al. |

(56) References Cited

U.S. PATENT DOCUMENTS

| | | |
|---|---|---|
| 2013/0008444 A1 | 1/2013 | Chalvignac et al. |
| 2013/0025591 A1 | 1/2013 | Clark et al. |
| 2013/0031784 A1 | 2/2013 | Chambers et al. |
| 2013/0087145 A1 | 4/2013 | Koebrich et al. |
| 2013/0087146 A1 | 4/2013 | Callaghan et al. |
| 2013/0092159 A1 | 4/2013 | Ulrichskoetter et al. |
| 2013/0098361 A1 | 4/2013 | Koebrich Rainer et al. |
| 2013/0104898 A1 | 5/2013 | Berthon-Jones |
| 2013/0125891 A1 | 5/2013 | Eddy |
| 2013/0186400 A1 | 7/2013 | Jafari et al. |
| 2013/0186401 A1 | 7/2013 | Jafari et al. |
| 2013/0199520 A1 | 8/2013 | Dhuper et al. |
| 2013/0255689 A1 | 10/2013 | Kim et al. |
| 2013/0272905 A1* | 10/2013 | Shelke .................. F04B 43/113 417/375 |
| 2013/0276789 A1 | 10/2013 | Garde et al. |
| 2014/0007878 A1 | 1/2014 | Armistead et al. |
| 2014/0116441 A1 | 5/2014 | Mcdaniel |
| 2014/0216446 A1 | 8/2014 | Wruck |
| 2014/0318535 A1 | 10/2014 | Bullock |
| 2015/0000660 A1 | 1/2015 | Martin |
| 2015/0224278 A1 | 8/2015 | Addington et al. |
| 2015/0283352 A1 | 10/2015 | Karkkainen |
| 2015/0320962 A1 | 11/2015 | Bafile |
| 2016/0243330 A1 | 8/2016 | Destefano |
| 2016/0279363 A1 | 9/2016 | Devries et al. |
| 2016/0279369 A1 | 9/2016 | Cipollone |
| 2016/0279378 A1 | 9/2016 | Cipollone |
| 2017/0000968 A1 | 1/2017 | Harrington et al. |
| 2017/0361058 A1 | 12/2017 | Gaw et al. |

FOREIGN PATENT DOCUMENTS

| | | |
|---|---|---|
| WO | 03045486 A1 | 6/2003 |
| WO | 2013033589 A1 | 3/2013 |
| WO | 2015126853 A1 | 8/2015 |
| WO | 2016067147 A1 | 5/2016 |

OTHER PUBLICATIONS

Branson, D R. et al., Branson, D. Richard et al., "Maximizing Oxygen Delivery During Mechanical Ventilation with a Portable Oxygen Concentrator," The Journal of Trauma® Injury, Infection, and Critical Care, vol. 69, No. 1, Jul. Supplement 2010, 7 pages, Jul. 2010, 7 pages.

Gustafson, et al., Gustafson et al., "Pulse Dose Delivery of Oxygen in Mechanically Ventilated Pigs with Acute Lung Injury," The Journal of Trauma and Acute Care Surgery, 75(5), Nov. 2013, pp. 775-779., 5 pages.

Extended European Search Report dated Sep. 24, 2018 in European Patent Application No. 16769634.3, 7 pages.

International Search Report and Written Opinion dated Jun. 10, 2016 in International Patent Application No. PCT/US2016/023828, 11 pages.

International Search Report and Written Opinion dated Sep. 6, 2017 in International Patent Application No. PCT/US2017/037738, 8 pages.

\* cited by examiner

ACTIVE EXHALATION VALVE

CROSS-REFERENCE TO RELATED APPLICATION(S)

This application is a divisional of U.S. patent application Ser. No. 14/939,789, filed Nov. 12, 2015, which is a continuation of U.S. patent application Ser. No. 14/819,165, filed Aug. 5, 2015, which is a continuation of U.S. patent application Ser. No. 14/803,799, filed Jul. 20, 2015, which is a continuation of U.S. patent application Ser. No. 14/749,397, filed Jun. 24, 2015, which is a continuation of U.S. patent application Ser. No. 14/695,708, filed Apr. 25, 2015, which is a continuation of U.S. patent application Ser. No. 14/667,451, filed Mar. 24, 2015, which is a continuation of U.S. patent application Ser. No. 14/667,480, filed Mar. 24, 2015, all of which applications are incorporated by reference herein in their entireties.

TECHNICAL FIELD

The present invention is directed generally to an active exhalation valve for use with a ventilator having a pressure source usable to control operation of the valve and thereby the flow of patient exhaled gases.

BACKGROUND

Respiration may be characterized as including both an inspiratory phase and an exhalation phase. During the inspiratory phase, inspiratory gases are drawn into the lungs, and during the exhalation phase, exhalation gases are expelled from the lungs.

Mechanical ventilators are used to assist with breathing. Conventional ventilators typically push inspiratory gases including oxygen into the patient's lungs. Many patients who use a ventilator also need other types of assistance related to treating and maintaining their airways and lungs. For example, some patients may use a nebulizer to deliver drugs to their lungs and/or airways. Further, some patients may need help clearing secretions from their lungs and/or airways. Such assistance is typically provided by a conventional suction device. Thus, in additional to a ventilator, many patients require multiple devices and traveling with such equipment can be particularly problematic.

Currently, to receive cough assistance, a patient must be disconnected from mechanical ventilation, and connected to a separate cough assist device. After a cough assist maneuver is performed, the patient must be disconnected from the cough assist device, and reconnected to the mechanical ventilation. Often, suctioning of the patient airway is also performed after the patient has been disconnected from the cough assist device and reconnected to the mechanical ventilation to remove secretions not adequately cleared from the patient airway during the cough assist maneuver. To minimize risk of patient hypoxemia during the period of time that the patient is not receiving mechanical ventilation, it is a common practice to deliver an elevated level of inspired oxygen before removing mechanical ventilation from the patient. Because this process may be tedious, it is often not performed in a manner that is most advantageous to the patient.

Thus, a need exists for ventilators configured to be portable and/or provide additional functionality beyond delivering inspiratory gases into the patient's lungs. The present application provides these and other advantages as will be apparent from the following detailed description and accompanying figures.

SUMMARY

One embodiment of an active exhalation valve is for use with a ventilator to control flow of patient exhaled gases. The active exhalation valve includes a patient circuit connection port, a patient connection port, an exhaled gas port, a pilot pressure port, a valve seat, and a movable poppet. The movable poppet includes an inner bellows member, an outer bellows member and a bellows poppet face. The pilot pressure port is configured such that an activation pressure applied to the pilot pressure port extends the inner and outer bellows members to move the bellows poppet face into engagement with the valve seat and restrict flow of patient exhaled gases to the exhaled gas port, and the reduction of the activation pressure to the pilot pressure port allows the inner and outer bellows members to move the bellows poppet face away from the valve seat and out of engagement with the valve seat to permit flow of patient exhaled gases to the exhaled gas port, thereby controlling the flow of patient exhaled gases from the valve.

Optionally, the inner and outer bellows members define an interior bellows chamber therebetween and the pilot pressure port is in fluid communication with the interior bellows chamber.

Optionally, the inner bellows member has an inner bellows fluid passageway extending therethrough in fluid communication with the patient circuit connection port and the patient connection port.

Optionally, the inner bellows fluid passageway is in continuous fluid communication with the patient circuit connection port and the patient connection port during operation of the exhalation valve, and out of fluid communication with the interior bellows chamber between the inner and outer bellows members.

Optionally, the inner bellows member has an inner bellows fluid passageway extending therethrough in continuous fluid communication with the patient circuit connection port and the patient connection port.

Another embodiment of an active exhalation valve is for use with a patient connection and a ventilator having a pressure source usable to control operation of the valve to control flow of patient exhaled gases. The active exhalation valve includes a patient circuit connection port for fluid communication with the ventilator, a patient connection port for fluid communication with the patient connection, an exhaled gas port for fluid communication with air exterior to the valve to remove patient exhaled gases from the valve, a pilot pressure port for fluid communication with the pressure source, a valve seat, and a movable poppet. The movable poppet includes an inner bellows member, an outer bellows member and a bellows poppet face. The pilot pressure port is configured such that an activation pressure applied by the pressure source to the pilot pressure port extends the inner and outer bellows members to move the bellows poppet face into sealing engagement with the valve seat and restrict flow of patient exhaled gases to the exhaled gas port, and the reduction of the activation pressure applied by the pressure source to the pilot pressure port allows the inner and outer bellows members to move the bellows poppet face away from the valve seat and out of sealing engagement with the valve seat to permit flow of patient exhaled gases to the exhaled gas port, thereby controlling the flow of patient exhaled gases from the valve.

Optionally, the inner and outer bellows members define an interior bellows chamber therebetween and the pilot pressure port is in fluid communication with the interior bellows chamber.

Optionally, the inner bellows member has an inner bellows fluid passageway extending therethrough in fluid communication with the patient circuit connection port and the patient connection port.

Optionally, the inner bellows fluid passageway is in continuous fluid communication with the patient circuit connection port and the patient connection port during operation of the exhalation valve, and out of fluid communication with the interior bellows chamber between the inner and outer bellows members.

Optionally, the inner bellows member has an inner bellows fluid passageway extending therethrough in continuous fluid communication with the patient circuit connection port and the patient connection port.

Yet another embodiment of an active exhalation valve is for use with a ventilator to control operation of the valve to control flow of patient exhaled gases. The active exhalation valve includes a patient circuit connection port, a patient connection port, an exhaled gas port, a pilot pressure port, a valve seat, and a movable poppet. The movable poppet includes an inner member, an outer member and a poppet face. The pilot pressure port is configured such that an activation pressure applied to the pilot pressure port moves the inner and outer members toward the valve seat to move the poppet face into engagement with the valve seat and restrict flow of patient exhaled gases to the exhaled gas port, and the reduction of the activation pressure to the pilot pressure port allows the inner and outer members to move away from the valve seat to move the poppet face out of engagement with the valve seat to permit flow of patient exhaled gases to the exhaled gas port, thereby controlling the flow of patient exhaled gases from the valve.

Optionally, the inner and outer members define an interior chamber therebetween and the pilot pressure port is in fluid communication with the interior chamber.

Optionally, the inner member has an inner member fluid passageway extending therethrough in fluid communication with the patient circuit connection port and the patient connection port.

Optionally, the inner member fluid passageway is in continuous fluid communication with the patient circuit connection port and the patient connection port during operation of the exhalation valve, and out of fluid communication with the interior bellows chamber between the inner and outer bellows members.

Optionally, the inner member has an inner member fluid passageway extending therethrough in continuous fluid communication with the patient circuit connection port and the patient connection port.

Another embodiment of an active exhalation valve is for use with a patient connection and a ventilator having a pressure source usable to control operation of the valve. The active exhalation valve includes a valve body having an internal body chamber with gasses therein having a body chamber pressure, a first body port in fluid communication with the body chamber and configured for fluid communication with the patient connection, a second body port in fluid communication with the body chamber and configured for fluid communication with the ventilator, a passageway in fluid communication with the body chamber and with ambient air exterior of the valve body, and a valve seal movable between a closed position sealing the passageway and an open position opening the passageway. The valve seal has an outer member, an inner member positioned within the outer member, an internal seal chamber located between the outer and inner members and in fluid communication with the pressure source, and a seal member extending between the inner and outer members and movable therewith. The seal member has a first surface portion inside the seal chamber configured for movement of the valve seal toward the closed position in response to pressure applied thereto by the pressure source and a second surface portion outside the seal chamber configured for movement of the valve seal toward the open position in response to pressure applied thereto by the body chamber pressure, with the amount and direction of movement of the valve seal being responsive to a resultant force generated by the pressure source and the body chamber pressure on the first and second surface portions.

Optionally, the inner member has an inner member fluid passageway extending therethrough in fluid communication with the body chamber and having a first end in fluid communication with the first body port and a second end in fluid communication with the second body port.

Optionally, the inner member fluid passageway is in continuous fluid communication with the first and second body ports during operation of the exhalation valve, and out of fluid communication with the seal chamber between the inner and outer members.

Optionally, the inner member has an inner member fluid passageway extending therethrough with a first opening in continuous fluid communication with the first body port and a second opening in continuous fluid communication with the second body port.

Optionally, the body has a wall portion positioned outward of the valve seal and defining another chamber positioned outward of the valve seal with the passageway being in the wall portion.

Optionally, the body has a perimeter wall portion extending circumferentially about the body chamber and positioned outward of the valve seal, and defining an elongated perimeter chamber extending at least partially about the body chamber, with the passageway being in the perimeter wall portion.

Optionally, the passageway comprises a plurality of apertures in an external wall of the body in fluid communication with the body chamber and with ambient air exterior of the valve body.

An additional embodiment of an active exhalation valve is for use with a patient connection and a ventilator having a pressure source usable to control operation of the valve. The active exhalation valve includes a valve body having an internal body chamber with gasses therein having a body chamber pressure and a body wall portion with a channel therein for fluid communication with the pressure source and an aperture in fluid communication with the channel, a first body port in fluid communication with the body chamber and configured for fluid communication with the patient connection, a second body port in fluid communication with the body chamber and configured for fluid communication with the ventilator, a passageway in fluid communication with the body chamber and with ambient air exterior of the valve body, and a valve seal movable between a closed position sealing the passageway and an open position opening the passageway. The valve seal has an outer longitudinally extending and longitudinally compressible wall, an inner longitudinally extending and longitudinally compressible wall positioned within the outer wall, each of the outer and inner walls having a first end and a second end, a seal end wall closing a space between the first ends of the outer and inner walls and being longitudinally movable with the first ends of the outer and inner walls, with the body wall portion closing a space between the second ends of the outer and inner walls, and an internal seal chamber located between the outer and inner walls and extending between the seal end wall and the body wall portion. The aperture of the body wall portion is in fluid communication with the seal chamber to provide fluid communication with the pressure source. The seal end wall is longitudinally movable within the valve body between the closed position with the outer and inner walls being in an extended configuration and the open position with the outer and inner walls being compressed into at least a partially longitudinally compressed position. The seal end wall has a first surface portion inside the seal chamber configured for movement of the valve seal toward the closed position in response to pressure applied thereto by the pressure source and a second surface portion outside the seal chamber configured for movement of the valve seal toward the open position in response to pressure applied thereto by the body chamber pressure, with the amount and direction of movement of the valve seal being responsive to a resultant force generated by the pressure source and the body chamber pressure on the first and second surface portions of the seal end wall.

Optionally, the inner wall has an inner wall fluid passageway extending therethrough in fluid communication with the body chamber and having a first end in fluid communication with the first body port and a second end in fluid communication with the second body port.

Optionally, the inner wall fluid passageway is in continuous fluid communication with the first and second body ports during operation of the exhalation valve, and out of fluid communication with the seal chamber between the inner and outer walls.

Optionally, the inner wall has an inner wall fluid passageway extending therethrough with a first opening in continuous fluid communication with the first body port and a second opening in continuous fluid communication with the second body port.

Optionally, the longitudinally compressible outer and inner walls are corrugated with a plurality of corrugations, and when in the at least partially longitudinally compressed position more than one of the corrugations is longitudinally compressed.

A final embodiment of an active exhalation valve is for use with a patient connection and a ventilator having a pressure source usable to control operation of the valve. The active exhalation valve includes a valve body having an internal body chamber with gasses therein having a body chamber pressure and a channel therein for fluid communication with the pressure source and an aperture in fluid communication with the channel, a first body port in fluid communication with the body chamber and configured for fluid communication with the patient connection, a second body port in fluid communication with the body chamber and configured for fluid communication with the ventilator, a passageway in fluid communication with the body chamber and with ambient air exterior of the valve body, and a valve seal movable between a closed position sealing the passageway and an open position opening the passageway. The valve seal has a seal chamber defined by first and second longitudinally spaced apart ends, and by an outer longitudinally extendable wall and an inner longitudinally extendable wall positioned within the outer wall. The aperture of the valve body is in fluid communication with the seal chamber to provide fluid communication with the pressure source. The first end of the seal chamber is longitudinally movable within the valve body between the closed position of the valve seal whereat the outer and inner walls are in a longitudinally extended configuration and the open position of the valve seal whereat the outer and inner walls are in a longitudinally retracted configuration. The valve seal is moved toward the closed position in response to pressure applied by the pressure source and toward the open position in response to pressure applied by the body chamber pressure, with the amount and direction of movement of the valve seal being responsive to a resultant force generated by the pressure source and the body chamber pressure.

Optionally, the inner wall has an inner wall fluid passageway extending therethrough in fluid communication with the body chamber and having a first end in fluid communication with the first body port and a second end in fluid communication with the second body port.

Optionally, the inner wall fluid passageway is in continuous fluid communication with the first and second body ports during operation of the exhalation valve, and out of fluid communication with the seal chamber between the inner and outer walls.

Optionally, the inner wall has an inner wall fluid passageway extending therethrough with a first opening in continuous fluid communication with the first body port and a second opening in continuous fluid communication with the second body port.

BRIEF DESCRIPTION OF THE DRAWINGS

Like reference numerals have been used in the figures to identify like components.

DETAILED DESCRIPTION

Figure 1:
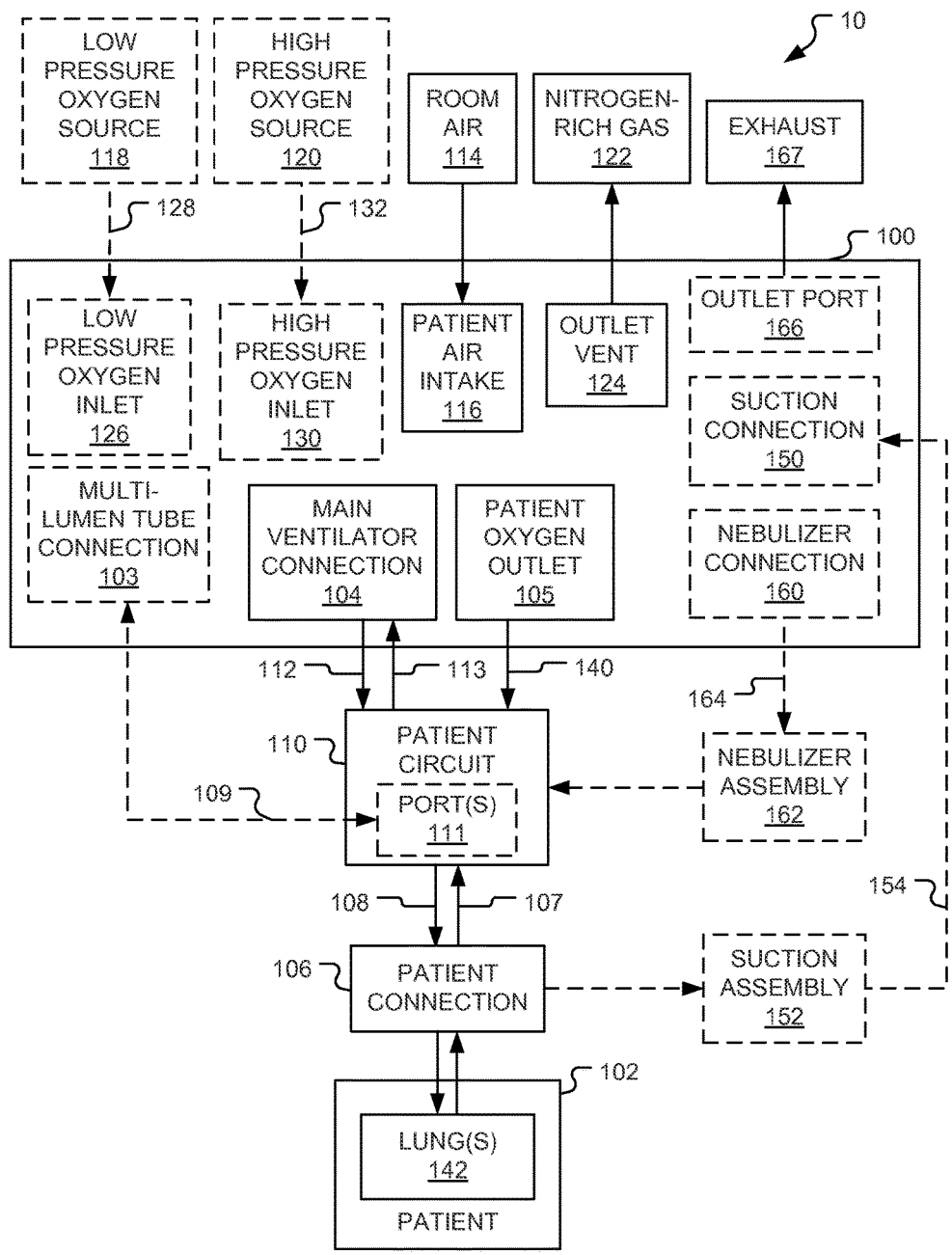
FIG. 1 is a block diagram illustrating an exemplary system that includes a ventilator for use by a human patient.

FIG. 1 is a block diagram illustrating an exemplary system 10 that includes a ventilator 100 with integrated cough assist functionality for use by a patient 102. The ventilator 100 may be configured to provide both traditional volume controlled ventilation and pressure controlled ventilation. The ventilator 100 has an optional multi-lumen tube connection 103, a main ventilator connection 104, and a patient oxygen outlet 105. The patient 102 has a patient connection 106 (e.g., a tracheal tube, a nasal mask, a mouthpiece, and the like) that is connectable to the main ventilator connection 104 and/or the patient oxygen outlet 105 by a patient circuit 110.

As will be described below, the patient circuit 110 may be implemented as an active patient circuit or a passive patient circuit. Optionally, when the patient circuit 110 is implemented as an active patient circuit, the patient circuit 110 may include one or more ports 111 configured to be connected to the optional multi-lumen tube connection 103. The port(s) 111 allow one or more pressure signals 109 to flow between the optional multi-lumen tube connection 103 and the patient circuit 110. As is apparent to those of ordinary skill in the art, a pressure signal may be characterized as gas(es) obtained from a fluid (and/or gas) source for which a pressure is to be measured. The gas(es) obtained are at the same pressure as the fluid (and/or gas) source.

The main ventilator connection 104 is configured to provide gases 112 that include room air 114 optionally mixed with oxygen. While identified as being "room air," those of ordinary skill in the art appreciate that the room air 114 may include air obtained from any source external to the ventilator 100. The gases 112 may be used as inspiratory gases (during the inspiratory phase of a breath) or insufflation gases used during the insufflation phase of a cough. The main ventilator connection 104 is configured to receive gases 113, which may include exsufflation gases exhaled by the patient 102 during an exsufflation phase of a cough.

The air 114 is received by the ventilator 100 via a patient air intake 116. The oxygen that is optionally mixed with the air 114 may be generated internally by the ventilator 100 and/or received from an optional low pressure oxygen source 118 (e.g., an oxygen concentrator), and/or an optional high pressure oxygen source 120. When the oxygen is generated internally, the ventilator 100 may output exhaust gases (e.g., nitrogen-rich gas 122) via an outlet vent 124. Optionally, the ventilator 100 may include a low pressure oxygen inlet 126 configured to be coupled to the optional low pressure oxygen source 118 and receive optional low pressure oxygen 128 therefrom. The ventilator 100 may include an optional high pressure oxygen inlet 130 configured to be coupled to the optional high pressure oxygen source 120 and receive optional high pressure oxygen 132 therefrom.

The patient oxygen outlet 105 is configured to provide doses or pulses of oxygen 140 to the patient connection 106 (via the patient circuit 110) that are synchronized with the patient's breathing. Unlike the gases 112 provided by the main ventilator connection 104, the pulses of oxygen 140 do not include the air 114.

The gases 112 and/or the pulses of oxygen 140 delivered to the patient circuit 110 are conducted thereby as inspiratory or insufflation gases 108 to the patient connection 106, which at least in part conducts those gases into the patient's lung(s) 142. Whenever the patient exhales during the exhalation phase of a breath or exsufflation phase of a cough, exhaled gases 107 enter the patient circuit 110 via the patient connection 106. Thus, the patient circuit 110 may contain one or more of the following gases: the gases 112 provided by the ventilator 100, the pulses of oxygen 140, and the exhaled gases 107. For ease of illustration, the gases inside the patient circuit 110 will be referred to hereafter as "patient gases."

Optionally, the ventilator 100 includes a suction connection 150 configured to be coupled to an optional suction assembly 152. The ventilator 100 may provide suction 154 to the optional suction assembly 152 via the optional suction connection 150. The suction assembly 152 may be configured to be connected to the patient connection 106, a suction catheter 812 (see FIG. 16) positionable inside the patient connection 106, and/or a drain 1280 (see FIG. 29).

Referring to FIG. 1, optionally, the ventilator 100 includes a nebulizer connection 160 configured to be coupled to an optional nebulizer assembly 162. The ventilator 100 may provide gases 164 (e.g., the air 114) to the optional nebulizer assembly 162 via the optional nebulizer connection 160. The optional nebulizer assembly 162 may be configured to be connected to the patient circuit 110. However, this is not a requirement.

Optionally, the ventilator 100 may include an outlet port 166 through which exhaust 167 may exit from the ventilator 100.

The ventilator 100 may be configured to be portable and powered by an internal battery (not shown) and/or an external power source (not shown) such as a conventional wall outlet.

Passive Patient Circuits

Figure 2A:
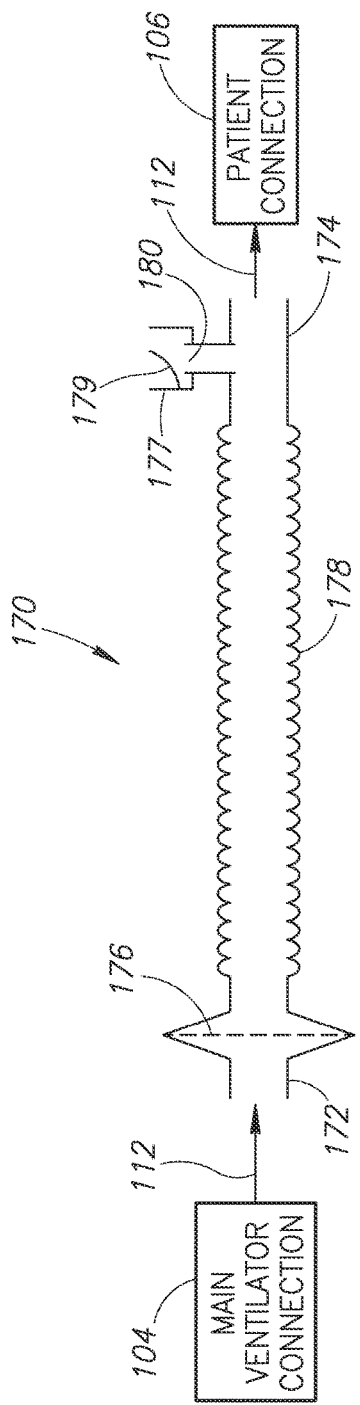
FIG. 2A is an illustration of a first embodiment of a passive patient circuit or use with the ventilator of FIG. 1.

FIG. 2A is an illustration of a first embodiment of a passive patient circuit 170 that may be used to implement the patient circuit 110. Referring to FIG. 2A, the passive patient circuit 170 has a first end portion 172 opposite a second end portion 174. The first end portion 172 is configured to be connected or coupled (e.g., directly or using a hose, flow line, conduit, or tube) to the main ventilator connection 104. The second end portion 174 is configured to be connected or coupled to the patient connection 106 (e.g., directly or using a hose, flow line, conduit, or tube). Optionally, a secretion trap 1250 (described below with respect to FIGS. 27-29) may be positioned between the second end portion 174 and the patient connection 106. The passive patient circuit 170 conducts the gases 112 (that include the air 114 optionally mixed with oxygen) from the main ventilator connection 104 into the patient connection 106 (optionally via the secretion trap 1250 illustrated in FIGS. 27-29).

In the embodiment illustrated, the passive patient circuit 170 includes an optional bacterial filter 176, a leak valve 177, and a flexible tube segment 178. The optional bacterial filter 176 may be positioned between the first end portion 172 and the flexible tube segment 178. The gases 112 may flow through the optional bacterial filter 176 and on to the patient connection 106. When present, the bacterial filter 176 helps prevent bacteria (e.g., received from the patient connection 106) from entering the ventilator 100 (via the main ventilator connection 104).

The leak valve 177 is coupled to the flexible tube segment 178 near the second end portion 174. The leak valve 177 is configured to allow gases to flow out of the passive patient circuit 170 and into the environment outside the passive patient circuit 170. The leak valve 177 may be implemented as a conventional fixed leak valve configured to allow at most a threshold amount of pressure inside the passive patient circuit 170 during both the inspiratory and exhalation phases.

The leak valve 177 may be implemented as a positive pressure valve that allows a portion of the patient gases to flow out of the passive patient circuit 170 and into the environment outside the passive patient circuit 170 whenever the pressure inside the passive patient circuit 170 is above the threshold amount (e.g., environmental pressure). The leak valve 177 includes a flexible member or flap 179 that covers and seals an outlet opening 180 when the pressure inside the passive patient circuit 170 is below the threshold amount. Thus, the leak valve 177 is closed when the pressure inside the passive patient circuit 170 is below the threshold amount.

On the other hand, the flap 179 is configured to be pushed outwardly and away from the outlet opening 180 when the pressure inside the passive patient circuit 170 exceeds the threshold amount (e.g., environmental pressure). Thus, the leak valve 177 is open when the pressure inside the passive patient circuit 170 is above the threshold amount. During normal ventilation, the leak valve 177 is open during both the inspiratory and exhalation phases. This means a portion of the patient gases inside the passive patient circuit 170 flow out of the passive patient circuit 170 through the outlet opening 180 and into the environment outside the passive patient circuit 170 during both the inspiratory and exhalation phases. On the other hand, as explained below, during an exsufflation phase of a cough, the leak valve 177 closes. This prevents the patient gases inside the passive patient circuit 170 from flowing out of the passive patient circuit 170 through the outlet opening 180. It also prevents air from entering the passive patient circuit 170 through the outlet opening 180.

Figure 2B:
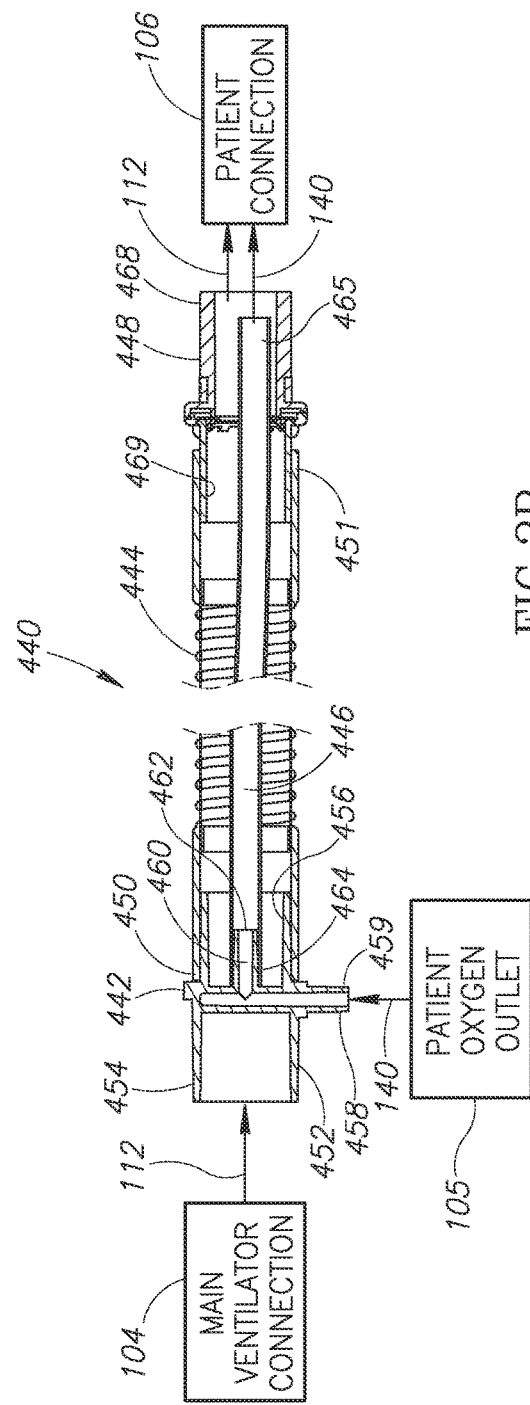
FIG. 2B is a cross-sectional view of a second embodiment of a passive patient circuit for use with the ventilator of FIG. 1.
Figure 2C:
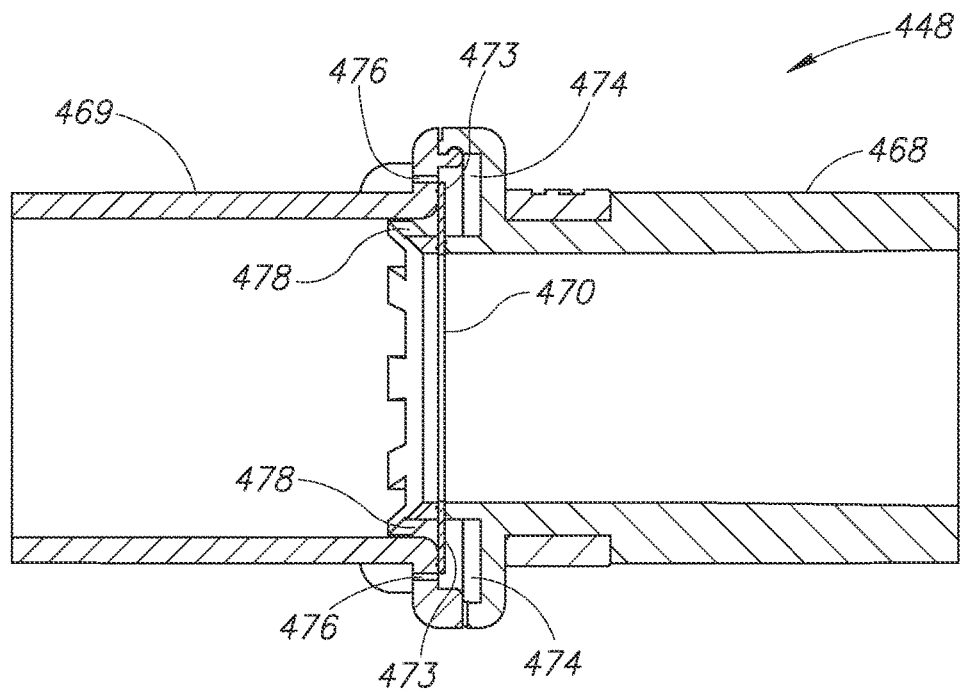
FIG. 2C is an enlarged cross-sectional view of a valve assembly of the passive patient circuit of FIG. 2B illustrated in a closed configuration.
Figure 2D:
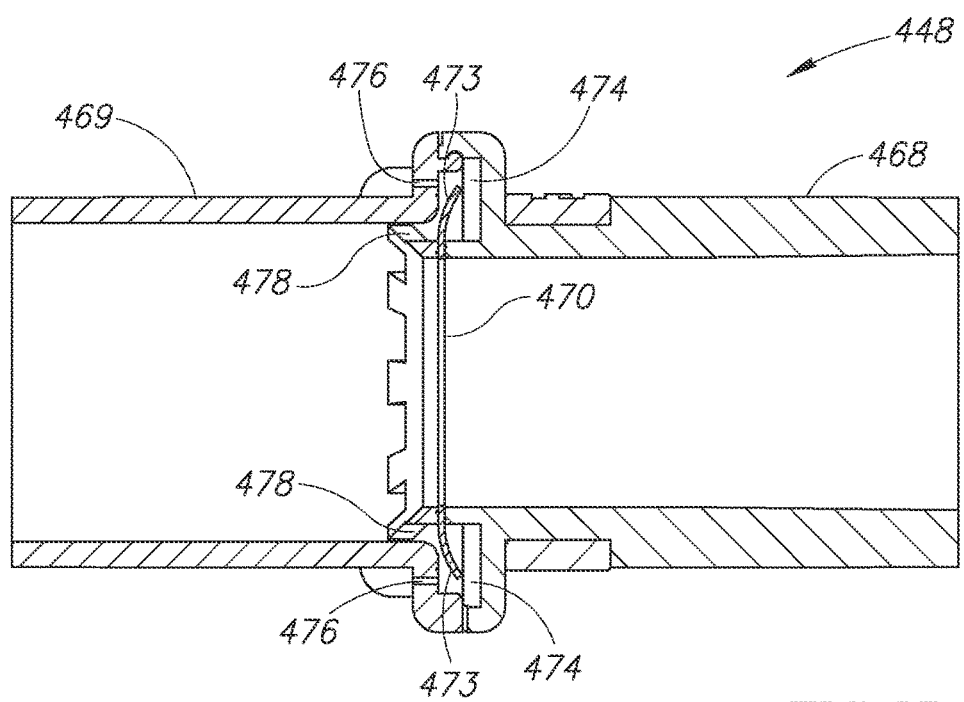
FIG. 2D is an enlarged cross-sectional view of the valve assembly of the passive patient circuit of FIG. 2B illustrated in an open configuration.
Figure 2E:
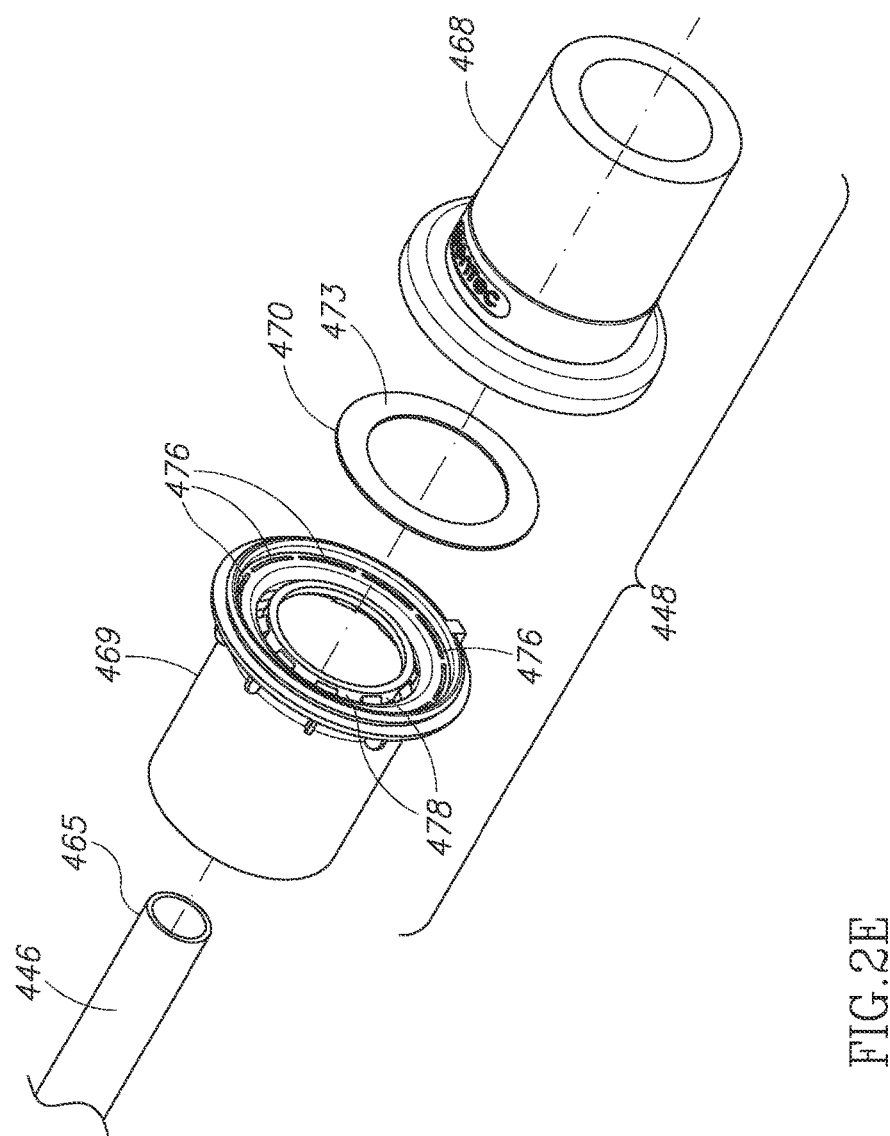
FIG. 2E is an exploded view of a valve assembly of the passive patient circuit of FIG. 2B.
Figure 2F:
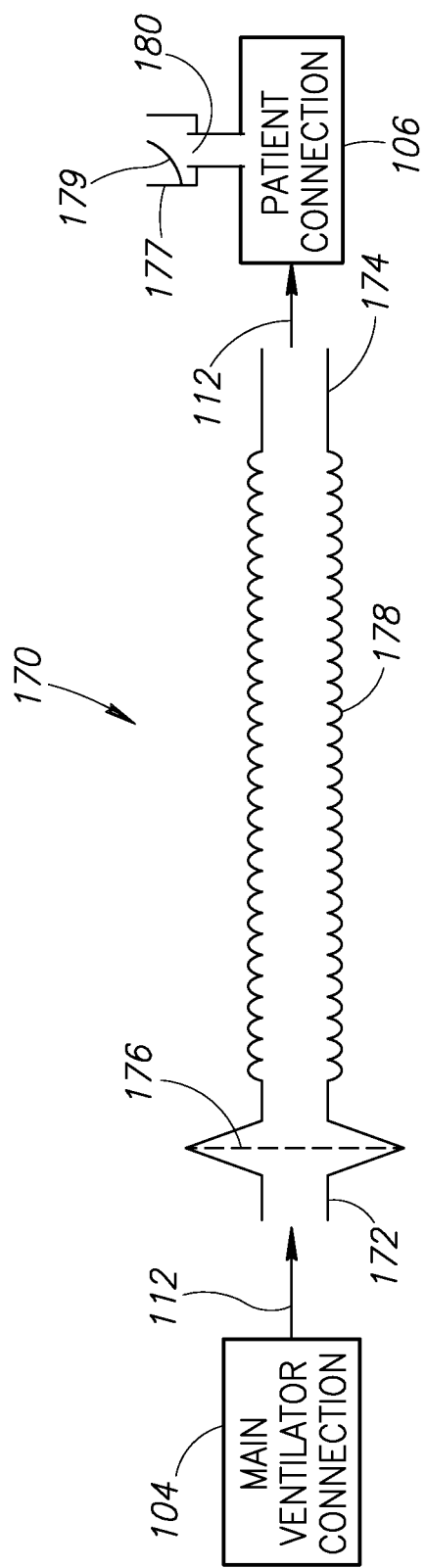
FIG. 2F is an illustration of an alternative embodiment of the first embodiment of the passive patient circuit shown in FIG. 2A with the leak valve incorporated into the patient connection.

FIG. 2F is an illustration of an alternative embodiment of the first embodiment of the passive patient circuit 170 shown in FIG. 2A with the leak valve 177 incorporated into the patient connection 106 and to which the second end portion 174 of the flexible tube segment 178 is connected or coupled. Alternatively, the leak valve 177 may be constructed as a separate part connected or coupled both to the second end portion 174 of the flexible tube segment 178 and to the patient connection 106.

FIG. 2B is an illustration of a second embodiment of a passive patient circuit 440 that may be used to implement the patient circuit 110. The passive patient circuit 440 includes a connector 442, a flexible tube segment 444, an open-ended oxygen pulse delivery tube 446, and a valve assembly 448. The flexible tube segment 444 may be implemented using a conventional corrugated or expanding ventilation hose or tubing (e.g., circuit tubing). The flexible tube segment 444 has a first end portion 450 opposite a second end portion 451. The first end portion 450 is configured to be connected or coupled to the connector 442. The second end portion 451 is configured to be connected or coupled to the valve assembly 448.

The connector 442 has a generally tube-shaped connector housing 452 with a first end portion 454 configured to be connected to the main ventilator connection 104 (e.g., directly or using a hose, flow line, conduit, or tube) and to receive the gases 112 (that include the air 114 optionally mixed with oxygen) from the main ventilator connection 104. Optionally, the bacterial filter 176 (see FIG. 2A) may be positioned between the connector 442 and the main ventilator connection 104. In such embodiments, the gases 112 flow through the bacterial filter 176 on their way to the connector 442. The bacterial filter 176 helps prevent bacteria (e.g., received from the patient connection 106) from entering the ventilator 100 (via the main ventilator connection 104).

The connector housing 452 has a second end portion 456 configured to be coupled to the first end portion 450 of the flexible tube segment 444 and to provide the gases 112 received by the first end portion 454 to the flexible tube segment 444. The flexible tube segment 444 conducts the gases 112 to the valve assembly 448.

The connector 442 includes a hollow tube section 458 that extends outwardly from the connector housing 452. In the embodiment illustrated, the tube section 458 is substantially transverse to the connector housing 452. However, this is not a requirement. The tube section 458 has an open free end portion 459 configured to be connected to the patient oxygen outlet 105 (e.g., directly or using a hose, flow line, conduit, or tube) and to receive the pulses of oxygen 140 therefrom. Inside the connector housing 452, the tube section 458 is connected to the oxygen pulse delivery tube 446 and provides the pulses of oxygen 140 thereto. In the embodiment illustrated, the tube section 458 is connected to or includes a branch tube 460 that extends longitudinally inside the connector housing 452. The branch tube 460 has an open free end 462 configured to be coupled to the oxygen pulse delivery tube 446 and provide the pulses of oxygen 140 thereto. While the tube section 458 extends into the connector housing 452, the tube section 458 only partially obstructs the flow of the gases 112 through the connector housing 452. In other words, the gases 112 pass by or alongside the tube section 458 and the branch tube 460, if present.

In the embodiment illustrated, the oxygen pulse delivery tube 446 extends through the flexible tube segment 444 and at least part way into the valve assembly 448. Thus, the oxygen pulse delivery tube 446 isolates the pulses of oxygen 140 from the gases in the flexible tube segment 444 along a majority portion of the passive patient circuit 440. The oxygen pulse delivery tube 446 has a first end portion 464 configured to be coupled to the branch tube 460. The oxygen pulse delivery tube 446 has a second end portion 465 that terminates at or near the patient connection 106. By way of a non-limiting example, the second end portion 465 may terminate within about two centimeters of the patient connection 106. The oxygen pulse delivery tube 446 conducts the pulses of oxygen 140 from the branch tube 460 to the patient connection 106. At the same time, the passive patient circuit 440 conducts the gases 112 (that include the air 114 optionally mixed with oxygen) from the main ventilator connection 104 into the patient connection 106.

In alternate embodiments, the oxygen pulse delivery tube 446 may be connected to the patient oxygen outlet 105 (e.g., directly or using a hose, flow line, conduit, or tube) to receive the pulses of oxygen 140 from the patient oxygen outlet 105. In such embodiments, the oxygen pulse delivery tube 446 may extend along the outside of the flexible tube segment 444. The second end portion 465 of the oxygen pulse delivery tube 446 may be connected to a portion of the passive patient circuit 440 at or near the patient connection 106 to provide the pulses of oxygen 140 from the branch tube 460 to the patient connection 106.

FIGS. 2C-2E illustrate exemplary components of the valve assembly 448. In the embodiment illustrated, the valve assembly 448 includes a first valve housing 468, a second valve housing 469, and a flexible ring-shaped leaf 470.

The first valve housing 468 is configured to be coupled to the patient connection 106 (see FIG. 2A). Optionally, the secretion trap 1250 (see FIGS. 27 and 28) may be coupled between the first valve housing 468 and the patient connection 106. The second valve housing 469 is configured to be coupled to the second end portion 451 of the flexible tube segment 444. The first and second valve housings 468 and 469 are configured to be coupled together with the ring-shaped leaf 470 positioned therebetween. A peripheral portion 473 of the leaf 470 is positioned within a ring-shaped chamber 474 defined by the first and second valve housings 468 and 469. One or more openings 476 are formed in the second valve housing 469 and connect the chamber 474 with the environment outside the passive patient circuit 440 (see FIG. 2B). Additionally, one or more openings 478 are formed in the second valve housing 469 and connect the patient gases inside the passive patient circuit 440 (see FIG. 2B) with the chamber 474.

Like the flap 179 (see FIG. 2A), the peripheral portion 473 of the leaf 470 is configured to transition or deflect from a closed position (see FIG. 2O) and an open position (see FIG. 2D) when the pressure inside the passive patient circuit 440 (see FIG. 2B) exceeds the threshold amount (e.g., environmental pressure). When the peripheral portion 473 of the leaf 470 is in the closed position depicted in FIG. 2O, the leaf 470 blocks off the one or more openings 478 and isolates the chamber 474 from the environment inside the passive patient circuit 440 (see FIG. 2B). On the other hand, when the peripheral portion 473 of the leaf 470 is in the open position depicted in FIG. 2D, the leaf 470 no longer blocks off the one or more openings 478 and allows the chamber 474 to communicate with the patient gases inside and outside the passive patient circuit 440 (see FIG. 2B). Thus, gases may exit the interior of the passive patient circuit 440 (see FIG. 2B) through the opening(s) 478, the chamber 474, and the opening(s) 476.

During the inspiratory phase, the ventilator 100 adjusts the pressure inside the passive patient circuit 440 to achieve a preset inspiratory pressure, which places or maintains the peripheral portion 473 of the leaf 470 in the open position with the peripheral portion 473 of the leaf leaving the openings 478 unblocked. Some of the patient gases flow to the patient 102 (see FIG. 1), and some of the patent gases flow out through the openings 476.

During the exhalation phase, the ventilator 100 adjusts the pressure inside the passive patient circuit 440 to achieve a baseline or positive end-expiratory pressure ("PEEP"), which places or maintains the peripheral portion 473 of the leaf 470 in the open position. Some of the exhaled gases 107 (see FIG. 1) from the patient 102 flow out through the openings 476, and some of the exhaled gases 107 flow into the passive patient circuit 440 (e.g., into the flexible tube segment 444).

The breath may pause between the end of the exhalation phase and the beginning of the inspiratory phase. This pause may be characterized as a dead time that occurs between the phases. During a pause, the ventilator 100 adjusts the pressure inside the passive patient circuit 440 to PEEP, which places or maintains the peripheral portion 473 of the leaf 470 in the open position, and causes the flow of the gases 112 from the ventilator 100 to flow out of the passive patient circuit 440 through the openings 476. Also, during this time, at least a portion of the exhaled gases 107 that flowed into the passive patient circuit 440 during the exhalation phase is "purged" out through the openings 476 by the forward moving flow of the gases 112 from the ventilator 100.

As explained below, during an exsufflation phase of a cough, the pressure inside the passive patient circuit 440 (see FIG. 2B) is less than the threshold amount (e.g., environmental pressure). This places the peripheral portion 473 of the leaf 470 in the closed position with the peripheral portion 473 of the leaf blocking the openings 478, which prevents the patient gases inside the passive patient circuit 440 from flowing out of the passive patient circuit 440 through the opening(s) 476. It also prevents air from entering the passive patient circuit 440 through the opening(s) 476.

The combined areas of the openings 476 may be characterized as providing a fixed orifice. Thus, the valve assembly 448 may be characterized as being a one-way valve with a fixed orifice. If the combined areas of the openings 476 is too large, most of the inspiratory flow will leak out through the openings 476, leaving little for the patient 102. Conversely, if the combined areas of the openings 476 is too small, the exhaled gases 107 will not be fully purged from the passive patient circuit 440 during the exhalation phase and the pause between the inspiratory and exhalation phases, By way of a non-limiting example, the valve assembly 448 may be configured to leak about 20-50 liters per minute ("LPM") when the pressure inside the passive patient circuit 440 is about 10 centimeters of water ("cmH20").

Figure 30:
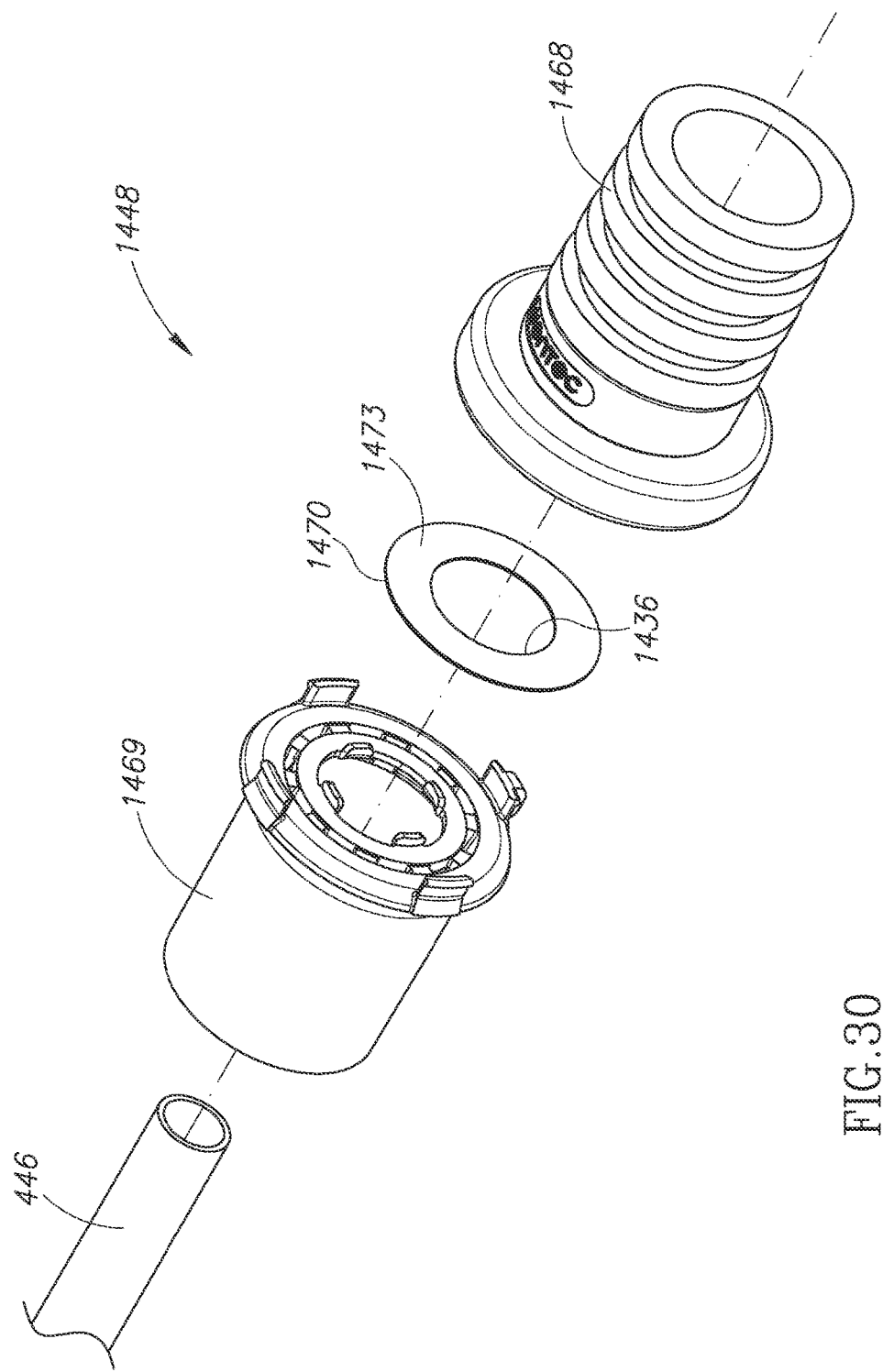
FIG. 30 is an exploded view of an alternate embodiment of a valve assembly for use in the passive patient circuit of FIG. 2B.

FIG. 30 is an exploded view of an alternate embodiment of a valve assembly 1448 that may be used in the passive patient circuit 440 (see FIG. 2B) instead of the valve assembly 448. In such embodiments, the flexible tube segment 444 (see FIG. 2B) conducts the gases 112 (see FIG. 2B) to the valve assembly 1448 and the oxygen pulse delivery tube 446 may extend through the flexible tube segment 444 (see FIG. 2B) and at least part way into the valve assembly 1448.

Figure 31A:
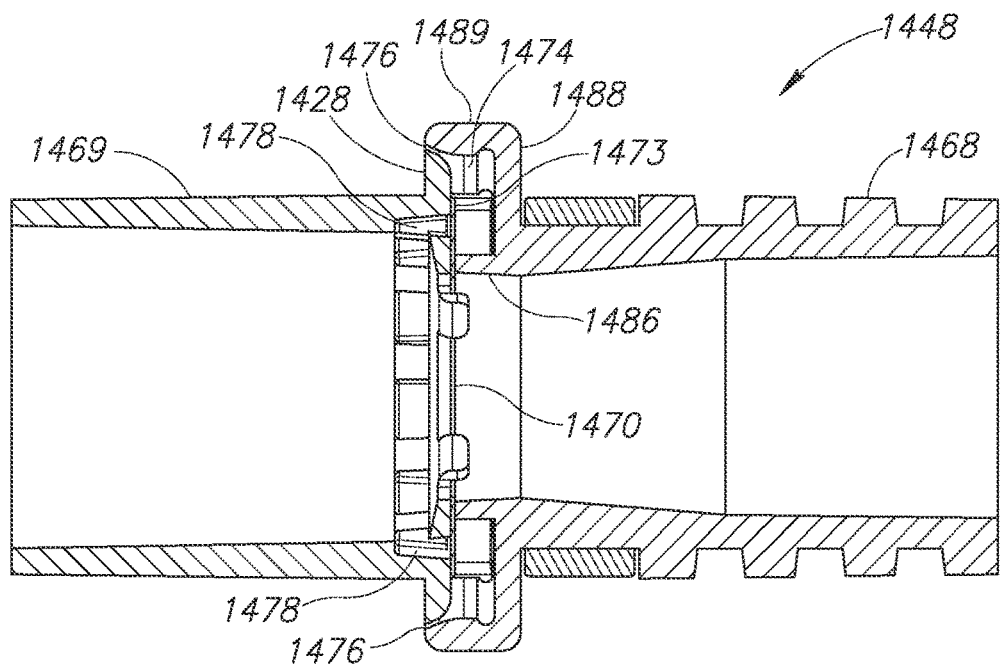
FIG. 31A is an enlarged longitudinal cross-sectional view of the valve assembly of FIG. 30 illustrated in a closed configuration.
Figure 31B:
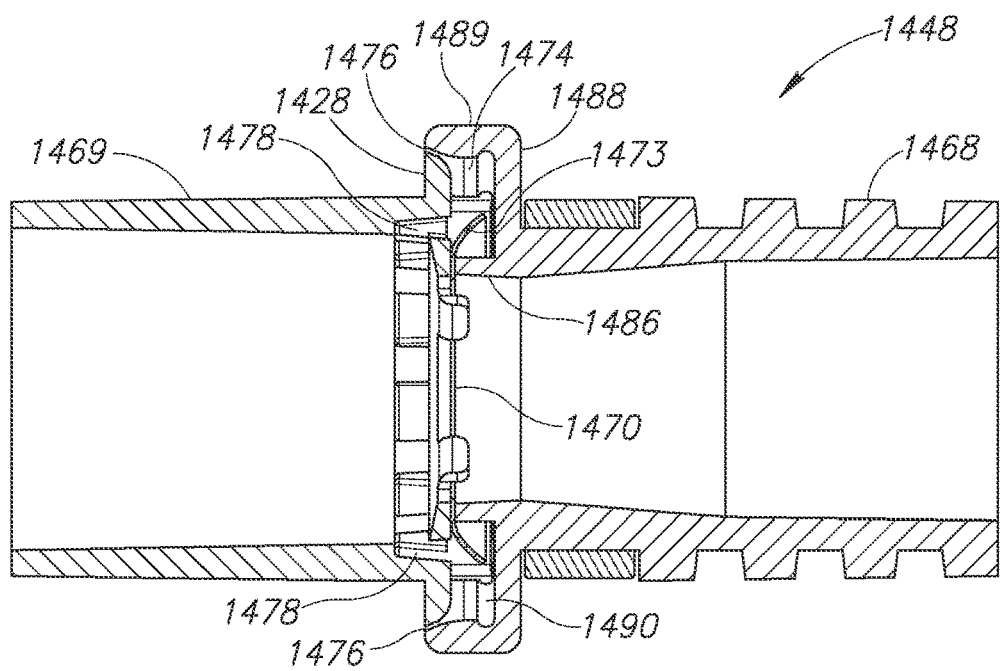
FIG. 31B is an enlarged longitudinal cross-sectional view of the valve assembly of FIG. 30 illustrated in an open configuration.
Figure 31C:
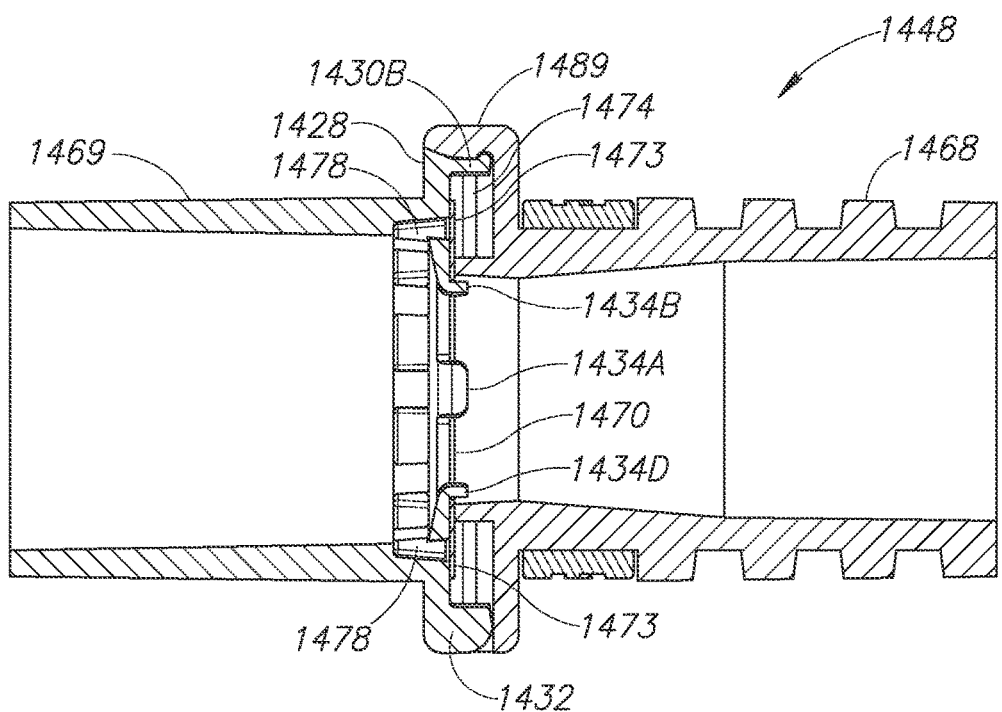
FIG. 31C is an enlarged longitudinal cross-sectional view of the valve assembly of FIG. 31A rotated approximately 45° about its longitudinal axis from the position depicted in FIG. 31A.

In the embodiment illustrated, the valve assembly 1448 includes a first valve housing 1468, a second valve housing 1469, and a flexible ring-shaped leaf 1470. As shown in FIGS. 31A-31C, the first and second valve housings 1468 and 1469 are configured to be coupled together with the ring-shaped leaf 1470 positioned therebetween.

Figure 32:
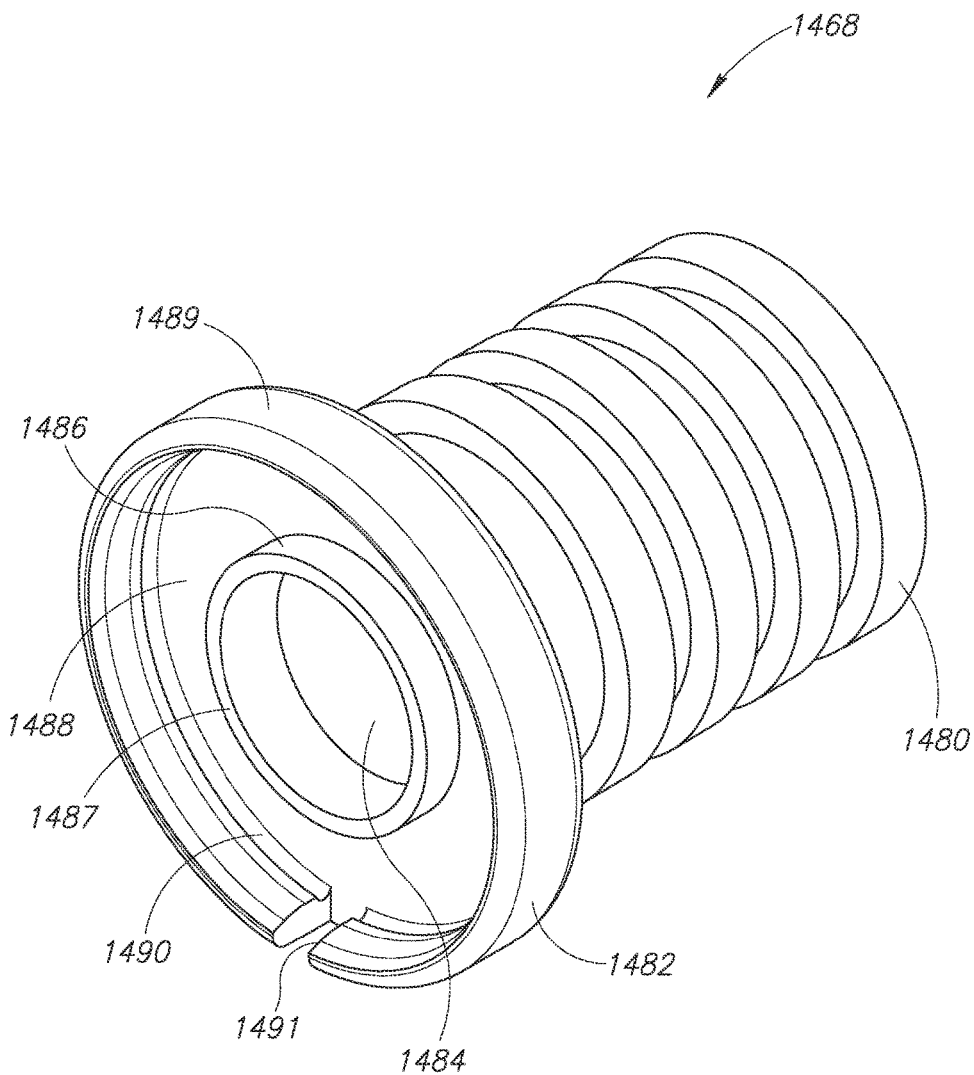
FIG. 32 is a perspective view of a first valve housing of the valve assembly of FIG. 30.

Referring to FIG. 32, in the embodiment illustrated, the first valve housing 1468 has a first end portion 1480 opposite a second end portion 1482. An open ended through channel 1484 extends through the first valve housing 1468 between its first and second end portions 1480 and 1482. The first end portion 1480 is configured to be coupled to the patient connection 106 (see FIG. 2B). Optionally, the secretion trap 1250 (see FIGS. 27-29) may be coupled between the first end portion 1480 of the first valve housing 1468 and the patient connection 106 (see FIG. 2B).

The second end portion 1482 is configured to be coupled to the second valve housing 1469 (see FIGS. 30-31C and 33). The second end portion 1482 includes a ring-shaped longitudinally extending inner wall 1486 positioned alongside the channel 1484 and defining a portion thereof. The second end portion 1482 includes a first wall portion 1488 that extends radially outwardly from the inner wall 1486 and terminates at a ring-shaped longitudinally extending outer wall 1489. The outer wall 1489 is concentric with and spaced apart from the inner wall 1486 by the first wall portion 1488. A distal edge portion 1487 of the inner wall 1486 is configured to abut the leaf 1470 (see FIGS. 30-31C) and press the leaf 1470 against the second valve housing 1469 (see FIGS. 30-31C and 33) to form an annular seal between the first and second valve housings 1468 and 1469 along the distal edge portion 1487 of the ring-shaped inner wall 1486. Near the location whereat the outer wall 1489 terminates the first wall portion 1488, the outer wall 1489 has a ring-shaped groove 1490 formed along its inner surface that opens toward the inner wall 1486. The outer wall 1489 has a longitudinally extending notch or keyway 1491 formed therein.

Figure 33:
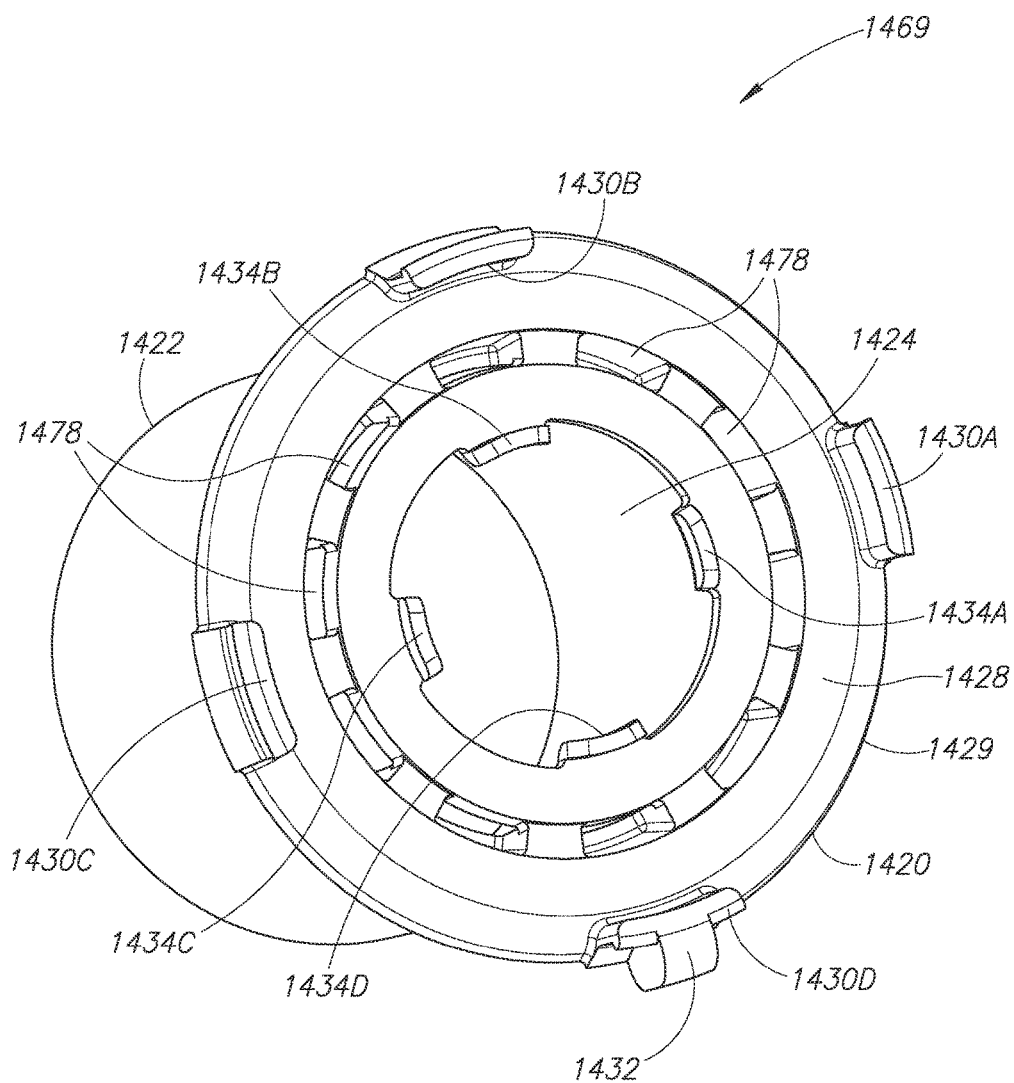
FIG. 33 is a perspective view of a second valve housing of the valve assembly of FIG. 30.

Referring to FIG. 33, in the embodiment illustrated, the second valve housing 1469 has a first end portion 1420 opposite a second end portion 1422. An open ended through channel 1424 extends through the second valve housing 1469 between its first and second end portions 1420 and 1422. The second end portion 1422 of the second valve housing 1469 is configured to be coupled to the second end portion 451 (see FIG. 2B) of the flexible tube segment 444 (see FIG. 2B).

The first end portion 1420 is configured to be coupled to the first valve housing 1468 (see FIGS. 30-32). The first end portion 1420 of the second valve housing 1469 includes a radially outwardly extending second wall portion 1428 having a distal portion 1429. A plurality of tabs 1430A-1430D are positioned along the distal portion 1429 of the second wall portion 1428. The tabs 1430A-1430D are configured to be received inside the ring-shaped groove 1490 (see FIG. 32) formed in the outer wall 1489 (see FIG. 32) of the first valve housing 1468 (see FIGS. 30-32). Engagement between the tabs 1430A-1430D and the groove 1490 couples the first and second valve housings 1468 and 1469 together. The tab 1430D includes a key member 1432 configured to be received inside the keyway 1491 (see FIG. 32) formed in the outer wall 1489 (see FIG. 32) of the first valve housing 1468 (see FIGS. 30-32). When the first and second valve housings 1468 and 1469 are coupled together, the key member 1432 is received inside the keyway 1491 to prevent rotation of the first valve housing 1468 relative to the second valve housing 1469.

The second valve housing 1469 includes a plurality of leaf positioning projections 1434A-1434D configured to be received inside a central through-hole 1436 (see FIG. 30) formed in the leaf 1470 (see FIGS. 30-31B). Referring to FIG. 31C, the leaf positioning projections 1434A-1434D help position the leaf 1470 with respect to the first and second valve housings 1468 and 1469. When the first and second valve housings 1468 and 1469 are coupled together, the leaf positioning projections 1434A-1434D extend into the channel 1484 (see FIG. 32) alongside the inner wall 1486 (see FIG. 32).

Referring to FIGS. 31A-31C, a peripheral portion 1473 of the leaf 1470 is positioned within a ring-shaped chamber 1474 defined by the first and second valve housings 1468 and 1469. Referring to FIGS. 31A and 31B, in the embodiment illustrated, the chamber 1474 is defined by the inner wall 1486, the first wall portion 1488, the outer wall 1489, and the second wall portion 1428.

One or more openings 1476 are defined between the first and second valve housings 1468 and 1469. In the embodiment illustrated, the second wall portion 1428 extends only partway toward the outer wall 1489 of the first valve housing 1468. However, as shown in FIG. 31C, the tabs 1430A-1430D (see FIG. 33), which are mounted on the distal portion 1429 (see FIG. 33) of the second wall portion 1428, contact the outer wall 1489 of the first valve housing 1468. Thus, referring to FIGS. 31A and 31B, the openings 1476 are defined between the distal portion 1429 (see FIG. 33) of the second wall portion 1428 and the outer wall 1489 of the first valve housing 1468 and positioned between the tabs 1430A-1430D (see FIG. 33).

The one or more openings 1476 connect the chamber 1474 with the environment outside the passive patient circuit 440 (see FIG. 2B). Additionally, one or more openings 1478 are formed in the second valve housing 1469 and connect the patient gases inside the passive patient circuit 440 (see FIG. 2B) with the chamber 1474. Referring to FIG. 33, the one or more openings 1478 are positioned between the distal portion 1429 of the second wall portion 1428 and the leaf positioning projections 1434A-1434D.

Figure 20:
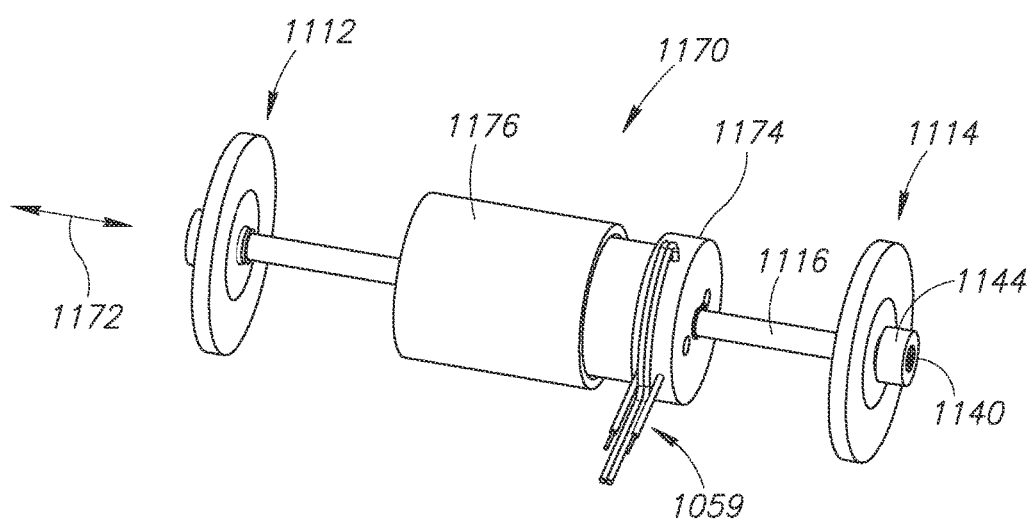
FIG. 20 is a perspective view of a subassembly of the cough assist valve including a moving coil actuator, a shaft, and a pair of poppet valve assemblies.

Referring to FIGS. 31A-310, the flexible ring-shaped leaf 1470 is substantially similar to the flexible ring-shaped leaf 470 (see FIGS. 20-2E). The peripheral portion 1473 of the leaf 1470 is configured to transition or deflect from a closed position (see FIGS. 31A and 31C) and an open position (see FIG. 31B) when the pressure inside the passive patient circuit 440 (see FIG. 2B) exceeds the threshold amount (e.g., environmental pressure). When the peripheral portion 1473 of the leaf 1470 is in the closed position depicted in FIGS. 31A and 310, the leaf 1470 blocks off the one or more openings 1478 into the chamber 1474 thereby isolating the chamber 1474 from the environment inside the passive patient circuit 440 (see FIG. 2B). On the other hand, when the peripheral portion 1473 of the leaf 1470 is in the open position depicted in FIG. 31B, the leaf 1470 no longer blocks off the one or more openings 1478 and allows the chamber 1474 to communicate with the patient gases inside the passive patient circuit 440 (see FIG. 2B). Thus, gases may exit the interior of the passive patient circuit 440 (see FIG. 2B) through the opening(s) 1478, the chamber 1474, and the opening(s) 1476.

As mentioned above, during the inspiratory phase, the ventilator 100 adjusts the pressure inside the passive patient circuit 440 to achieve a preset inspiratory pressure, which places or maintains the peripheral portion 1473 of the leaf 1470 in the open position (see FIG. 31B). Some of the patient gases flow to the patient 102 (see FIG. 1), and some of the patent gases flow out through the openings 1476.

During the exhalation phase, the ventilator 100 adjusts the pressure inside the passive patient circuit 440 to achieve a baseline or positive end-expiratory pressure ("PEEP"), which places or maintains the peripheral portion 1473 of the leaf 1470 in the open position (see FIG. 31B). Some of the exhaled gases 107 (see FIG. 1) from the patient 102 flow out through the openings 1476, and some of the exhaled gases 107 flow into the passive patient circuit 440 (e.g., into the flexible tube segment 444).

During a pause between the end of the exhalation phase and the beginning of the inspiratory phase, the ventilator 100 adjusts the pressure inside the passive patient circuit 440 to PEEP, which places or maintains the peripheral portion 1473 of the leaf 1470 in the open position (see FIG. 31B), and causes the flow of the gases 112 from the ventilator 100 to flow out of the passive patient circuit 440 through the openings 1476. Also, during this time, at least a portion of the exhaled gases 107 that flowed into the passive patient circuit 440 during the exhalation phase is "purged" out through the openings 1476 by the forward moving flow of the gases 112 from the ventilator 100.

The combined areas of the openings 1476 may be characterized as providing a fixed orifice. Thus, the valve assembly 1448 may be characterized as being a one-way valve with a fixed orifice. If the combined areas of the openings 1476 is too large, most of the inspiratory flow will leak out through the openings 1476, leaving little for the patient 102. Conversely, if the combined areas of the openings 1476 is too small, the exhaled gases 107 will not be fully purged from the passive patient circuit 440 during the exhalation phase and the pause between the inspiratory and exhalation phases. By way of a non-limiting example, the valve assembly 1448 may be configured to leak about 20-50 LPM when the pressure inside the passive patient circuit 440 is about 10 cmH20.

As explained below, during an exsufflation phase of a cough, the pressure inside the passive patient circuit 440 (see FIG. 2B) is less than the threshold amount (e.g., environmental pressure). When the passive patient circuit 440 (see FIG. 2B) includes the valve assembly 1448 (instead of the valve assembly 448), the peripheral portion 1473 of the leaf 1470 is placed in the closed position (see FIGS. 31A and 31C) when the pressure inside the passive patient circuit 440 (see FIG. 2B) is less than the threshold amount, which prevents the patient gases inside the passive patient circuit 440 from flowing out of the passive patient circuit 440 through the opening(s) 1476. It also prevents air from entering the passive patient circuit 440 through the opening(s) 1476.

It should be noted that the passive valve assemblies described herein may be integrated into the patient connection 106, such as into a patient mask serving as the patient connection, rather than being part of the passive patient circuit 170 or the passive patient circuit 440. As stated above and as shown in FIG. 1, the patient 102 has a patient connection 106 which may be a tracheal tube, a nasal mask, a mouthpiece or the like, that is connectable to the main ventilator connection 104 and/or the patient oxygen outlet 105 by a patient circuit 110.

Active Patient Circuit

Figure 3A:
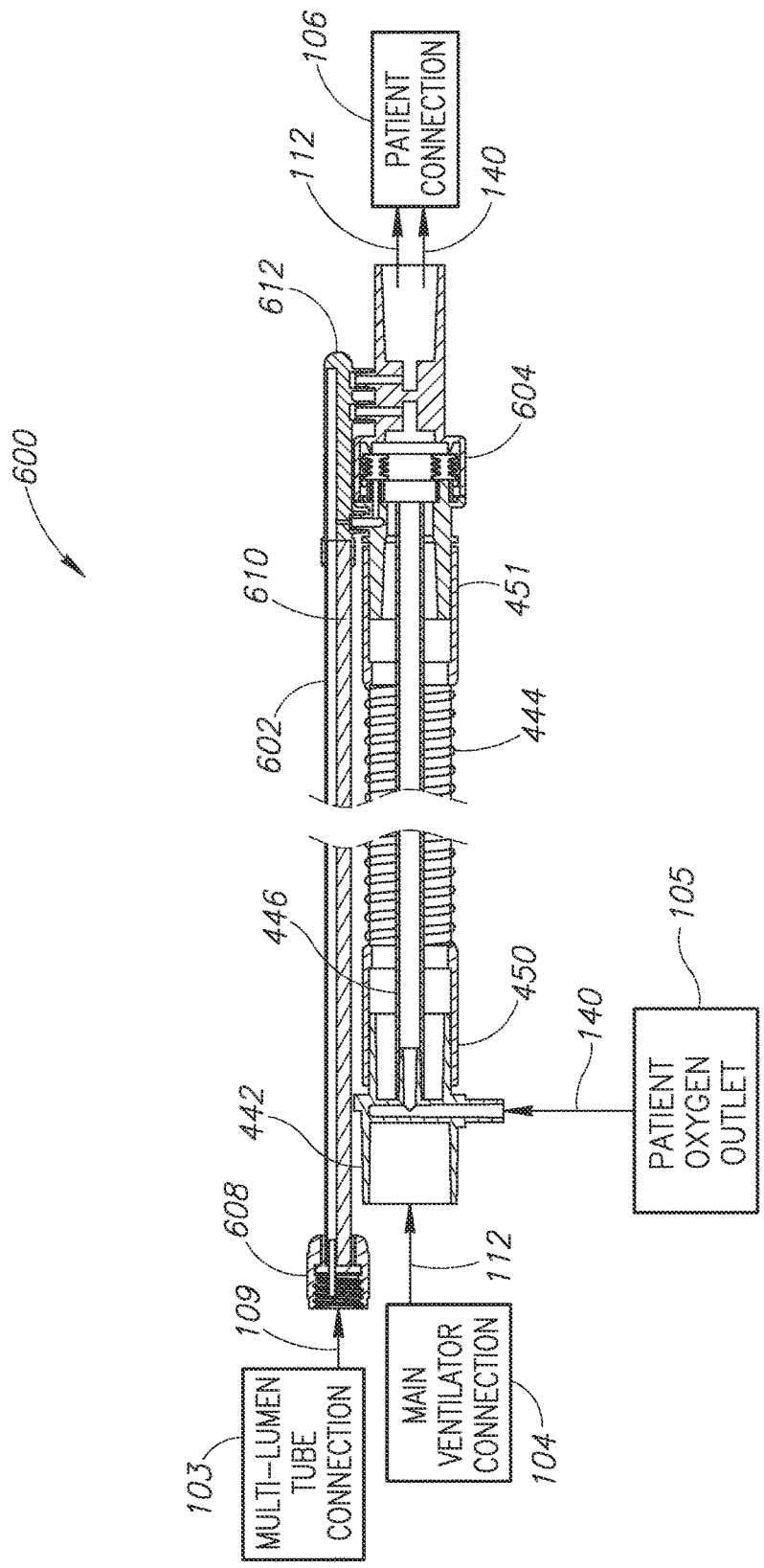
FIG. 3A is a cross-sectional view of an embodiment of an active patient circuit for use with the ventilator of FIG. 1.

FIG. 3A depicts an active patient circuit 600 that may be used to implement the patient circuit 110 (see FIG. 1). Referring to FIG. 3A, the active patient circuit 600 includes the connector 442, the flexible tube segment 444, the oxygen pulse delivery tube 446, a multi-lumen tube assembly 602, and an active exhalation valve assembly 604.

Like in the passive patient circuit 440 (see FIG. 28), the connector 442 is coupled to both the first end portion 450 of the flexible tube segment 444 and the oxygen pulse delivery tube 446. The connector 442 receives the gases 112 and provides them to the flexible tube segment 444. Further, the connector 442 receives the pulses of oxygen 140 and provides them to the oxygen pulse delivery tube 446. The pulses of oxygen 140 exit the oxygen pulse delivery tube 446 at or near the patient connection 106. By way of a non-limiting example, the pulses of oxygen 140 may exit the oxygen pulse delivery tube 446 within about 10 centimeters of the patient connection 106. In the embodiment illustrated, the pulses of oxygen 140 exit the oxygen pulse delivery tube 446 at or near the active exhalation valve assembly 604.

Optionally, the bacterial filter 176 (see FIG. 2A) may be positioned between the connector 442 and the main ventilator connection 104. In such embodiments, the gases 112 flow through the bacterial filter 176 on their way to the connector 442. When present, the bacterial filter 176 helps prevent bacteria (e.g., received from the patient connection 106) from entering the ventilator 100 (via the main ventilator connection 104).

The second end portion 451 of the flexible tube segment 444 is configured to be coupled to the active exhalation valve assembly 604. As mentioned above with respect to FIG. 1, the patient circuit 110 may include one or more ports 111 configured to allow the one or more pressure signals 109 to flow between the optional multi-lumen tube connection 103 and the patient circuit 110. Referring to FIG. 3C, in the embodiment illustrated, the ports 111 (see FIG. 1) include ports 111A-111C spaced apart from one another longitudinally. The ports 111A-111C are each formed in the active exhalation valve assembly 604. The port 1110 is referred to hereafter as the pilot port 111C.

Figure 3B:
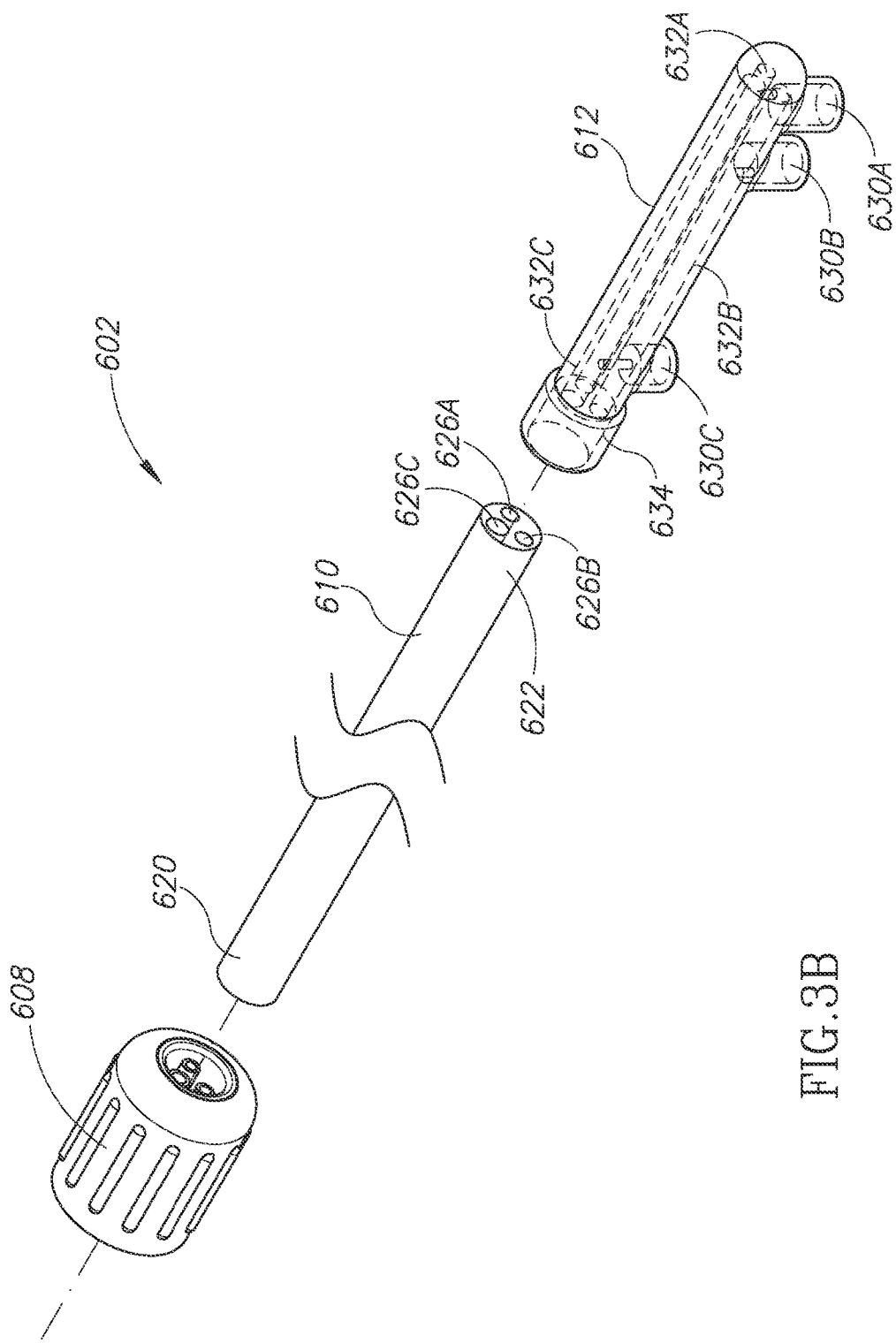
FIG. 3B is an exploded view of a multi-lumen tube assembly of the active patient circuit of FIG. 3A.
Figure 3C:
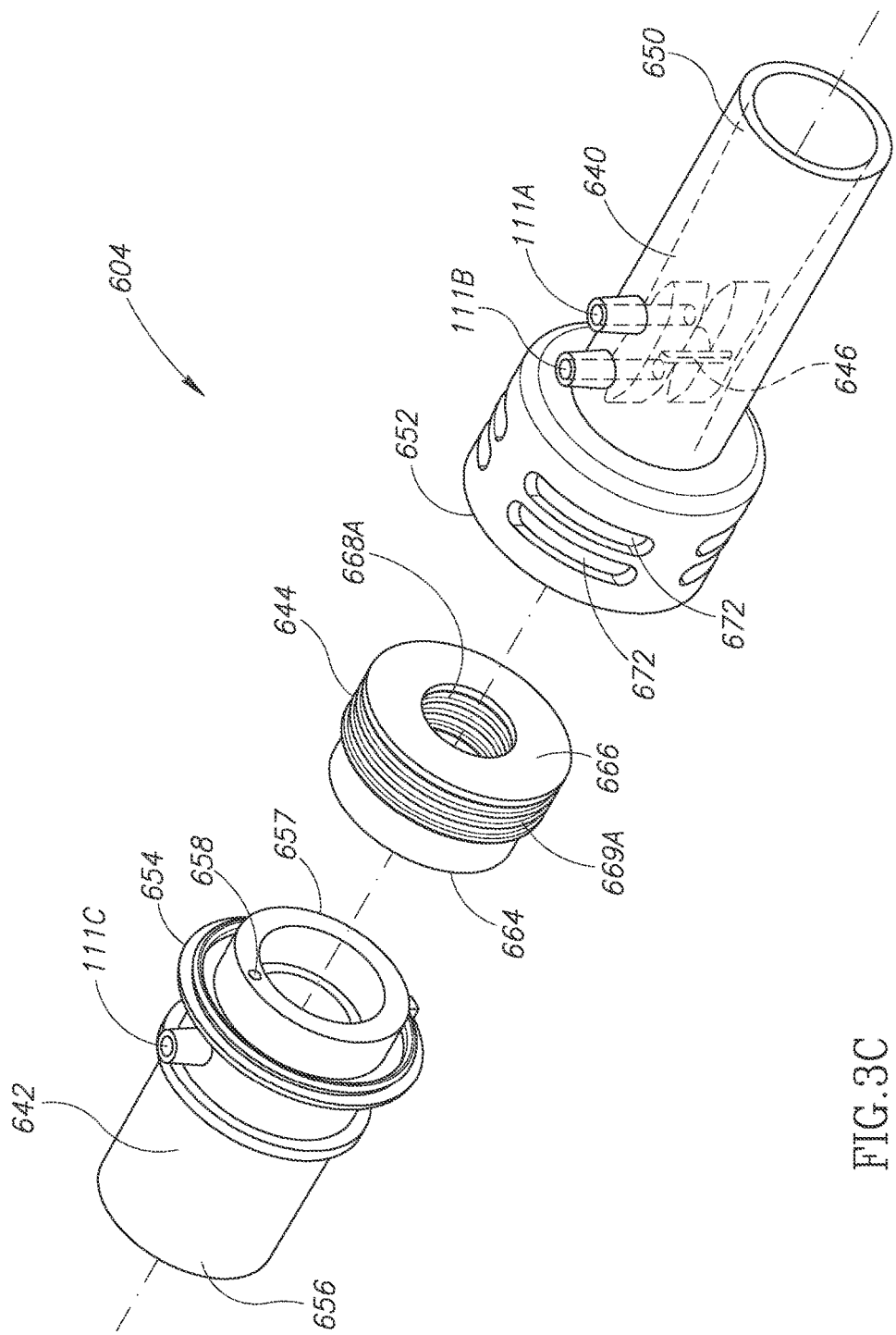
FIG. 3C is an exploded view of an active exhalation valve assembly of the active patient circuit of FIG. 3A.

FIG. 3B is exploded perspective view of the multi-lumen tube assembly 602. Referring to FIG. 3B, the multi-lumen tube assembly 602 includes a coupler 608, an elongated tube segment 610, and a connector member 612. The coupler 608 is configured to couple a first end portion 620 of the tube segment 610 to the optional multi-lumen tube connection 103 (see FIG. 3A). The tube segment 610 has a second end portion 622 opposite the first end portion 620. The second end portion 622 is connected to the connector member 612. Three separate and continuous open-ended channels 626A-626C extend longitudinally through the tube segment 610.

The connector member 612 has three connectors 630A-630C configured to connected to the ports 111A-111C (see FIG. 3C), respectively. The connectors 630A and 630B receive pressure signals 109A and 109B (see FIG. 5A), respectively, from the ports 111A and 111B, respectively. The connector 630C conducts a pressure signal 109C (see FIG. 5A) to and from the pilot port 111C.

Continuous channels 632A-632C extend from the connectors 630A-630C, respectively, to an end portion 634 of the connector member 612. When the connector member 612 is connected to the tube segment 610, the continuous channels 626A-626C of the tube segment 610 are aligned and communicate with the continuous channels 632A-632C, respectively. Thus, the multi-lumen tube assembly 602 may be used to conduct the separate pressure signals 109A and 109B, respectively, from the ports 111A and 111B, respectively, to the optional multi-lumen tube connection 103. Further, the multi-lumen tube assembly 602 may be used to conduct the pressure signal 109C to the pilot port 111C from the optional multi-lumen tube connection 103 and vice versa.

Referring to FIG. 3C, the active exhalation valve assembly 604 includes a first valve housing member 640, a double bellows member 644, and a second valve housing member 642. The ports 111A and 111B are formed in the first valve housing member 640 and extend laterally outwardly therefrom. The pilot port 1110 is formed in the second valve housing member 642 and extends laterally outwardly therefrom.

Figure 3D:
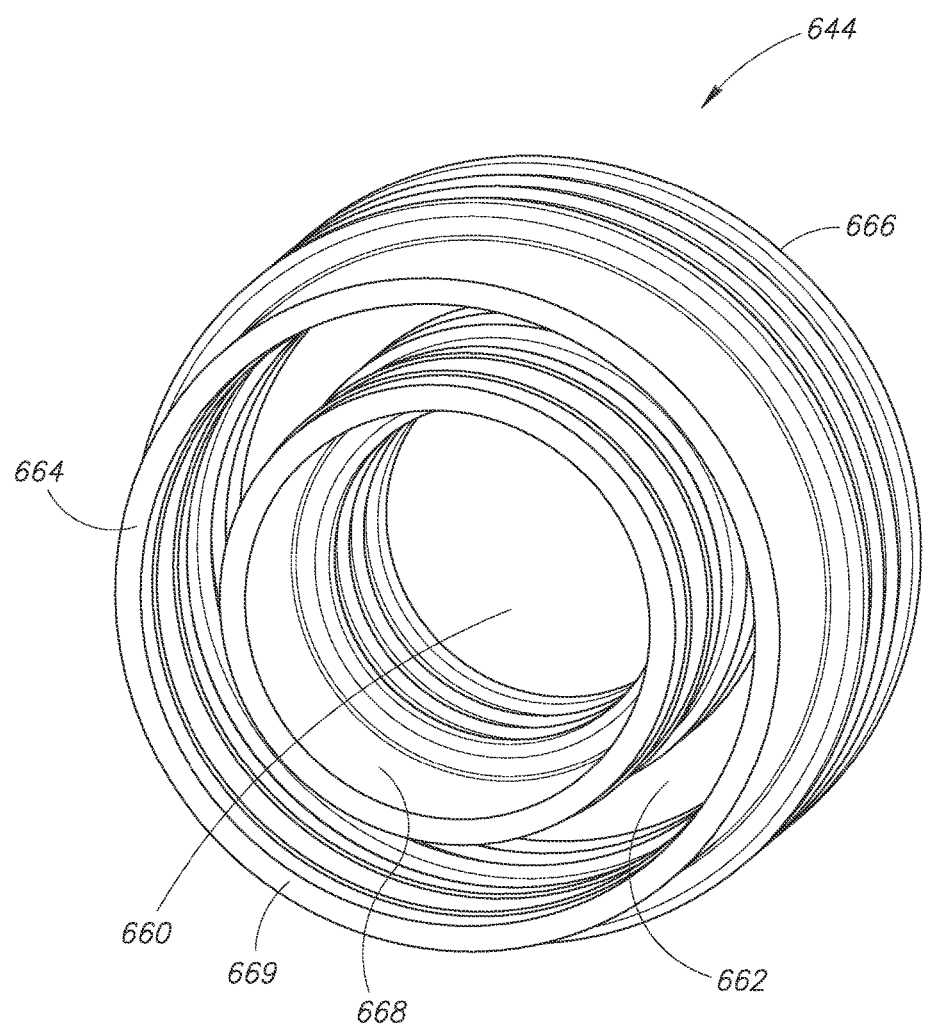
FIG. 3D is an enlarged perspective view of a double bellows member of the active exhalation valve assembly of FIG. 3C.
Figure 3E:
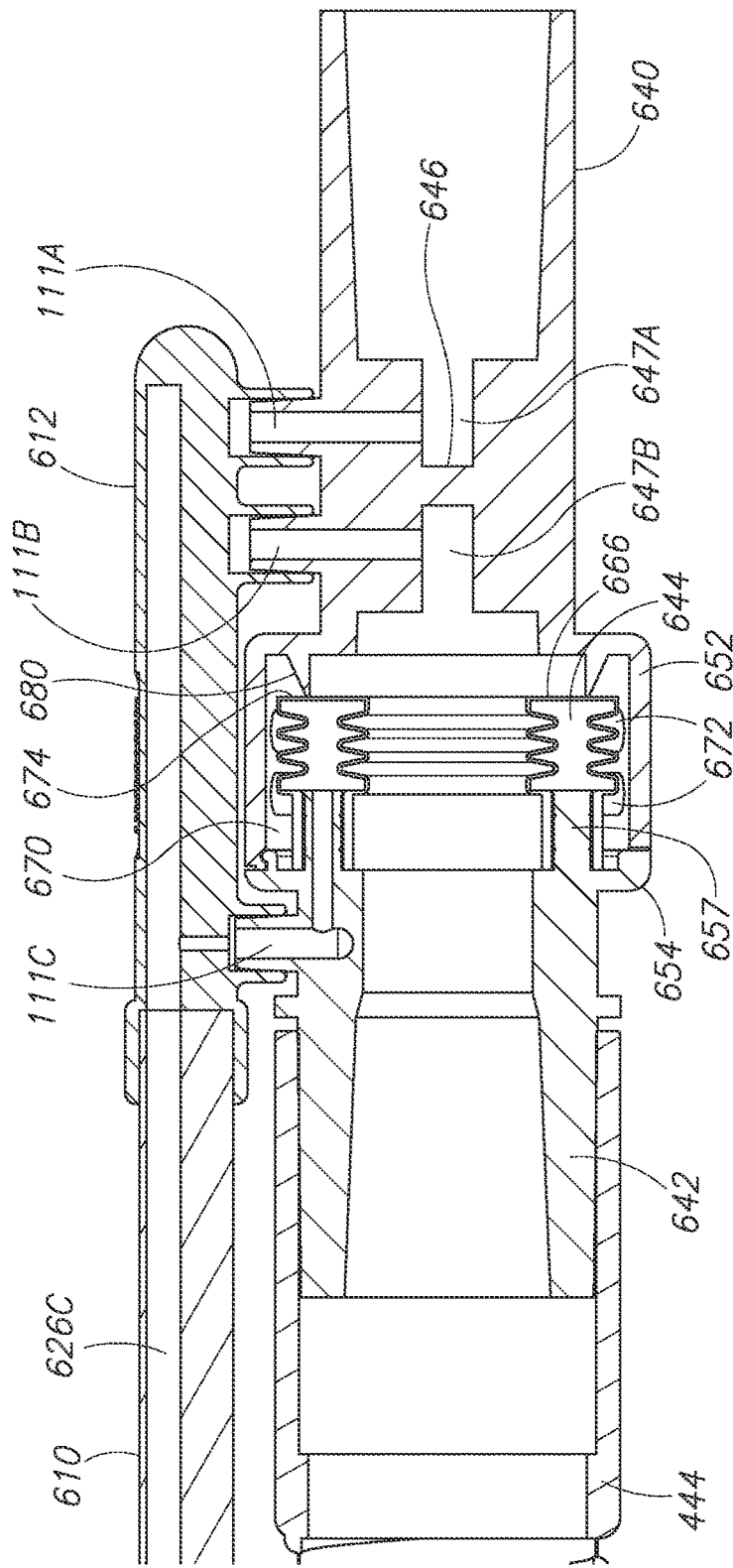
FIG. 3E is an enlarged cross-sectional view of the active patient circuit of FIG. 3A illustrated with the double bellows member of the active exhalation valve assembly in a closed position.
Figure 3F:
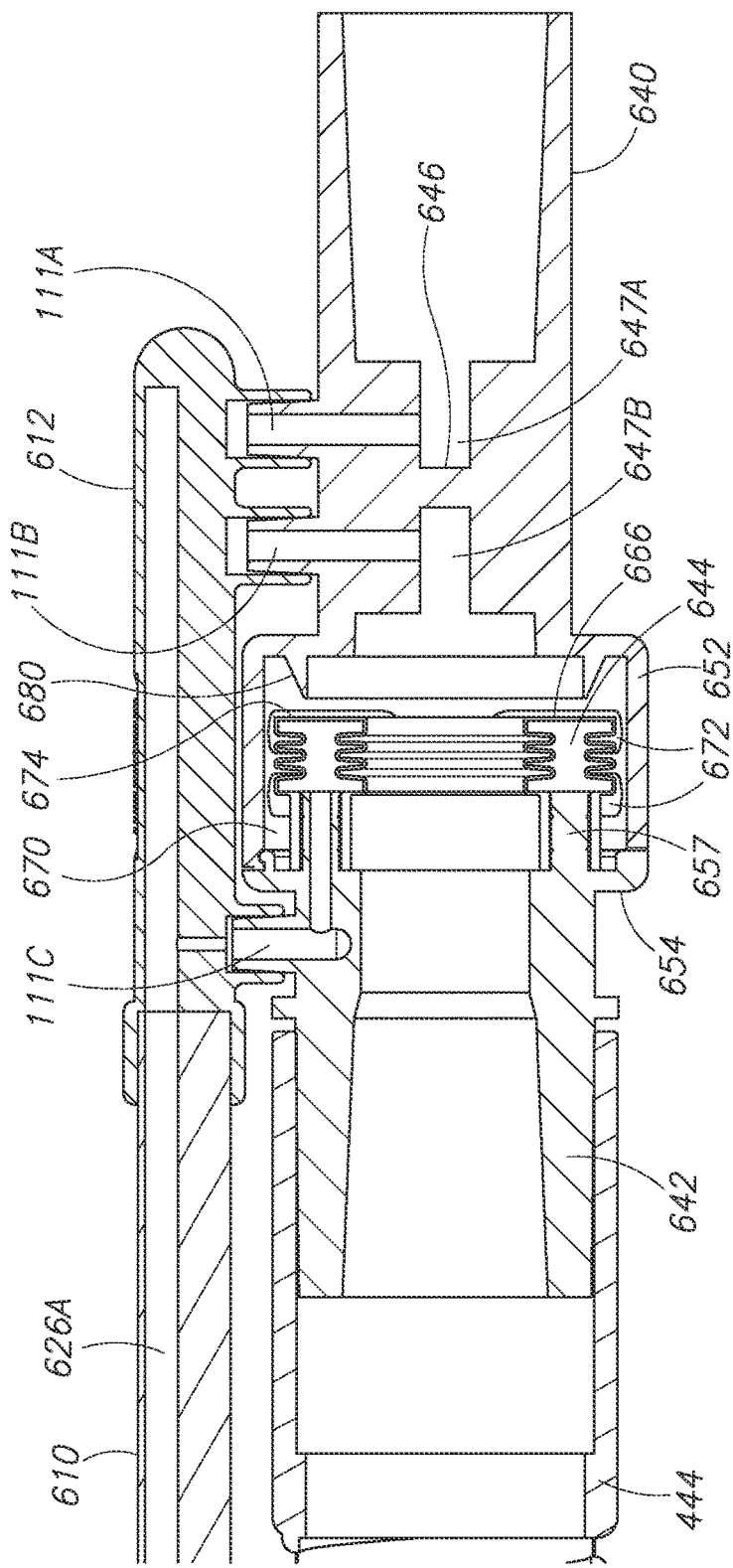
FIG. 3F is a first enlarged cross-sectional view of the active patient circuit of FIG. 3A illustrated with the double bellows member of the active exhalation valve assembly in an open position.

FIGS. 3E and 3F are enlarged longitudinal cross sectional views that each show a portion of the active patient circuit 600 that includes the active exhalation valve assembly 604. The oxygen pulse delivery tube 446 has been omitted from FIGS. 3E and 3F. In the embodiment illustrated, the first valve housing member 640 includes an internal obstruction 646 positioned between the ports 111A and 111B and configured to partially restrict flow through the first valve housing member 640. Further, as shown in FIGS. 3E and 3F, the interior of the first valve housing member 640 includes a first narrowed portion 647A that is adjacent to the obstruction 646 and the port 111A, and a second narrowed portion 647B that is adjacent to the obstruction 646 and the port 111B. Thus, the first and second narrowed portions 647A and 647B are positioned opposite one another longitudinally with respect to the obstruction 646 with the first narrowed portion 647A being nearer to the patient connection 106 (see FIG. 3A) than the second narrowed portion 647B. The ports 111A and 111B open into the first and second narrowed portions 647A and 647B, respectively.

Figure 3G:
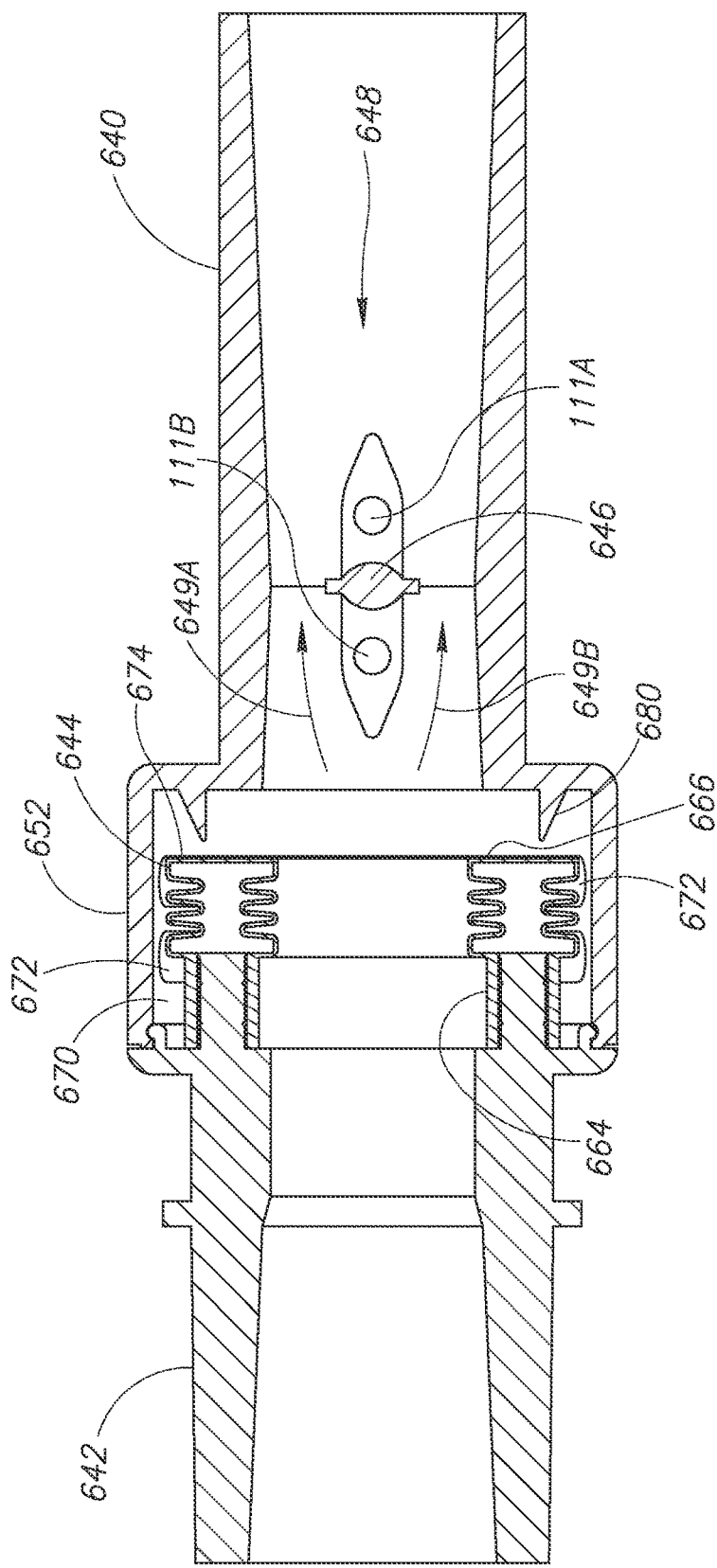
FIG. 3G is a second enlarged cross-sectional view of the active patient circuit of FIG. 3A illustrated with the double bellows member of the active exhalation valve assembly in the open position.

Referring to FIG. 3G, together the obstruction 646, the first and second narrowed portions 647A and 647B, and the ports 111A and 111B define an airway flow transducer 648 (e.g., a fixed orifice differential pressure type flow meter) inside the interior of the first valve housing member 640. During the inspiration phase, the gases 112 may flow around the obstruction 646 along flow paths identified by curved arrows 649A and 649B. During the exhalation phase, the exhaled gases 107 may flow around the obstruction 646 along flow paths opposite those identified by the curved arrows 649A and 649B.

Referring to FIG. 3C, the first valve housing member 640 has a first end portion 650 configured to be coupled to the patient connection 106 (see FIG. 3A). Optionally, the secretion trap 1250 (see FIGS. 27 and 28) may be coupled between the first end portion 650 and the patient connection 106. The first valve housing member 640 has a second end portion 652 configured to be coupled to the second valve housing member 642. The second valve housing member 642 has a first end portion 654 configured to be coupled to the second end portion 652 of the first valve housing member 640, and a second end portion 656 configured to be coupled to the second end portion 451 of the flexible tube segment 444. The first end portion 654 of the second valve housing member 642 has a generally cylindrical shaped bellows connector portion 657. An opening 658 of the pilot port 111C is formed in the bellows connector portion 657 of the second valve housing member 642.

Referring to FIG. 3D, the double bellows member 644 has a generally ring-like outer shape with a centrally located through-channel 660. The double bellows member 644 has a hollow interior 662 with a ring-shaped open end 664 opposite a ring-shaped closed end 666 (see FIG. 3C). In the embodiment illustrated, the double bellows member 644 has concertinaed inner and outer sidewalls 668 and 669. The inner sidewall 668 extends between the open end 664 and the closed end 666 along the centrally located through-channel 660. The outer sidewall 669 extends between the open end 664 and the closed end 666 and is spaced radially outwardly from the inner sidewall 668. The hollow interior 662 is defined between the inner and outer sidewalls 668 and 669. Each of the inner and outer sidewalls 668 and 669 have bellows portions 668A and 669A (see FIG. 3C), respectively, which each have an undulating longitudinal cross-sectional shape (also referred to as a corrugated or convoluted tubular shape). In alternate embodiments, the inner and outer sidewalls 668 and 669 may include different numbers of convolutions that define a single convolute or more than two convolutes.

The open end 664 is configured to fit over the bellows connector portion 657 of the second valve housing member 642 like a sleeve. When the bellows connector portion 657 of the second valve housing member 642 is received inside the open end 664 of the double bellows member 644, the bellows portions 668A and 669A (see FIG. 3C) of the inner and outer sidewalls 668 and 669, respectively, are positioned adjacent to the bellows connector portion 657 of the second valve housing member 642. Thus, the opening 658 of the pilot port 111C is in communication with a portion of the hollow interior 662 positioned between the bellows portions 668A and 669A (see FIG. 3C) of the inner and outer sidewalls 668 and 669, respectively.

Referring to FIG. 3C, when the bellows connector portion 657 of the second valve housing member 642 is received inside the open end 664 of the double bellows member 644, the opening 658 of the pilot port 111C may provide the pressure signal 109C to the interior of the double bellows member 644.

Referring to FIGS. 3E and 3F, as mentioned above, the second end portion 652 of the first valve housing member 640 is configured to be coupled to the first end portion 654 of the second valve housing member 642. When so coupled together, a ring-shaped chamber 670 is defined between the second end portion 652 of the first valve housing member 640 and the first end portion 654 of the second valve housing member 642. One or more openings 672 (see FIG. 3C) are formed in the first valve housing member 640 and connect the chamber 670 with the environment outside the active patient circuit 600 (see FIG. 3A). The bellows portion 668A and 669A (see FIG. 3C) of the outer sidewall 669 and a peripheral portion 674 of the closed end 666 is positioned within the chamber 670.

The double bellows member 644 is constructed from a flexible material (e.g., silicone rubber and the like). The bellows portions 668A and 669A (see FIG. 3C) of the inner and outer sidewalls 668 and 669, respectively, are configured to compress to transition the closed end 666 from a closed position (see FIG. 3E) to an open position (see FIG. 3F). When the bellows portions 668A and 669A (see FIG. 3C) are not compressed, the closed end 666 is in the closed position depicted in FIG. 3E. In this configuration, the closed end 666 of the double bellows member 644 abuts a ring-shaped seat 680 formed in the first valve housing member 640 and defining a portion of the chamber 670. This seals the chamber 670 from the interior of the active patient circuit 600. On the other hand, when the bellows portions 668A and 669A (see FIG. 3C) are compressed toward the second valve housing member 642, the closed end 666 is in the open position depicted in FIG. 3F. In this configuration, the closed end 666 is spaced away from the seat 680. This opens the chamber 670 by connecting the chamber 670 with the inside of the active patient circuit 600. Thus, when the closed end 666 of the double bellows member 644 is in the open position, patient gases inside the active patient circuit 600 may exit therefrom through the chamber 670 and the opening(s) 672 (see FIG. 3C).

The closed end 666 of the double bellows member 644 is selectively moved between the open and closed positions by controlling the pressure inside the double bellows member 644 using the pilot port 111C. For example, the closed end 666 of the double bellows member 644 may be placed in the closed position (see FIG. 3E) during the inspiratory phase, and in the open position during the expiratory phase. In such embodiments, at the start of the inspiratory phase, the pilot port 111C provides a flow of gases (as the pressure signal 109C) having the same pressure as the gases 112 (provided to the active patient circuit 600) to the hollow interior 662 of the double bellows member 644. An area of the double bellows member 644 exposed to a pressure provided by the patient 102 (see FIG. 1) via the patient connection 106 is less than an area exposed to the pressure of the pressure signal 109C, so that even if the two pressures are equal, the closed end 666 of the double bellows member 644 will move to or remain in the closed position against the seat 680. At the end of the inspiratory phase, the pilot port 111C provides a flow of gases (as the pressure signal 109C) having a pilot pressure to the hollow interior 662 of the double bellows member 644. The pilot pressure is less than the pressure provided by the patient 102 (see FIG. 1) via the patient connection 106 and causes the closed end 666 of the double bellows member 644 to move to or remain in the open position (see FIG. 3F) spaced apart from the seat 680. Thus, during normal ventilation, the pressure inside the hollow interior 662 of the double bellows member 644 may be alternated between a closed pressure that is the same pressure as the gases 112 (provided to the active patient circuit 600), and an open pressure that is equal to the pilot pressure. If desired, the pressure inside the hollow interior 662 of the double bellows member 644 may be adjusted by allowing the flow of gases (in the pressure signal 109C) to flow from the hollow interior 662 to the pilot port 111C.

As explained below, during an exsufflation phase of a cough, the closed end 666 of the double bellows member 644 may be placed in the closed position (see FIG. 3E). This prevents exsufflation gases (exhaled by the patient 102) into the active patient circuit 600 from exiting the active patient circuit 600 through the opening(s) 672 (see FIG. 3C). It also prevents air from entering the active patient circuit 600 through the opening(s) 672 (see FIG. 3C). It is noted that during the beginning of the exsufflation phase, when the pressure is still positive, the double bellows member 644 is in the open position and automatically closes when the pressure provided by the patient 102 drops below ambient.

Ventilator

Figure 4:
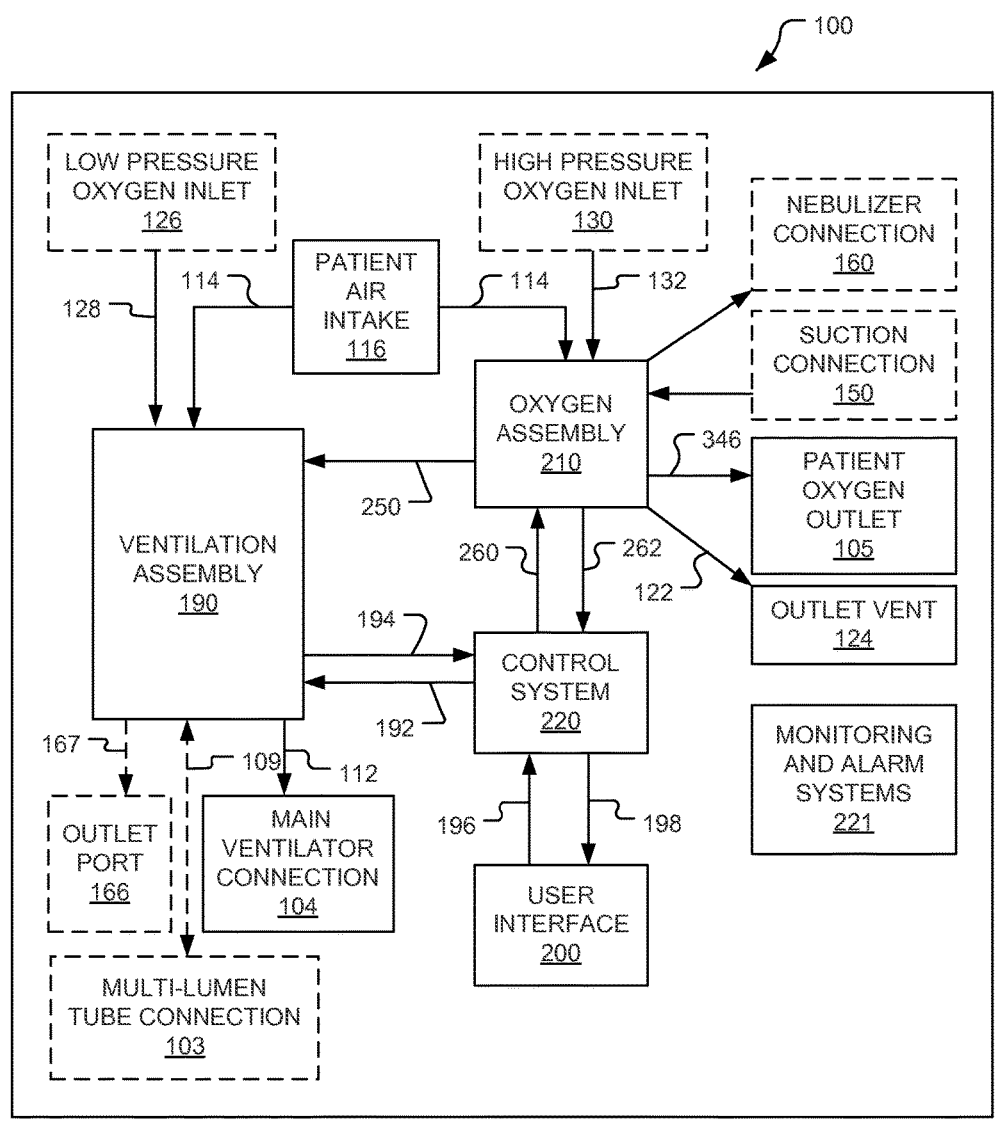
FIG. 4 is block diagram illustrating some exemplary components of the ventilator of FIG. 1.

FIG. 4 is a block diagram illustrating some exemplary components of the ventilator 100. Referring to FIG. 4, in addition to the components discussed with respect to FIG. 1, the ventilator 100 includes a ventilation assembly 190, a user interface 200, an oxygen assembly 210, a control system 220, and conventional monitoring and alarm systems 221. Because those of ordinary skill in the art are familiar with conventional monitoring and alarm systems 221, they will not be described in detail herein.

The control system 220 receives input information 196 (e.g., settings, parameter values, and the like) from the user interface 200, and provides output information 198 (e.g., performance information, status information, and the like) to the user interface 200. The user interface 200 is configured to receive input from a user (e.g., a caregiver, a clinician, and the like associated with the patient 102 depicted in FIG. 1) and provide that input to the control system 220 in the input information 196. The user interface 200 is also configured to display the output information 198 to the user.

As mentioned above, referring to FIG. 1, the patient circuit 110 may include the optional port(s) 111 configured to allow one or more pressure signals 109 to flow between the optional multi-lumen tube connection 103 and the patient circuit 110. Referring to FIG. 3, the optional multi-lumen tube connection 103 is configured to provide the pressure signal(s) 109 to the ventilation assembly 190.

As will be explained below, the ventilation assembly 190 may receive one or more control signals 192 from the control system 220, and the ventilation assembly 190 may provide one or more data signals 194 to the control system 220. Similarly, the oxygen assembly 210 may receive one or more control signals 260 from the control system 220, and the oxygen assembly 210 may provide one or more data signals 262 to the control system 220. The control signals 192 and 260 and the data signals 194 and 262 may be used by the control system 220 to monitor and/or control internal operations of the ventilator 100.

Ventilation Assembly

Figure 5A:
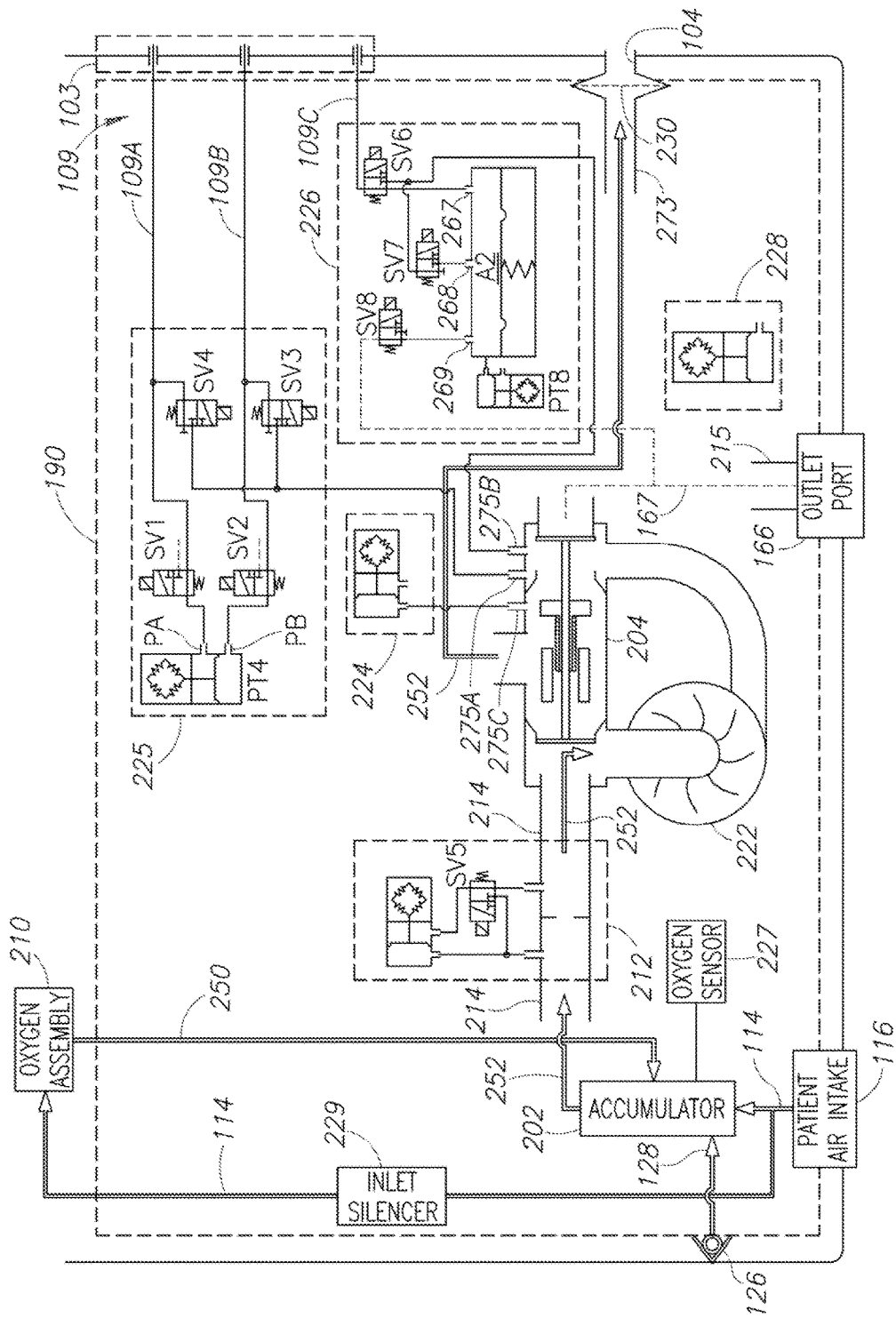
FIG. 5A is a schematic diagram illustrating some exemplary components of a ventilator assembly of the ventilator of FIG. 1 with a cough assist valve of the ventilator assembly depicted in a first configuration.
Figure 5B:
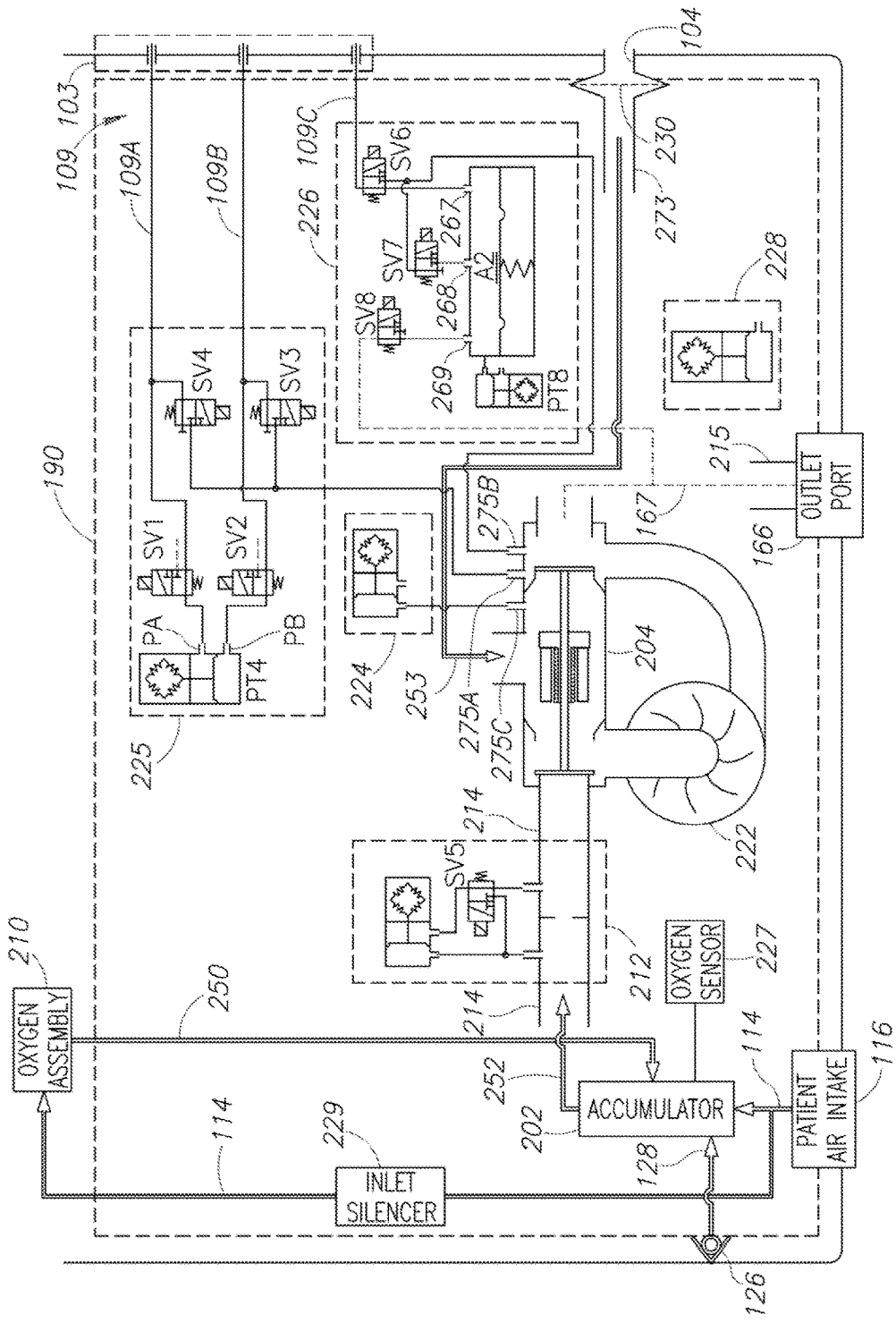
FIG. 5B is a schematic diagram illustrating the cough assist valve of the ventilator assembly in a second configuration.

FIGS. 5A and 5B are schematic diagrams illustrating some exemplary components of the ventilation assembly 190. FIG. 5E is a block diagram illustrating exemplary components of the control system 220, the control signal(s) 192 sent by the control system 220 to exemplary components of the ventilation assembly 190, and the data signals 194 received by the control system 220 from exemplary components of the ventilation assembly 190.

Referring to FIGS. 5A and 5B, the ventilation assembly 190 includes a cough assist valve 204, an accumulator 202, an internal flow transducer 212, a blower 222, an airway pressure transducer 224, an airway flow transducer module 225, an exhalation control assembly 226, an oxygen sensor 227, an ambient pressure transducer 228, an inlet silencer 229, and an internal bacteria filter 230.

The cough assist valve 204 is connected to the accumulator 202 by a conduit or flow line 214. For ease of illustration, a portion of the flow line 214 between the accumulator 202 and the internal flow transducer 212 has been omitted from FIGS. 5A and 5B.

The cough assist valve 204 is connected to the outlet port 166 by a conduit or flow line 215. For ease of illustration, a portion of the flow line 215 between the cough assist valve 204 and the outlet port 166 has been omitted from FIGS. 5A and 5B.

The cough assist valve 204 is connected to the main ventilator connection 104 by a conduit or flow line 273. For ease of illustration, a portion of the flow line 273 between the cough assist valve 204 and the internal bacteria filter 230 has been omitted from FIGS. 5A and 5B.

FIG. 5A depicts the cough assist valve 204 in a first configuration and FIG. 5B depicts the cough assist valve 204 in a second configuration. Referring to FIG. 5A, in the first configuration, the cough assist valve 204 receives a gas 252 from the accumulator 202 (via the flow line 214), and outputs the gas 252 to the main ventilator connection 104

(via the flow line 273). During normal breathing and ventilation, the cough assist valve 204 remains in the first configuration. When cough assist functionality (described below) is used to perform a cough assist maneuver, the cough assist valve 204 is in the first configuration during the insufflation phase of a cough and the cough assist valve 204 is in the second configuration during the exsufflation phase of the cough. Referring to FIG. 5B, in the second configuration, the cough assist valve 204 receives exsufflation gases 253 via the flow line 273, and outputs the exsufflation gases 253 (as the exhaust 167) to the outlet port 166 via the flow line 215.

Figure 5C:
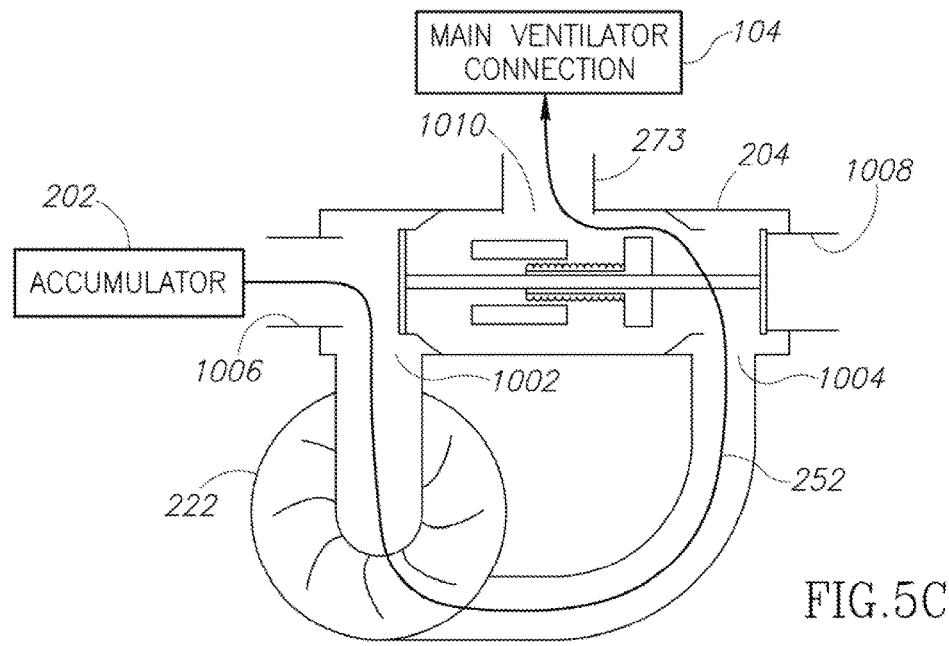
FIG. 5C is an enlarged portion of the schematic diagram of FIG. 5A showing the cough assist valve in the first configuration.

FIG. 5C is an enlarged schematic diagram of the cough assist valve 204 in the first configuration. FIG. 5C illustrates the gas 252 flowing through both the blower 222 and the cough assist valve 204 during the inspiratory phase of a breath or the insufflation phase of a cough assist maneuver performed by the ventilator 100 (see FIGS. 1 and 4).

Figure 5D:
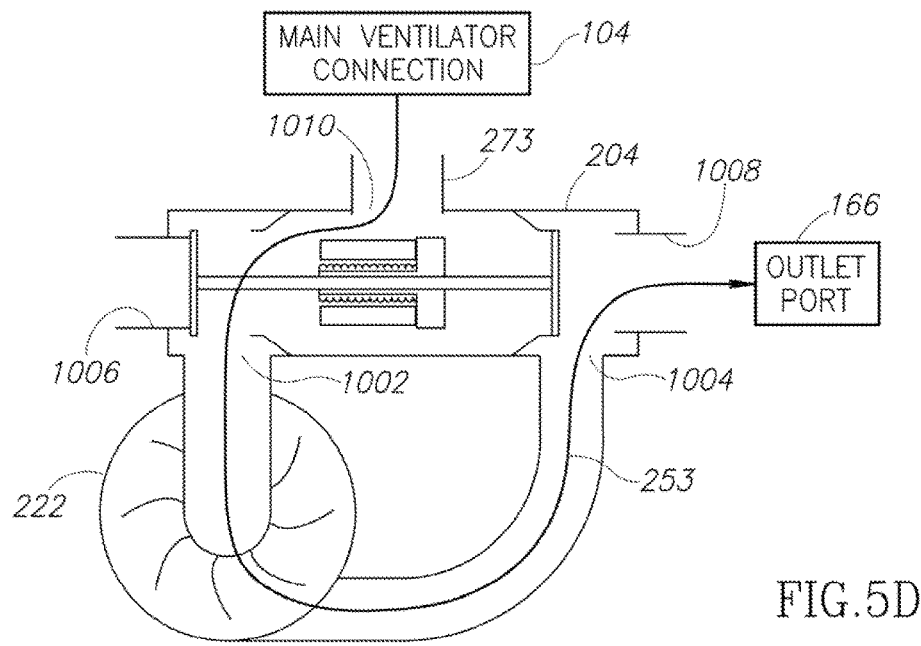
FIG. 5D is an enlarged portion of the schematic diagram of FIG. 5B showing the cough assist valve in the second configuration.
Figure 5E:
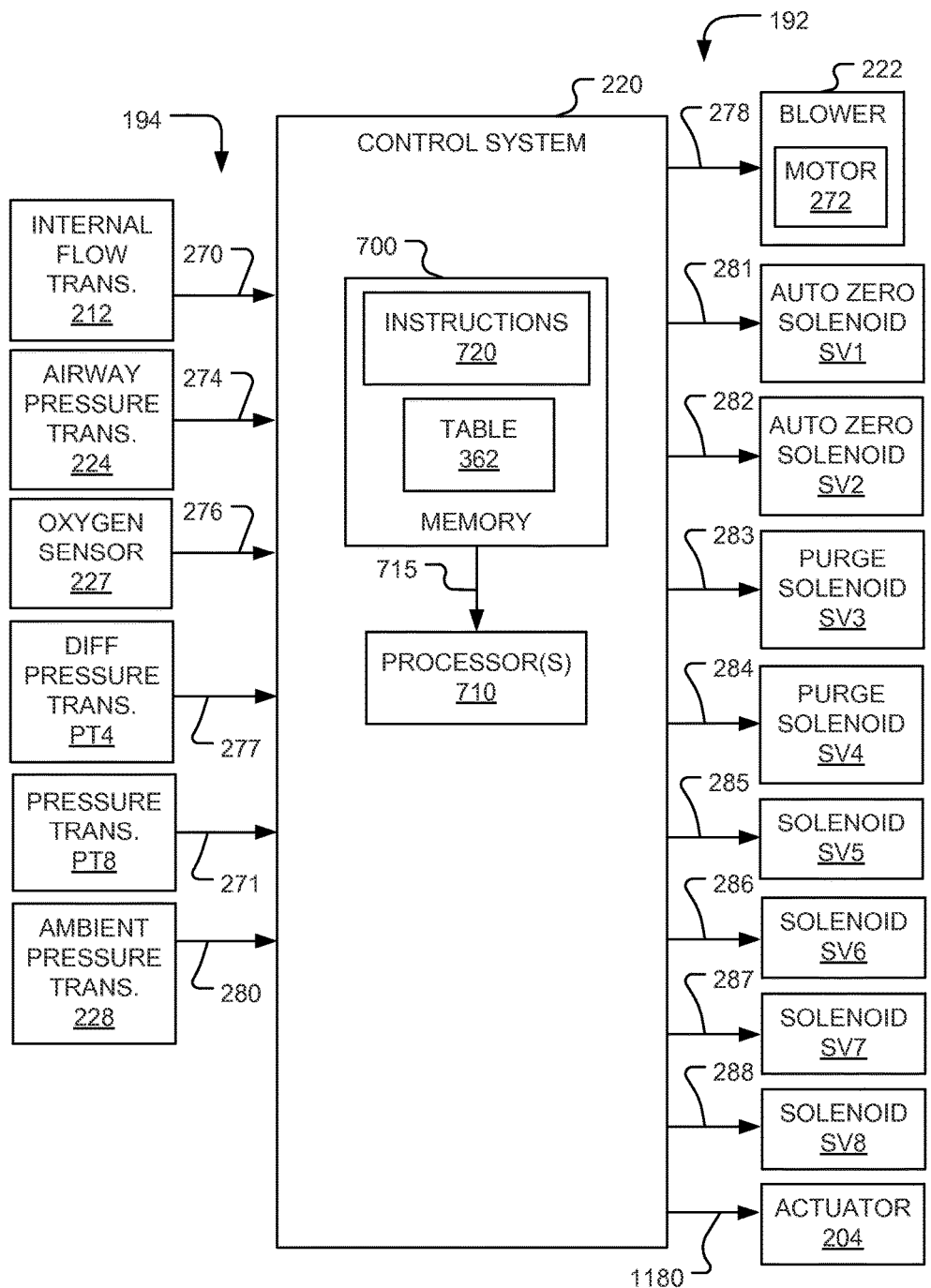
FIG. 5E is block diagram illustrating exemplary components of a control system of the ventilator, control signals sent by the control system to exemplary components of the ventilation assembly, and the data signals received by the control system from exemplary components of the ventilation assembly.

FIG. 5D is an enlarged schematic diagram of the cough assist valve 204 in the second configuration. FIG. 5D illustrates the exsufflation gases 253 flowing through both the blower 222 and the cough assist valve 204 during an exsufflation phase of a cough assist maneuver performed by the ventilator 100 (see FIGS. 1 and 4). For ease of illustration, ports 275A-275C (see FIGS. 5A and 5B) have been omitted from FIGS. 5C and 5D.

Referring to FIGS. 5C and 5D, the cough assist valve 204 has a valve-to-blower outlet 1002, a blower-to-valve inlet 1004, an air intake 1006, an exhaust outlet 1008, and an aperture 1010. The aperture 1010 is connected to the main ventilator connection 104 by the flow line 273. As shown in FIG. 5C, when the cough assist valve 204 is in the first configuration, the air intake 1006 is in fluid communication with the valve-to-blower outlet 1002, and the blower-to-valve inlet 1004 is in fluid communication with the aperture 1010. Further, the exhaust outlet 1008 is closed, and both the valve-to-blower outlet 1002 and the air intake 1006 are out of fluid communication with the aperture 1010 except via the blower 222. Thus, the gas 252 may flow into the air intake 1006, through a portion of the cough assist valve 204 and out of the valve-to-blower outlet 1002, and into the blower 222. The gas 252 exiting the blower 222 flows into the blower-to-valve inlet 1004, through a portion of the cough assist valve 204, and exits the cough assist valve 204 through the aperture 1010. The aperture 1010 is connected to the flow line 273, which conducts the gas 252 (see FIG. 5A) to the main ventilator connection 104.

As shown in FIG. 5D, when the cough assist valve 204 in the second configuration, the air intake 1006 is closed, and both the blower-to-valve inlet 1004 and the exhaust outlet 1008 are out of fluid communication with the aperture 1010 except via the blower 222. Further, the aperture 1010 is in fluid communication with the valve-to-blower outlet 1002, and the blower-to-valve inlet 1004 is in fluid communication with the exhaust outlet 1008. Thus, the exsufflation gases 253 flow into the aperture 1010, through a portion of the cough assist valve 204 and out the valve-to-blower outlet 1002, and into the blower 222. The exsufflation gases 253 exiting the blower 222 flow into the blower-to-valve inlet 1004, through a portion of the cough assist valve 204, and exit the cough assist valve 204 though the exhaust outlet 1008. The exhaust outlet 1008 is connected to the flow line 215 (see FIGS. 5A and 5B), which conducts the exsufflation gases 253 (as the exhaust 167 illustrated in FIGS. 5A and 5B) to the outlet port 166.

Figure 17A:
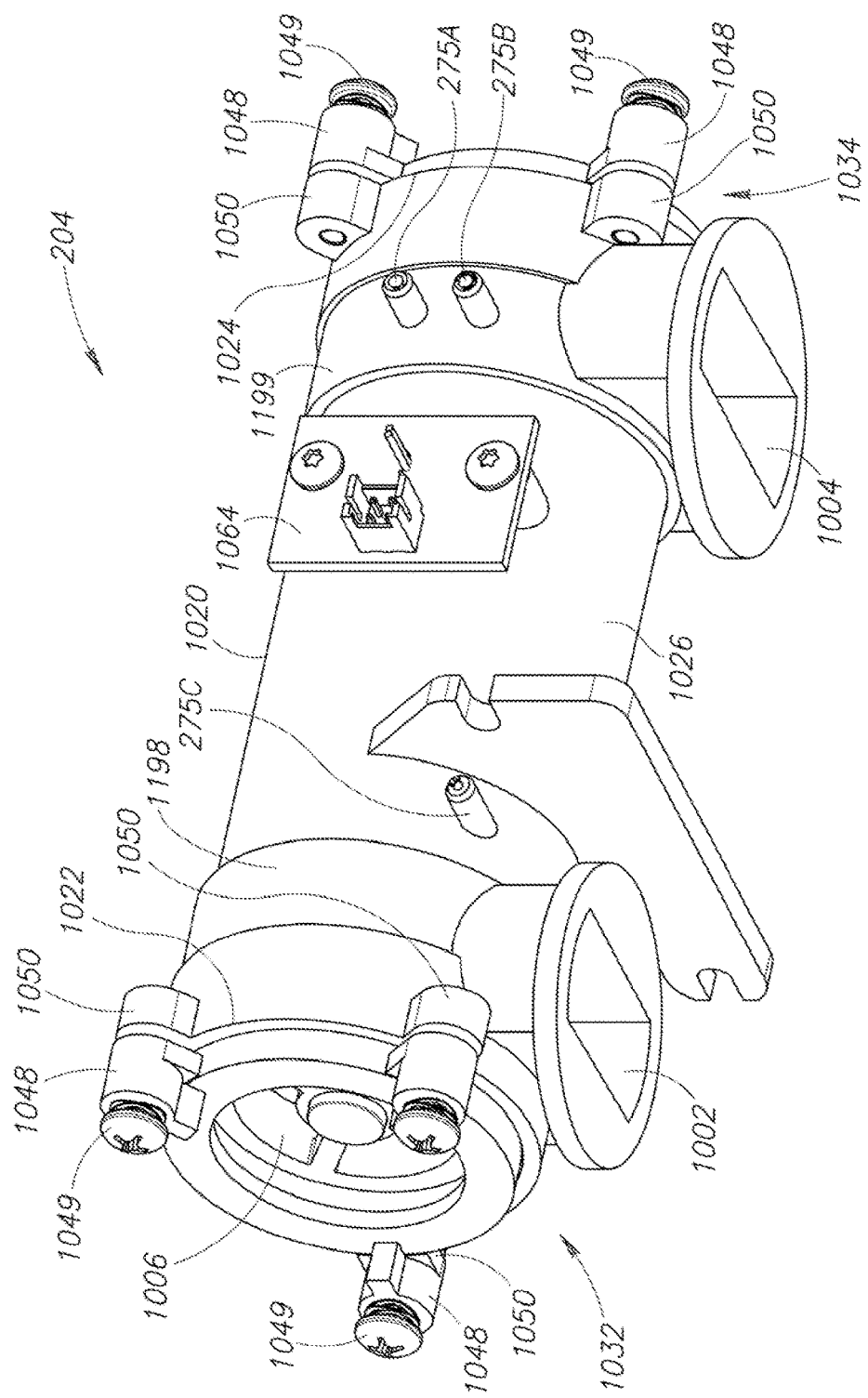
FIG. 17A is a perspective view of a cough assist valve of the ventilator assembly showing an air intake side of the cough assist valve.
Figure 17B:
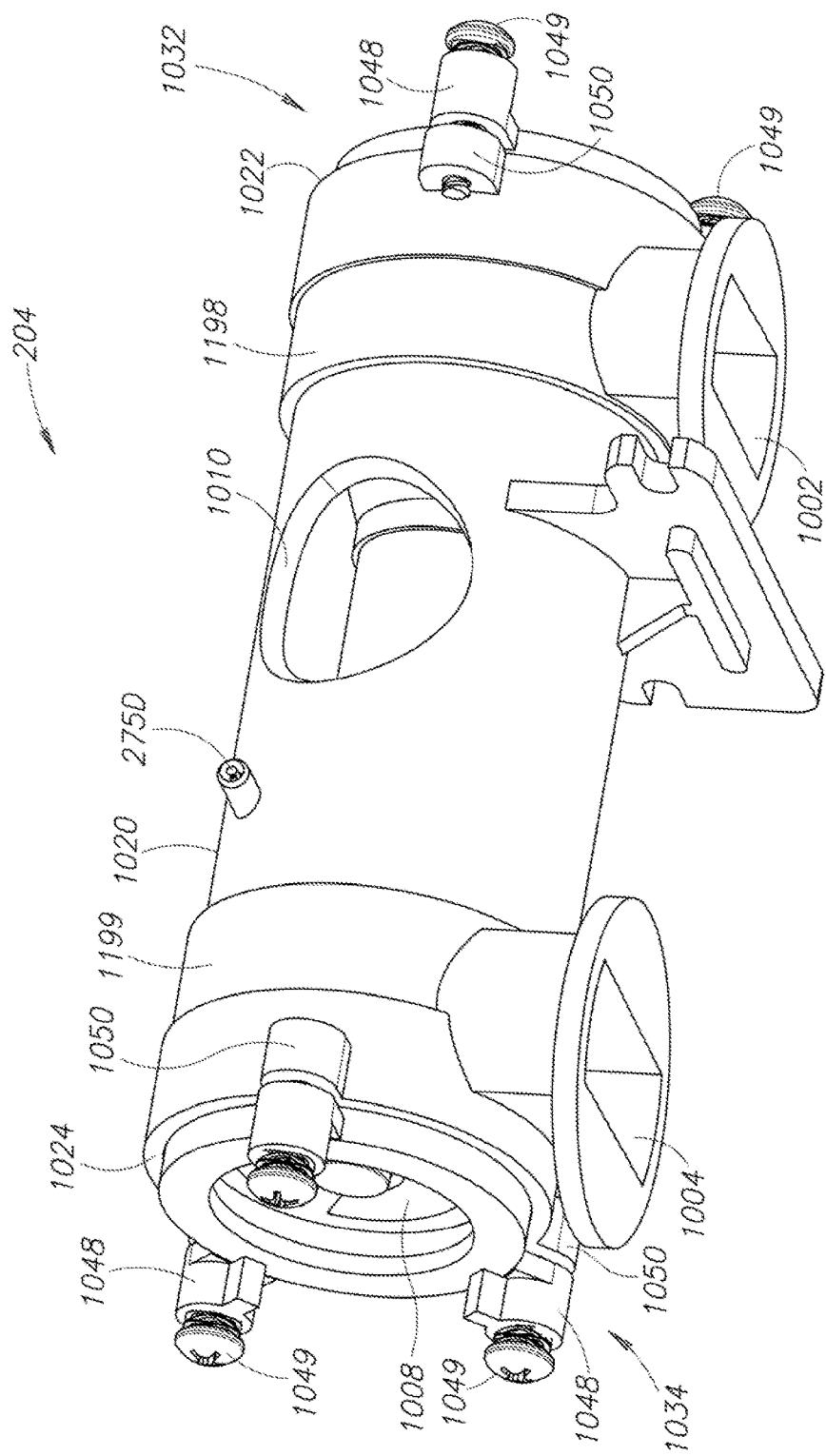
FIG. 17B is a perspective view of the cough assist valve showing an exhaust outlet side of the cough assist valve.
Figure 18A:
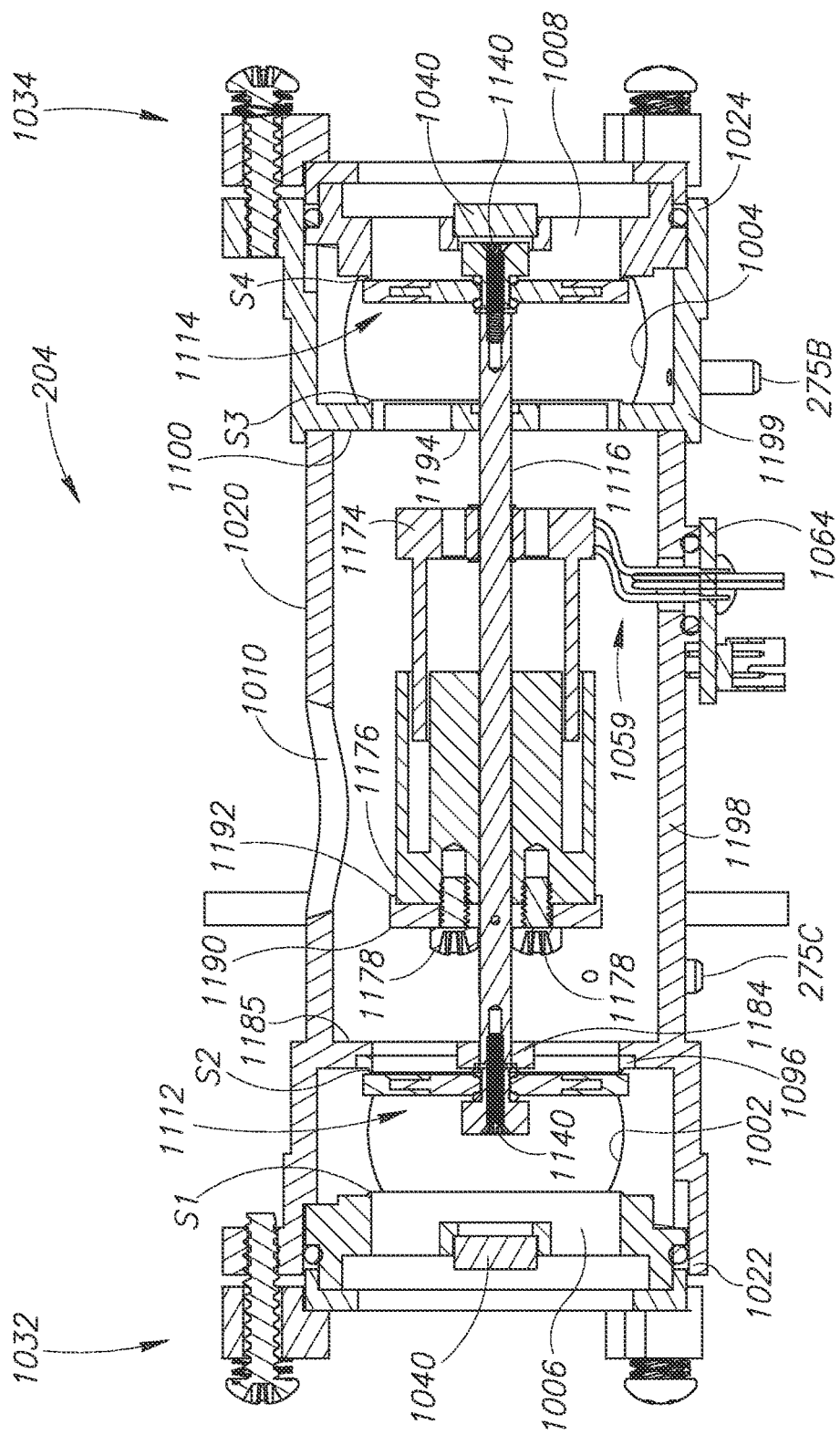
FIG. 18A is a cross-sectional view of the cough assist valve in a first configuration used during normal ventilation and an insufflation phase of a cough.
Figure 18B:
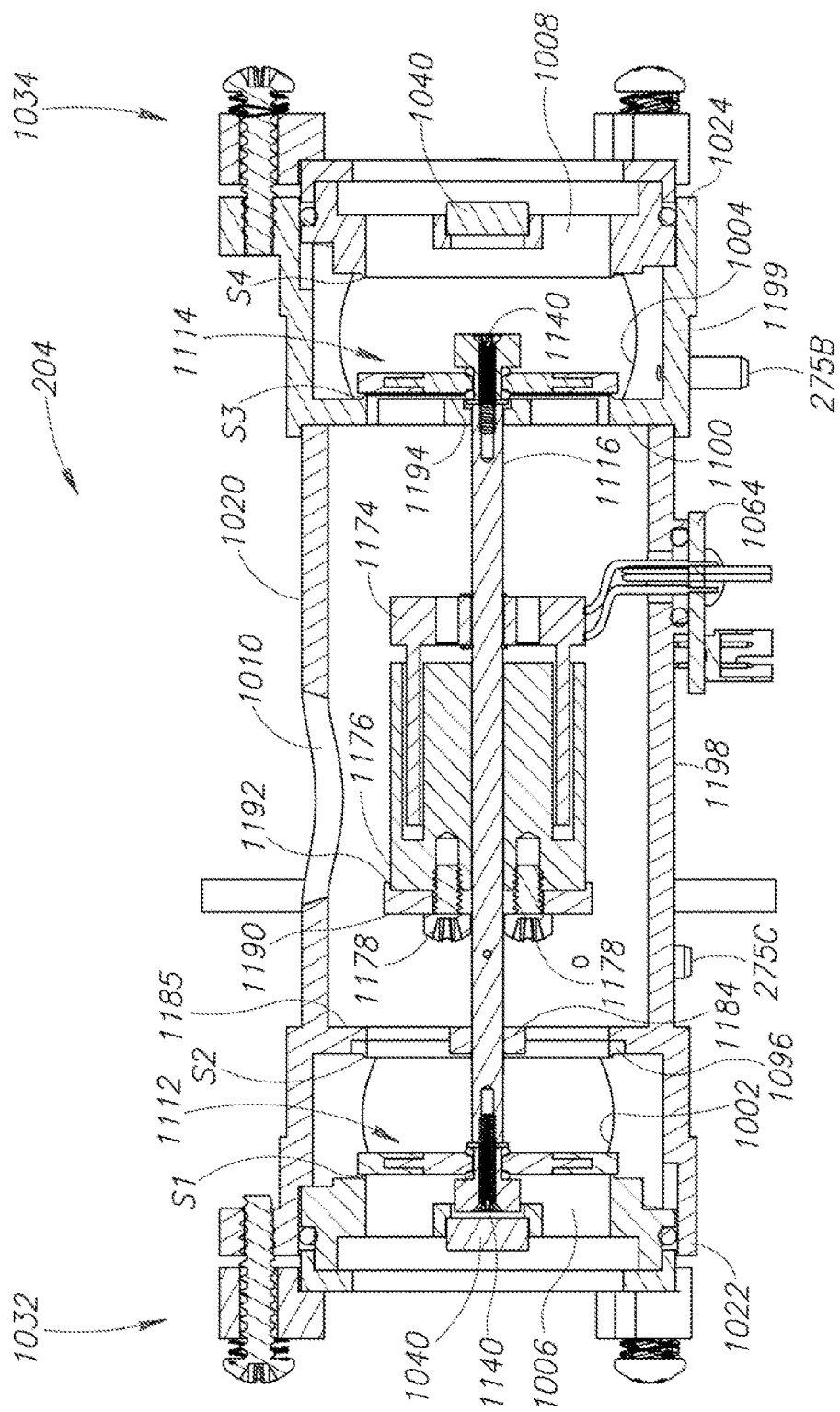
FIG. 18B is a cross-sectional view of the cough assist valve in a second configuration used during an exsufflation phase of a cough.

FIGS. 17A and 17B are perspective views of the cough assist valve 204. FIGS. 18A and 18B are cross-sectional views of the cough assist valve 204. FIG. 18A depicts the cough assist valve 204 in the first configuration, and FIG. 18B depicts the cough assist valve 204 in the second configuration.

Referring to FIG. 17A, the cough assist valve 204 includes a generally cylindrically shaped housing 1020. In the embodiment illustrated, the air intake 1006 is formed in a first open end 1022 of the housing 1020 and the exhaust outlet 1008 (see FIG. 17B) is located at a second open end 1024 of the housing 1020 with the second open end 1024 being opposite the first open end 1022. The valve-to-blower outlet 1002, the blower-to-valve inlet 1004, and the aperture 1010 (see FIG. 17B) are formed in a sidewall 1026 of the housing 1020 extending between the first and second open ends 1022 and 1024 thereof.

Figure 19A:
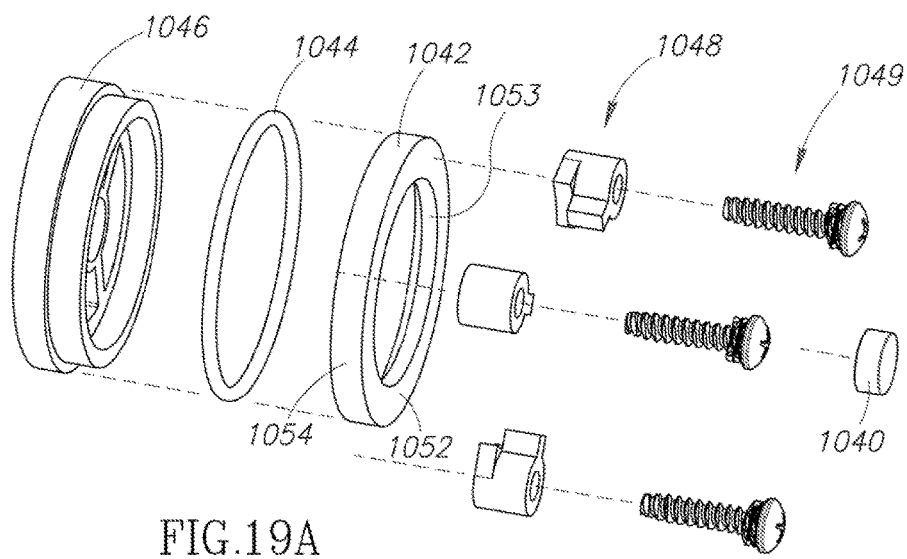
FIG. 19A is an exploded perspective view of an end cap assembly of the cough assist valve.

A first end cap assembly 1032 may be coupled to the first open end 1022, and a second end cap assembly 1034 may be coupled to the second open end 1024. The first and second end cap assemblies 1032 and 1034 are substantially identical to one another. Referring to FIG. 19A, each of the first and second end cap assemblies 1032 and 1034 (see FIGS. 17A, 17B, 18A and 18B) includes a magnet 1040, a retaining member 1042, a sealing member 1044 (e.g., an O-ring), and a seat member 1046. The sealing member 1044 is positioned between the seat member 1046 and the retaining member 1042. Each of the first and second end cap assemblies 1032 and 1034 may be coupled to the housing 1020 by one or more tabs 1048 and one or more fasteners 1049. Referring to FIGS. 17A and 17B, in the embodiment illustrated, the housing 1020 includes an outwardly extending mounting portion 1050 at each of the first and second open ends 1022 and 1024 of the housing 1020, each configured to receive one of the each fasteners 1049.

In the embodiment illustrated, the magnet 1040 is generally cylindrically or disk shaped. However, this is not a requirement.

Referring to FIG. 19A, the retaining member 1042 has a ring-shaped base portion 1052 defining an opening 1053. A sidewall 1054 extends inwardly from the base portion 1052 toward the seat member 1046. Each tab 1048 is configured to abut the base portion 1052 and avoid obstructing the opening 1053. Thus, gas (e.g., the gas 252 or the exsufflation gases 253) may pass through the opening 1053 unobstructed by the tab(s) 1048.

Figure 19B:
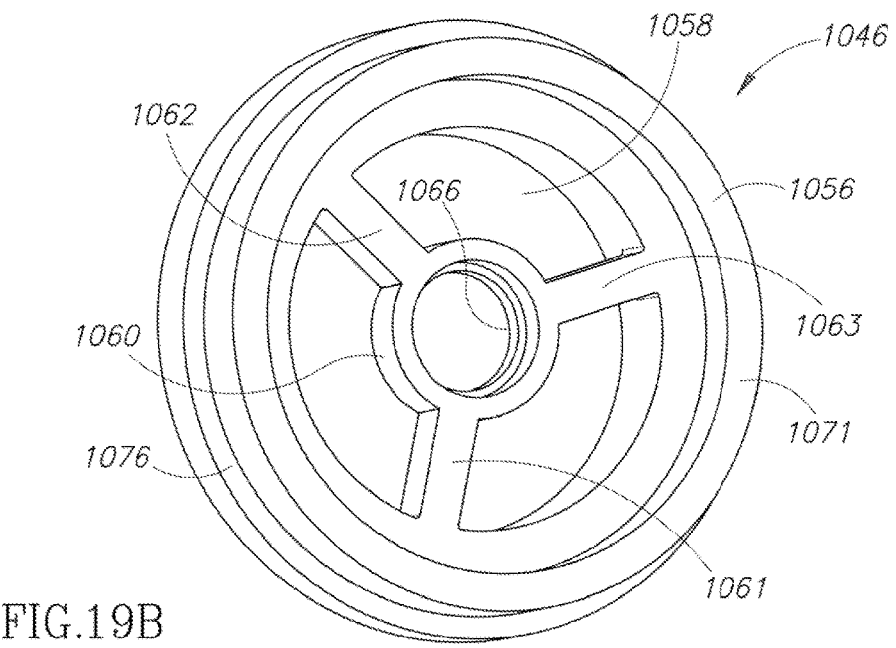
FIG. 19B is an enlarged perspective view of a second side of a seat member of the end cap assembly of FIG. 19A.
Figure 19C:
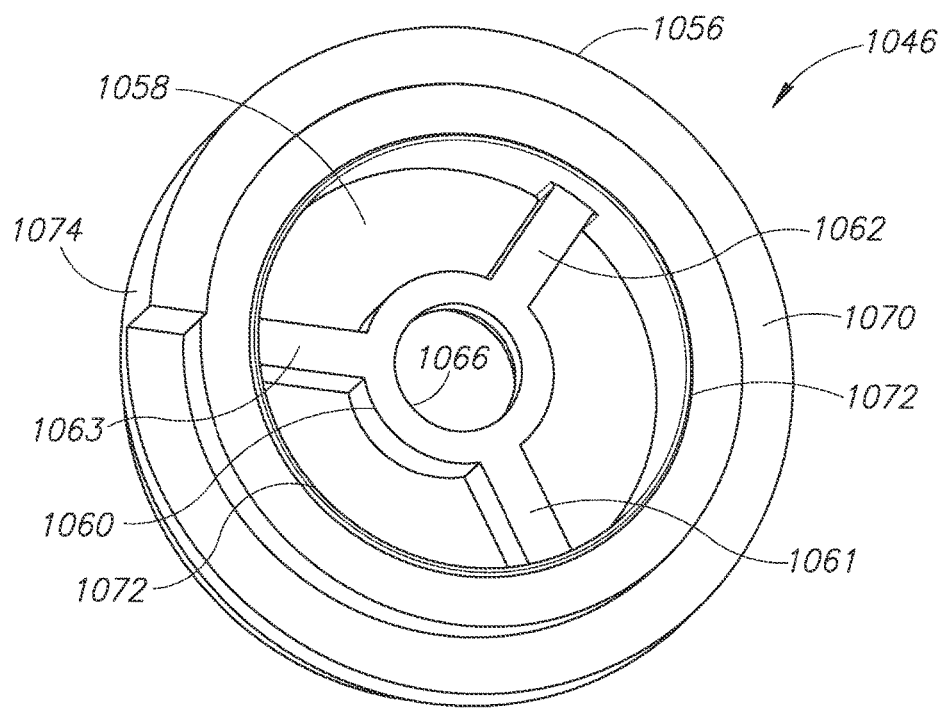
FIG. 19C is an enlarged perspective view of a first side of a seat member of the end cap assembly of FIG. 19A.

Referring to FIGS. 19B and 19C, the seat member 1046 has a ring-shaped peripheral portion 1056 defining an opening 1058 therewithin. A central magnet receiving portion 1060 is supported within the opening 1058 by radially extending support arms 1061-1063 connected to the peripheral portion 1056. Together the magnet receiving portion 1060 and the support arms 1061, 1062 and 1063 which only partially obstruct or occlude the opening 1058. Thus, gas (e.g., the gas 252 or the exsufflation gases 253) may pass through the opening 1058 around the magnet receiving portion 1060 and the support arms 1061, 1062 and 1063.

The seat member 1046 has an inwardly facing side 1070 (see FIG. 19C) opposite an outwardly facing side 1071 (see FIG. 19B). Referring to FIG. 19C, the peripheral portion 1056 along the inwardly facing side 1070 is configured to be at least partially received inside one of the first and second open ends 1022 and 1024 (see FIGS. 17A-18B) of the housing 1020. Along the inwardly facing side 1070, the peripheral portion 1056 has an inwardly extending annular projection 1072 positioned adjacent the opening 1058. In the embodiment illustrated, the peripheral portion 1056 has a longitudinally inwardly facing, annularly extending helical ramp portion 1074 along the inwardly facing side 1070. As will be described in greater detail below, the ramp portion 1074 is used to adjustably longitudinally position the seat members 1046 of the first and second end cap assemblies 1032 and 1034 within the housing 1020.

Referring to FIG. 19B, in the embodiment illustrated, the peripheral portion 1056 has an annular shaped recessed portion 1076 along the outwardly facing side 1071. The recessed portion 1076 is configured to receive the sealing member 1044 and at least a free end portion of the inwardly extending sidewall 1054 of the retaining member 1042 with the sealing member 1044 sandwiched between the seat member 1046 and the retaining member 1042.

At the outwardly facing side 1071, the magnet receiving portion 1060 is configured to receive the magnet 1040 (see FIG. 19A). In the embodiment illustrated, the magnet receiving portion 1060 has been implemented as an open ended cylinder. However, this is not a requirement. Along the inwardly facing side 1070 (see FIG. 19C), the magnet receiving portion 1060 has an inner stop wall 1066 configured to prevent the magnet 1040 from passing through the central magnet receiving portion 1060 into the housing 1020. By way of a non-limiting example, the magnet 1040 (see FIG. 19A) may be retained inside the magnet receiving portion 1060 by friction or an adhesive.

Figure 23A:
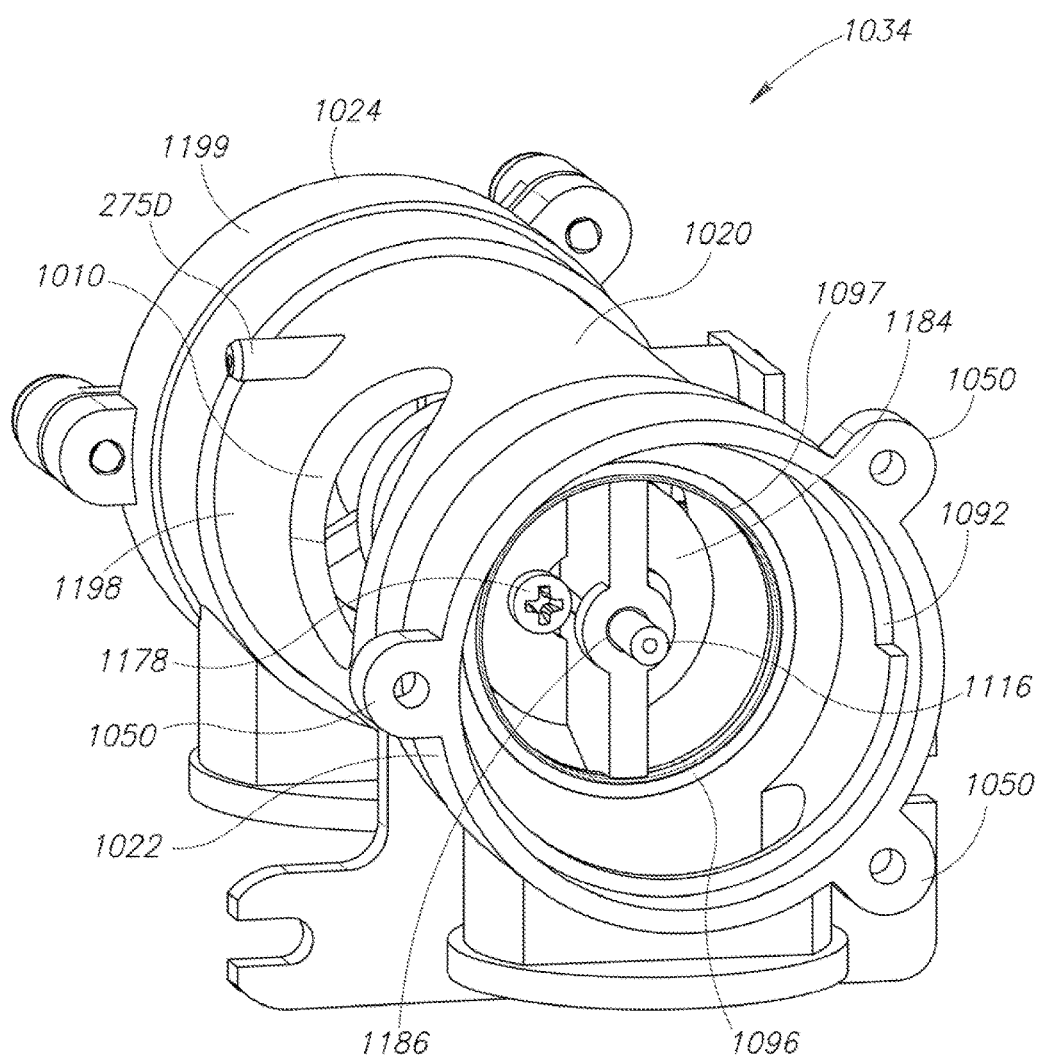
FIG. 23A is a perspective view of the air intake side of the cough assist valve omitting both its end cap assembly and poppet valve assembly.

Referring to FIG. 23A, the first open end 1022 of the housing 1020 has a longitudinally outward facing, annularly extending first inside helical ramp portion 1092 configured to mate with the helical ramp portion 1074 (see FIG. 19C) of the first end cap assembly 1032 (see FIGS. 17A, 18A and 18B). A ring-shaped inner seat member 1096 is positioned inside the housing 1020 at a circumferentially extending, radially projecting, inner wall 1185 near but inward of the first open end 1022. The inner seat member 1096 has a longitudinally outwardly extending annular projection 1097 substantially similar to the inwardly annular projection 1072 (see FIG. 19C).

Referring to FIG. 19O, the annular projection 1072 formed on the inwardly facing side 1070 of the seat member 1046 of the first end cap assembly 1032 functions as a first seat "S1" (see FIGS. 18A and 18B). The annular projection 1097 within the housing 1020 at the first open end 1022 functions as a second seat "S2" (see FIGS. 18A and 18B). As may be seen in FIGS. 18A and 18B, the second seat "S2" is positioned longitudinally inward from the first cap assembly 1032. The first and second seats "S1" and "S2" extend toward and face one another.

Figure 23B:
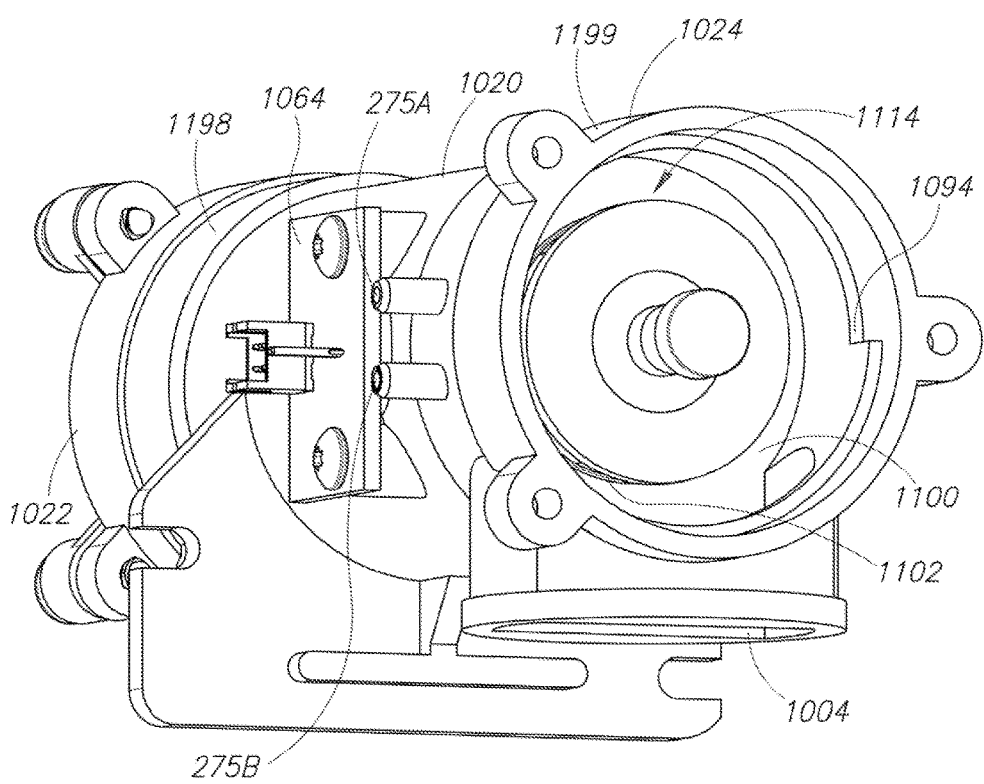
FIG. 23B is a perspective view of the exhaust outlet side of the cough assist valve omitting its end cap assembly.

Referring to FIG. 23B, the second open end 1024 of the housing 1020 has a longitudinally outward facing, annularly extending second inside helical ramp portion 1094 configured to mate with the helical ramp portion 1074 (see FIG. 19C) of the second end cap assembly 1034 (see FIGS. 17B, 18A and 18B). The housing 1020 has circumferentially extending, radially inwardly projecting, inner wall 1100 near but inward of the second open end 1024. The inner wall 1100 has a longitudinally outwardly extending annular projection 1102 substantially similar to the annular projection 1072 (see FIG. 19C). The annular projection 1102 within the housing 1020 at the second open end 1024 functions as a third seat "S3" (see FIGS. 18A and 18B). As shown in FIGS. 18A and 18B, the third seat "S3" is positioned longitudinally inward from the second end cap assembly 1034. The annular projection 1072 (see FIG. 19C) of the seat member 1046 (see FIG. 19C) of the second end cap assembly 1034 functions as a fourth seat "S4." The third and fourth seats "S3" and "S4" extend toward and face one another.

The first seat "S1" is positioned adjacent to the air intake 1006, and the fourth seat "S4" is positioned adjacent to the exhaust outlet 1008. The valve-to-blower outlet 1002 is positioned between the first seat "S1" and the second seat "S2" inside the housing 1020. Similarly, the blower-to-valve inlet 1004 is positioned between the third seat "S3" and the fourth seat "S4" formed in the housing 1020.

The cough assist valve 204 includes first and second poppet valve assemblies 1112 and 1114 connected together by a shaft 1116 so as to move together in unison. The cough assist valve 204 has first, second and third interior chambers, as will be described below. The first poppet valve assembly 1112 is located in the first chamber between the first and second seats "S1" and "S2," and moves longitudinally between the first and second seats "S1" and "S2," and the second poppet valve assembly 1114 is located in the third chamber between the third and fourth seats "S3" and "S4," and moves longitudinally between the third and fourth seats "S3" and "S4." The second chamber is located between the second and third seats "S2" and "S3," respectively, and hence is located between the first and third chambers. The second seat "S2" defines a first aperture through which the first and second chambers are in fluid communication and the first poppet valve assembly 1112 controls flow through the first aperture, and the third seat "S3" defines a second aperture through which the second and third chambers are in fluid communication and the second poppet valve assembly 1114 controls flow through the second aperture. As shown in FIG. 18A, when the first poppet valve assembly 1112 is pressed against the second seat "S2," the cough assist valve 204 is in the first configuration illustrated in FIGS. 5A and 5C. In the first configuration, the first poppet valve assembly 1112 permits the flow of gas 252 from the accumulator 202 to flow through the air intake 1006 into the first chamber and then to the valve-to-blower outlet 1002, and enter the blower 222, while blocking flow of the gas 252 directly to the aperture 1010, thus sealing the aperture 1010 from both the air intake 1006 and the valve-to-blower outlet 1002. At the same time, the second poppet valve assembly 1114 is pressed against the fourth seat "S4," so that the second poppet valve assembly 1114 closes the exhaust outlet 1008 and directs the flow of the gas 252 into the third chamber and then through the second aperture into the second chamber for exit through the aperture 1010 to the main ventilator connection 104. In this configuration, the gas 252 from the accumulator 202 entering the air intake 1006 is directed to the blower 222 through the valve-to-blower outlet 1002. The gas 252 is then blown by the blower 222 into the blower-to-valve inlet 1004 and exit the cough assist valve 204 through the aperture 1010 to the main ventilator connection 104.

As shown in FIG. 18B, when the first poppet valve assembly 1112 is pressed against the first seat "S1," the cough assist valve 204 is in the second configuration illustrated in FIGS. 5B and 5D. In the second configuration, the first poppet valve assembly 1112 permits the flow of exsufflation gases 253 from the main ventilator connection 104 to flow through the aperture 1010 into the second chamber and then through the first aperture into the first chamber for exit through the valve-to-blower outlet 1002, and entry to the blower 222, while blocking flow of the exsufflation gases to the air intake 1006 and also preventing gas 252 from the accumulator 202 reaching the valve-to-blower outlet 1002. At the same time, the second poppet valve assembly 1114 is pressed against the third seat "S3," so that the second poppet valve assembly 1114 opens the exhaust outlet 1008 and blocks the flow of the exsufflation gases 253 through the second aperture into the second chamber and to the aperture 1010. In this configuration, the exsufflation gases 253 from the main ventilator connection 104 entering the aperture 1010, pass through the first chamber and are directed to the blower 222 through the valve-to-blower outlet 1002. The exsufflation gases 253 are then blown by the blower 222 into the blower-to-valve inlet 1004 and into the third chamber and exit the cough assist valve 204 through the exhaust outlet 1008 to the outlet port 166.

Figure 21:
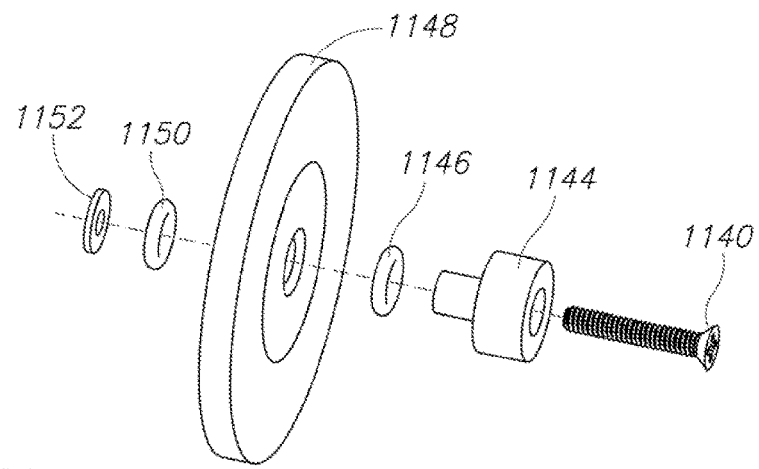
FIG. 21 is an exploded perspective view of one of the poppet valve assemblies of the cough assist valve.
Figure 22:
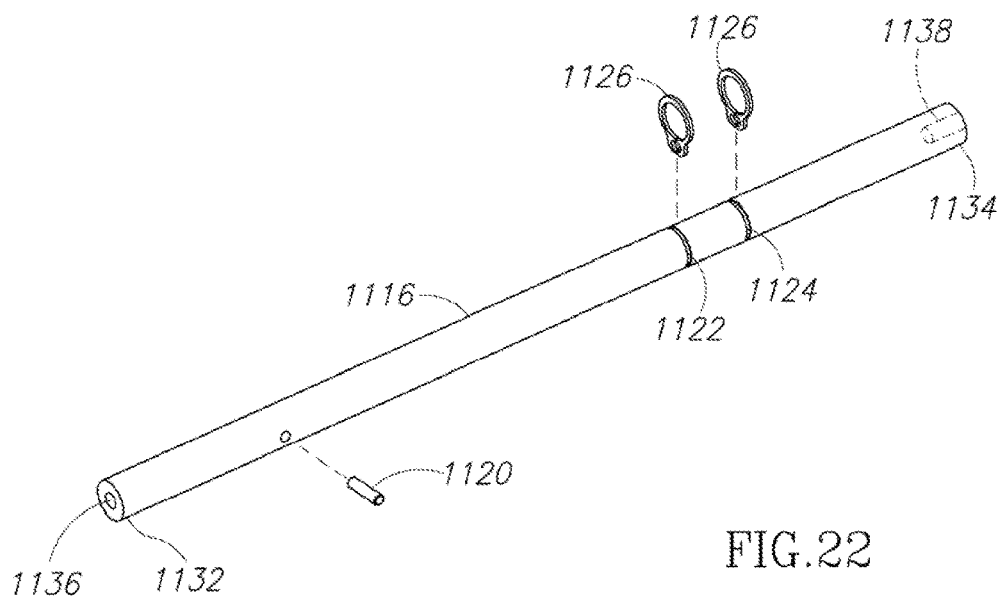
FIG. 22 is an exploded perspective view of a subassembly of the cough assist valve including the shaft, a guide member, and retaining rings.

The first and second poppet valve assemblies 1112 and 1114 are coupled to opposite ends of the shaft 1116 to move therewith as a unit in unison. Referring to FIG. 22, in the embodiment illustrated, a guide member 1120 (e.g., a pin, dowel, and the like) extends laterally outwardly from the shaft 1116. The shaft 1116 may include one or more circumferentially extending grooves 1122 and 1124 each configured to receive a different retaining ring 1126. The shaft 1116 has a first end portion 1132 opposite a second end portion 1134. Longitudinal channels 1136 and 1138 extend inwardly into the shaft at the first and second end portions 1132 and 1134, respectively. Each of the channels 1136 and 1138 is configured to receive a fastener 1140 (see FIG. 21).

The shaft 1116 is configured to move longitudinally within the housing 1020 between a first position (see FIG. 18A) whereat the cough assist valve 204 is in the first configuration and a second position (see FIG. 18B) whereat the cough assist valve 204 is in the second configuration. Referring to FIGS. 18A and 18B, as the shaft 1116 moves, the first poppet valve assembly 1112 moves between the first and second seats "S1" and "S2," and the second poppet valve assembly 1114 moves between the third and fourth seats "S3" and "S4." When the shaft 1116 is in the first position (see FIG. 18A), the first poppet valve assembly 1112 is in sealing position against the first seat "S1," and the second poppet valve assembly 1114 is in sealing position against the third seat "S3." When the shaft 1116 is in the second position (see FIG. 18B), the first poppet valve assembly 1112 is in sealing position against the second seat "S2," and the second poppet valve assembly 1114 is in sealing position against the fourth seat "S4."

The ramp portion 1074 of seat member 1046 of the first end cap assembly 1032 is in sliding engagement with the ramp portion 1092 within the first open end 1022 of the housing 1020 such that rotation of the seat member 1046 causes adjustable longitudinal movement relative to the housing 1020 to precisely adjust the position of the first seat S1 of the seat member 1046, during assembly and calibration, with respect to the first poppet valve assembly 1112 to achieve the desired seal and seating therebetween. Similarly, the ramp portion 1074 of seat member 1046 of the second end cap assembly 1034 is in sliding engagement with the ramp portion 1094 within the second open end 1024 of the housing 1020 such that rotation of the seat member 1046 causes adjustable longitudinal movement relative to the housing 1020 to precisely adjust the position of the fourth seat S4 of the seat member 1046, during assembly and calibration, with respect to the second poppet valve assembly 1114 to achieve the desired seal and seating therebetween.

The first and second poppet valve assemblies 1112 and 1114 are substantially identical to one another. Referring to FIG. 21, each of the first and second poppet valve assemblies 1112 and 1114 includes the fastener 1140, a ferromagnetic member 1144, a first sealing member 1146 (e.g., an O-ring), a disk shaped poppet member 1148, a second sealing member 1150 (e.g., an O-ring), and an optional washer 1152.

The fastener 1140 of the first poppet valve assembly 1112 fastens the other components (namely, the ferromagnetic member 1144, the first sealing member 1146, the poppet member 1148, the second sealing member 1150, and optionally, the washer 1152) of the first poppet valve assembly 1112 to the first end portion 1132 of the shaft 1116. Similarly, the fastener 1140 of the second poppet valve assembly 1114 fastens the other components of the second poppet valve assembly 1114 to the second end portion 1134 of the shaft 1116. The first and second sealing members 1146 and 1150 of each of the first and second poppet valve assemblies 1112 and 1114 serve to both seal the poppet valve assemblies to the end portion of the shaft 1116 and provide a flexible coupling between the shaft and the poppet members 1148 of the poppet valve assemblies.

Referring to FIG. 18A, the magnet 1040 of the first end cap assembly 1032 attracts the ferromagnetic member 1144 of the first poppet valve assembly 1112 and when in proximity therewith maintains the shaft 1116 in the first position after the shaft has been moved to the first position and holds the first poppet valve assembly 1112 in place at the first seat 51 of the first end cap assembly 1032. Similarly, referring to FIG. 18B, the magnet 1040 of the second end cap assembly 1034 attracts the ferromagnetic member 1144 of the second poppet valve assembly 1114 and when in proximity therewith maintains the shaft 1116 in the second position after the shaft has been moved to the second position and holds the second poppet valve assembly 1114 in place at the fourth seat S4 of the second end cap assembly 1034. The ferromagnetic members 1144 holds the poppet valve assemblies 1112 and 1114 in place with respect to the first and fourth seats S1 and S4, respectively, even when power is not being applied to the actuator used to move the poppet valve assemblies.

Referring to FIG. 20, the cough assist valve 204 includes an actuator 1170 configured to selectively move the shaft 1116 between the first position (see FIG. 18A) and the second position (see FIG. 18B) along longitudinal directions identified by double headed arrow 1172. In the embodiment illustrated, the actuator 1170 is a linear actuator implemented using a voice coil that includes a movable coil subassembly 1174 and a stationary magnet subassembly 1176. The shaft 1116 is coupled to the movable coil subassembly 1174 and moves therewith as a unit. Referring to FIGS. 18A and 18B, the stationary magnet subassembly 1176 is coupled to an actuator mounting portion 1190 of the housing 1020 (e.g., by one or more fasteners 1178).

Referring to FIG. 18A, the movable coil subassembly 1174 is connected by one or more wires 1059 to a printed circuit board ("PCB") 1064 mounted to the outside of the housing 1020. In the embodiment illustrated, the wire(s) 1059 provide power to the movable coil subassembly 1174. The housing 1020 includes one or more apertures 1065 (see FIG. 24A) through which the wire(s) 1059 may pass. The PCB 1064 is connected to the control system 220 (see FIG. 5E) by one or more wires (not shown). The actuator 1170 is configured to receive a control signal 1180 (see FIG. 5E) from the control system 220 (via the PCB 1064 and the wire(s) 1059) and move in accordance with one or more instructions in the control signal 1180. The PCB 1064 serves as a connector and passes the control signal 1180 to the movable coil subassembly 1174.

The control signal 1180 (see FIG. 5E) selectively powers the movable coil subassembly 1174 to move toward either the first end cap assembly 1032 or the second end cap assembly 1034. When the movable coil subassembly 1174 moves toward the first end cap assembly 1032, the movable coil subassembly 1174 moves the shaft 1116 toward the first position. Referring to FIG. 18A, after the shaft 1116 has moved to the first position, the movable coil subassembly 1174 is powered down and the magnet 1040 of the first end cap assembly 1032 (which, as described above is attracted to at least a portion of the first poppet valve assembly 1112) maintains the shaft 1116 in the first position. On the other hand, when the movable coil subassembly 1174 moves toward the second end cap assembly 1034, the movable coil subassembly 1174 moves the shaft 1116 toward the second position. Referring to FIG. 18B, after the shaft 1116 has moved to the second position, the movable coil subassembly 1174 is powered down and the magnet 1040 of the second end cap assembly 1034 (which, as described above is attracted to at least a portion of the second poppet valve assembly 1114) maintains the shaft 1116 in the second position. Thus, additional power is not needed to maintain the shaft 1116 in either the first position or the second position, which helps extend battery life in embodiments powered by one or more batteries.

Figure 24A:
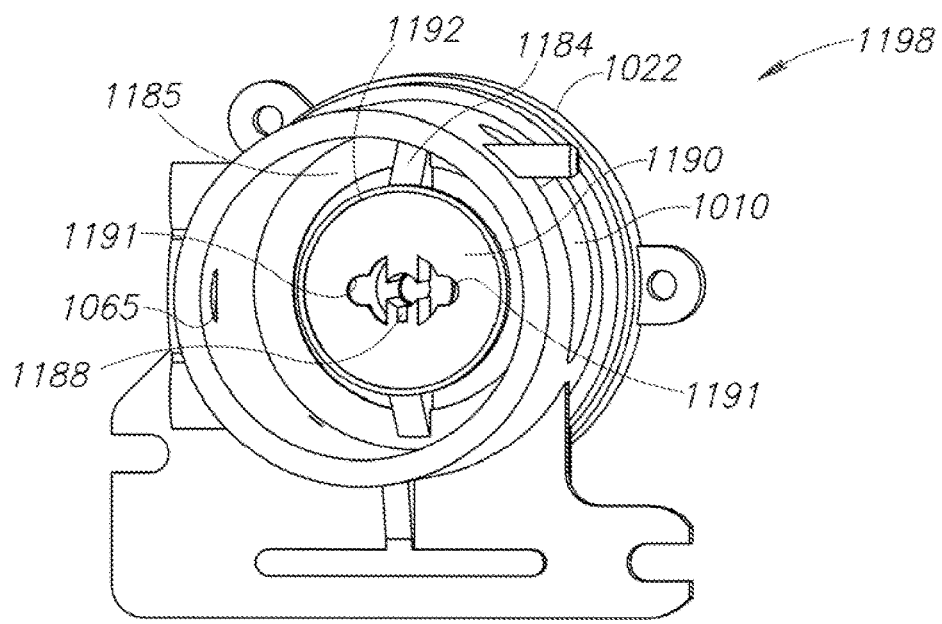
FIG. 24A is a perspective view of a first side of an intake body portion of a housing of the cough assist valve.
Figure 24B:
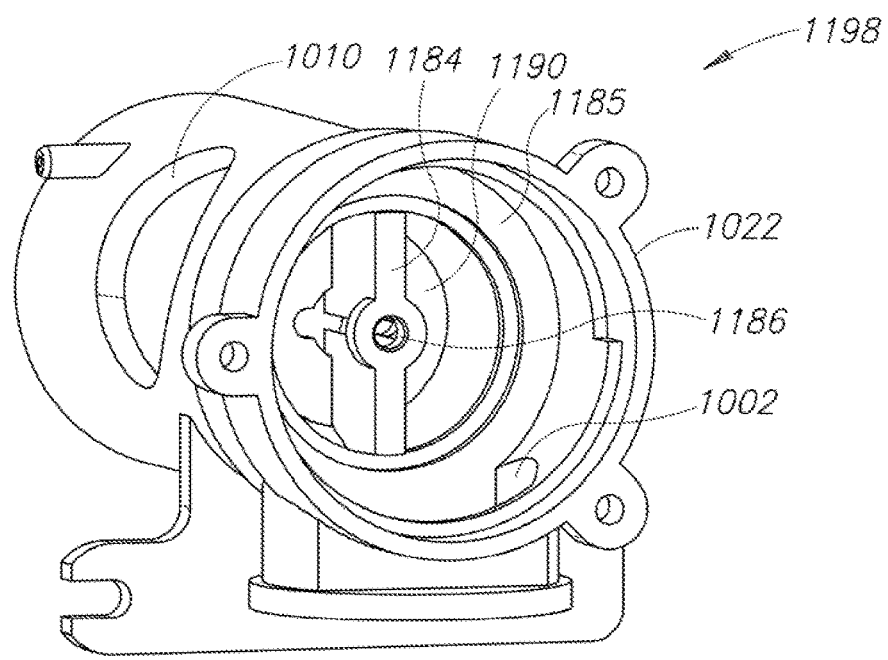
FIG. 24B is a perspective view of a second side of the intake body portion of the housing of the cough assist valve.

Referring to FIG. 24B, the housing 1020 (see FIGS. 18A and 18B) includes a first internal support 1184 spaced inwardly from the first open end 1022. In the embodiment illustrated, the first internal support 1184 extends radially inward from the circumferentially inwardly extending inner wall 1185. The first internal support 1184 has a longitudinally extending channel 1186 formed therein. Referring to FIGS. 18A and 18B, the channel 1186 (see FIG. 24B) is configured to allow the shaft 1116 to pass fully therethrough to position the first poppet valve assembly 1112 between the first internal support 1184 and the first end cap assembly 1032. As may be viewed in FIG. 23A, the channel 1186 opens alongside the inner seat member 1096, and as shown in FIGS. 18A and 18B, positions the first poppet valve assembly 1112 between the first and second seats "S1" and "S2." A portion of the shaft 1116 near the first end portion 1132 including the guide member 1120 (see FIG. 22) is positioned inside the channel 1186 (see FIG. 24B) and reciprocates therein. Referring to FIG. 24A, an open-ended, longitudinally extending guide groove 1188 is formed in the first internal support 1184 alongside the channel 1186. The guide member 1120 (see FIG. 22) is positioned in and moves within the guide groove 1188. (This prevents rotation of the poppet assembly, which could damage the wires.)

The first internal support 1184 has the actuator mounting portion 1190 which optionally includes one or more through-holes configured to receive the fastener(s) 1178 (see FIGS. 18A and 18B). The stationary magnet subassembly 1176 (see FIGS. 18A and 18B) is coupled to the actuator mounting portion 1190 which anchors the stationary magnet subassembly to the housing 1020 (see FIGS. 18A and 18B). In the embodiment illustrated, the actuator mounting portion 1190 includes an inwardly extending peripheral sidewall 1192 configured to extend around a portion of the stationary magnet subassembly 1176.

Figure 25:
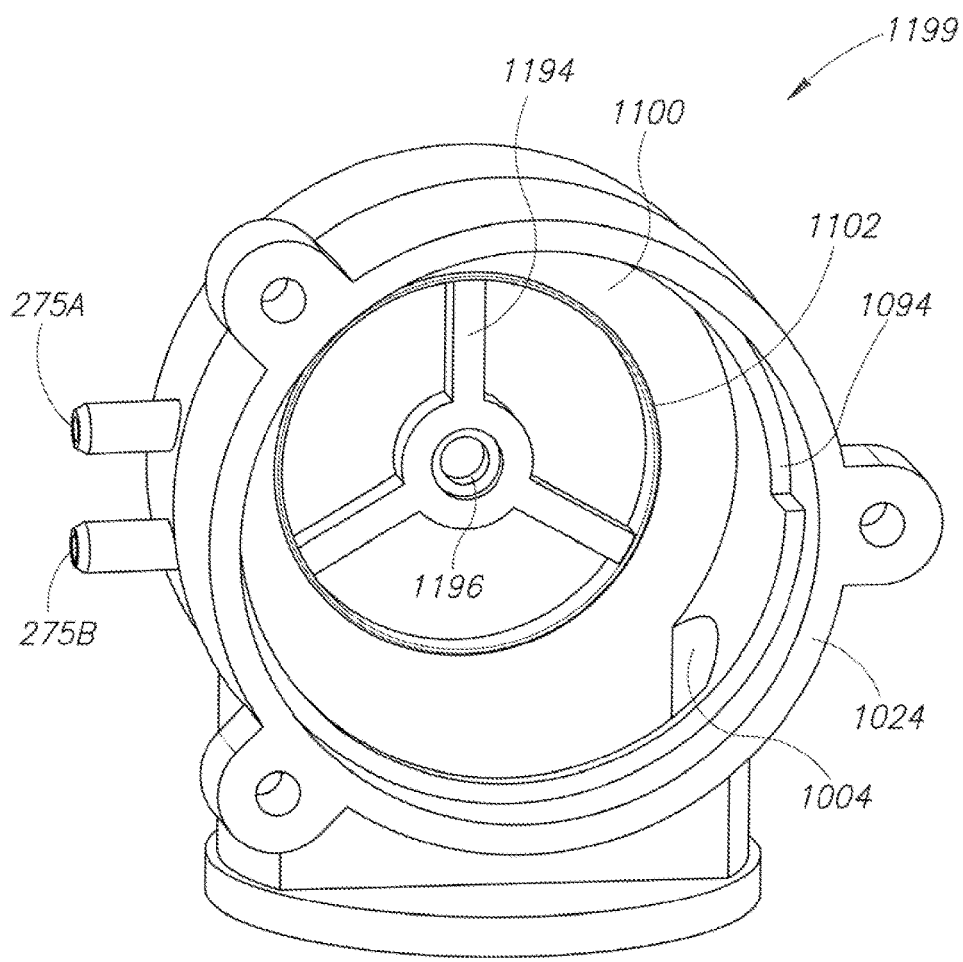
FIG. 25 is a perspective view of an exhaust body portion of a housing of the cough assist valve.

Referring to FIG. 25, the housing 1020 (see FIGS. 18A and 18B) includes a second internal support 1194 spaced inwardly from the second open end 1024. In the embodiment illustrated, the second internal support 1194 extends radially inward from the inner wall 1100. The second internal support 1194 has a through-hole 1196 formed therein. Referring to FIGS. 18A and 18B, the through-hole 1196 (see FIG. 25) is configured to allow the shaft 1116 to pass therethrough to position the second poppet valve assembly 1114 between the second internal support 1194 and the second end cap assembly 1034. As may be viewed in FIG. 25, the through-hole 1196 opens alongside the annular projection 1102, and as shown in FIGS. 18A and 18B, positions the second poppet valve assembly 1114 between the third and fourth seats "S3" and "S4."

Referring to FIGS. 17A, 17B, 18A, 18B, 23A, and 23B, in the embodiment illustrated, the housing 1020 includes an intake body portion 1198 coupled to an exhaust body portion 1199. The valve-to-blower outlet 1002, the air intake 1006, the aperture 1010, the first open end 1022, and the first internal support 1184 are formed in the intake body portion 1198. The blower-to-valve inlet 1004, the exhaust outlet 1008, the second open end 1024, and the second internal support 1194 are formed in the exhaust body portion 1199.

In the embodiment illustrated, the cough assist valve 204 includes the ports 275A, 275B and 275C (described below) formed in the housing 1020. The ports 275A and 275B may be formed in the exhaust body portion 1199, and the port 275C may be formed in the intake body portion 1198. However, this is not a requirement. Optionally, the cough assist valve 204 includes a port 275D (see FIGS. 17B and 23A) configured to be connected to a redundant airway pressure transducer (not shown).

Figure 34A:
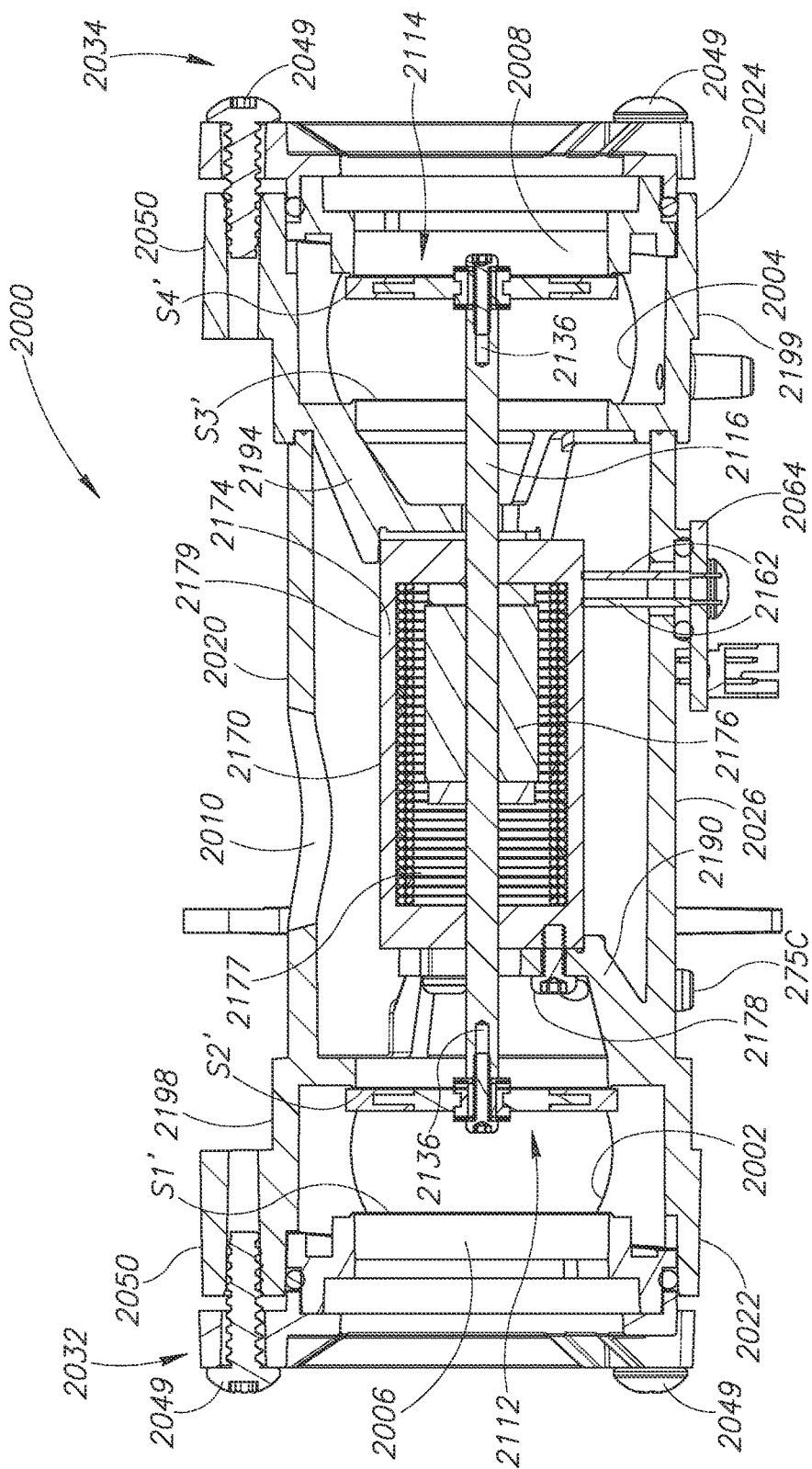
FIG. 34A is a longitudinal cross-sectional view of an alternate embodiment of a cough assist valve for use with the ventilator assembly of FIG. 5A depicted in a first configuration used during normal ventilation and an insufflation phase of a cough.
Figure 34B:
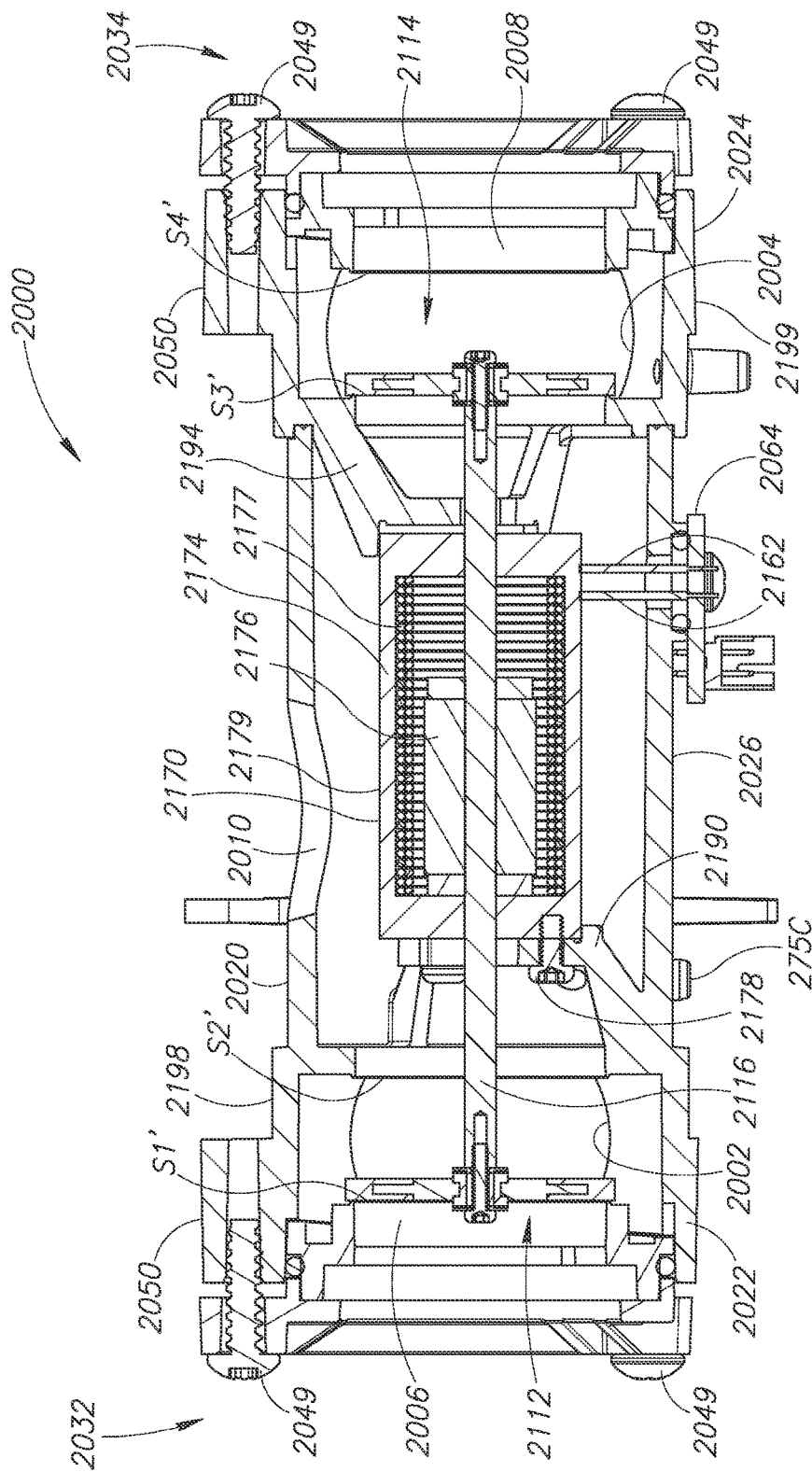
FIG. 34B is a longitudinal cross-sectional view of the cough assist valve of FIG. 34A depicted in a second configuration used during an exsufflation phase of a cough.

FIGS. 34A and 34B are cross-sectional views of an alternate embodiment of a cough assist valve 2000 that may be used in the ventilation assembly 190 (see FIGS. 4 and 5A), instead of the cough assist valve 204 (see FIGS. 5A-5D and 17A-18B). Referring to FIGS. 5A and 5B, like the cough assist valve 204, the cough assist valve 2000 (see FIGS. 34A and 34B) is configured to be connected to the accumulator 202 by the flow line 214, to the outlet port 166 by the flow line 215, and to the main ventilator connection 104 by the flow line 273.

FIG. 34A depicts the cough assist valve 2000 in a first configuration and FIG. 34B depicts the cough assist valve 2000 in a second configuration. The first and second configurations of the cough assist valve 2000 correspond and provide identical functionality to the first and second configurations, respectively, of the cough assist valve 204 (see FIGS. 5A-5D and 17A-18B). Thus, during normal breathing and ventilation, the cough assist valve 2000 remains in the first configuration. When cough assist functionality (described below) is used to perform a cough assist maneuver, the cough assist valve 2000 is in the first configuration during the insufflation phase of a cough and the cough assist valve 2000 is in the second configuration during the exsufflation phase of the cough.

Referring to FIGS. 34A, 34B, 18A, and 18B, the cough assist valve 2000 has a valve-to-blower outlet 2002, a blower-to-valve inlet 2004, an air intake 2006, an exhaust outlet 2008, and an aperture 2010 substantially identical to the valve-to-blower outlet 1002, the blower-to-valve inlet 1004, the air intake 1006, the exhaust outlet 1008, and the aperture 1010, respectively, of the cough assist valve 204. The valve-to-blower outlet 2002 and the blower-to-valve inlet 2004 are each connected to the blower 222. The air intake 2006 is connected to the accumulator 202 by the flow line 214. The exhaust outlet 2008 is connected to the outlet port 166 by the flow line 215. The aperture 2010 is connected to the main ventilator connection 104 by the flow line 273. The cough assist valve 2000 has seats "S1" to "S4" that are substantially identical to the seats "S1" to "S4," respectively, of the cough assist valve 204.

Referring to FIGS. 34A and 34B, the cough assist valve 2000 includes a generally cylindrically shaped housing 2020. The air intake 2006 is formed in a first open end 2022 of the housing 2020 and the exhaust outlet 2008 is formed at a second open end 2024 of the housing 2020. The valve-to-blower outlet 2002, the blower-to-valve inlet 2004, and the aperture 2010 are formed in a sidewall 2026 of the housing 2020 extending between the first and second open ends 2022 and 2024 thereof.

Figure 35:
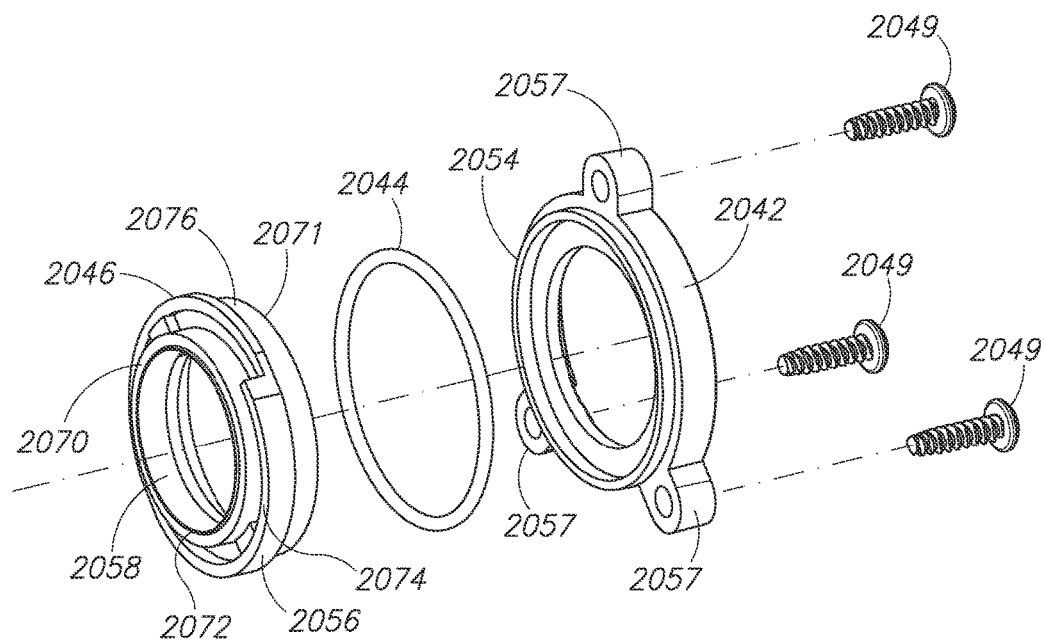
FIG. 35 is an exploded perspective view of an end cap assembly of the cough assist valve of FIG. 34A.

First and second end cap assemblies 2032 and 2034 may be coupled to the first and second open ends 2022 and 2024, respectively. The first and second end cap assemblies 2032 and 2034 are substantially identical to one another. Referring to FIG. 35, each of the first and second end cap assemblies 2032 and 2034 (see FIGS. 34A and 34B) includes a retaining member 2042, a sealing member 2044 (e.g., an 0-ring), and a seat member 2046. Referring to FIGS. 34A and 34B, each of the first and second end cap assemblies 2032 and 2034 may be coupled to the housing 2020 by one or more fasteners 2049. In the embodiment illustrated, the housing 2020 includes one or more outwardly extending mounting portions 2050 at each of the first and second open ends 2022 and 2024 of the housing 2020 each configured to receive one of the fasteners 2049.

Referring to FIG. 35, the seat member 2046 has a ring-shaped peripheral portion 2056 defining an opening 2058. The seat member 2046 has an inwardly facing side 2070 opposite an outwardly facing side 2071. Along the inwardly facing side 2070, the seat member 2046 has an inwardly extending annular projection 2072 positioned adjacent the opening 2058. In the embodiment illustrated, the peripheral portion 2056 has an outside threaded portion 2074 along the inwardly facing side 2070 and an annular shaped recessed portion 2076 along the outwardly facing side 2071. The recessed portion 2076 is configured to receive the sealing member 2044 and at least a free end portion of an inwardly extending sidewall 2054 of the retaining member 2042 with the sealing member 2044 sandwiched between the seat member 2046 and the retaining member 2042.

The first and second end cap assemblies 2032 and 2034 (see FIGS. 34A and 34B) do not include the tabs 1048 (see FIG. 19A). Instead, the retaining member 2042 of the first end cap assembly 2032 (see FIGS. 34A and 34B) includes an outwardly extending mounting portion 2057 for each of the outwardly extending mounting portions 2050 (see FIGS. 34A, 34B, and 37) located at the first open end 2022 (see FIGS. 34A and 34B) of the housing 2020. Similarly, each mounting portion 2057 of the retaining member 2042 of the second end cap assembly 2034 (see FIGS. 34A and 34B) corresponds to one of the outwardly extending mounting portions 2050 (see FIGS. 34A, 34B, and 38) located at the second open end 2024 of the housing 2020. Each mounting portion 2057 is configured to receive one of the fasteners 2049 and be fastened thereby to the mounting portion 2050 (see FIGS. 34A, 34B, and 38) that corresponds to the mounting portion 2057.

Figure 37:
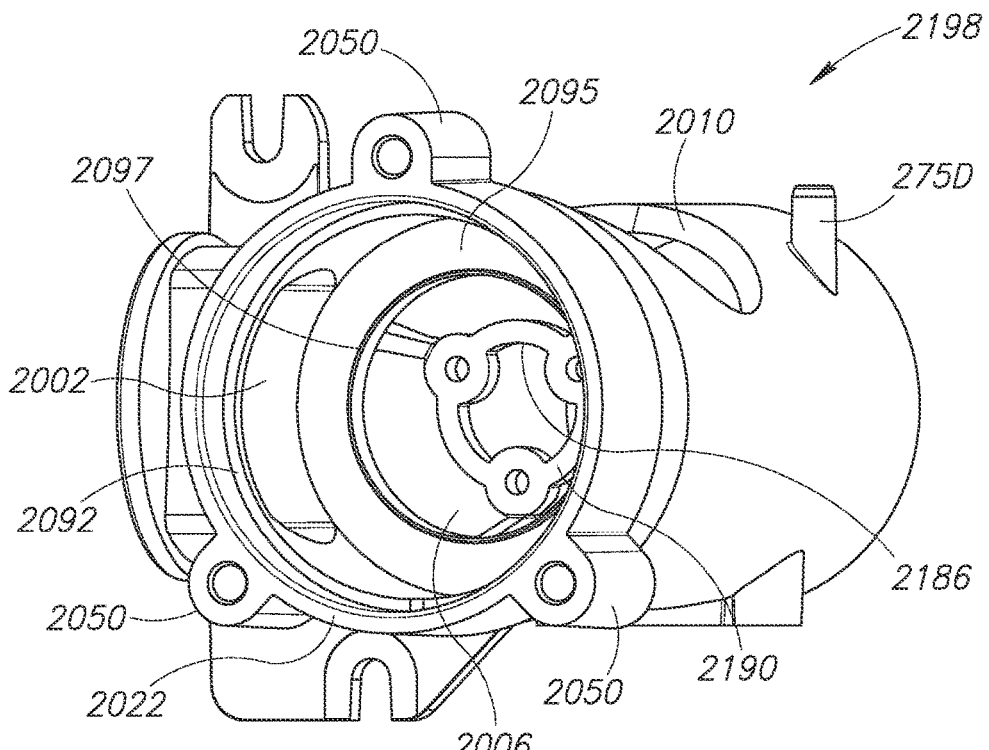
FIG. 37 is a perspective view of an intake body portion of a housing of the cough assist valve of FIG. 34A.

Referring to FIG. 37, the first open end 2022 of the housing 2020 (see FIGS. 34A and 34B) has a first inside threaded portion 2092 configured to mate with the outside threaded portion 2074 (see FIG. 35) of the first end cap assembly 2032 (see FIGS. 34A and 34B). The housing 2020 (see FIGS. 34A and 34B) has circumferentially extending, radially inwardly projecting, inner wall 2095 near but inward of the first open end 2022. The inner wall 2095 has a longitudinally outwardly extending annular projection 2097 substantially similar to the annular projection 2072 (see FIG. 35).

Referring to FIG. 35, the annular projection 2072 of the seat member 2046 of the first end cap assembly 2032 (see FIGS. 34A and 34B) functions as the first seat "511" (see FIGS. 34A and 34B). Referring to FIG. 37, the annular projection 2097 inside the first open end 2022 of the housing 2020 functions as the second seat "S21" (see FIGS. 34A and 34B). As may be seen in FIGS. 34A and 34B, the second seat "S21" is positioned longitudinally inward from the first cap assembly 2032. The first and second seats "S1" and "S2" extend toward and face one another.

Figure 38:
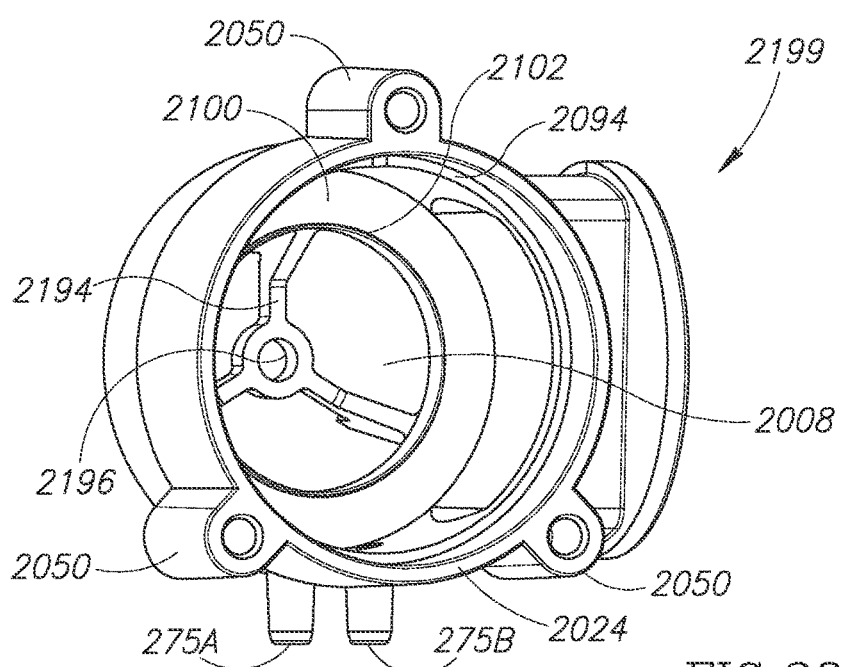
FIG. 38 is a perspective view of an exhaust body portion of a housing of the cough assist valve of FIG. 34A.

Referring to FIG. 38, the second open end 2024 of the housing 2020 (see FIGS. 34A and 34B) has a second inside threaded portion 2094 configured to mate with the outside threaded portion 2074 (see FIG. 35) of the second end cap assembly 2034 (see FIGS. 34A and 34B). The housing 2020 (see FIGS. 34A and 34B) has circumferentially extending, radially inwardly projecting, inner wall 2100 near but inward of the second open end 2024. The inner wall 2100 has a longitudinally outwardly extending annular projection 2102 substantially similar to the annular projection 2072 (see FIG. 35). Referring to FIGS. 34A and 34B, the annular projection 2102 (see FIG. 38) within the housing 2020 at the second open end 2024 functions as the third seat "S3'." The third seat "S3" is positioned longitudinally inward from the second end cap assembly 2034. The annular projection 2072 (see FIG. 35) of the seat member 2046 (see FIG. 35) of the second end cap assembly 2034 functions as a fourth seat "S4'." The third and fourth seats "S3" and "S4" extend toward and face one another.

Referring to FIGS. 34A and 34B, the cough assist valve 2000 includes first and second poppet valve assemblies 2112 and 2114 connected together by a shaft 2116 so as to move together in unison. The first poppet valve assembly 2112 is located and moves longitudinally between the first and second seats "Si" and "S2'," and the second poppet valve assembly 2114 is located and moves longitudinally between the third and fourth seats "S3" and "S4'."

Referring to FIGS. 34A and 34B, the shaft 2116 is configured to move longitudinally within the housing 2020 between a first position (see FIG. 34A) whereat the cough assist valve 2000 is in the first configuration and a second position (see FIG. 34B) whereat the cough assist valve 2000 is in the second configuration. As the shaft 2116 moves, the first poppet valve assembly 2112 moves between the first and second seats "S1" and "S2'," and the second poppet valve assembly 2114 moves between the third and fourth seats "S3'" and "S4'." When the shaft 2116 is in the first position (see FIG. 34A), the first poppet valve assembly 2112 is in sealing position against the first seat "Si'," and the second poppet valve assembly 2114 is in sealing position against the third seat "S3'." When the shaft 2116 is in the second position (see FIG. 34B), the first poppet valve assembly 2112 is in sealing position against the second seat "S2'," and the second poppet valve assembly 2114 is in sealing position against the fourth seat "S4'."

Figure 36:
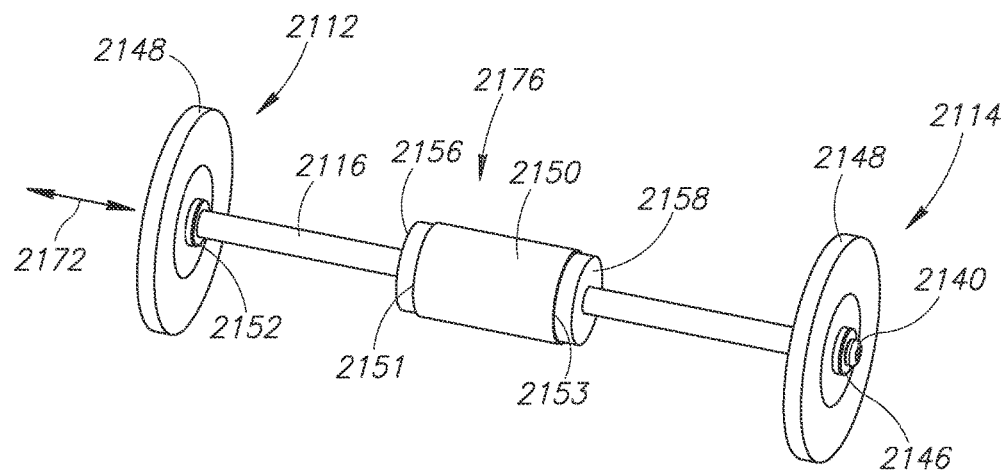
FIG. 36 is a perspective view of a subassembly of the cough assist valve of FIG. 34A including a movable magnet subassembly of an actuator, a shaft, and a pair of poppet valve assemblies.

Referring to FIG. 34A, a longitudinal channel 2136 extends inwardly into the shaft 2116 at each of its ends. Referring to FIG. 36, each of the channels 2136 (see FIG. 34A) is configured to receive a fastener 2140 (see FIG. 21). The first and second poppet valve assemblies 2112 and 2114 are substantially identical to one another. Referring to FIG. 36, each of the first and second poppet valve assemblies 2112 and 2114 includes the fastener 2140, an optional first washer 2146, a disk shaped poppet member 2148, and an optional second washer 2152. While not visible in FIG. 36, the first and second poppet valve assemblies 2112 and 2114 each include first and second sealing members 1146 and 1150, much as shown in FIG. 21, which serve to both seal the poppet valve assemblies to the end portion of the shaft 2116 and provide a flexible coupling between the shaft and the poppet valve members 2148 of the poppet valve assemblies. The fastener 2140 of the first poppet valve assembly 2112 fastens the other components (namely, the optional first washer 2146, the disk shaped poppet member 2148, and the optional second washer 2152) of the first poppet valve assembly 2112 to one of the ends of the shaft 2116. Similarly, the fastener 2140 of the second poppet valve assembly 2114 fastens the other components of the second poppet valve assembly 2114 to the other end of the shaft 2116.

Referring to FIGS. 34A and 34B, the cough assist valve 2000 includes an actuator 2170 configured to selectively move the shaft 2116 between the first position (see FIG. 34A) and the second position (see FIG. 34B) along longitudinal directions identified by double headed arrow 2172 (see FIG. 36). In the embodiment illustrated, the actuator 2170 is a linear actuator that includes a stationary coil subassembly 2174 and a movable magnet subassembly 2176. The shaft 2116 is coupled to the movable magnet subassembly 2176 and moves therewith as a unit.

Referring to FIGS. 34A and 34B, the stationary coil subassembly 2174 includes a coil 2177 housed inside an outer housing 2179. The outer housing 2179 is coupled to an actuator mounting portion 2190 of the housing 2020 (e.g., by one or more fasteners 2178). The outer housing 2179 is constructed from a magnetic material. The coil 2177 is connected by one or more wires 2062 to a printed circuit board ("PCB") 2064 mounted to the outside of the housing 2020. In the embodiment illustrated, the wire(s) 2062 provide power to the coil 2177. The outer housing 2179 and the housing 2020 each include one or more apertures through which the wire(s) 2062 may pass. The PCB 2064 is connected to the control system 220 (see FIG. 5E) by one or more wires (not shown). The actuator 2170 is configured to receive the control signal 1180 (see FIG. 5E) from the control system 220 (via the PCB 2064 and the wire(s) 2062) and move in accordance with one or more instructions in the control signal 1180. The PCB 2064 serves as a connector and passes the control signal 1180 to the coil 2177.

Referring to FIG. 36, the movable magnet subassembly 2176 has a main magnet 2150 with a first end 2151 opposite a second end 2153. A first latch magnet 2156 is mounted to the first end 2151 and a second latch magnet 2158 is mounted to the second end 2153. The first and second latch magnets 2156 and 2158 are each attracted to the magnetic outer housing 2179 (see FIGS. 34A and 34B). Referring to FIG. 34A, attraction between the first latch magnet 2156 (see FIG. 36) and the outer housing 2179 maintains the shaft 2116 in the first position after the shaft 2116 has been moved to the first position (by powering the coil 2177). Similarly, referring to FIG. 34B, attraction between the second latch magnet 2158 (see FIG. 36) and the outer housing 2179 maintains the shaft 2116 in the second position after the shaft 2116 has been moved to the second position (by powering the coil 2177). Thus, the shaft 2116 may remain in a desired position after the coil 2177 is powered down.

The control signal 1180 (see FIG. 5E) selectively powers the coil 2177 to move the movable magnet subassembly 2176 toward either the first end cap assembly 2032 or the second end cap assembly 2034. When the movable magnet subassembly 2176 moves toward the first end cap assembly 2032, the shaft 2116 moves therewith toward the first position. Referring to FIG. 34A, after the shaft 2116 has moved to the first position, the coil 2177 is powered down and attraction between the first latch magnet 2156 (see FIG. 36) and the outer housing 2179 maintains the shaft 2116 in the first position. On the other hand, when the movable magnet subassembly 2176 moves toward the second end cap assembly 2034, the shaft 2116 moves therewith toward the second position. Referring to FIG. 34B, after the shaft 2116 has moved to the second position, the coil 2177 is powered down and attraction between the second latch magnet 2158 (see FIG. 36) and the outer housing 2179 maintains the shaft 2116 in the second position. Thus, additional power is not needed to maintain the shaft 2116 in either the first position or the second position, which helps extend battery life in embodiments powered by one or more batteries.

Referring to FIG. 37, the actuator mounting portion 2190 is spaced inwardly from the first open end 2022 and optionally includes one or more through-holes configured to receive the fastener(s) 2178 (see FIGS. 34A and 34B). Referring to FIGS. 34A and 34B, the outer housing 2179 is coupled to an inwardly facing side of the actuator mounting portion 2190 by the fastener(s) 2178, which anchor the stationary coil subassembly 2174 to the housing 2020. Referring to FIGS. 34A and 34B, the actuator mounting portion 2190 has a through-hole 2186 (see FIG. 37) configured to allow the shaft 2116 to pass fully therethrough to position the first poppet valve assembly 2112 between the first and second seats "Si" and "S2'."

Referring to FIG. 38, the housing 2020 (see FIGS. 34A and 34B) includes an internal support 2194 spaced inwardly from the second open end 2024. In the embodiment illustrated, the internal support 2194 extends radially inward from the inner wall 2100. The internal support 2194 has a through-hole 2196 formed therein. Referring to FIGS. 34A and 34B, the through-hole 2196 (see FIG. 38) is configured to allow the shaft 2116 to pass therethrough to position the second poppet valve assembly 2114 between the third and fourth seats "S3" and "S4°." Referring to FIGS. 34A and 34B, the internal support 2194 abuts and helps position the outer housing 2179 of the actuator 2170. In the embodiment illustrated, the actuator mounting portion 2190 is coupled to an end of the outer housing 2179 near the second seat "S2" and the internal support 2194 abuts an opposite end of the outer housing 2179 near the third seat "S3'."

Referring to FIGS. 34A and 34B, the housing 2020 includes an intake body portion 2198 (also illustrated in FIG. 37) coupled to an exhaust body portion 2199 (also illustrated in FIG. 38). The valve-to-blower outlet 2002, the air intake 2006, the aperture 2010, the first open end 2022, and the actuator mounting portion 2190 are formed in the intake body portion 2198. The blower-to-valve inlet 2004, the exhaust outlet 2008, the second open end 2024, and the internal support 2194 are formed in the exhaust body portion 2199.

Referring to FIG. 34A, in the first configuration, the first poppet valve assembly 2112 is pressed against the second seat "S2'," and the second poppet valve assembly 2114 is pressed against the fourth seat "S4'." Referring to FIGS. 5A and 34A, in the first configuration, the first poppet valve assembly 2112 permits the flow of gas 252 from the accumulator 202 to flow through the air intake 2006, out the valve-to-blower outlet 2002, and into the blower 222. Further, the first poppet valve assembly 2112 blocks the gas 252 from directly entering the aperture 2010, thus sealing the aperture 2010 from both the air intake 2006 and the valve-to-blower outlet 2002. At the same time, the second poppet valve assembly 2114, which is pressed against the fourth seat "S4'," closes the exhaust outlet 2008 and permits the flow of the gas 252 to the main ventilator connection 104. In this configuration, the gas 252 from the accumulator 202 entering the air intake 2006 is directed to the blower 222 through the valve-to-blower outlet 2002. The gas 252 is then blown by the blower 222 into the blower-to-valve inlet 2004 and out through the aperture 2010 to the main ventilator connection 104.

Referring to FIG. 34B, in the second configuration, the first poppet valve assembly 2112 is pressed against the first seat "S1'," and the second poppet valve assembly 2114 is pressed against the third seat "S3'." Referring to FIGS. 5B and 34B, in the second configuration, the first poppet valve assembly 2112 permits the flow of exsufflation gases 253 from the main ventilator connection 104 to flow through the aperture 2010, out the valve-to-blower outlet 2002, and into the blower 222. Further the first poppet valve assembly 2112 blocks the flow of exsufflation gases to the air intake 2006, thus preventing gas 252 from the accumulator 202 from reaching the valve-to-blower outlet 2002. At the same time, the second poppet valve assembly 2114, which is pressed against the third seat "ST," opens the exhaust outlet 2008 and blocks the flow of the exsufflation gases 253 to the aperture 2010. In this configuration, the exsufflation gases 253 from the main ventilator connection 104 entering the aperture 2010 are directed to the blower 222 through the valve-to-blower outlet 2002. The exsufflation gases 253 are then blown by the blower 222 into the blower-to-valve inlet 2004 and out through the exhaust outlet 2008.

In the embodiment illustrated, the cough assist valve 2000 (see FIGS. 34A and 34B) includes the ports 275A, 275B and 275C (described below and illustrated in FIGS. 5A and 5B) formed in the housing 2020 (see FIGS. 34A and 34B). Referring to FIG. 38, the ports 275A and 275B may be formed in the exhaust body portion 2199. Referring to FIGS. 34A and 34B, the port 275C may be formed in the intake body portion 2198. However, this is not a requirement. Optionally, referring to FIG. 37, the cough assist valve 2000 includes the port 275D configured to be connected to a redundant airway pressure transducer (not shown).

The cough assist valve, whether it be the cough assist valve 204 or the cough assist valve 2000, is designed so that the pressures working against the first and second poppet valve assemblies 1112 and 1114 of cough assist valve 204 or the first and second poppet valve assemblies 2112 and 2114 of cough assist valve 2000, are balanced. This results in the actuator 1170 of cough assist valve 204 and the actuator 2170 of cough assist valve 2000 never having to work against the patient pressure. Since all of the seat areas of seats S1-S4 of cough assist valve 204 are the same, as are all of the seat areas of seats 51'-S4° of cough assist valve 2000, the patient pressure inside the cough assist valve coming through port 1010 (e.g., see FIGS. 5C and 5D) working against the poppet valve assemblies of the cough assist valve, creates forces that are equal and opposite. Thus, the force on the first and second poppet valve assemblies 1112 and 1114 of cough assist valve 204, when seated against the first and third seats 51 and S3, respectively, and when seated against the second and fourth seats S2 and S4, respectively, are substantially equal and in opposite directions. Similarly, the force on the first and second poppet valve assemblies 2112 and 2114 of cough assist valve 2000, when seated against the first and third seats 51' and S3', respectively, and when seated against the second and fourth seats S2' and S4', respectively, are substantially equal and in opposite directions. If the forces on the first and second poppet valve assemblies of the cough assist valve were not balanced, the actuator 1170/2170 of the cough assist valve would need to be much larger, and the power required to actuate the actuator would be greater.

As mentioned above, the ventilation assembly 190 may include either the cough assist valve 204 or the cough assist valve 2000. If the ventilation assembly 190 includes the cough assist valve 204, during normal ventilation, the cough assist valve 204 is in the first configuration shown in FIGS. 5A and 18A. On the other hand, if the ventilation assembly 190 includes the cough assist valve 2000 (see FIGS. 34A and 34B), during normal ventilation, the cough assist valve 2000 is in the first configuration shown in FIG. 34A.

Referring to FIG. 5A, at the beginning of the inspiratory phase of a breath (and the beginning of the insufflation phase of a cough), the air 114 may be drawn into the ventilator 100 (see FIGS. 1 and 4) through the patient air intake 116, which may be configured to filter dust and/or other types of particles from the air. At least a portion of the air 114 flows into the accumulator 202 where the air 114 may optionally be mixed with oxygen 250 received from the oxygen assembly 210, the low pressure oxygen 128 (received from the external low-pressure oxygen source 118 depicted in FIG. 1), combinations and/or sub-combinations thereof, and the like. As illustrated in FIG. 4, the high pressure oxygen 132 (received from the high-pressure external oxygen source 120 depicted in FIG. 1) flows into the oxygen assembly 210 and may be delivered to the accumulator 202 (see FIG. 5A) as the oxygen 250.

Referring to FIG. 5A, the accumulator 202 may also serve as a muffler for the patient air intake 116.

Figure 7A:
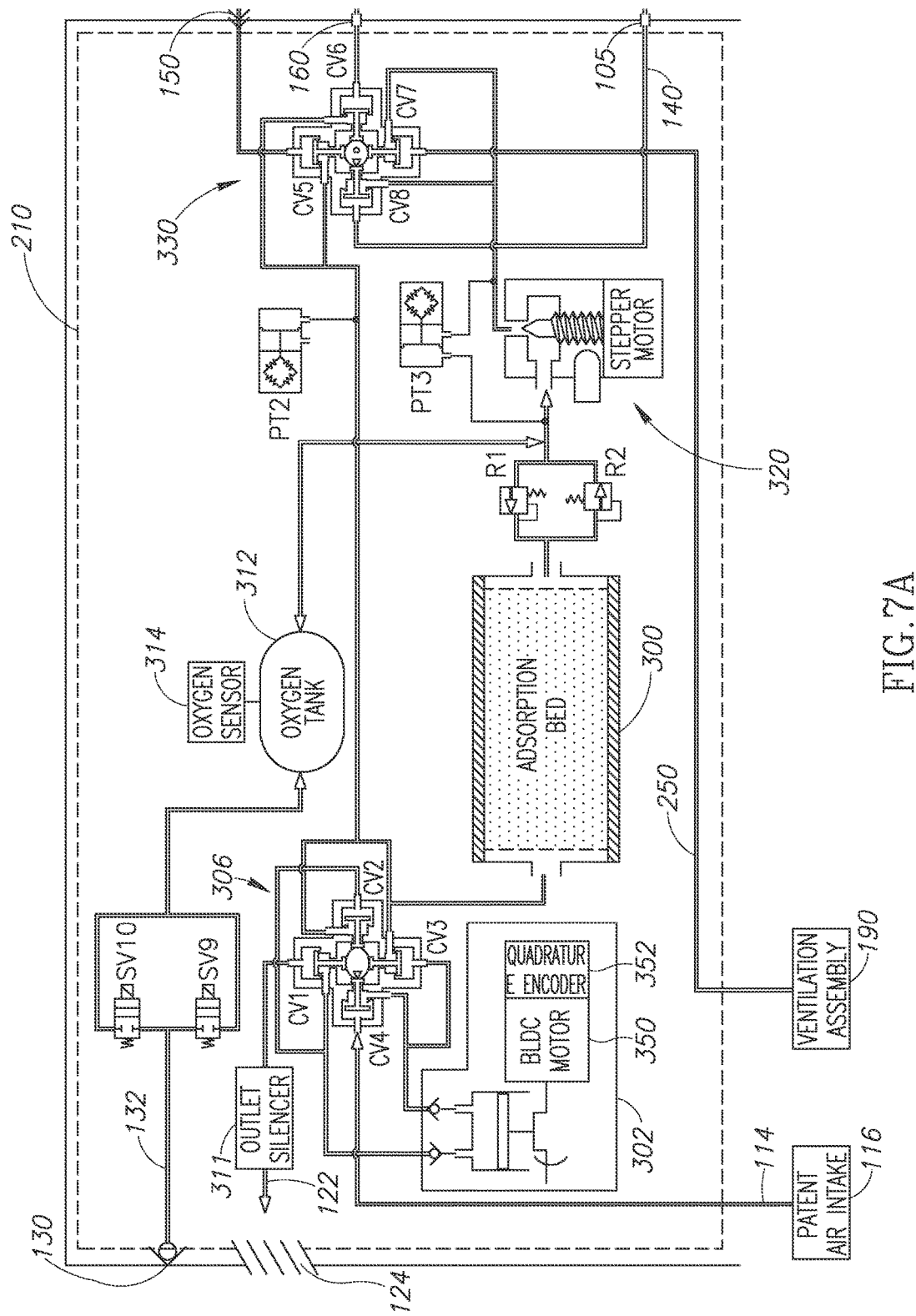
FIG. 7A is a schematic diagram illustrating some exemplary components of an oxygen assembly of the ventilator of FIG. 1.

The inlet silencer 229 helps muffle sounds created by the oxygen assembly 210 (e.g., by a compressor 302 illustrated in FIG. 7A).

The oxygen sensor 227 is connected to the accumulator 202 and measures an oxygen concentration value of the gas(es) inside the accumulator 202. This value approximates the oxygen concentration value of the gas 252 that exits the accumulator 202. Referring to FIG. 5E, the oxygen sensor 227 provides an oxygen concentration signal 276 encoding the oxygen concentration value to the control system 220. The control system 220 processes the oxygen concentration signal 276 to obtain a measure of how much oxygen is in the gas 252 (e.g., expressed as a percentage). Referring to FIG. 4, the output information 198 sent by the control system 220 to the user interface 200 may include the measure of how much oxygen is in the gas 252. The user interface 200 may display this measure to the user (e.g., the patient 102 depicted in FIG. 1).

Referring to FIG. 5A, optionally, the accumulator 202 includes or is connected to the low-pressure oxygen inlet 126. When the low-pressure oxygen 128 is supplied by the external low-pressure oxygen source 118 (see FIG. 1), the control system 220 may not control the resulting oxygen concentration flowing to the patient 102. In other words, the low-pressure oxygen 128 may simply flow into the accumulator 202, be mixed with the air 114, and pushed into the patient circuit 110 (see FIG. 1) by the blower 222. When this occurs, the ventilator 100 does not control the oxygen concentration delivered to the patient 102 in the inspiratory gases 108 (see FIG. 1), but does control the delivery of the inspiratory gases 108 during the inspiratory phase of each breath.

The gas 252 exiting the accumulator 202 includes the air 114 and optionally one or more of the oxygen 250 and the oxygen 128. The gas 252 may be conducted via the flow line 214 to the internal flow transducer 212. The gas 252 flows through the internal flow transducer 212, which measures a flow rate of the gas 252 and provides a flow signal 270 (see FIG. 5E) encoding the flow rate to the control system 220 (see FIG. 5E). The flow signal 270 may be implemented as an analog electric signal. Referring to FIG. 5E, the control system 220 uses the flow signal 270 to control the blower 222. By way of a non-limiting example and as shown in FIG. 5A, the internal flow transducer 212 may be implemented using a flow transducer having a fixed orifice differential pressure configuration.

The internal flow transducer 212 may be used to detect when the patient 102 (see FIG. 1) has initiated a breath. In particular, the internal flow transducer 212 may be used in this manner when the patient circuit 110 (see FIG. 1) is implemented as a passive patient circuit (e.g., the passive patient circuit 170, the passive patient circuit 440, and the like). The flow of gases through the flow line 214 is not determined entirely by the blower 222. Instead, the patient's breathing efforts may cause a change in the flow rate through the flow line 214. Thus, the control system 220 may identify that the patient 102 has initiated a breath by identifying a change in the flow rate (encoded in the flow signal 270) through the flow line 214.

The internal flow transducer 212 may include or be connected to an auto zero solenoid valve SV5 configured to be selectively activated and deactivated by a control signal 285 (see FIG. 5E) sent by the control system 220. The internal flow transducer 212 may drift over time, causing flow rate measuring errors. To compensate for this error, occasionally (e.g., periodically) the control system 220 energizes (or activates) the auto zero solenoid valve SV5 (using the control signal 285) and determines an offset value for the internal flow transducer 212. After determining the offset value, the control system 220 uses the offset value to compensate future readings (based on the flow signal 270) accordingly.

Referring to FIG. 5A, after the internal flow transducer 212, the gas 252 is conducted into the blower 222 via the flow line 214 and the cough assist valve 204 (or the cough assist valve 2000). Referring to FIG. 5E, the blower 222 may be implemented as a radial blower driven by a motor 272. By way of a non-limiting example, the motor 272 may be implemented as a brushless direct current motor. By way of additional non-limiting examples, the blower 222 may be implemented as a compressor, a pump, and the like. The motor 272 has an operating speed that is controlled by the control system 220. By way of a non-limiting example, the control system 220 may continuously control the operating speed of the motor 272.

Referring to FIG. 5A, the gas 252 flows out of the blower 222 and into the cough assist valve 204 (or the cough assist valve 2000). The ports 275A-275C are each configured to provide access to the flow of the gas 252 in the cough assist valve 204 (or the cough assist valve 2000). The flow line 273 conducts the flow of the gas 252 from the cough assist valve 204 (or the cough assist valve 2000) to the internal bacteria filter 230.

Referring to FIG. 5A, the airway pressure transducer 224 measures airway pressure of the gas 252 flowing out of the blower 222 and toward the main ventilator connection 104. In the embodiment illustrated, the airway pressure transducer 224 is connected to the port 275C. Referring to FIG. 5E, the airway pressure transducer 224 provides an electrical pressure signal 274 encoding these pressure values to the control system 220. The electrical pressure signal 274 is used to control patient pressure during the inspiratory and exhalation phases. The electrical pressure signal 274 is also used by the monitoring and alarm systems 221 (see FIG. 4). Optionally, the ventilator 100 (see FIGS. 1 and 4) may include one or more redundant airway pressure transducers (not shown) like the airway pressure transducer 224 to provide a failsafe backup for the airway pressure transducer 224. In embodiments including a redundant airway pressure transducer (not shown), the redundant airway pressure transducer may be connected to the port 275D (see FIG. 17B).

The airway pressure transducer 224 may be used by the control system 220 to detect a pressure change and in response to detecting a pressure change, instruct the blower 222 to increase or decrease its speed to adjust the pressure inside the flow line 273. Thus, the control system 220 may use the electrical pressure signal 274 to deliver pressure ventilation and/or help ensure the pressure inside the flow line 273 does not exceed an user supplied peak inspiratory pressure value (e.g., entered via the pressure control input 237 depicted in FIG. 6).

Referring to FIG. 5A, the airway flow transducer module 225 includes a differential pressure transducer PT4, auto zero solenoid valves SV1 and SV2, and purge solenoid valves SV3 and SV4. Referring to FIG. 5E, the control system 220 may selectively activate or deactivate the solenoid valves SV1-SV4 using control signals 281-284, respectively.

Referring to FIG. 1, as mentioned above, the patient circuit 110 may include the one or more optional ports 111. FIG. 5A illustrates an implementation of the ventilation assembly 190 configured for use with the patient circuit 110 implemented as an active patient circuit (e.g., the active patient circuit 600 depicted in FIG. 3A, and the like). In alternate embodiments configured for use with the patient circuit 110 implemented as a passive patient circuit (e.g., the passive patient circuit 170 depicted in FIG. 2A, the passive patient circuit 440 depicted in FIG. 2B, and the like), the ports 275A and 275B, the airway flow transducer module 225, and the exhalation control assembly 226 may be omitted from the ventilation assembly 190.

The airway flow transducer module 225, and the exhalation control assembly 226 illustrated in FIG. 5A are configured for use with an active patient circuit (e.g., the active patient circuit 600 depicted in FIG. 3A) that includes the airway flow transducer 648 (see FIG. 3G). Referring to FIG. 5A, the first and second ports 111A and 111B (see FIG. 3C) send first and second pressure signals 109A and 109B, respectively, (e.g., via separate lines or channels) to the differential pressure transducer PT4. The differential pressure transducer PT4 has input ports PA and PB configured to receive the first and second pressure signals 109A and 109B, respectively. The differential pressure transducer PT4 determines a differential pressure based on the first and second pressure signals 109A and 109B, converts the differential pressure to a signal 277 (see FIG. 5E), and (as illustrated in FIG. 5E) transmits the signal 277 to the control system 220 for further processing thereby. By way of a non-limiting example, the signal 277 may be an analog signal.

The signal 277 may be used to detect when the patient 102 (see FIG. 1) has initiated a breath. The flow of gases through the active patient circuit 600 (see FIG. 3A) is not determined entirely by the blower 222. Instead, the patient's breathing efforts may cause a change in the flow rate through the active patient circuit 600. Thus, the control system 220 may identify that the patient 102 has initiated a breath by identifying a change in the flow rate (encoded in the signal 277) through the active patient circuit 600.

The auto zero solenoid valves SV1 and SV2 are connected to the input ports PA and PB, respectively, of the differential pressure transducer PT4. Further, each of the auto zero solenoid valves SV1 and SV2 is connected to ambient pressure. The differential pressure transducer PT4 can drift over time causing flow measuring errors. To compensate for this error, occasionally (e.g., periodically) the control system 220 energizes (or activates) the auto zero solenoid valves SV1 and SV2 (using the control signals 281 and 282, respectively) and determines an offset value for the differential pressure transducer PT4. Then, the control system 220 deactivates the auto zero solenoid valves SV1 and SV2 (using the control signals 281 and 282, respectively). After determining the offset value, the control system 220 uses the offset value to compensate future readings (based on the signal 277) accordingly.

The purge solenoid valves SV3 and SV4 are connected to the port 275A. Referring to FIG. 5E, the control system 220 occasionally (e.g., periodically) energizes (or activates) the purge solenoid valves SV3 and SV4 (using the control signals 283 and 284, respectively), which allows dry gas from the cough assist valve 204 illustrated in FIG. 5A (or the cough assist valve 2000 illustrated in FIG. 34A) to flow through the lines, ports, and/or channels (e.g., the optional multi-lumen tube connection 103, the channels 626A and 626B, the channels 632A and 632B, the ports 111A and 111B, and the like) conducting the pressure signals 109A and 109B to purge those structures of any moisture that may have condensed from the humid patient breathing gas.

Referring to FIG. 5E, the exhalation control assembly 226 includes an accumulator A2, a pressure transducer PT8, and solenoid valves SV6-SV8. The accumulator A2 has three ports 267-269 and an internal pressure (referred as the "pilot pressure"). The pressure transducer PT8 is connected to the accumulator A2, measures the internal pressure inside the accumulator A2, and transmits this value to the control system 220 in an electrical pressure signal 271 (see FIG. 5E).

Referring to FIG. 5E, the solenoid valves SV6-SV8 are configured to be selectively activated and deactivated by control signals 286-288, respectively, sent by the control system 220 to the solenoid valves SV6-SV8, respectively. Turning to FIG. 5A, the solenoid valve SV6 is connected to the first port 267 of the accumulator A2, the port 275B, and the pilot port 111C (see FIG. 3C) of the active patient circuit 600 (see FIG. 3A). The solenoid valve SV7 is connected to the second port 268 of the accumulator A2 and the port 275B. The solenoid valve SV8 is connected between the third port 269 of the accumulator A2 and the outlet port 166.

The exhalation control assembly 226 provides the pilot pressure (from the accumulator A2) to the pilot port 111C (see FIG. 3C) of the active patient circuit 600 (see FIG. 3A), which as described above, controls the active exhalation valve assembly 604. At the start of the inspiratory phase of a breath, the control system 220 activates the solenoid valve SV6 (using the control signal 286), which connects the pressure of the gases 252 (via the port 275B) to the pilot port 111C. This closes the active exhalation valve assembly 604. At the end of the inspiratory phase of a breath, the control system 220 deactivates the solenoid valve SV6 (using the control signal 286), which connects the internal pressure of the accumulator A2 (or the pilot pressure) to the active exhalation valve assembly 604, which opens the active exhalation valve assembly 604.

Similarly, at the start of the insufflation phase of a cough, the control system 220 activates the solenoid valve SV6 (using the control signal 286), which connects the pressure of the gases 252 (via the port 275B) to the pilot port 111C. This closes the active exhalation valve assembly 604. At the end of the insufflation phase, the control system 220 deactivates the solenoid valve SV6 (using the control signal 286), which connects the internal pressure of the accumulator A2 (or the pilot pressure) to the active exhalation valve assembly 604. As discussed below, instead of opening the active exhalation valve assembly 604, this maintains the active exhalation valve assembly 604 in the closed configuration. It is noted that during the beginning of the exsufflation phase, the double bellows member 644 may move into the open position as a result of the patient pressure applied to the double bellows member being higher than ambient, but will automatically close when the pressure provided by the patient 102 drops below ambient.

The control system 220 uses the solenoid valves SV7 and SV8 to control the pilot pressure inside the accumulator A2 using feedback provided by the pressure transducer PT8 (via the electrical pressure signal 271 depicted in FIG. 5E) to set a pilot pressure for the exhalation phase of a breath that will achieve the desired PEEP. For example, the control system 220 may lower the pilot pressure inside the accumulator A2 by activating the solenoid valve SV8 (using the control signal 288) to vent some of the gases inside the accumulator A2 via the outlet port 166 as the exhaust 167. Conversely, the control system 220 may increase the pilot pressure by activating the solenoid valve SV7 (using the control signal 287) to add some of the gases 252 (obtained via the port 275B) to the inside of the accumulator A2.

Referring to FIG. 5E, the control system 220 uses the electrical pressure signal 274 (received from the airway pressure transducer 224) to help control the blower 222. The control system 220 sends a control signal 278 to the motor 272, which directs the blower 222 to provide a desired flow rate and/or a desired amount of pressure to the patient 102. As mentioned above, the flow signal 270 is used to help control the flow rate of the gas 252 during the inspiratory and exhalation phases of a breath. Similarly, the electrical pressure signal 274 is used to control the patient pressure during the inspiratory and exhalation phases of a breath. The flow signal 270 may be used to help control the flow rate of the gas 252 during the insufflation phase and/or the flow rate of the exsufflation gases 253 during the exsufflation phase of a cough. Similarly, the electrical pressure signal 274 is used to control the patient pressure during the insufflation phase and/or the exsufflation phase of a cough.

As explained above, the ventilator 100 adjusts the pressure inside the patient circuit 110 (e.g., the passive patient circuit 440 illustrated in FIG. 2B) to achieve the preset inspiratory pressure during the inspiratory phase, the baseline pressure or PEEP during the exhalation phase, and PEEP during the pause between the inspiratory and exhalation phases. These adjustments (and adjustments performed during a cough assist maneuver) are made by the control system 220, which monitors the electrical pressure signal 274, and uses the control signal 278 to increase or decrease the speed of the motor 272 to achieve the desired pressure inside the patient circuit 110.

The ambient pressure transducer 228 measures an atmospheric pressure value. The ambient pressure transducer 228 provides an ambient electrical pressure signal 280 encoding the atmospheric pressure value to the control system 220. The control system 220 uses the ambient electrical pressure signal 280 to correct the flow rate values (received via the flow signal 270), and/or the exhaled tidal volume value (calculated by the control system 220) to desired standard conditions.

Referring to FIG. 5A, as mentioned above, the flow line 273 conducts the flow of the gas 252 from the cough assist valve 204 (or the cough assist valve 2000) to the internal bacteria filter 230. After the gas 252 passes through the internal bacteria filter 230, they exit the internal bacteria filter 230 as the gases 112 and enter the patient circuit 110 (see FIG. 1) via the main ventilator connection 104. The internal bacteria filter 230 helps prevent bacteria in the patient circuit 110 from contaminating the ventilator 100.

User Interface

Figure 6:
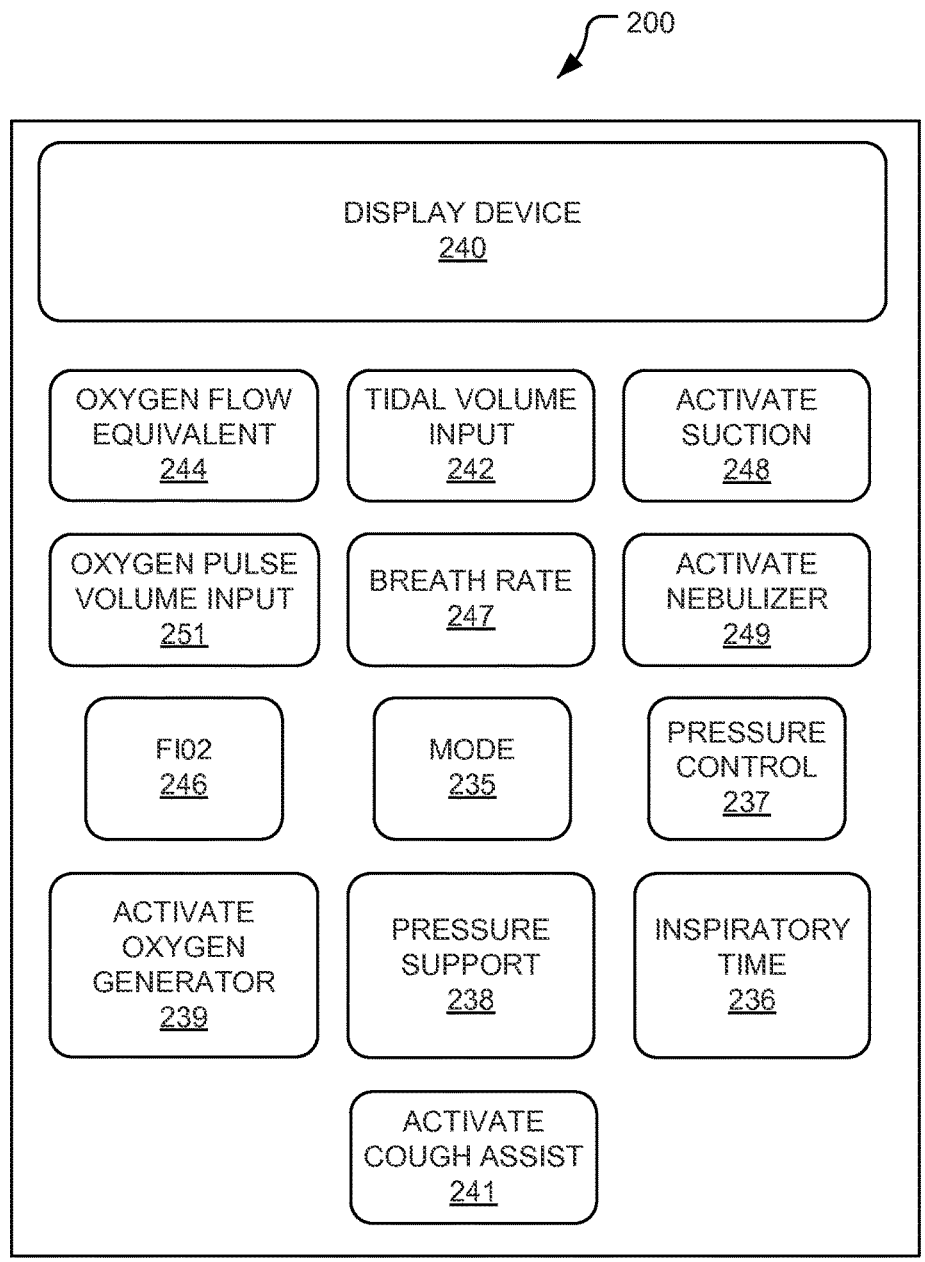
FIG. 6 is block diagram illustrating some exemplary components of a user interface of the ventilator of FIG. 1.

FIG. 6 is a block diagram illustrating some exemplary components of the user interface 200. As mentioned above, FIG. 4 illustrates the output information 198 sent by the control system 220 to exemplary components of the user interface 200, and the input information 196 received by the control system 220 from exemplary components of the user interface 200.

Referring to FIG. 6, the user interface 200 is configured to receive operating parameter values from a user (e.g., a clinician) and to display information to the user. For example, the user interface 200 may include a display device 240 (e.g., a liquid crystal display), a mode input 235, an inspiratory time input 236, a pressure control input 237, a pressure support input 238, an activate oxygen generator input 239 for activating oxygen generation (described below), a tidal volume input 242, an oxygen flow equivalent 244, a fraction of inspired oxygen ("F1O2") input 246, a breath rate input 247, an oxygen pulse volume input 251, an activate cough assist input 241, an activate suction input 248 for activing the suction assembly 152 (see FIG. 1), and an activate nebulizer input 249 for activing the nebulizer assembly 162 (see FIG. 1).

The beginning of the inspiratory phase is referred to as "initiation." The mode input 235 is configured to receive an indication as to whether the ventilator 100 determines when each breath is initiated or the patient 102 determines when each breath is initiated. The breath rate input 247 is configured to receive a rate (e.g., breaths per minute) at which breaths are to be delivered. If the user has indicated (using the mode input 235) that the ventilator 100 determines when each breath is initiated, the ventilator 100 will deliver breaths in accordance with the rate received by the breath rate input 247 (e.g., at regularly timed intervals). On the other hand, If the user has indicated (using the mode input 235) that the patient 102 initiates each breath, the ventilator 100 will automatically deliver breaths as needed to ensure the patient 102 receives breaths at least as frequently as indicated by the rate received by the breath rate input 247.

The ventilator 100 may identify the end of the inspiratory phase using time or a rate of flow of the gases 112 to the patient 102. In the latter case, the patient 102 determines when the inspiratory phase ends. The inspiratory time input 236 is configured to receive a value indicating a duration T, from the initiation of each breath to the end of the inspiratory phase. The ventilator 100 may use the value (indicating the duration T,) to identify the end of the inspiratory phase. The pressure support input 238 receives an indication that the user would like to use the rate of flow of the gases 112 to the patient 102 (instead of the value indicating the duration T,) to end the inspiratory phase. For example, the ventilator 100 may end the inspiratory phase of a breath when the flow rate of the gases 112 is only about 25% of a peak flow rate that occurred during the breath.

The ventilator 100 is configured to deliver the gases 112 alone, or a combination of the gases 112 and the pulses of oxygen 140. As mentioned above, the ventilator 100 may be configured to provide both traditional volume controlled ventilation and pressure controlled ventilation. To use pressure control, the user may use the pressure control input 237 to enter a peak inspiratory pressure value. The ventilator 100 uses the peak inspiratory pressure value to configure the gases 112 alone, or the combination of the gases 112 and the pulses of oxygen 140 such that the pressure during the inspiratory phases is at most the peak inspiratory pressure value.

The F1O2 input 246 is configured to receive an oxygen concentration value. The ventilator 100 uses the oxygen concentration value to configure the gases 112 to have an oxygen concentration equal to or approximating the oxygen concentration value.

The oxygen pulse volume input 251 is configured to receive an oxygen pulse volume value (e.g., expressed in milliliters, or a value within a predefined range, such as from 1 to 10, and the like). The ventilator 100 uses the oxygen pulse volume value to configure each of the pulses of oxygen 140 to have a volume equal to or approximating the oxygen pulse volume value.

Figure 15A:
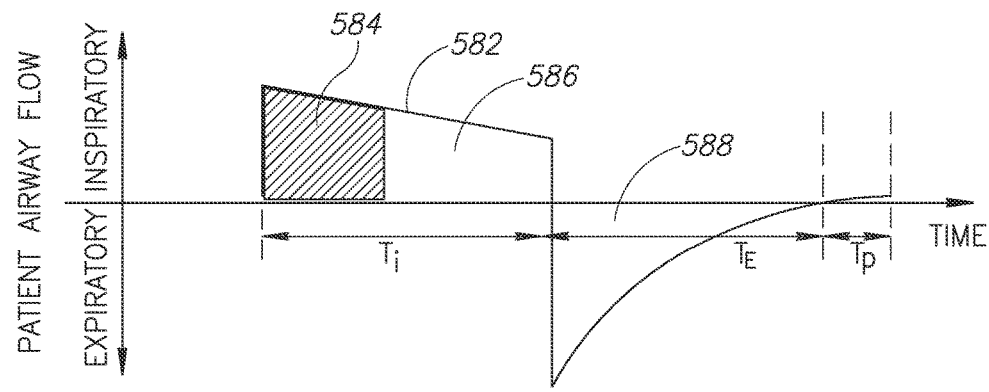
FIG. 15A is a graph showing patient airway flow using the ventilator of FIG. 1 during both inspiratory and expiratory phases.

The tidal volume input 242 is configured to receive a desired total tidal volume value. Referring to FIG. 15A, the ventilator 100 uses the desired total tidal volume value to output a volume of the gases 112 (illustrated by area 586 and described below) and one of the pulses of oxygen 140 (illustrated by area 584 and described below) during each breath. For each breath delivered, the total tidal volume delivered is the combined volumes of gases 112 and the pulse of oxygen 140 delivered during the breath.

The oxygen flow equivalent 244 is configured to receive a desired oxygen delivery rate (expressed in liters per minute) that identifies a rate at which a hypothetical continuous oxygen flow may be bled into a conventional ventilator or the patient circuit 110 (see FIG. 1) from an external source (e.g., a standalone oxygen concentrator). The ventilator 100 uses this value to configure each of the pulses of oxygen 140 (see FIG. 1) to deliver an amount of oxygen that would provide equivalent oxygenation to the patient 102 (see FIG. 1) as the hypothetical continuous oxygen flow.

The activate cough assist input 241 indicates that the user would like to perform a cough assist maneuver (discussed below).

Oxygen Assembly

Figure 7B:
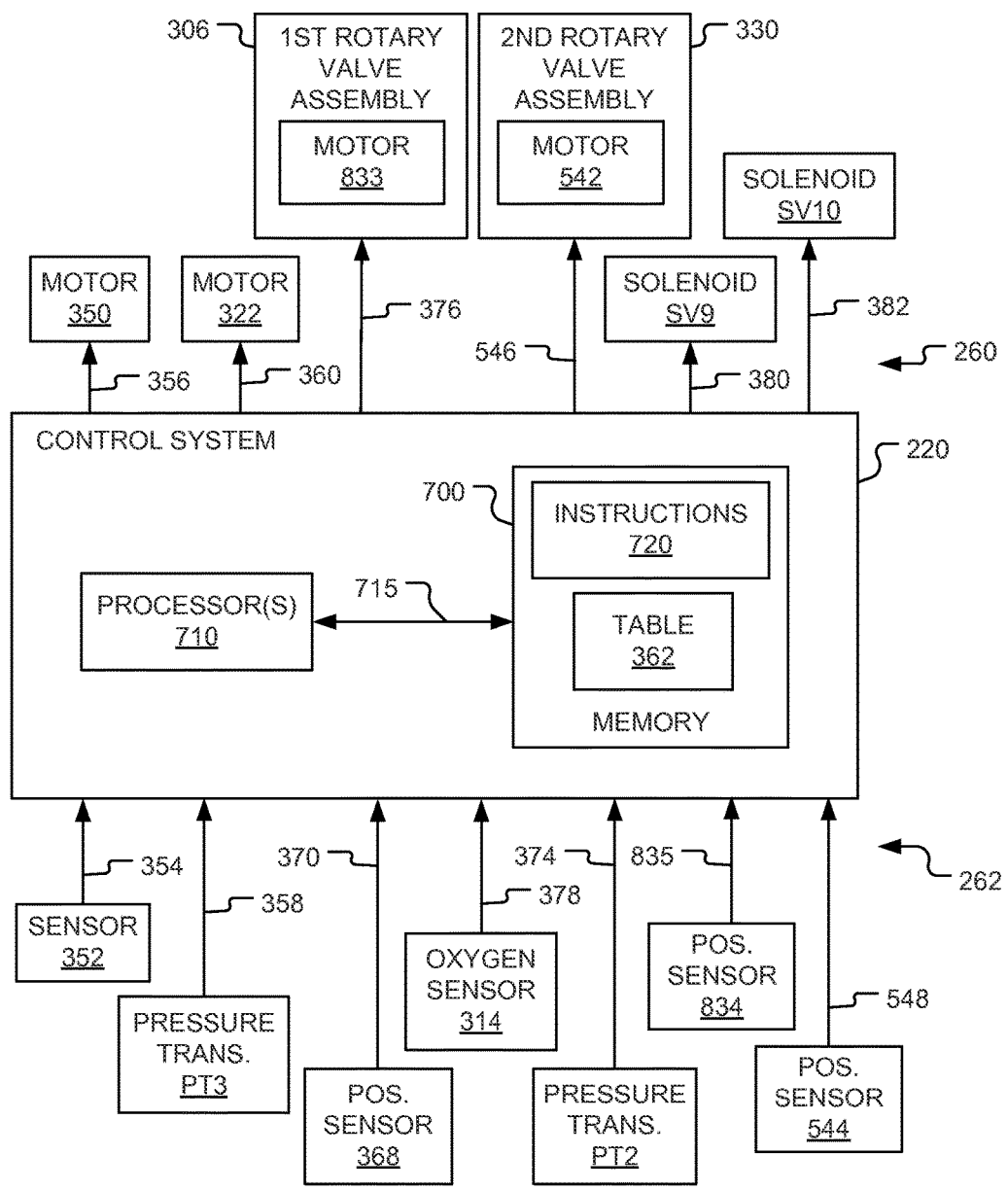
FIG. 7B is block diagram illustrating exemplary control signals sent by the control system to exemplary components of the oxygen assembly, and the data signals received by the control system from exemplary components of the oxygen assembly.

FIG. 7A is a schematic diagram illustrating some exemplary components of the oxygen assembly 210. FIG. 7B illustrates the control signals 260 sent by the control system 220 to exemplary components of the oxygen assembly 210, and the data signals 262 received by the control system 220 from exemplary components of the oxygen assembly 210.

Referring to FIG. 7A, the oxygen assembly 210 is configured to receive the high-pressure oxygen 132 and/or generate oxygen 346 (see FIG. 8B) and provide the oxygen 250 to the accumulator 202 (see FIG. 5A) of the ventilation assembly 190 and/or provide the pulses of oxygen 140 to the patient oxygen outlet 105. The oxygen assembly 210 may be configured to provide up to about two liters per minute ("LPM") of approximately 90% pure oxygen. In the embodiment illustrated, the oxygen assembly 210 includes an adsorption bed 300, the compressor 302, a first rotary valve assembly 306, two pressure transducers PT2 and PT3, two pressure regulators R1 and R2, an outlet silencer 311, optional solenoid valves SV9 and SV10, an oxygen tank 312, an oxygen sensor 314, a metering valve 320, and an optional second rotary valve assembly 330. Together the compressor 302, the first rotary valve assembly 306, the adsorption bed 300, and the pressure regulators R1 and R2 may be characterized as being an oxygen generator or oxygen concentrator. The oxygen generator illustrated in the figures and described below implements a vacuum pressure swing adsorption ("VPSA") process. In alternate embodiments, the ventilator 100 may include an oxygen generator that implements at least one of a polymer membrane separation process, an ion transport separation process, a cryogenic process, and the like. Further, the VPSA process described below is a subset of Pressure Swing Adsorption (PSA) and the oxygen generator may be configured to implement a PSA process other than the VPSA process described below.

The adsorption bed 300 is configured to harvest oxygen from the air 114 received via the patient air intake 116. As will be explained below, the adsorption bed 300 may be configured to at least partially implement a VPSA process that includes a cycle with four phases (described below). The cycle alternately generates the oxygen 346 (see FIG. 8B) and the nitrogen-rich gas 122. As the ventilator 100 operates, the cycle is repeated until enough oxygen has been generated to fill the oxygen tank 312. When the oxygen tank 312 is full, the cycles are halted or slowed until a sufficient amount of the oxygen in the oxygen tank 312 has been removed. Then, the cycles are resumed again or sped up as appropriate. The nitrogen-rich gas 122 generated by each cycle is exhausted to the outside environment via the outlet vent 124.

FIGS. 8A-8D are block diagrams illustrating some exemplary components of the adsorption bed 300. Referring to FIGS. 8A-8D, in the embodiment illustrated, the adsorption bed 300 includes at least one housing 340 having a first end 341 opposite a second end 343. The housing 340 contains a bed of nitrogen adsorbent material 344 (such as zeolite) between its first and second ends 341 and 343. The bed of nitrogen adsorbent material 344 preferentially absorbs nitrogen. For ease of illustration, the adsorption bed 300 will be described as including a single housing containing a single bed of nitrogen adsorbent material. In alternate embodiments, the adsorption bed 300 may include two or more beds like the bed of nitrogen adsorbent material 344 that are each housed inside separate housings like the housing 340.

Figure 8A:
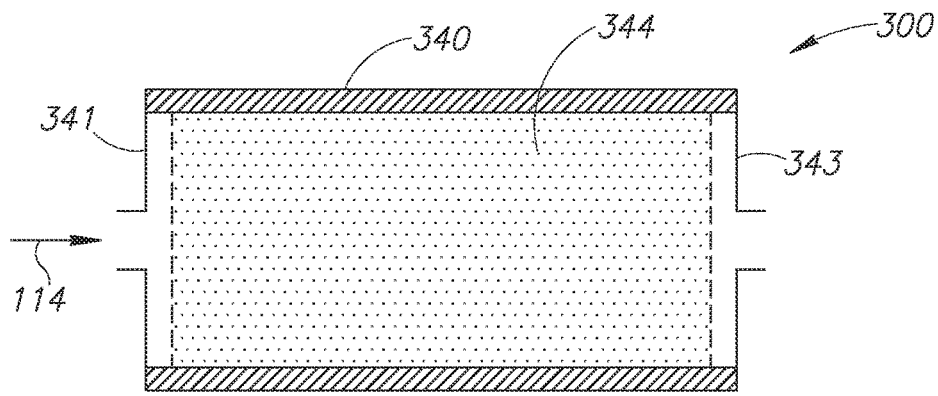
FIG. 8A is a block diagram illustrating an adsorption bed of the oxygen assembly during a first phase of a vacuum pressure swing adsorption ("VPSA") process.

As mentioned above, the VPSA process includes a cycle with four phases. FIG. 8A illustrates the adsorption bed 300 during a first phase. Referring to FIG. 8A, during the first phase, the air 114 is pumped into the housing 340 by the compressor 302 (see FIG. 7A). When the housing 340 is pressurized with the air 114 (by the compressor 302), nitrogen in the air is preferentially adsorbed by the bed of nitrogen adsorbent material 344, which leaves behind unadsorbed oxygen. The bed of nitrogen adsorbent material 344 may include interstitial spaces in which the unadsorbed oxygen is held or trapped.

Figure 8B:
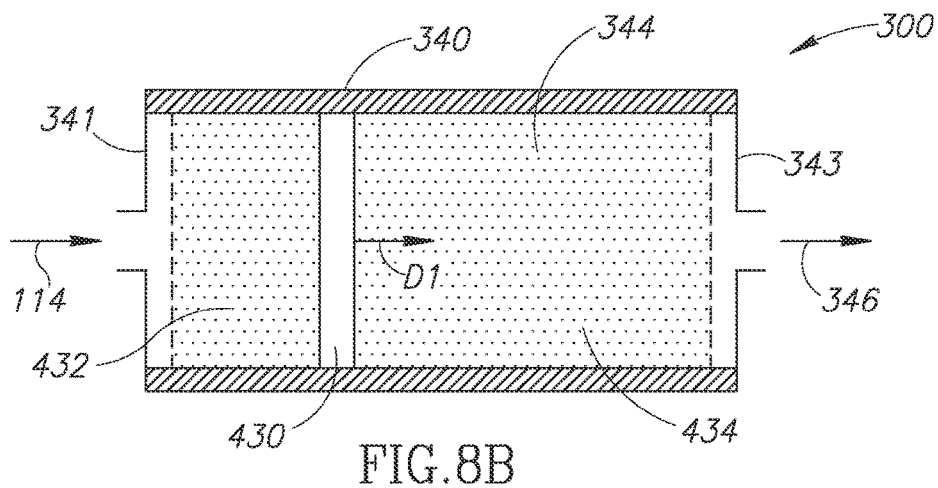
FIG. 8B is a block diagram illustrating the adsorption bed of the oxygen assembly during a second phase of the VPSA process.

FIG. 8B illustrates the adsorption bed 300 during a second phase of a cycle of the VPSA process. During the second phase, the oxygen 346 is pumped from the housing 340. The oxygen 346 flows from the interstitial spaces and into the oxygen tank 312 (see FIG. 7A).

Figure 8C:
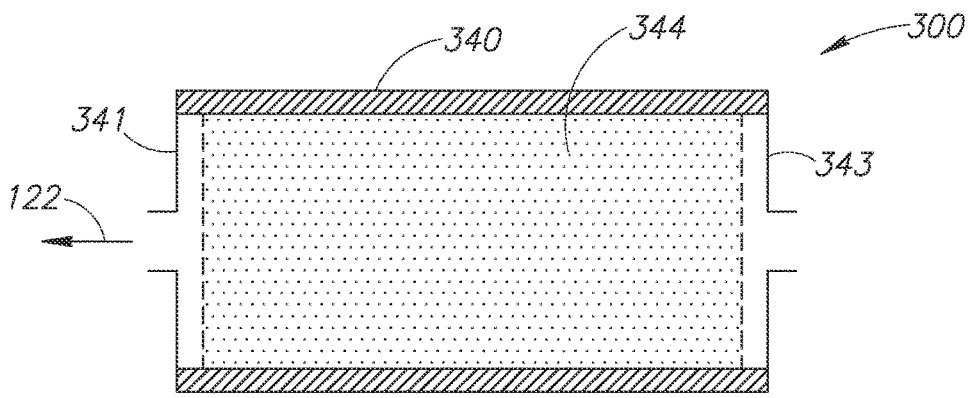
FIG. 8O is a block diagram illustrating the adsorption bed of the oxygen assembly during a third phase of the VPSA process.
FIG. 8D is a block diagram illustrating the adsorption bed of the oxygen assembly during a fourth phase of the VPSA process.

FIG. 8C illustrates the adsorption bed 300 during a third phase of a cycle of the VPSA process. During the third phase, the nitrogen-rich gas 122 is pulled from the bed of nitrogen adsorbent material 344 in the housing 340 (by the compressor 302 illustrated in FIG. 7A) and vented to the outside environment via the outlet vent 124 (see FIG. 7A).

Figure 8D:
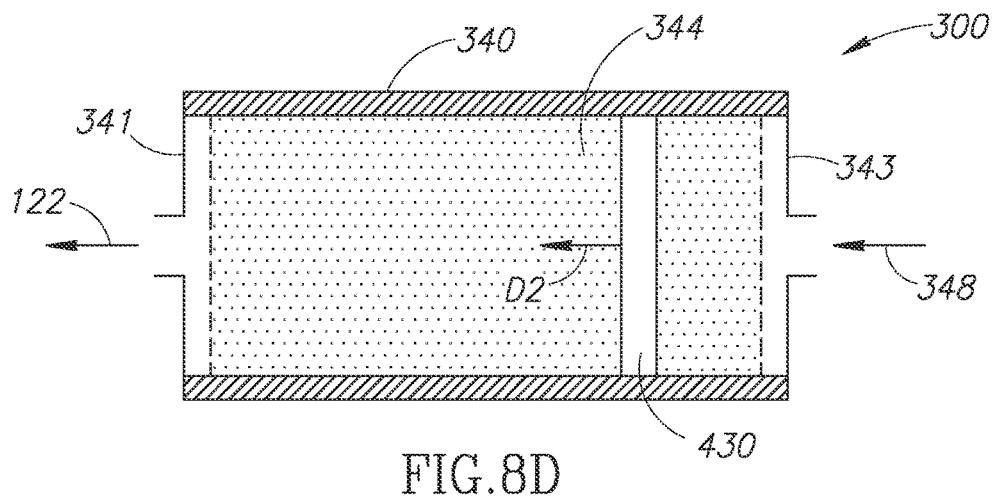

FIG. 8D illustrates the adsorption bed 300 during a fourth phase of a cycle of the VPSA process. During the fourth phase, a flow of "purge" oxygen 348 (e.g., from the oxygen tank 312 illustrated in FIG. 7A) may be used to help draw out the nitrogen-rich gas 122 and regenerate the bed of nitrogen adsorbent material 344.

Returning to FIG. 7A, the oxygen 346 (see FIG. 8B) removed from the adsorption bed 300 flows through the pressure regulator R2, and into the oxygen tank 312 where the oxygen 346 is stored. While this is occurring, the metering valve 320 may be closed, and the pressure regulator R1 may be closed to prevent flow back into the adsorption bed 300. Alternatively, the metering valve 320 may be at least partially open to allow some of the oxygen 346 to flow to the optional second rotary valve assembly 330.

During each cycle, the compressor 302 is configured to alternately push the air 114 into the adsorption bed 300 (through the first rotary valve assembly 306) and pull the nitrogen-rich gas 122 out of the adsorption bed 300 (through the first rotary valve assembly 306). The compressor 302 may be driven by a motor 350 and may include a sensor 352 (e.g., an encoder) configured to provide a signal 354 encoding the direction and speed of rotation of the motor 350 to the control system 220. Referring to FIG. 7B, the motor 350 is configured to receive instructions from the control system 220 encoded in a control signal 356. The instructions in the control signal 356 instruct the motor 350 to switch on or off and/or indicate in which direction the motor 350 is to rotate when switched on. Further, the control signal 356 may instruct the motor 350 at which speed to run. Referring to FIG. 7A, when the motor 350 runs in a first direction, the compressor 302 pushes air into the adsorption bed 300. On the other hand, when the motor 350 runs in a second direction, the compressor 302 pulls the nitrogen-rich gas 122 (see FIGS. 8C and 8D) from the adsorption bed 300. By way of a non-limiting example, the motor 350 may be implemented as a brushless direct current motor.

Figure 9:
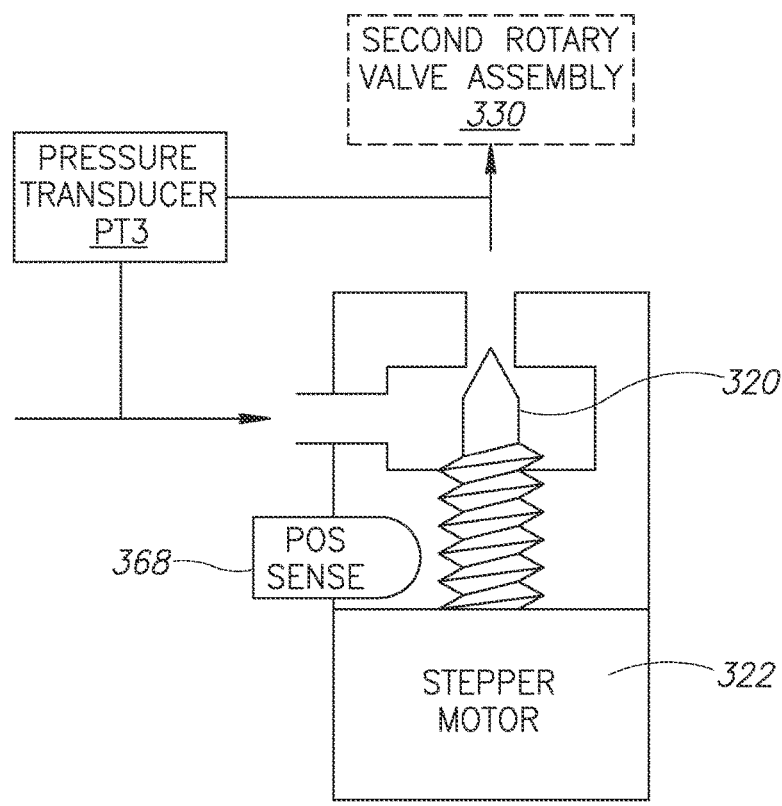
FIG. 9 is an illustration of a metering valve of the oxygen assembly.

FIG. 9 is an illustration of the metering valve 320. Referring to FIG. 9, the pressure transducer PT3 is connected across the metering valve 320. Thus, the pressure transducer PT3 may determine a pressure differential value across the metering valve 320. Referring to FIG. 7B, the pressure transducer PT3 provides a pressure differential signal 358 encoding the pressure differential value to the control system 220.

Referring to FIGS. 7B and 9, the metering valve 320 may be driven by a stepper motor 322 configured to receive a control signal 360 from the control system 220 encoding a stepper position value. The stepper motor 322 is configured to move to the stepper position value encoded in the control signal 360. In the embodiment illustrated, the metering valve 320 is a stepper driven proportioning valve characterized by three variables: (1) valve position, (2) differential pressure across the valve (as measured by the pressure transducer PT3), and (3) flow rate. When a particular flow rate is desired (e.g., entered by the user via the flow rate input 248 depicted in FIG. 6), the control system 220 uses the pressure differential signal 358 (encoding the pressure differential value) and the particular flow rate to "look up" a corresponding stepper position value in a characterization table 362. In other words, the characterization table 362 stores stepper position values each associated with a flow rate value and a pressure differential value. Thus, a particular pressure differential value and a particular flow rate value may be used by the control system 220 to determine a stepper position value. Then, the control system 220 encodes the stepper position value in the control signal 360 and sends it to the stepper motor 322. This process may be repeated occasionally (e.g., every few milliseconds) to provide an instantaneously desired oxygen flow rate.

Referring to FIG. 9, a position sensor 368 may be operatively coupled to the metering valve 320 and used to determine a home position. The position sensor 368 provides a position signal 370 to the control system 220 that encodes whether the metering valve 320 is in the home position (e.g., true or "on") or at a position other than the home position (e.g., false or "off").

Referring to FIG. 7A, the pressure regulator R2 may be characterized as being a back pressure regulator. The pressure regulator R2 may be configured to prevent the pressure inside the adsorption bed 300 from exceeding a first threshold pressure value (e.g., approximately 10 pounds per square inch ("PSIG")). For example, the pressure regulator R2 may be configured to allow oxygen to flow automatically from the adsorption bed 300 when the pressure inside the adsorption bed 300 reaches the first threshold value. The pressure regulator R2 may also be configured to prevent gases from flowing into the adsorption bed 300. This allows the pressure regulator R2 to control the pressure during the first phase (see FIG. 8A) and the second phase (see FIG. 8B).

The pressure regulator R1 may be characterized as being a vacuum regulator. The pressure regulator R1 may be configured to prevent the pressure inside the adsorption bed 300 from falling below a second threshold pressure value (e.g., approximately −7 PSIG). Thus, the pressure regulator R1 regulates the pressure in the adsorption bed 300 to the second threshold pressure during the third phase (see FIG. 8C) and the fourth phase (see FIG. 8D). For example, the pressure regulator R1 may be configured to allow oxygen to flow automatically into the adsorption bed 300 (e.g., from the oxygen tank 312) when the pressure inside the adsorption bed 300 falls below the second threshold value. The pressure regulator R1 may also be configured to prevent gases inside the adsorption bed 300 from flowing out of the adsorption bed 300 toward the metering valve 320 (see FIG. 1).

The optional solenoid valves SV9 and SV10 may be configured to maintain the pressure inside the oxygen tank 312 between a minimum threshold pressure value (e.g., approximately 4 PSIG) and a maximum threshold pressure value (e.g., approximately 10 PSIG). The solenoid valves SV9 and SV10 are connected in a parallel arrangement to a conduit or flow line (not shown) that conducts the high-pressure oxygen 132 (e.g., from the high-pressure oxygen source 120 illustrated in FIG. 1) to the oxygen tank 312. The control system 220 selectively activates and deactivates the solenoid valves SV9 and SV10 using control signals 380 and 382 (see FIG. 7B), respectively, to maintain the pressure in oxygen tank 312 between the minimum and maximum threshold pressure values. Thus, together the control system 220 and the solenoid valves SV9 and SV10 perform the functions of a digital (on/off) regulator.

The control system 220 may automatically stop the oxygen assembly 210 from performing the VPSA process when the high-pressure external oxygen source 120 is connected. For example, the control system 220 may slow or shut down the VPSA process when pressure in the oxygen tank 312 exceeds an upper threshold (e.g., 10 PSIG). In this manner, the control system 220 may slow or shut down the VPSA process when the adsorption bed 300 is operating or the high-pressure external oxygen source 120 is connected. On the other hand, when the pressure inside the oxygen tank 312 falls below a lower pressure threshold (e.g., 4 PSIG), the control system 220 may restart or accelerate the VPSA process.

The oxygen tank 312 may be implemented as a rigid chamber configured to store a predetermined amount of oxygen (e.g., about 56 cubic inches of oxygen). The outlet silencer 311 helps muffle sounds created by the compressor 302.

Referring to FIGS. 7A and 7B, the oxygen sensor 314 measures oxygen concentration in the oxygen tank 312, and encodes an oxygen concentration value in an oxygen concentration signal 378 provided to the control system 220. The control system 220 may use the oxygen concentration signal 378 to monitor the oxygen assembly 210 to ensure it is working properly. If the oxygen concentration signal 378 indicates the oxygen concentration is too low, the control system 220 may conclude that the oxygen assembly 210 is not functioning properly.

The pressure transducer PT2 monitors the pressure between the first and second rotary valve assemblies 306 and 330 (which may be characterized as being a pump pressure supplied to the second rotary valve assembly 330).

Referring to FIG. 7B, the pressure transducer PT2 provides an electrical pressure signal 374 encoding that pressure value to the control system 220.

First Rotary Valve Assembly

Figure 10A:
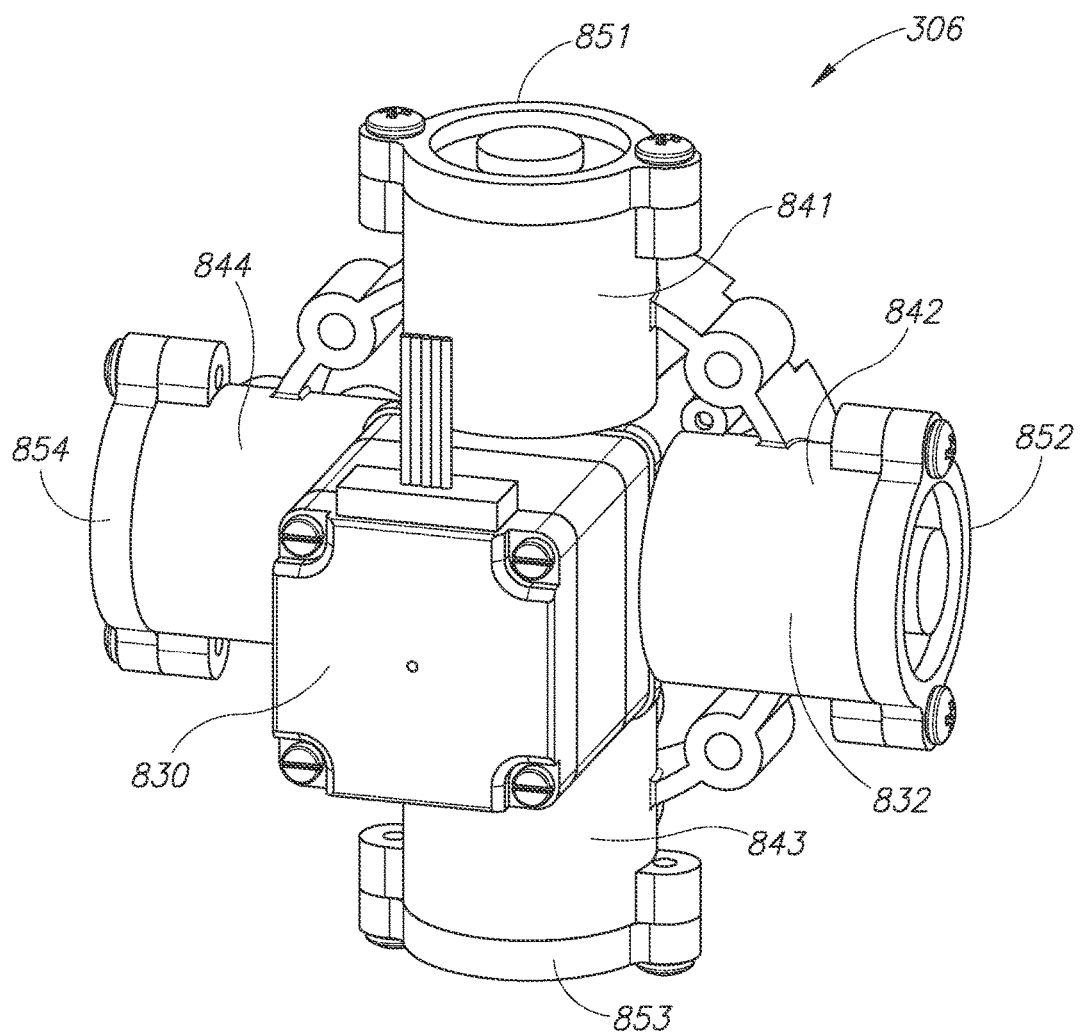
FIG. 10A is a perspective view of a first side of a first rotary valve assembly of the oxygen assembly.
Figure 10B:
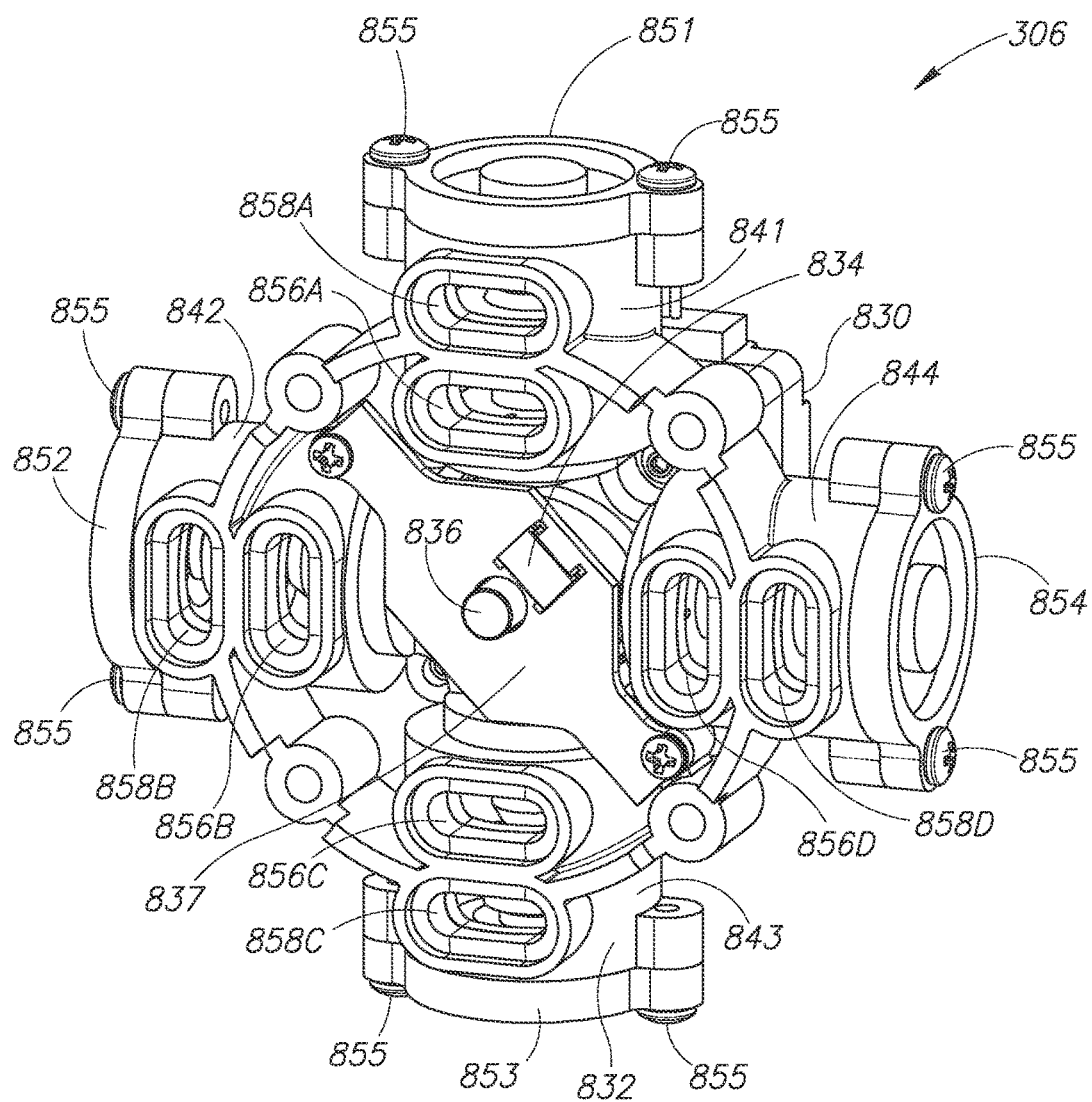
FIG. 10B is a perspective view of a second side of the first rotary valve assembly.

FIG. 10A is a perspective view of a first side of an exemplary embodiment of the first rotary valve assembly 306. FIG. 10B is a perspective view of a second side of the first rotary valve assembly 306 opposite the first side. Referring to FIG. 10A, the first rotary valve assembly 306 includes a motor assembly 830 mounted to an outer housing 832. The motor assembly 830 includes a stepper motor 833 (see FIG. 7B) and a shaft 836 (see FIGS. 10B and 100). The stepper motor 833 is configured to rotate the shaft 836.

Referring to FIG. 10B, a position sensor 834 may be mounted on a printed circuit board ("PCB") 837 fastened to the outer housing 832 opposite the motor assembly 830. In such embodiments, the PCB 837 may include an opening through which an end of the shaft 836 opposite the motor assembly 830 may pass.

Figure 10C:
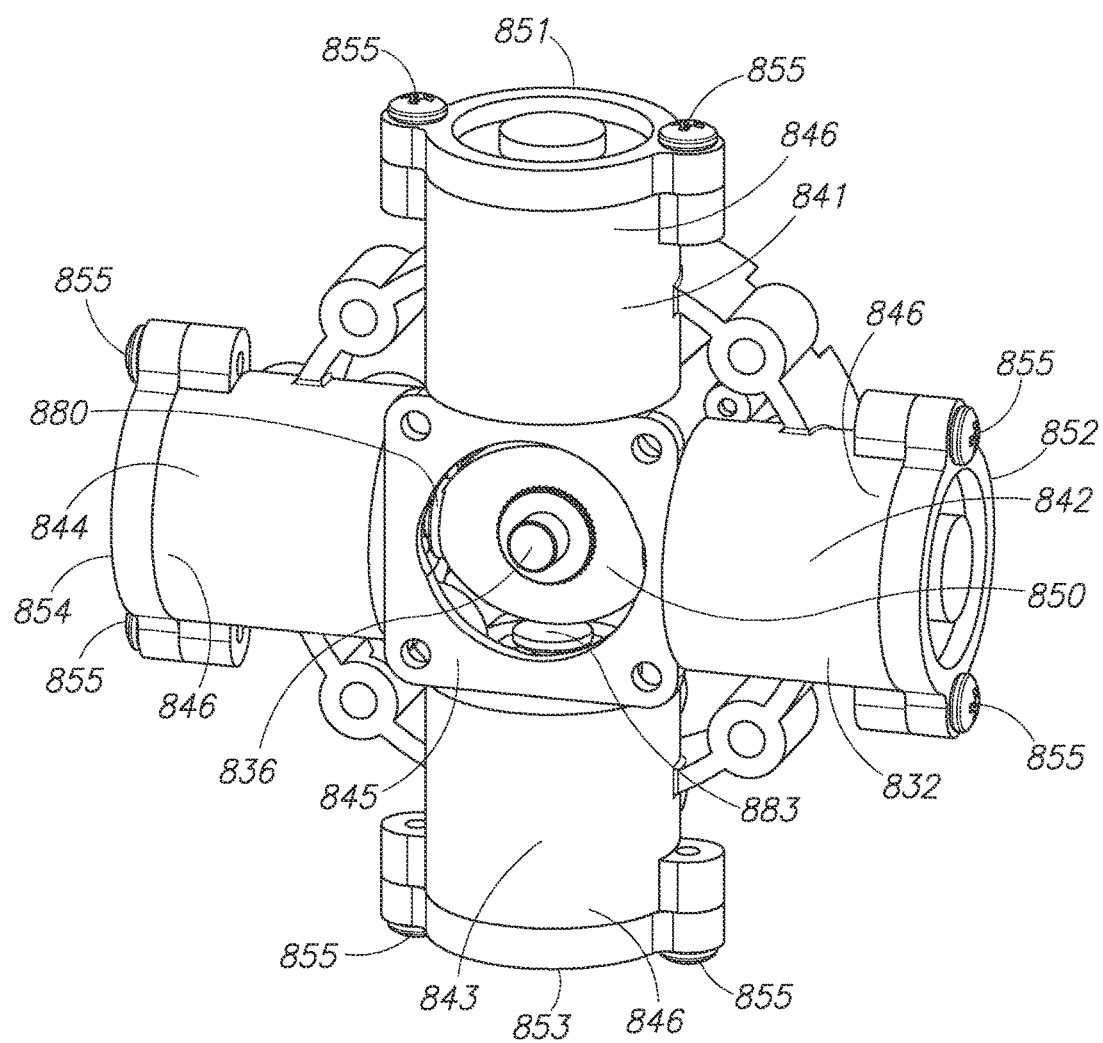
FIG. 10C is a perspective view of the first side of the first rotary valve assembly including a shaft of a motor assembly and omitting other parts of the motor assembly.

FIG. 10C depicts the first side of the first rotary valve assembly 306 and the shaft 836 of the motor assembly 830. Other parts of the motor assembly 830 have been omitted in FIG. 10C. Referring to FIG. 10C, in the embodiment illustrated, the outer housing 832 has an outer shape that is generally cross or cruciform-shaped. Thus, the outer housing 832 has four arms 841-844 that extend outwardly from a central region 845 of the outer housing 832. In the embodiment illustrated, the motor assembly 830 (see FIG. 10A) is mounted to the central region 845.

Figure 10D:
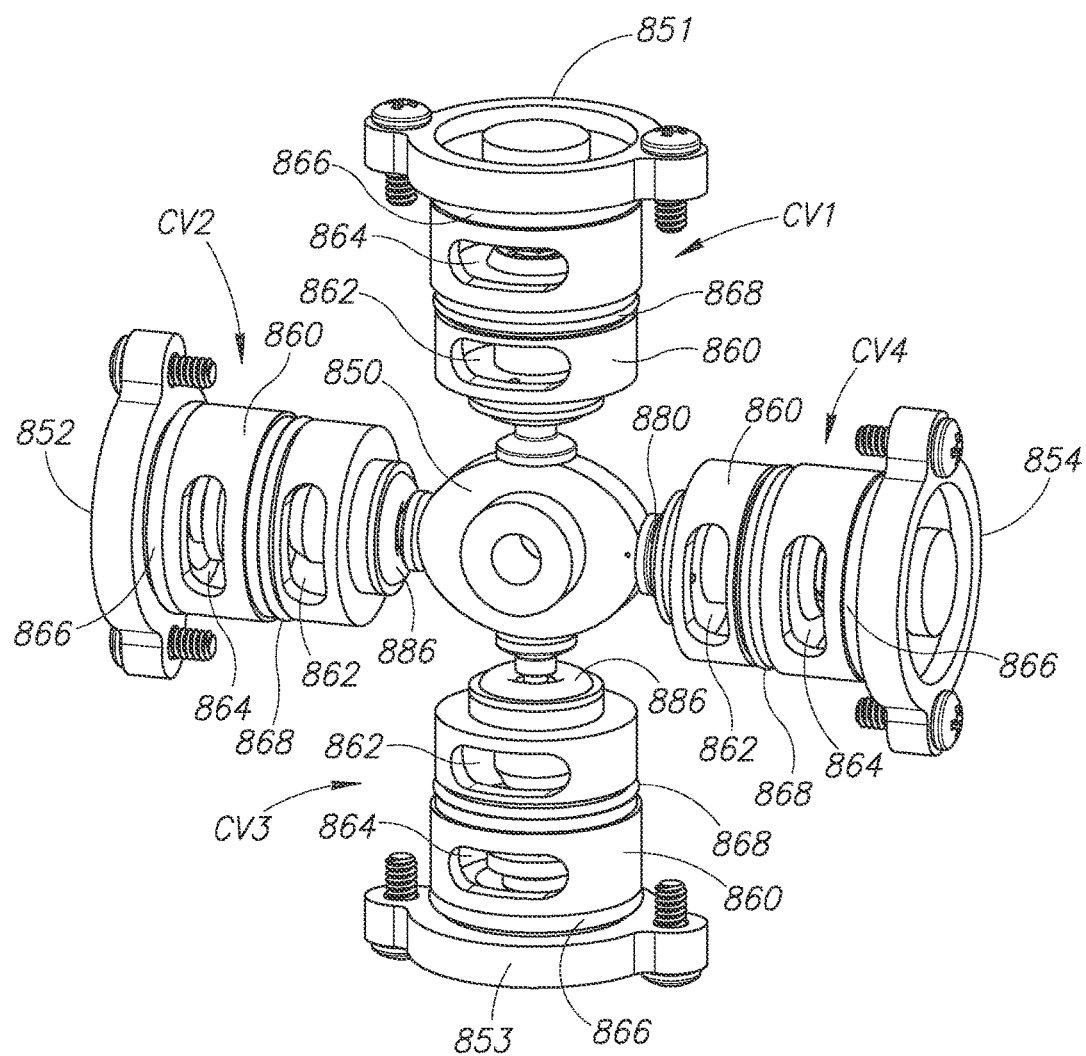
FIG. 10D is a perspective view of the second side of the first rotary valve assembly with its outer housing and printed circuit board removed.

FIG. 10D depicts the second side of the first rotary valve assembly 306 with the outer housing 832 and the PCB 837 removed. As shown in FIG. 10D, the arms 841-844 (see FIG. 10B) house poppet valves CV1-CV4, respectively. Inside the outer housing 832 (see FIG. 10B), the poppet valves CV1 and CV3 are positioned opposite one another, and the poppet valves CV2 and CV4 are positioned opposite one another. The first rotary valve assembly 306 includes a cam 850 mounted on the shaft 836 (see FIGS. 10B and 100) and configured to selectively actuate the poppet valves CV1-CV4. The cam 850 rotates with the shaft 836 as the motor assembly 830 (see FIG. 10A) rotates the shaft 836. Referring to FIG. 7B, the position sensor 834 provides a position signal 835 to the control system 220 that encodes whether the cam 850, the stepper motor 833 (see FIGS. 10A and 10B), and/or the shaft 836 (see FIGS. 10B and 100) is in a home position (e.g., true or "on") or at a position other than the home position (e.g., false or "off").

Referring to FIG. 100, each of the arms 841-844 is open at its distal end 846. The open distal ends 846 of the arms 841-844 are closed by end caps 851-854, respectively. The end caps 851-854 may be fastened to the outer housing 832 by fasteners 855.

Referring to FIG. 10B, the arms 841-844 include inlet openings 856A-856D, respectively, configured to receive a gas or mixture of gases, and outlet openings 858A-858D, respectively, through which a gas or mixture of gases may exit.

Referring to FIG. 10D, each of the poppet valves CV1-CV4 includes an open ended housing 860 with a lateral inlet 862 and a lateral outlet 864. The lateral inlets 862 of the poppet valves CV1-CV4 are aligned and in fluid communication with the inlet openings 856A-856D, respectively, of the outer housing 832. Similarly, the lateral outlets 864 of the poppet valves CV1-CV4 are aligned and in fluid communication with the outlet openings 858A-858D, respectively, of the outer housing 832.

One or more seals 866 and 868 (e.g., 0-ring type seals) may be positioned between the outer housing 832 and the housing 860. For example, the seal 868 may be positioned between the lateral inlet 862 and the lateral outlet 864. By way of another non-limiting example, one of the seals 866 may be positioned between each of the open distal ends 846 of the arms 841-844 and the end caps 851-854, respectively.

Figure 10E:
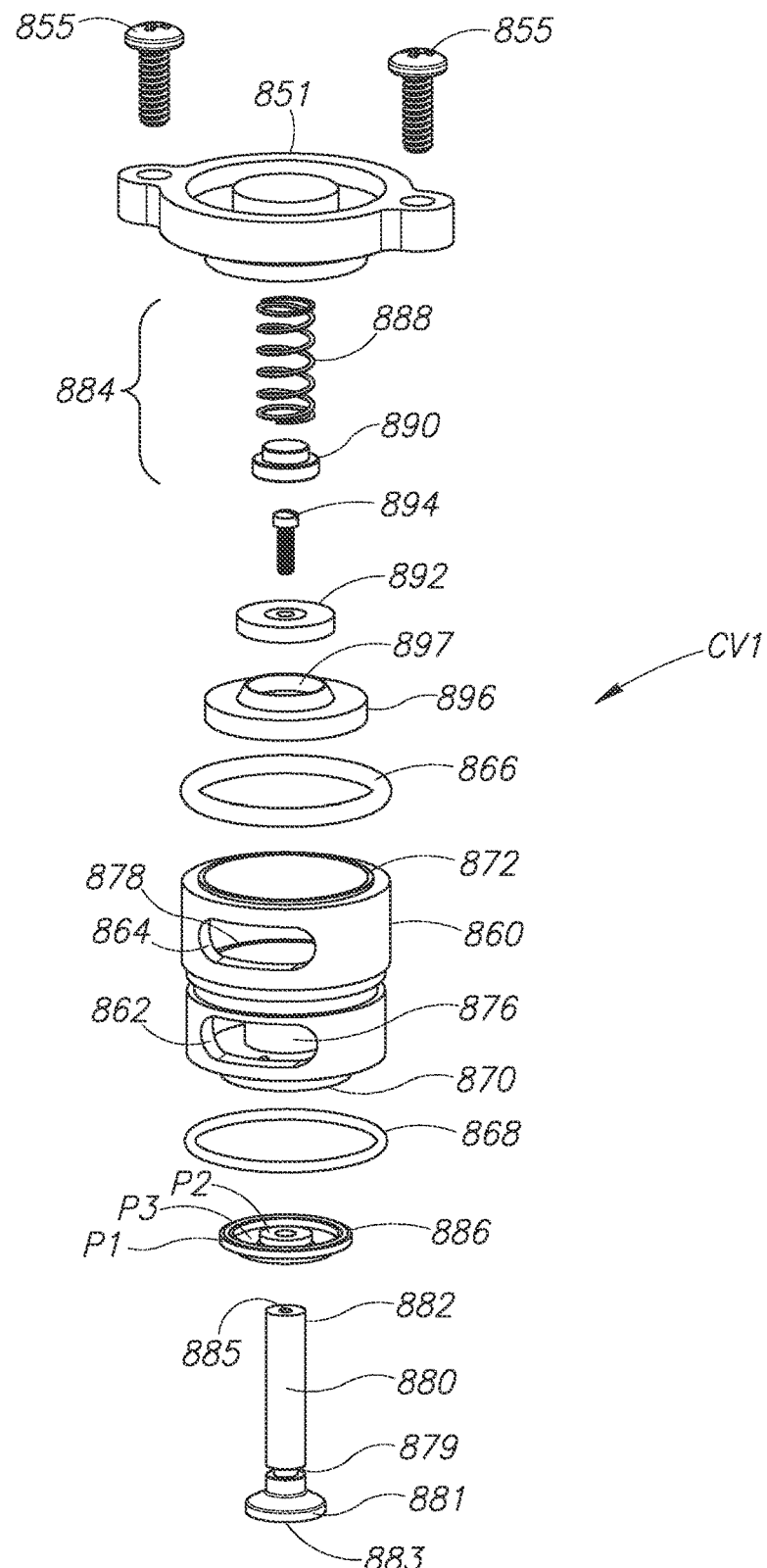
FIG. 10E is an exploded perspective view of one of four poppet valves of the first rotary valve assembly illustrated with an end cap and fasteners.

The poppet valves CV1-CV4 are substantially identical to one another. For the sake of brevity, only the poppet valve CV1 will be described in detail. FIG. 10E is an exploded perspective view of the poppet valve CV1, the end cap 851, and the fasteners 855. Referring to FIG. 10E, the housing 860 has an open proximal end portion 870 opposite an open distal end portion 872. The open distal end portion 872 is closed by the end cap 851 when the end cap 851 is fastened to the outer housing 832. Similarly, the housings 860 of the poppet valves CV2-CV4 are closed at their open distal end portions 872 by the end caps 852-853, respectively, when the end caps 852-854 are fastened to the outer housing 832

Figure 10F:
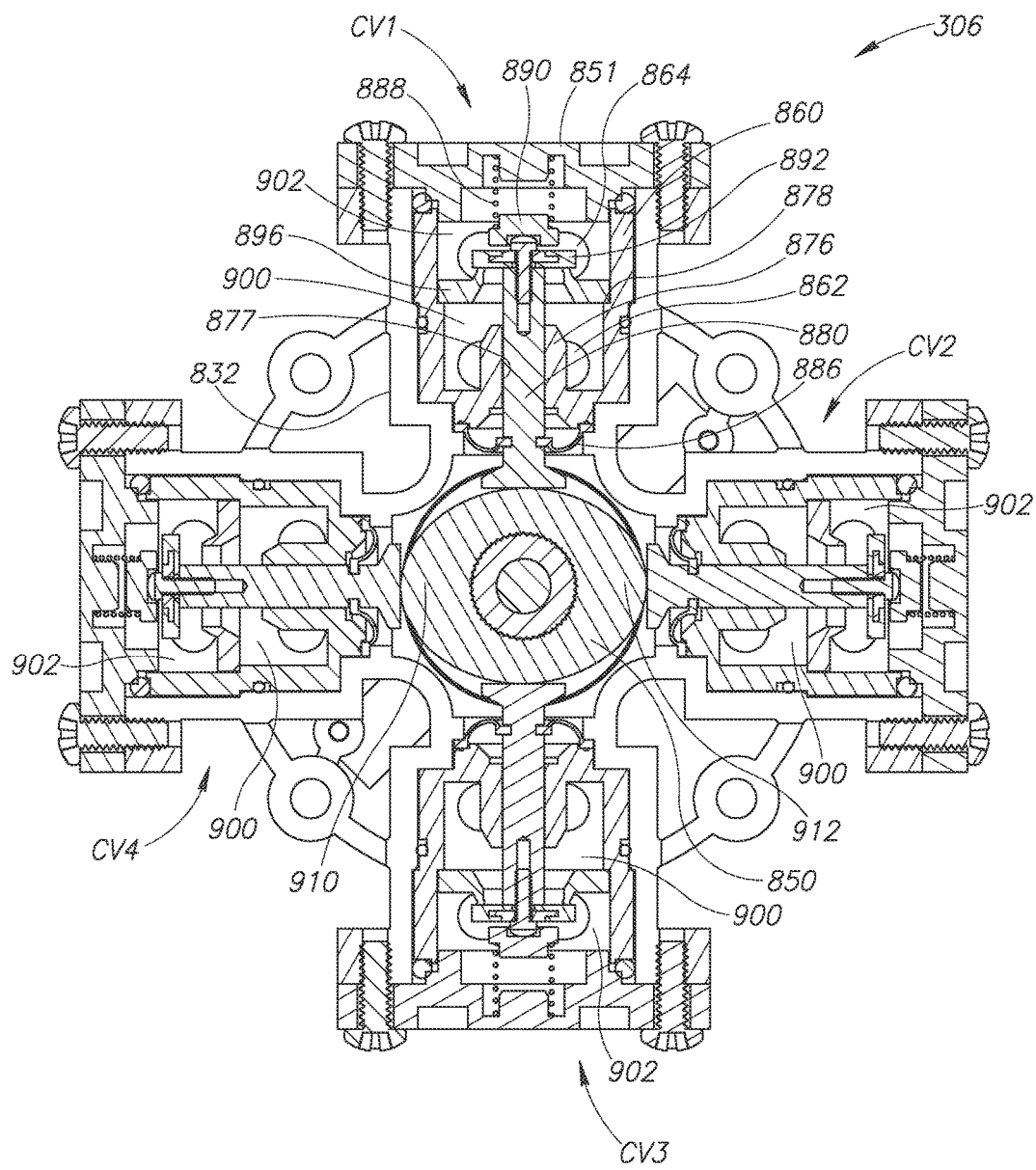
FIG. 10F is a cross-sectional view of the first rotary valve assembly with its second and fourth poppet valves open.
Figure 10G:
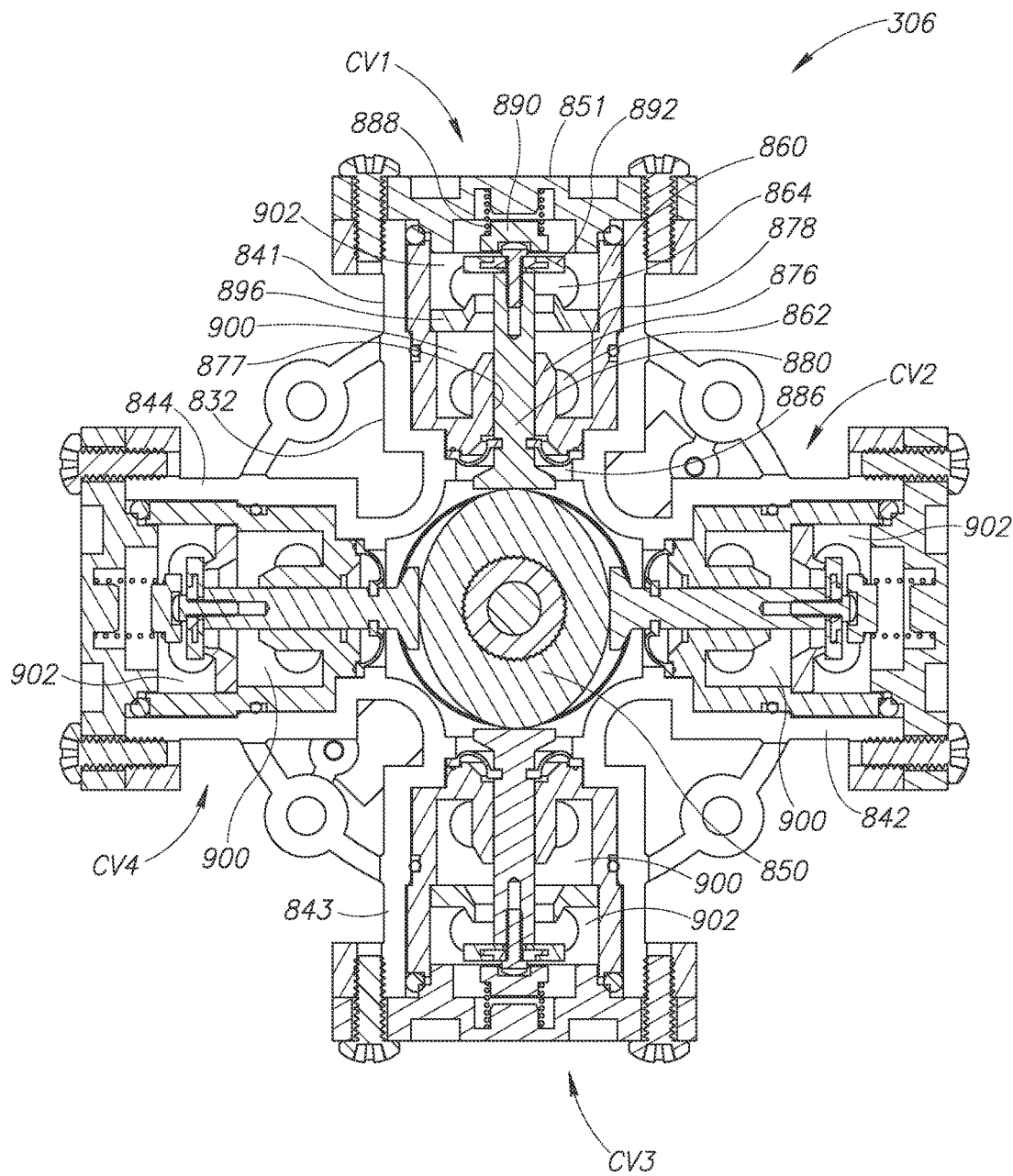
FIG. 10G is a cross-sectional view of the first rotary valve assembly with its first and third poppet valves open.

FIG. 10F is a cross sectional view of the first rotary valve assembly 306 with the cam 850 positioned to open the poppet valves CV2 and CV4. FIG. 10G is a cross sectional view of the first rotary valve assembly 306 with the cam 850 positioned to open the poppet valves CV1 and CV3.

Referring to FIG. 10F, a generally cylindrically shaped guide portion 876 extends inwardly from the open proximal end portion 870 (see FIG. 10E) of the housing 860. An open-ended channel 877 is formed in the guide portion 876. A shoulder 878 is formed on the inside the housing 860 between the lateral inlet and outlet 862 and 864.

Turning to FIG. 10E, inside the housing 860, the poppet valve CV1 has a pushrod 880 biased away from the end cap 851 by a biasing assembly 884. Referring to FIG. 10F, the pushrod 880 extends through the channel 877 and exits the housing 860 though the open proximal end portion 870 (see FIG. 10E). Turning to FIG. 10E, the pushrod 880 may have a circumferential recess 879 form near its proximal end portion 881.

A ring-shaped diaphragm 886 may extend around the pushrod 880 near the proximal end portion 881. In the embodiment illustrated, the diaphragm 886 has a circular central portion P2 having a center aperture 887 through which the pushrod 880 extends with the inner edge portion of the central portion P2 positioned within the recess 879, and thereby the central portion P2 firmly grips the pushrod 880. The diaphragm 886 may close and seal the open proximal end portion 870 of the housing 860. However, the diaphragm 886 may flex or stretch longitudinally to allow the pushrod 880 to move longitudinally with respect to the housing 860. In the embodiment illustrated in FIG. 10F, the diaphragm 886 has a circular outer peripheral portion P1 positioned between the open proximal end portion 870 of the housing 860 and the outer housing 832, and thereby the outer peripheral portion P1 is firmly clamped in place.

Referring to FIG. 10E, the circular outer peripheral portion P1 of the diaphragm 886 is connected to the circular central portion P2 by a curved or contoured intermediate portion P3. The intermediate portion P3 may be characterized as being a convolute. A circle positioned midway between the outer peripheral portion P1 and the central portion P2 may be characterized as being located at the center of the convolute. The diaphragm 886 has an effective area which extends from the circle at the center of the convolute to the central portion P2.

Turning to FIG. 10E, the pushrod 880 has a distal end portion 882 opposite the proximal end portion 881. The proximal end portion 881 has a cam follower 883 (see FIGS. 10O and 10E) formed therein. In the embodiment illustrated, the proximal end portion 881 may taper outwardly and be generally cone-shaped. The cam follower 883 (see FIG. 10C) may be implemented as a planar or contoured lower surface of the proximal end portion 881.

A ring-shaped seat 896 is fixedly attached to the shoulder 878 formed on the inside the housing 860. In the embodiment illustrated, the seat 896 has a central through-hole 897 through which the pushrod 880 extends unobstructed.

The distal end portion 882 of the pushrod 880 has a longitudinally extending channel 885 formed therein. The channel 885 is open at the distal end portion 882 of the pushrod 880. A disc-shaped poppet member 892 is fastened to the distal end portion 882 of the pushrod 880 by a fastener 894 (e.g., a bolt, screw, and the like) that extends into the open end of the channel 885. Thus, the fastener 894 couples the poppet member 892 to the distal end portion 882 of the pushrod 880, which moves therewith as a unit when the pushrod 880 moves inside the housing 860.

Referring to FIG. 10F, when the poppet member 892 is pressed against the seat 896, the poppet member 892 closes the central through-hole 897 and divides the interior of the housing 860 into a proximal chamber 900 and a distal chamber 902. Thus, the poppet member 892 may seal the proximal and distal chambers 900 and 902 from one another. The lateral inlet 862 is in communication with the proximal chamber 900, and the lateral outlet 864 is in communication with the proximal chamber 900. On the other hand, referring to FIG. 10G, when the poppet member 892 is spaced apart distally from the seat 896, the central through-hole 897 is uncovered and the proximal and distal chambers 900 and 902 are in communication with one another. Thus, in this configuration, a gas or mixture of gases may flow between the proximal and distal chambers 900 and 902. In other words, a pathway is opened between the lateral inlet and outlet 862 and 864.

The distal end portion 882 of the pushrod 880 is adjacent the biasing assembly 884. In the embodiment illustrated, the biasing assembly 884 includes a biasing member 888 (e.g., a coil spring), and an end cap 890. The biasing member 888 applies an inwardly directed force on the pushrod 880, which helps insure the pushrod 880 maintains contact with the cam 850. The end cap 890 rests upon the fastener 894 and is positioned between the disc-shaped poppet member 892 and the end cap 851. The biasing member 888 extends between the end cap 890 and the end cap 851 and applies the biasing force to the end cap 890, which translates that force to the fastener 894 and/or the poppet member 892. In turn, the fastener 894 and/or the poppet member 892 translates the biasing force to the pushrod 880.

The cam 850 may be characterized as having two lobes or high points 910 and 912 opposite one another. When one of the high points 910 and 912 is adjacent the cam follower 883 (see FIGS. 10O and 10E) of the pushrod 880 of the poppet valve CV1, the high point 910 or 912 pushes the pushrod 880 outwardly toward the end cap 851. This pushes the disc-shaped poppet member 892 away from the seat 896 (as illustrated in FIG. 10G) and opens the central through-hole 897. This opens the poppet valve CV1 and allows a gas or mixture of gases to flow though the poppet valve CV1. On the other hand, as illustrated in FIG. 10G, when neither of the high points 910 and 912 are adjacent the cam follower 883 (see FIGS. 10O and 10E) of the pushrod 880 of the poppet valve CV1, the pushrod 880 is biased inwardly away from the end cap 851 by the biasing assembly 884. The pushrod 880 thereby pulls the disc-shaped poppet member 892 toward the seat 896 causing the poppet member 892 to cover or close the central through-hole 897. This closes the poppet valve CV1 and prevents a gas or mixture of gases from flowing though the poppet valve CV1.

Because the ventilator 100 may be required to function over a long life span (e.g., more than about 30,000 hours), the first rotary valve assembly 306 may experience about 15,000,000 VPSA cycles. To satisfy this requirement, each of the poppet valves CV1-CV4 may have a "balanced" valve configuration. Whenever one of the poppet valves CV1-CV4 is closed, pressure inside the proximal chamber 900 acts upon both the effective area of the diaphragm 886 and a portion of the poppet member 892 covering (or closing) the central through-hole 897 of the seat 896. The area of the portion of the poppet member 892 covering (or closing) the central through-hole 897 of the seat 896 is approximately equal to the effective area of the diaphragm 886. When the pressure inside the proximal chamber 900 is negative (or a vacuum), an inwardly (toward the proximal chamber 900) directed force acts upon the effective area of the diaphragm 886. At the same time, an inwardly (toward the proximal chamber 900) directed force acts on the portion of the poppet member 892 covering the central through-hole 897 of the seat 896. Similarly, when the pressure inside the proximal chamber 900 is positive, an outwardly (away from the proximal chamber 900) directed force acts upon the effective area of the diaphragm 886 and an outwardly (or distally) directed force acts on the portion of the poppet member 892 covering the central through-hole 897 of the seat 896. Thus, when the proximal chamber 900 is sealed by the poppet member 892, forces directed in opposite directions act upon the effective area of the diaphragm 886 and the area of the portion of the poppet member 892 covering (or closing) the central through-hole 897 of the seat 896. Because (as mentioned above), the effective area of the diaphragm 886 and the area of the portion of the poppet member 892 covering (or closing) the central through-hole 897 of the seat 896 are approximately equal, net force on the pushrod 880 is zero. This balancing feature helps reduce the force of the pushrod 880 on the cam follower 883 and the cam 850, thereby reducing the wear and extending the life.

As explained above, each of the poppet valves CV1-CV4 is biased into a closed position by its biasing assembly 884. Each of the poppet valves CV1-CV4 includes the cam follower 883 (see FIGS. 10O and 10E) that abuts the cam 850. As the cam 850 rotates, it pushes opposing ones of the poppet valves CV1-CV4 outwardly opening them. If the poppet valves CV1 and CV3 are in open positions, the poppet valves CV2 and CV4 are in closed positions and vice versa. Referring to FIG. 7B, the first rotary valve assembly 306 (e.g., the stepper motor 833) is configured to receive a control signal 376 from the control system 220 encoding a cam position. The first rotary valve assembly 306 (e.g., the stepper motor 833) is also configured to rotate the cam 850 to the position encoded in the control signal 376.

Referring to FIG. 7A, the poppet valve CV3 (see FIG. 10G) is connected to the compressor 302 and the adsorption bed 300. The control system 220 makes the pressure inside the distal chamber 902 of the poppet valve CV3 less than the pressure inside the proximal chamber 900 of the poppet valve CV3 by configuring the compressor 302 to provide suction to the distal chamber 902.

The poppet valve CV1 (FIG. 10G) is connected to the compressor 302 and the outlet vent 124. The control system 220 makes the pressure inside the distal chamber 902 of the poppet valve CV1 less than the pressure inside the proximal chamber 900 of the poppet valve CV1 by configuring the compressor 302 to push the nitrogen-rich gas 122 (see FIGS. 8C and 8D) into the proximal chamber 900.

When the poppet valves CV1 and CV3 are open as illustrated in FIG. 10G, the poppet valve CV3 receives the nitrogen-rich gas 122 (see FIGS. 8C and 8D) from the adsorption bed 300 and provides it to the compressor 302. At the same time, the poppet valve CV1 allows the nitrogen-rich gas 122 pumped from the adsorption bed 300 (via the poppet valve CV3) by the compressor 302 to flow out of the compressor 302 and exit the ventilator 100 via the outlet vent 124. Optionally, the poppet valve CV3 may be connected to the second rotary valve assembly 330. As will be explained below, the compressor 302 may provide the suction 154 to the suction assembly 152 via the second rotary valve assembly 330.

Referring to FIG. 7A, the poppet valve CV4 (see FIG. 10F) is connected to the compressor 302 and the patient air intake 116. The control system 220 makes the pressure inside the proximal chamber 900 of the poppet valve CV4 less than the pressure inside the distal chamber 902 of the poppet valve CV4 by configuring the compressor 302 to provide suction to the proximal chamber 900.

The poppet valve CV2 (see FIG. 10F) is connected to the compressor 302 and the adsorption bed 300. The control system 220 makes the pressure inside the distal chamber 902 of the poppet valve CV2 greater than the pressure inside the proximal chamber 900 of the poppet valve CV2 by configuring the compressor 302 to provide the pressurized air 114 pumped by the compressor 302 to the distal chamber 902.

When the poppet valves CV2 and CV4 are open as illustrated in FIG. 10F, the poppet valve CV4 allows the air 114 to be pumped via the patient air intake 116 into the compressor 302. At the same time, the poppet valve CV2 provides the pressurized air 114 from the compressor 302 to the adsorption bed 300. Optionally, the poppet valve CV2 may be connected to the second rotary valve assembly 330. As will be explained below, the gases 164 provided to the second rotary valve assembly 330 may be used to implement the nebulizer assembly 162.

Figure 11:
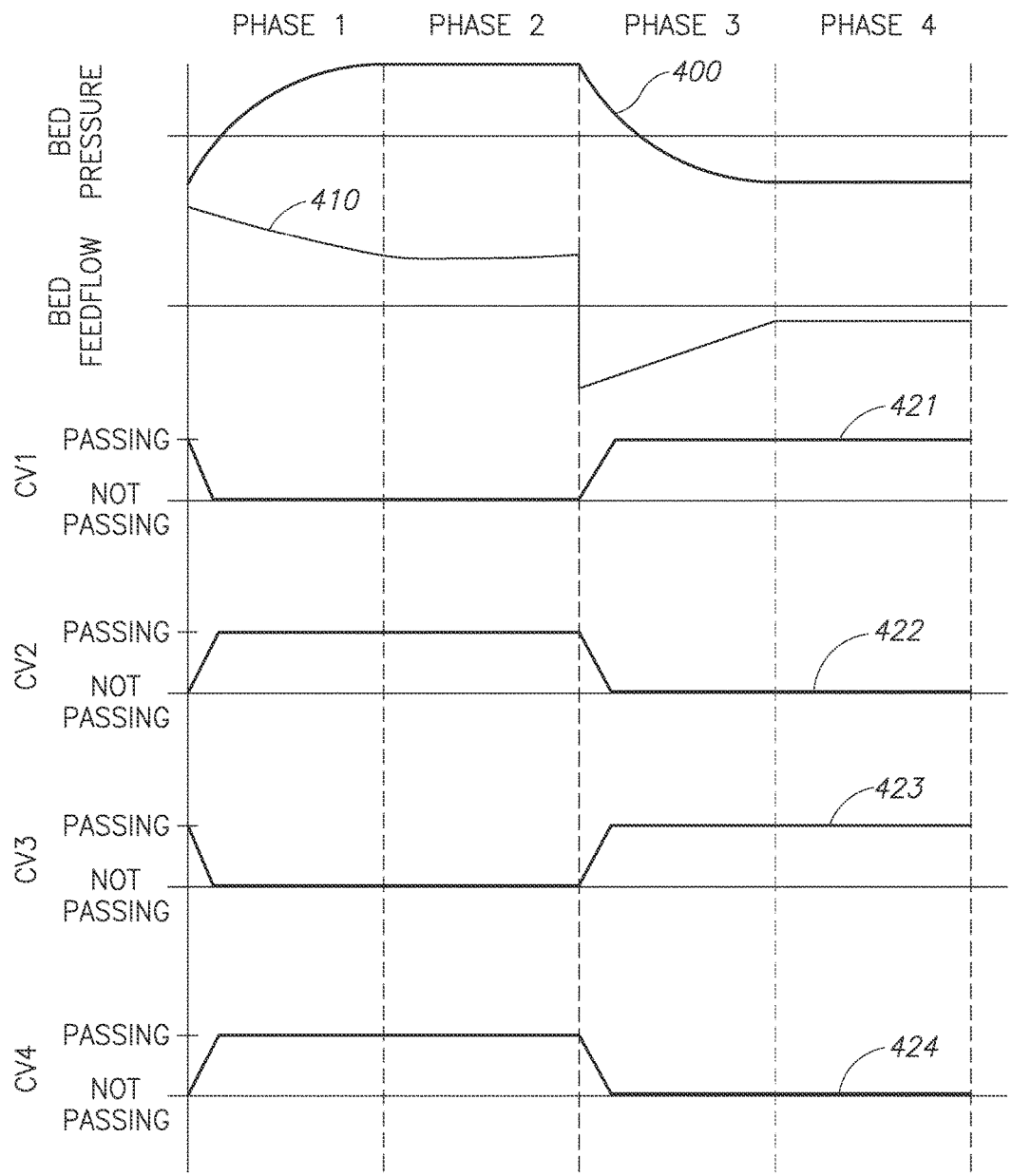
FIG. 11 is a graph showing pressure and feed flow experienced by a bed of nitrogen adsorbent material of the oxygen generator during the four phases of the VPSA process.

As mentioned above, in the embodiment illustrated, the oxygen assembly 210 generates the oxygen 364 (see FIG. 8B) using the VPSA process, which may have four phases that are labeled "PHASE 1," "PHASE 2," "PHASE 3," and "PHASE 4" across the top of FIG. 11.

In FIG. 11, an upper line 400 depicts pressure experienced by the bed of nitrogen adsorbent material 344 (see FIGS. 8A-8D) during the four phases of the VPSA process. Referring to FIG. 11, the line 400 may be determined by the control system 220 based on the electrical pressure signal 374 (see FIG. 7B) provided by the pressure transducer PT2. A lower line 410 depicts feed flow rate through the bed of nitrogen adsorbent material 344 (see FIGS. 8A-8D) during the four-phases of the VPSA process.

Lines 421 and 423 show that the poppet valves CV1 and CV3, respectively, are transitioned from open ("passing") to closed ("not passing") at the beginning of the first phase and then the poppet valves CV1 and CV3 are transitioned from closed ("not passing") to open ("passing") at the beginning of third phase. Thus, the poppet valves CV1 and CV3 are closed during most of the first phase and all of the second phase. Further, the poppet valves CV1 and CV3 are open during most of the third phase and all of the fourth phase.

Conversely, lines 422 and 424 show that the poppet valves CV2 and CV4, respectively, are transitioned from closed ("not passing") to open ("passing") at the beginning of the first phase and then the poppet valves CV2 and CV4 are transitioned from open ("passing") to closed ("not passing") at the beginning of third phase. Thus, the poppet valves CV2 and CV4 are open during most of the first phase and all of the second phase. Further, the poppet valves CV2 and CV4 are closed during most of the third phase and all of the fourth phase.

Figure 12:
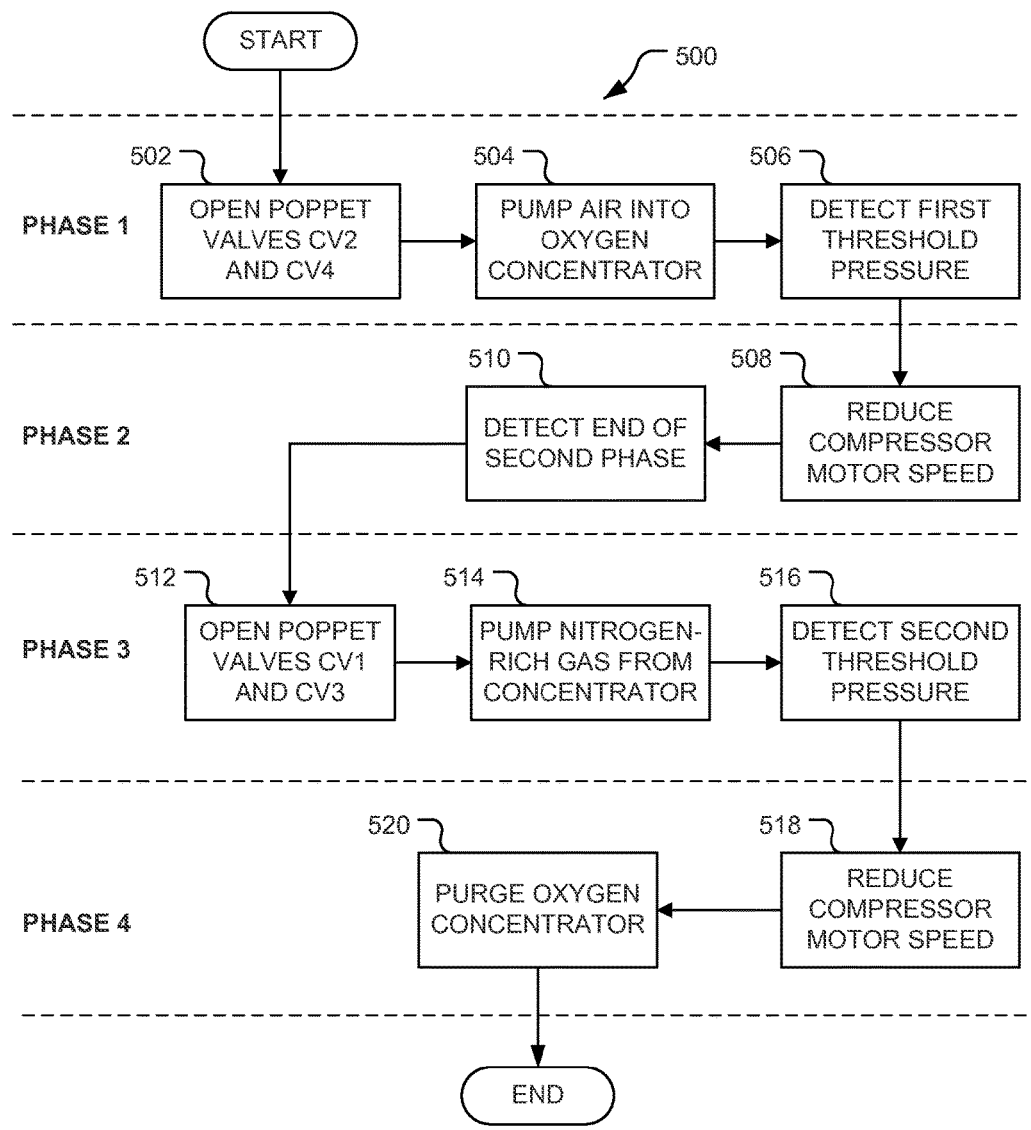
FIG. 12 is a flow diagram of a method performed by the control system of the ventilator of FIG. 1.

FIG. 12 is a flow diagram of a method 500 performed by the control system 220. The method 500 at least partially implements the VPSA process. As the method 500 is performed, the pressure transducer PT2 (see FIGS. 7A and 7B) occasionally obtains pressure values for the adsorption bed 300 and sends the electrical pressure signal 374 to the control system 220.

In first block 502, the control system 220 begins the first phase of the VPSA process by opening the poppet valves CV2 and CV4, and closing the poppet valves CV1 and CV3. At this point, the pressure regulator R2 is closed.

In next block 504, the control system 220 instructs the motor 350 of the compressor 302 to pump the air 114 from the patient air intake 116 into the adsorption bed 300. The motor 350 of the compressor 302 may run at a relatively high speed while drawing the air 114 from the patient air intake 116.

In block 506, the control system 220 determines that the pressure inside the adsorption bed 300 has reached the first threshold pressure value (e.g., approximately 10 PSIG). When the pressure inside the adsorption bed 300 reaches the first threshold pressure value, the pressure regulator R2 automatically opens. At this point, the first phase ends and the second phase begins. During the second phase, nitrogen is adsorbed by the adsorption bed 300 from the air 114 and referring to FIG. 8B, the oxygen 346 (e.g., 90% pure oxygen) flows out of the adsorption bed 300 through the pressure regulator R2. The oxygen that passes through the pressure regulator R2 during the second phase is stored in the oxygen tank 312.

Returning to FIG. 12, in next block 508, at the start of the second phase, the control system 220 reduces the speed of the motor 350. Referring to FIG. 8B, during the second phase, a mass transfer zone 430 moves away from the first end 341 (in a direction identified by an arrow "DI") through to the second end 343. Gas on a first side 432 of the mass transfer zone 430 near the first end 341 is air, and gas on a second side 434 of the mass transfer zone 430 near the second end 343 is about 90% oxygen. The compressor 302 may run relatively slowly during the second phase to facilitate effective nitrogen adsorbtion. In block 510, the control system 220 detects the end of the second phase, which ends when the mass transfer zone 430 reaches the second end 343. The control system 220 may determine the second phase has ended after a predetermined amount of time (e.g., about one second) has elapsed. In some embodiments, the control system 220 may also use a secondary means (e.g., pressure) to help determine when the second phase has ended. At this point, the adsorption bed 300 is fully saturated with nitrogen, the second phase ends, and the third phase begins.

At the start of the third phase, in block 512, the control system 220 opens the poppet valves CV1 and CV3, and closes the poppet valves CV2 and CV4. At this point, the pressure regulator R1 is closed.

In next block 514, the control system 220 instructs the motor 350 of the compressor 302 to pump the nitrogen-rich gas 122 from the adsorption bed 300 and into the external environment through the outlet vent 124. The compressor 302 may run at a relatively high speed as it draws the nitrogen-rich gas 122 out of the adsorption bed 300.

In block 516, the control system 220 determines that the pressure inside the adsorption bed 300 has reached the second threshold pressure value (e.g., approximately −7 PSIG). At this point, the third phase ends and the fourth phase begins.

At the beginning of the fourth phase, in block 518, the control system 220 may reduce the speed of the motor 350 to a relatively slow speed.

In block 520, the control system 220 purges the adsorption bed 300 with oxygen from the oxygen tank 312. In block 520, the pressure regulator R1 opens automatically to allow the flow of "purge" oxygen 348 (see FIG. 8D) from the oxygen tank 312 to flow through the adsorption bed 300 (e.g., in a direction identified by an arrow "D2"). The mass transfer zone 430 also moves away from the second end 343 (in a direction identified by an arrow "D2") through to the first end 341. The low pressure inside the adsorption bed 300 combined with the flow of purge oxygen 348 draws the nitrogen out and regenerates the adsorption bed 300. When the purge is completed, the fourth phase ends, which completes one four-phase cycle, and the method 500 terminates. The control system 220 may begin another cycle by returning to block 502 of the method 500.

FIGS. 13A-13D are schematic diagrams of the second rotary valve assembly 330. The second rotary valve assembly 330 may be substantially similar to the first rotary valve assembly 306 (see FIGS. 10A and 10B). However, the second rotary valve assembly 330 includes a cam 530 with a single lobe or high point 532, which is unlike the cam 850 of the first rotary valve assembly 306, which has two high points 910 and 912 (see FIG. 10F) opposite one another.

Referring to FIGS. 13A-13D, the cam 530 of the second rotary valve assembly 330 is configured to selectively actuate four poppet valves CV5¬CV8 one at a time. Each of the poppet valves CV5-CV8 may be substantially similar to the poppet valve CV1 illustrated in FIG. 10E.

In the second rotary valve assembly 330, the poppet valves CV5 and CV7 are positioned opposite one another. Similarly, the poppet valves CV6 and CV8 are positioned opposite one another. The poppet valves CV5-CV8 are biased into a closed position. Each of the poppet valves CV5-CV8 has a pushrod 538 (substantially similar to the pushrod 880 depicted in FIG. 10E) with a cam follower 540 (substantially similar to the cam follower 883 depicted in FIG. 10O) that abuts the cam 530. As the cam 530 rotates, it pushes only one of the pushrods 538 of the poppet valves CV5-CV8 at a time outwardly and into an open position.

Further, as explained above with respect to the first rotary valve assembly 306, each of the poppet valves CV5-CV8 may include a poppet member (substantially identical to the poppet member 892) configured to move with respect to a seat (substantially identical to the seat 896) to selectively connect a proximal chamber (like the proximal chamber 900) with a distal chamber (like the distal chamber 902). In such embodiments, after the cam 530 pushes the pushrod 538 of a selected one of the poppet valves CV5-CV8 outwardly, the selected poppet valve opens.

Referring to FIG. 7B, the second rotary valve assembly 330 includes a stepper motor 542 and a position sensor 544 substantially similar to the stepper motor 833 and the position sensor 834 of the first rotary valve assembly 306.

The second rotary valve assembly 330 (e.g., the stepper motor 542) is configured to receive a control signal 546 from the control system 220 encoding a cam position. The second rotary valve assembly 330 (e.g., the stepper motor 542) is also configured to rotate the cam 530 to the position encoded in the control signal 546. The position sensor 544 provides a position signal 548 to the control system 220 that encodes whether the stepper motor 542 and/or the cam 530 is in a home position (e.g., true or "on") or at a position other than the home position (e.g., false or "off").

Figure 13A:
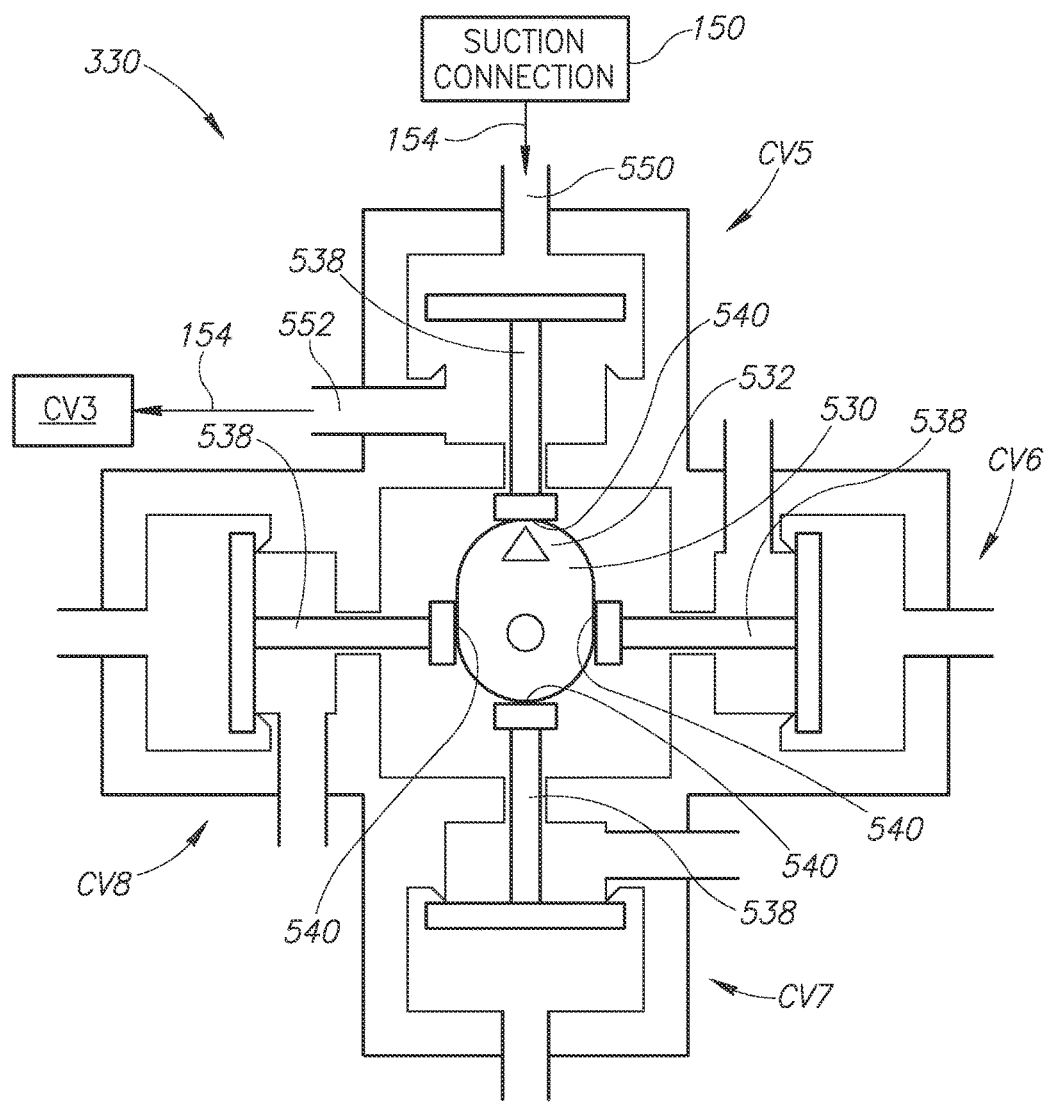
FIG. 13A is an illustration of an optional second rotary valve assembly of the oxygen assembly depicted with a first one of its four poppet valves open.

Referring to FIG. 13A, the poppet valve CV5 has an inlet 550 connected to the suction connection 150 and an outlet 552 connected to the poppet valve CV3 (see FIGS. 10D, 10F, and 10G). When the poppet valves CV1 and CV3 are open, the poppet valve CV5 may be opened (as shown in FIG. 13A) to receive the suction 154 from the compressor 302 and provide the suction 154 to the suction connection 150. Any gases received from the suction assembly 152 (see FIG. 1) via the suction connection 150, may be pumped by the compressor 302 out the outlet vent 124 via the poppet valve CV1. The nitrogen-rich gas 122 may be pumped by the compressor 302 at the same time the suction 154 is provided.

Figure 13B:
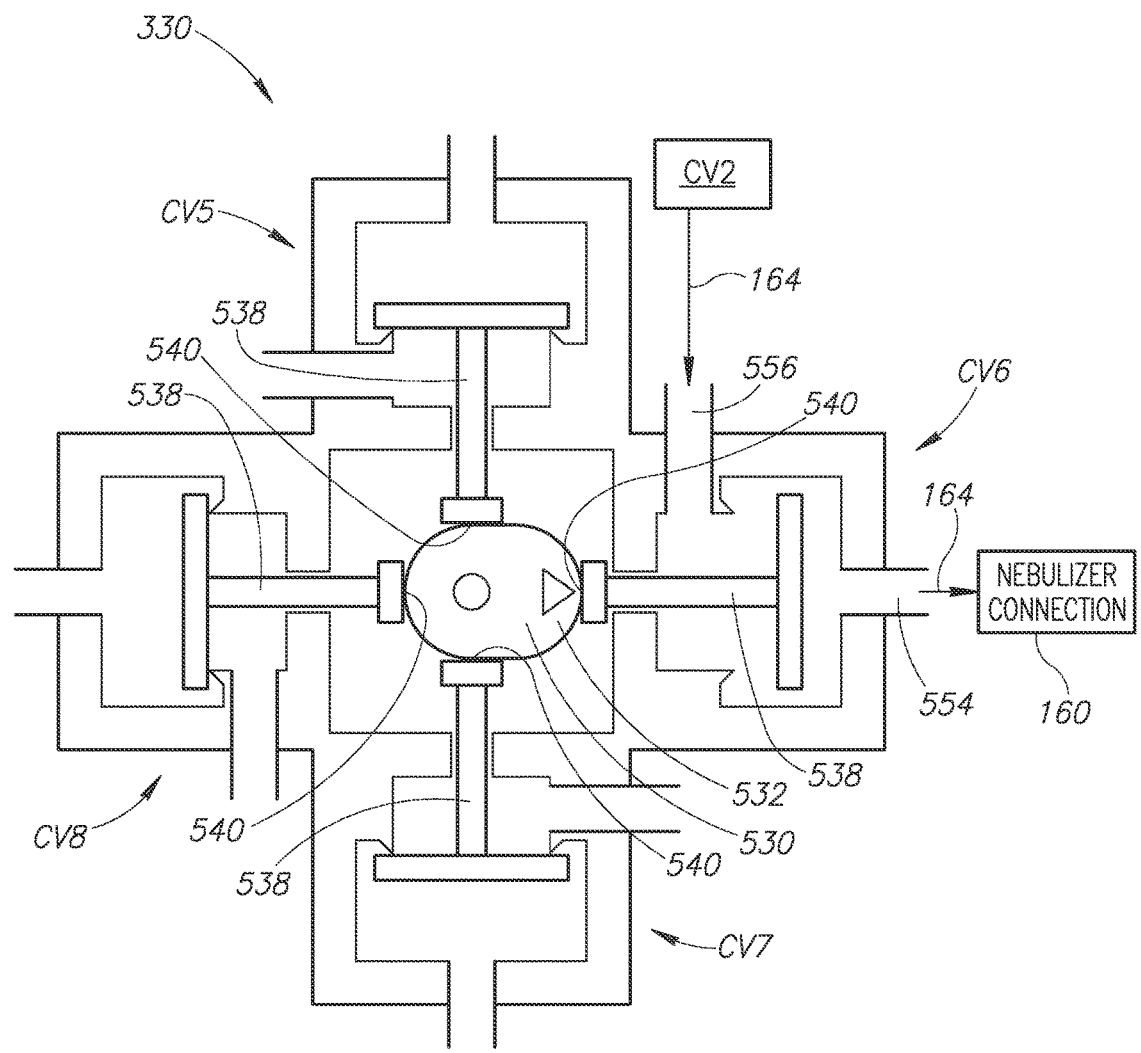
FIG. 13B is an illustration of the optional second rotary valve assembly of the oxygen assembly depicted with a second one of its four poppet valves open.

Referring to FIG. 13B, the poppet valve CV6 has an inlet 554 connected to the nebulizer assembly 162 and an outlet 556 connected to the poppet valve CV2. When the poppet valves CV2 and CV4 are open, the poppet valve CV6 may be opened (as shown in FIG. 13B) to provide the gases 164 to the nebulizer connection 160 instead of providing the air 114 to the adsorption bed 300. Thus, the compressor 302 may power the nebulizer assembly 162 (see FIG. 1).

Figure 13C:
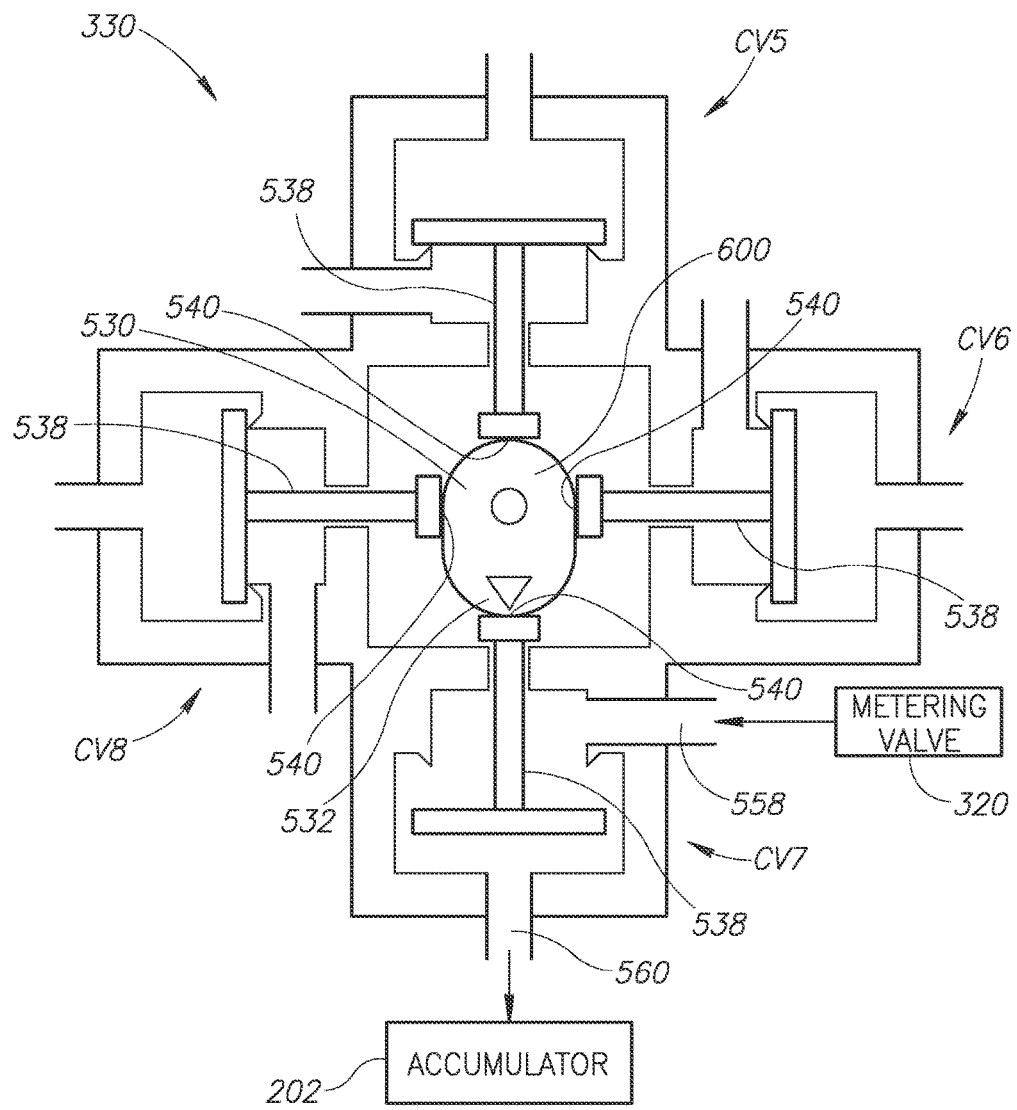
FIG. 13C is an illustration of the optional second rotary valve assembly of the oxygen assembly depicted with a third one of its four poppet valves open.

Referring to FIG. 13C, the poppet valve CV7 has an inlet 558 connected to the metering valve 320 and an outlet 560 connected to the accumulator 202. When the poppet valve CV7 is open as shown in FIG. 13C, oxygen output from the metering valve 320 is provided to the accumulator 202.

Figure 13D:
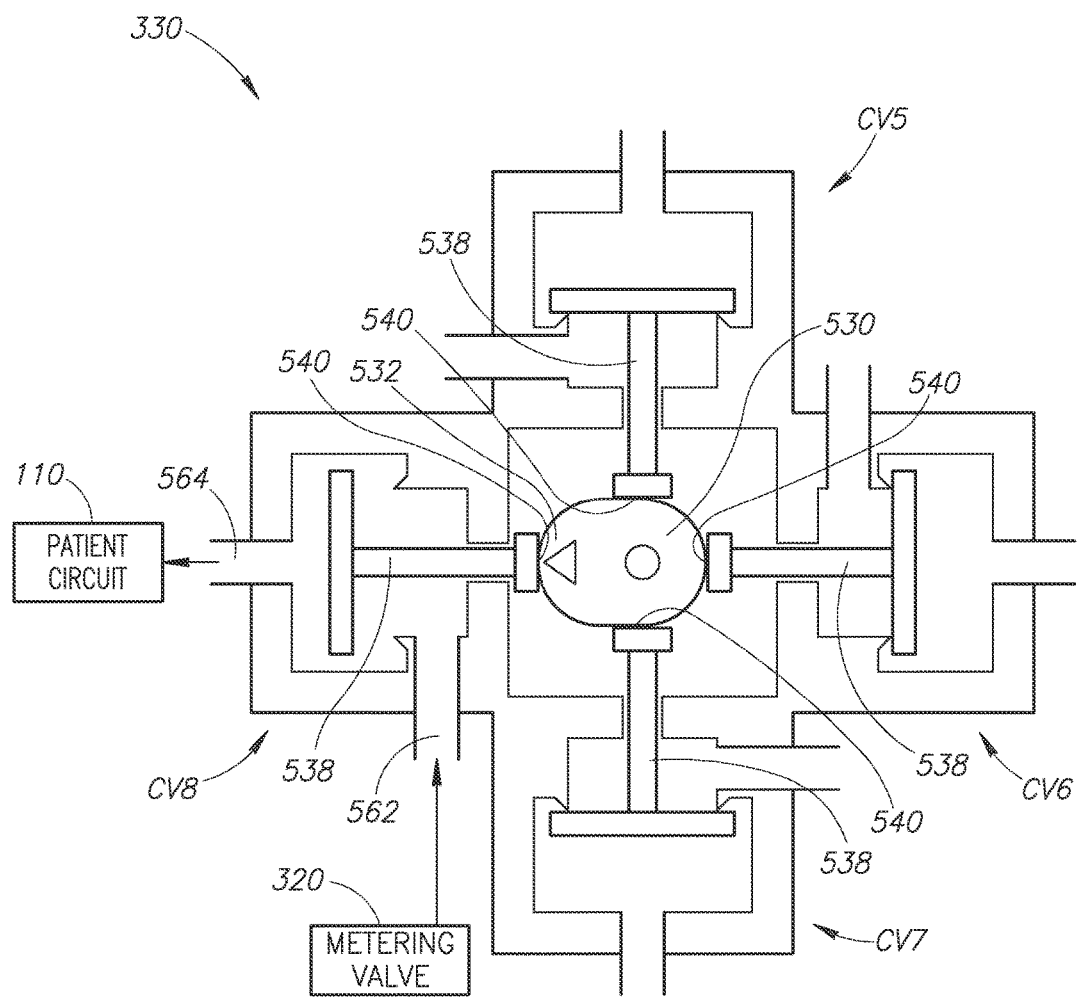
FIG. 13D is an illustration of the optional second rotary valve assembly of the oxygen assembly depicted with a fourth one of its four poppet valves open.

Referring to FIG. 13D, the poppet valve CV8 has an inlet 562 connected to the metering valve 320 and an outlet 564 connected to the patient circuit 110. When the poppet valve CV8 is open as shown in FIG. 13D, the oxygen 364 (from the adsorption bed 300) and/or the oxygen from the oxygen tank 312 is provided directly to the patient circuit 110.

Control System

Referring to FIGS. 5E and 7B, the control system 220 includes a memory 700 connected to one or more processors 710. The memory stores the table 362 and instructions 720 executable by the processor(s) 710.

The processor(s) 710 may be implemented by one or more microprocessors, microcontrollers, application-specific integrated circuits ("ASIC"), digital signal processors ("DSP"), combinations or sub-combinations thereof, or the like. The processor(s) 710 may be integrated into an electrical circuit, such as a conventional circuit board, that supplies power to the processor(s) 710. The processor(s) 710 may include internal memory and/or the memory 700 may be coupled thereto. The present invention is not limited by the specific hardware component(s) used to implement the processor(s) 710 and/or the memory 700.

The memory 700 is a computer readable medium that includes instructions or computer executable components that are executed by the processor(s) 710. The memory 700 may be implemented using transitory and/or non-transitory memory components. The memory 700 may be coupled to the processor(s) 710 by an internal bus 715.

The memory 700 may include random access memory ("RAM") and read-only memory ("ROM"). The memory 700 contains instructions and data that control the operation of the processor(s) 710. The memory 700 may also include a basic input/output system ("BIOS"), which contains the basic routines that help transfer information between elements within the ventilator 100.

Optionally, the memory 700 may include internal and/or external memory devices such as hard disk drives, floppy disk drives, and optical storage devices (e.g., CD-ROM, R/W CD-ROM, DVD, and the like). The ventilator 100 may also include one or more I/O interfaces (not shown) such as a serial interface (e.g., RS-232, RS-432, and the like), an IEEE-488 interface, a universal serial bus ("USB") interface, a parallel interface, and the like, for the communication with removable memory devices such as flash memory drives, external floppy disk drives, and the like.

The processor(s) 710 is configured to execute software implementing the VPSA process (which may include performing the method 500 illustrated in FIG. 12) and/or delivering oxygen in accordance with oxygen delivery methods described below. Such software may be implemented by the instructions 720 stored in memory 700.

Oxygen Delivery

Referring to FIG. 1, as mentioned above, the ventilator 100 delivers the inspiratory gases 108 directly to the patient connection 106 (via the patient circuit 110). Oxygen may be delivered to the patient 102 in one of two ways: (1) as pulses of oxygen 140 delivered directly to the patient connection 106, or (2) in the gases 112 that contain the air 114 optionally blended with the oxygen 250 and/or the low pressure oxygen 128 in the accumulator 202.

Figure 14A:
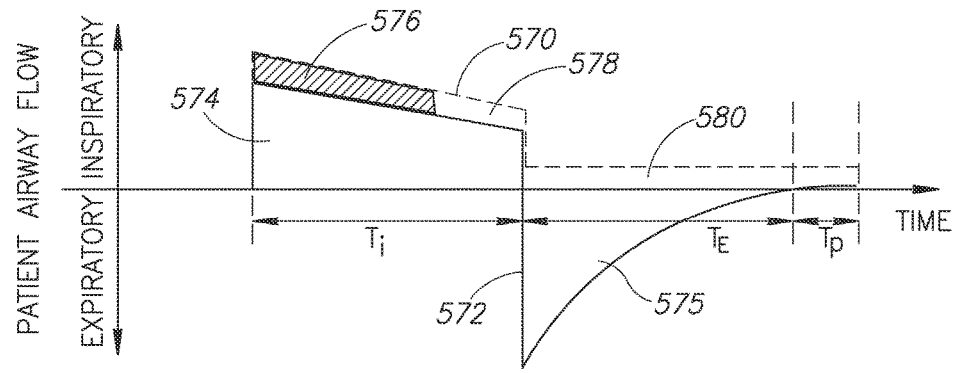
FIG. 14A is a graph showing patient airway flow using a prior art ventilator during both inspiratory and expiratory phases.
Figure 14B:
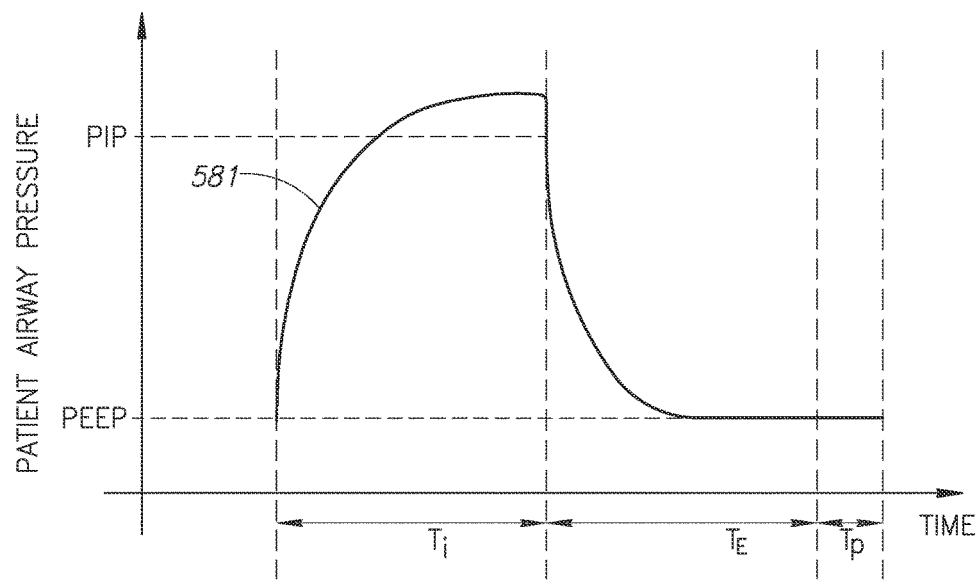
FIG. 14B is a graph showing patient airway pressure using the prior art ventilator during both the inspiratory and expiratory phases.

FIGS. 14A and 14B are graphs illustrating traditional delivery of oxygen by a conventional portable ventilator connected to an external low pressure continuous flow source, such as a stand-alone oxygen concentrator. In FIG. 14A, the conventional portable ventilator is using traditional volume controlled ventilation to deliver breaths. In both FIGS. 14A and 14B, the x-axis is time. The inspiratory phase occurs during the duration $T_I$. The exhalation phase occurs during a duration $T_E$. The pause occurs during a duration $T_P$.

In FIG. 14A, the y-axis is flow rate within the patient's airway. Referring to FIG. 14A, a dashed line 570 illustrates a continuous flow of oxygen delivered during both the inspiratory and expiratory phases. A solid line 572 illustrates a flow of air provided by the conventional portable ventilator during both the inspiratory and expiratory phases. The solid line 572 is determined by a set of desired ventilator settings.

An area 574 illustrates an inspiratory volume of air received by the patient, and an area 575 illustrates an expiratory volume of air expelled by the patient. The area 574 represents the desired total tidal volume selected by the user.

A shaded area 576 illustrates a volume of effective oxygen provided to the patient during the inspiratory phase. An area 578 illustrates a volume of oxygen that is delivered by the conventional portable ventilator during the inspiratory phase but is unusable (e.g., trapped in one or more anatomical dead spaces). Together the areas 576 and 578 form a volume of gases that exceed the desired ventilator settings (e.g., a desired total tidal volume). Specifically, together the areas 574, 576, and 578 form a total inspiratory volume (of oxygen and air) delivered by the conventional portable ventilator that exceeds the desired total tidal volume. An area 580 illustrates a volume of oxygen delivered by the conventional portable ventilator during the exhalation phase that is wasted by the conventional portable ventilator.

In FIG. 14B, the conventional portable ventilator is using traditional pressure controlled ventilation to deliver breaths. Referring to FIG. 14B, the y-axis is pressure within the patient's airway. A pressure value "PIP" identifies the peak inspiratory pressure input or desired by the user. A solid line 581 illustrates patient airway pressure during both the inspiratory and expiratory phases. Unfortunately, as FIG. 14B illustrates, the continuous flow of oxygen (illustrated in FIG. 14A by the dashed line 570) causes the pressure within the patient's airway to exceed the peak inspiratory pressure input by the user (the pressure value "PIP").

As shown in FIGS. 14A and 14B, the conventional portable ventilator is inefficient. For example, the conventional portable ventilator wastes all of the continuous flow of oxygen (illustrated in FIG. 14A by the dashed line 570) delivered during non-inspiratory time. Further, because the continuous flow of oxygen delivered to the patient is not controlled (e.g., by ventilator volume or inspiratory pressure settings), only a portion of the oxygen (illustrated by the shaded area 576) delivered is actually effective. Further, the continuous flow of oxygen causes the peak inspiratory pressure input by the user to be exceeded when pressure controlled ventilation is used. One reason for this problem is that the conventional ventilator does not know how much oxygen (e.g., volume or rate) is being delivered to the patient.

While FIGS. 14A and 14B depict the conventional portable ventilator using traditional volume controlled ventilation and traditional pressure controlled ventilation, respectively, to deliver breaths, a similar result occurs when the conventional portable ventilator uses other types of ventilation because the ventilator does not know how much oxygen (e.g., volume or rate) is being delivered to the patient. Thus, the ventilator cannot accurately configure the breaths delivered (e.g., to achieve either a desired flow rate or pressure in the patient's airway).

Figure 15B:
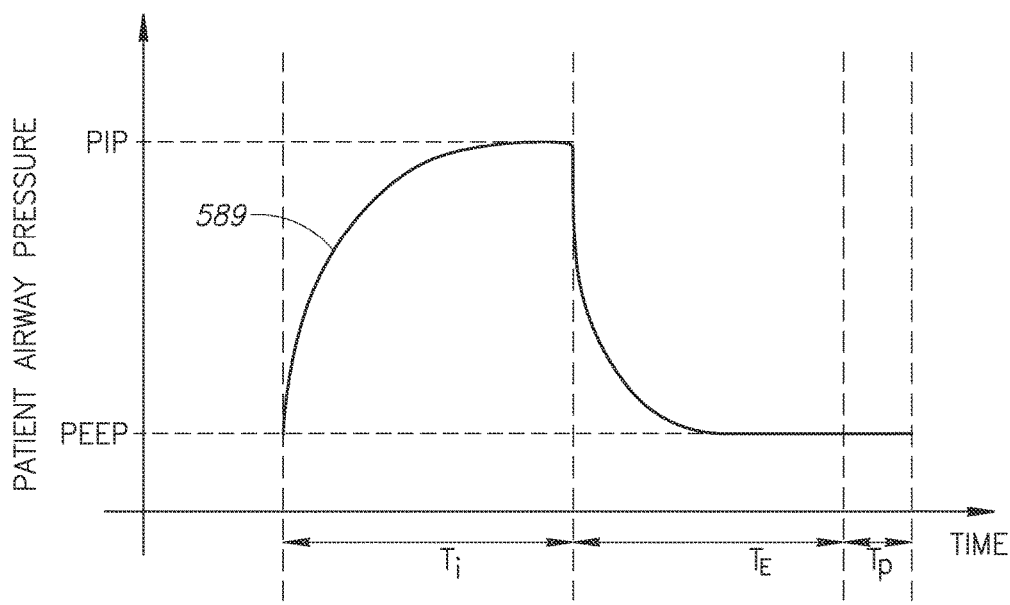
FIG. 15B is a graph showing patient airway pressure using the ventilator of FIG. 1 during both the inspiratory and expiratory phases.

FIGS. 15A and 15B are graphs illustrating oxygen delivery provided by the ventilator 100 illustrated in FIGS. 1 and 4. In FIG. 15A, the ventilator 100 is using volume controlled ventilation to deliver breaths. In both FIGS. 15A and 15B, the x-axis is time. The inspiratory phase occurs during the duration $T_I$. The exhalation phase occurs during the duration $T_E$. The pause occurs during the duration $T_P$.

Referring to FIG. 15A, a solid line 582 illustrates a flow of air provided by the ventilator 100 during both the inspiratory and expiratory phases. The solid line 582 is determined by a set of desired ventilator settings (e.g., values entered via the user interface 200 illustrated in FIG. 6). A shaded area 584 illustrates a volume of effective oxygen provided to the patient 102 at the beginning of the inspiratory phase. An area 586 illustrates a volume of air provided to the patient 102 during the inspiratory phase. Together the areas 584 and 586 form a total inspiratory volume (of oxygen and air) delivered by the ventilator 100. As mentioned above, this volume is also referred to as the total tidal volume. An area 588 illustrates an expiratory volume of air expelled by the patient 102.

FIG. 15A illustrates delivering one of the pulses of oxygen 140 (see FIG. 1) at the start of the inspiration phase before the gases 112 (see FIG. 1) are provided. For example, the ventilator 100 may wait until after the pulse of oxygen has been delivered before delivering the gases 112. Thus, at the start of each inspiration phase of each breath, the patient 102 (see FIG. 1) may be receiving only the pulse (or bolus) of oxygen from the ventilator 100. However, this is not a requirement. In alternate embodiments, the flow of the gases 112 may begin before the delivery of the bolus of oxygen has completed. In any event, the flow of the gases 112 are started before the end of the inspiration phase.

In FIG. 15B, the ventilator 100 is using pressure controlled ventilation to deliver breaths. Referring to FIG. 15B, the y-axis is pressure within the patient's airway. A solid line 589 illustrates patient airway pressure during both the inspiratory and expiratory phases. As FIG. 15B illustrates, the pressure within the patient's airway does not exceed the peak inspiratory pressure value input by the user (the pressure value "PIP") using the pressure control input 237 (see FIG. 6).

As shown in FIGS. 15A and 15B, the ventilator 100 is more efficient than the conventional portable ventilator. For example, the ventilator 100 does not provide a continuous flow of oxygen and therefore, avoids wasting oxygen during non-inspiratory times. Further, the total inspiratory volume is in accordance with (and does not exceed) the desired ventilator settings. And furthermore, the oxygen is delivered in the first part of the breath where the oxygen provides better oxygenation, as opposed to during the last part of the breath when the oxygen becomes trapped in the anatomical dead spaces. Further, because the ventilator 100 knows the total tidal volume delivered, the ventilator 100 may configure the breaths not to exceed a user supplied peak inspiratory pressure value (e.g., when pressure ventilation is used). Thus, one of ordinary skill in the art through application of the present teachings could configure the ventilator 100 to deliver any desired type of ventilation in which oxygen is delivered in the first part of the breath. Further, the delivery of the pulses of oxygen 140 (see FIG. 1) may begin before the initiation of each breath.

Referring to FIG. 13D, for pulse dose delivery, the control system 220 instructs the second rotary valve assembly 330 (via the control signal 546 depicted in FIG. 7B) to rotate the cam 530 to open the poppet valve CV8. The inspiratory phase may be initiated by either the control system 220 or the patient 102. After detecting the beginning of an inspiratory phase, the control system 220 instructs the stepper motor 322 of the metering valve 320 to deliver a desired dose or pulse of oxygen to the patient circuit 110, referred to as a "bolus." Thus, the ventilator 100 is configured to synchronize a bolus of oxygen with the patient's breathing. For example, the ventilator 100 may be configured to provide the volume (or bolus) of oxygen depicted by the area 584 of FIG. 15A.

The user interface 200 may be used to determine parameter values for the bolus. For example, if the oxygen flow equivalent input 244 (see FIG. 6) allows the user to select a numerical value (e.g., from 1 to 10), each successive number may represent an amount of "equivalent oxygenation" relative to a continuous flow of oxygen. For example, the number "2" may provide a bolus of oxygen at the beginning of a breath that would provide oxygenation equivalent to a bleed-in flow of oxygen at two liters per minute from an external source (e.g., the low pressure oxygen source 118 depicted in FIG. 1). By way of another non-limiting example, the user may select a numerical value within a predetermined range that represents from about 0.2 liters per minute to about 9 liters per minute in increments of about 0.1 liters per minute.

Because at least some of the oxygen delivered using a hypothetical continuous flow of oxygen is wasted, the control system 220 is configured to deliver an amount of oxygen in the bolus that is less than an amount of oxygen that would be delivered by the continuous flow of oxygen during the inspiration phase.

In alternate embodiments, the user may enter a pulse volume value using the oxygen pulse volume input 251 (see FIG. 6) that specifies the size of the bolus. The pulse volume value may be expressed in milliliters or a dimensionless value within a predetermined numerical range (e.g., from 1 to 10). In such embodiments, each successive number may represent a greater amount of oxygen.

The control system 220 adjusts the delivery of the breath to account for the bolus, and ensures that the breath is delivered in accordance with the user setting of tidal volume (entered via the tidal volume input 242 depicted in FIG. 6) or the peak inspiratory pressure value (e.g., entered via the pressure control input 237 depicted in FIG. 6). By way of a non-limiting example, the control system 220 may configure the bolus to have a volume that is less than about 75% of the total tidal volume delivered. By way of another non-limiting example, the control system 220 may configure the bolus to have a volume that is between about 50% and about 75% of the total tidal volume delivered.

Further, the ventilator 100 is configured to adjust the parameter values (e.g., volume, pressure, etc.) of the inspiratory gases 108 to assure the inspiratory gases 108 are delivered correctly. For example, if the user (e.g., a clinician) uses the tidal volume input 242 (see FIG. 6) to set the total tidal volume value to 500 ml, and the oxygen pulse volume input 251 (see FIG. 6) to set the pulse volume value to 100 ml, the control system 220 will set the air delivery from the accumulator 202 to 400 ml, thus providing the correct total volume (500 ml=400 ml+100 ml) to the patient circuit 110.

The control system 220 may deliver a user-set bolus of oxygen (e.g., in the gases 112 and/or the pulses of oxygen 140) to the patient connection 106. The size of the bolus is controlled by the metering valve 320. The control system 220 reduces the flow of the gases 252 (see FIG. 5A) as measured by the internal flow transducer 212 (and encoded in the flow signal 270 illustrated in FIG. 5E) to satisfy a user set tidal volume value (when volume ventilation is used) or a user set peak inspiratory pressure value (when pressure ventilation is used).

The total inspiratory flow rate and volume of the gases 112 (see FIG. 1) may be determined using the flow signal 270 (see FIG. 5E), and the pulse volume may be determined using the signal 358 (see FIG. 7B) and the stepper position value (described above) of the metering valve 320. Further, the control system 220 controls the pulse (or bolus) volume using the control signal 360 (see FIG. 7B) sent to the stepper motor 322 (see FIG. 7B) of the metering valve 320. The control system 220 sets the air delivery from the accumulator 202 using the control signal 278 (see FIG. 5E) sent to the motor 272 of the blower 222.

Referring to FIG. 13C, for mixed oxygen delivery, the cam 530 of the second rotary valve assembly 330 is positioned so that the poppet valve CV7 is in the open position. The control system 220 determines the oxygen flow required at a given time to achieve a FI02 input by the user (e.g., via the FI02 input 246 depicted in FIG. 6). The FI02 may be expressed within a range (e.g., about 21% to about 100%). The control system 220 may use the control signal 360 (see FIG. 7B) to position the metering valve 320 to achieve the desired oxygen flow. The control system 220 may use the oxygen concentration signal 276 (see FIG. 5E) from the oxygen sensor 227 to monitor the gases 252 that pass through the internal bacterial filter 230 and emerge as the gases 112.

Suction Assembly

Figure 16:
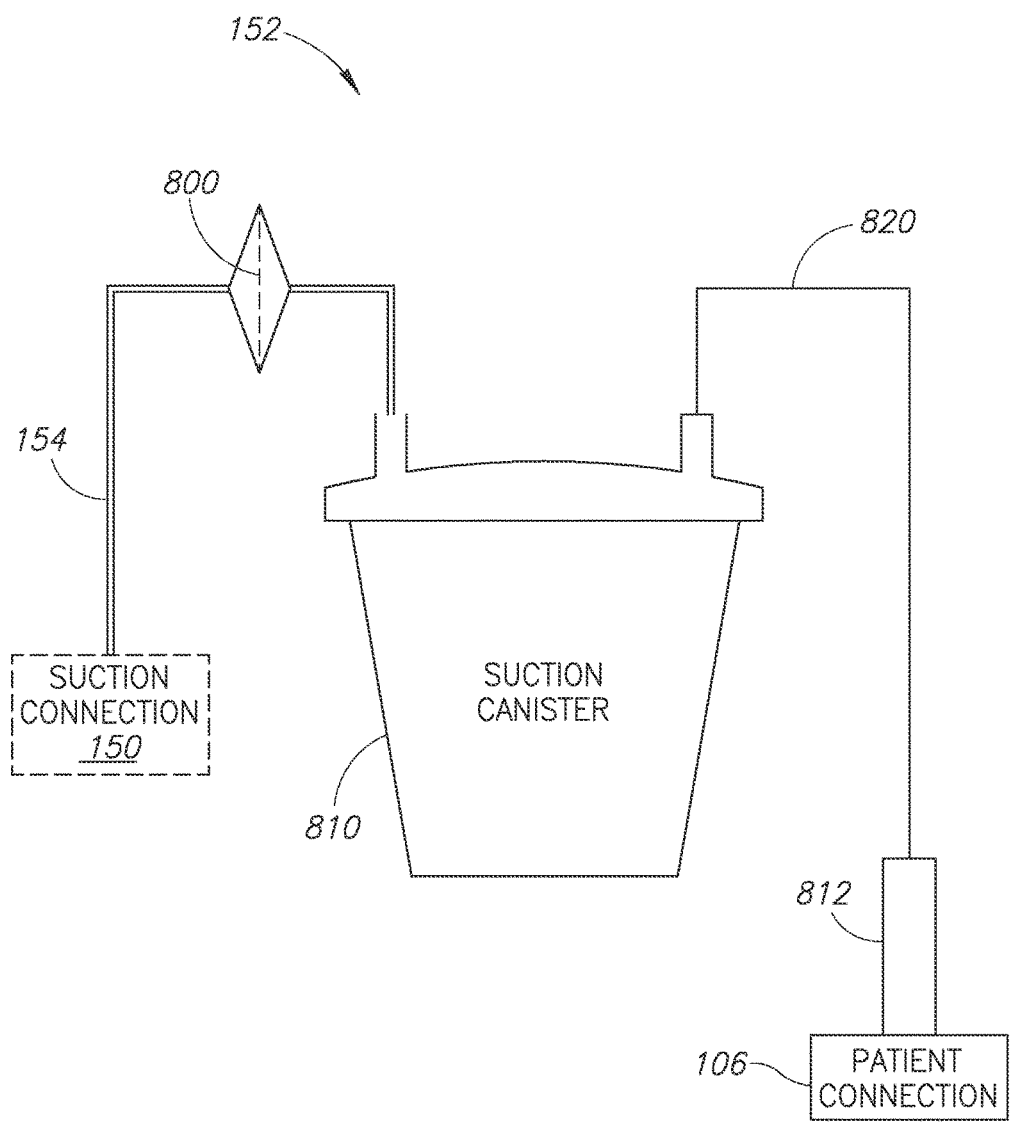
FIG. 16 is a block diagram illustrating an exemplary suction assembly for use with the ventilator of FIG. 1.

Referring to FIG. 16, the suction assembly 152 may include a filter 800, a conventional suction canister 810, a conventional suction catheter 812, and tubing 820 configured to be connected to the suction catheter 812. The suction catheter 812 may be configured to be inserted inside the patient connection 106.

Referring to FIG. 1, the suction assembly 152 provides a means to use the suction 154 provided by the ventilator 100 to "vacuum" secretions from the patient's airway. Referring to FIG. 10G, the control system 220 positions the cam 850 of the first rotary valve assembly 306 to open the poppet valves CV1 and CV3, and, referring to FIG. 13A, the control system 220 positions the cam 530 of the second rotary valve assembly 330 to open the poppet valve CV5. In this configuration, the compressor 302 pulls gas and secretions from the suction catheter 812 (see FIG. 16), through the tubing 820 and into the suction canister 810 (see FIG. 16) where the liquid secretions are trapped. The filter 800 (e.g., a hydrophobic filter) may be used to further prevent patient secretions from entering the ventilator 100 through the suction connection 150. However, gas pulled into the ventilator 100 continues through the first and second rotary valve assemblies 306 and 330, and enters the compressor 302. The control system 220 controls the speed of the motor 350 of the compressor 302 to achieve the user set suction pressure, as measured by the pressure transducer PT2.

Nebulizer Assembly

Referring to FIG. 1, the nebulizer assembly 162 provides a means to use the gases 164 provided by the ventilator 100 for delivering aerosolized medications to the patient's lung(s) 142. Referring to FIG. 10F, the control system 220 positions the cam 850 of the first rotary valve assembly 306 to open the poppet valves CV2 and CV4, and, referring to FIG. 13B, the control system 220 positions the cam 530 of the second rotary valve assembly 330 to open the poppet valve CV6. In this configuration, gas flows from the compressor 302, through the first and second rotary valve assemblies 306 and 330, and on to the nebulizer assembly 162. The control system 220 controls the speed of the motor 350 of the compressor 302 to maintain a desired pressure (e.g., about 12 PSIG) as measured by the pressure transducer PT2. The first rotary valve assembly 306 may be cycled to synchronize medication delivery with the inspiratory phase as desired. In a manner similar to that used for pulse dose oxygen delivery, the control system 220 may compensate (or adjust) the breaths delivered to account for the additional volume delivered by the nebulizer assembly 162.

Cough Assist

As mentioned above, a normal cough may be characterized as having an insufflation phase followed by an exsufflation phase. During the insufflation phase, the patient 102 (see FIG. 1) draws gases into the patient's lung(s) 142 (see FIG. 1). During the exsufflation phase, the patient 102 exhales at least a portion of the gases in the patient's lung(s) 142 (which may include secretions from the patient's lung(s) 142) using a peak flow rate and a peak pressure that are both greater than that used during the exhalation phase of normal breathing. The ventilator 100 (see FIGS. 1 and 4) is configured to provide cough assist functionality that facilitates secretion clearance by creating an exhaled flow rate and/or pressure that simulates a normal cough. Referring to FIG. 6, the user may use the activate cough assist input 241 to instruct the ventilator 100 (see FIGS. 1 and 4) to switch from a normal breathing mode to a cough assist mode during which the cough assist functionality is used to perform a cough assist maneuver with the patient 102 (see FIG. 1).

As mentioned above, the ventilation assembly 190 may include either the cough assist valve 204 or the cough assist valve 2000. Referring to FIG. 50, if the ventilation assembly 190 includes the cough assist valve 204, at the beginning of the insufflation phase, the control system 220 places the cough assist valve 204 in the first configuration (FIGS. 5A, 5C and 18A). Thus, the blower 222 can deliver the gas 252 to the main ventilator connection 104 in the same manner that a normal breath is delivered. The control system 220 (see FIG. 5E) instructs the blower 222 (using the control signal 1180) to deliver flow to achieve pressure in accordance with the user input settings for insufflation and exsufflation pressure. These settings are usually for greater flow rate and/or pressure than used during a normal breath but that many not always be the case. In other words, the blower 222 adds energy to the gas 252 (e.g., increases its flow rate and/or pressure) that exits the blower 222 and flows into the blower-to-valve inlet 1004 of the cough assist valve 204. The gas 252 flows through a portion of the cough assist valve 204 and exits the cough assist valve 204 into the flow line 273 via the aperture 1010. The flow line 273 conducts the gas 252 to the main ventilator connection 104. The main ventilator connection 104 is coupled (e.g., directly or using a hose, flow line, conduit, or tube) to the patient circuit 110 (see FIG. 1), which conducts the inspiratory gases 108 to the patient connection 106, which in turn conducts the inspiratory gases 108 on to the patient 102. The inspiratory gases 108 inflate the lung(s) 142 and raise the pressure to a desired insufflation pressure (see FIG. 26).

At the end of the insufflation phase, the control system 220 (see FIG. 5E) instructs the cough assist valve 204 (using the control signal 1180) to transition to the second configuration (see FIGS. 5B, 5D, and 18B). The control system 220 also instructs the blower 222 (using the control signal 1180) to increase its speed to achieve a desired exsufflation pressure (see FIG. 26). This creates a high peak exsufflation flow rate. At the end of the exsufflation phase, if desired, the cough assist maneuver may repeated.

If the ventilation assembly 190 includes the cough assist valve 2000 (see FIGS. 34A and 34B) instead of the cough assist valve 204, at the beginning of the insufflation phase, the control system 220 places the cough assist valve 2000 in the first configuration (see FIG. 34A). The control system 220 (see FIG. 5E) instructs the blower 222 (using the control signal 1180) to apply a selected flow rate and/or pressure which often is greater than used during a normal breath. The gas 252 exits the blower 222 and flows into the blower-to¬valve inlet 2004 of the cough assist valve 2000. The gas 252 flows through a portion of the cough assist valve 2000 and exits the cough assist valve 2000 into the flow line 273 via the aperture 2010. The flow line 273 conducts the gas 252 to the main ventilator connection 104. The main ventilator connection 104 is coupled (e.g., directly or using a hose, flow line, conduit, or tube) to the patient circuit 110 (see FIG. 1), which conducts the inspiratory gases 108 to the patient connection 106, which in turn conducts the inspiratory gases 108 on to the patient 102. The inspiratory gases 108 inflate the lung(s) 142 and raise the pressure to a desired insufflation pressure (see FIG. 26). At the end of the insufflation phase, the control system 220 (see FIG. 5E) instructs the cough assist valve 2000 (using the control signal 1180) to transition to the second configuration (see FIG. 34B). The control system 220 also instructs the blower 222 (using the control signal 1180) to increase its speed to achieve a desired exsufflation pressure (see FIG. 26). This creates a high peak exsufflation flow rate. At the end of the exsufflation phase, if desired, the cough assist maneuver may repeated.

Figure 26:
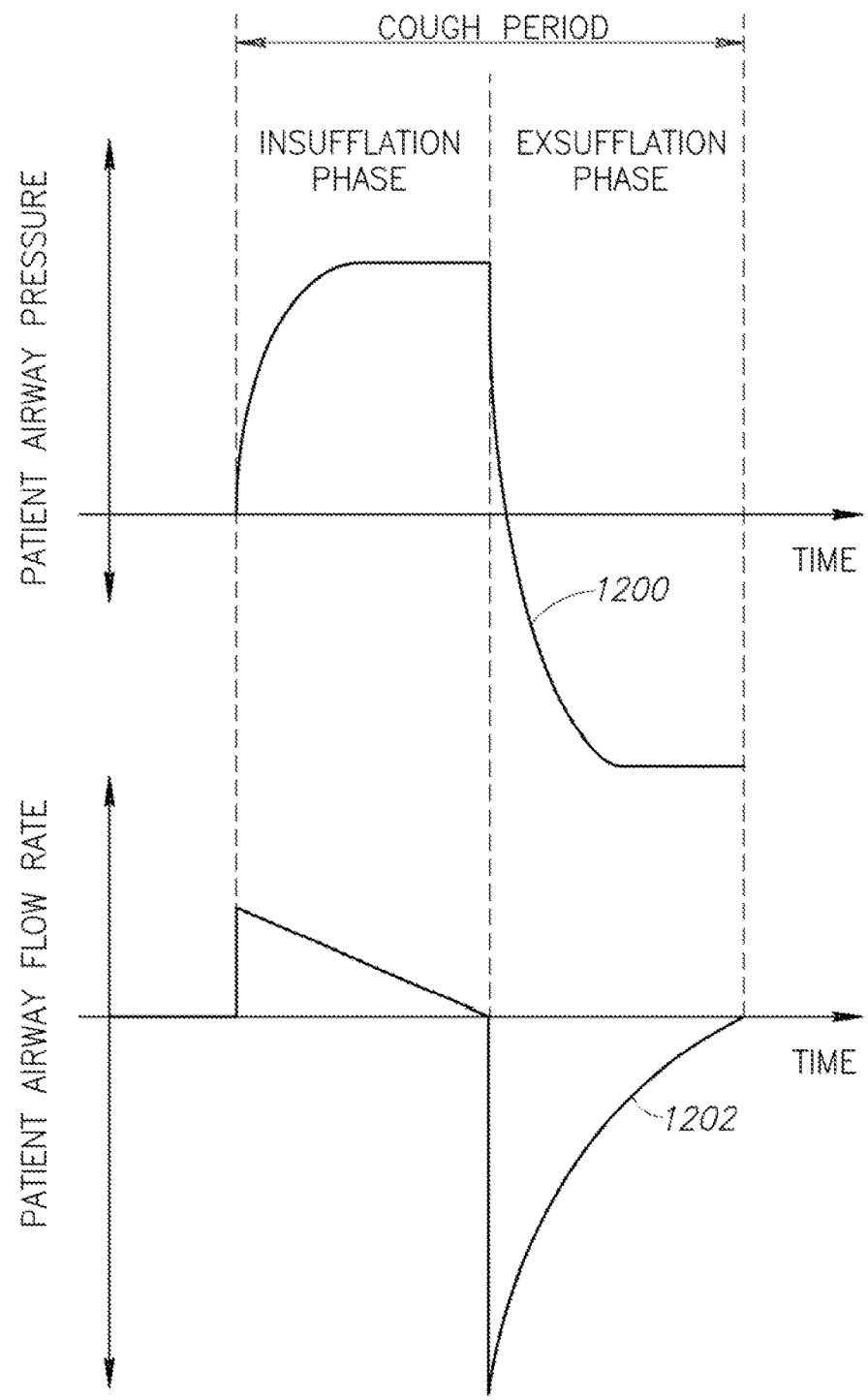
FIG. 26 is a pair of graphs with the top graph showing airway pressure during both insufflation and exsufflation phases of a cough assist maneuver performed using the ventilator, and the bottom graph showing airway flow rate during both the insufflation and exsufflation phases of the cough assist maneuver performed using the ventilator.

Referring to FIG. 26, a line 1200 illustrates airway pressure during both the insufflation and exsufflation phases of a cough assist maneuver performed using the ventilator 100. Referring to FIG. 26, a line 1202 illustrates airway flow rates during both the insufflation and exsufflation phases of a cough assist maneuver performed using the ventilator 100.

Because the ventilator 100 combines both mechanical ventilation and cough assist functions into one device, it is desirable to use the same tubing for both ventilation and cough assist so the user does not have to change tubing connections between operations. Keeping the tubing connection intact may also provide one or more of the following benefits:

1. better maintenance of the patient's oxygenation level,
2. reduced likelihood of ventilator-associated pneumonia, and
3. reduced risks associated with possible errors of reconnection.

Unfortunately, prior art passive patient circuits are inadequate for use with cough assist because they include a fixed leak valve that reduces the negative pressure in the patient circuit during the exsufflation phase. This reduction in negative pressure causes an undesirable reduction in the flow rate from the patient's lungs, which in turn compromises secretion clearance.

The passive patient circuit 440 illustrated in FIG. 2B avoids this problem because the passive patient circuit 440 includes the valve assembly 448 or the valve assembly 1448 (see FIGS. 30-31C). When the passive patient circuit 440 includes the valve assembly 448, the peripheral portion 473 of the leaf 470 of the valve assembly 448 is configured to transition or deflect from the open position (see FIG. 2D) to the closed position (see FIG. 2C) when the pressure inside the passive patient circuit 440 (see FIG. 2B) is less than the threshold amount (e.g., environmental pressure). When the peripheral portion 473 of the leaf 470 is in the closed position depicted in FIG. 2C, the leaf 470 blocks off the one or more openings 478 and isolates the chamber 474 from the environment inside the passive patient circuit 440 (see FIG. 2B). Thus, the leaf 470 prevents a flow of air into the passive patient circuit 440 (through the one or more openings 478) while the patient circuit pressure is less than the threshold amount (e.g., when the patient circuit pressure is negative). The valve assembly 448 may be characterized as being a positive pressure leak valve in embodiments in which the valve assembly 448 is open when the patient circuit pressure is positive and closed when the patient circuit pressure is negative.

Similarly, referring to FIGS. 31A and 31B, when the passive patient circuit 440 (see FIG. 2B) includes the valve assembly 1448, the peripheral portion 1473 of the leaf 1470 of the valve assembly 1448 is configured to transition or deflect from the open position (see FIG. 31B) to the closed position (see FIG. 31A) when the pressure inside the passive patient circuit 440 (see FIG. 2B) is less than the threshold amount (e.g., environmental pressure). When the peripheral portion 1473 of the leaf 1470 is in the closed position depicted in FIG. 31A, the leaf 1470 blocks off the one or more openings 1478 and isolates the chamber 1474 from the environment inside the passive patient circuit 440 (see FIG. 2B). Thus, the leaf 1470 prevents a flow of air into the passive patient circuit 440 (through the one or more openings 1478) while the patient circuit pressure is less than the threshold amount (e.g., when the patient circuit pressure is negative). The valve assembly 1448 may be characterized as being a positive pressure leak valve in embodiments in which the valve assembly 1448 is open when the patient circuit pressure is positive and closed when the patient circuit pressure is negative.

When a passive patient circuit (e.g., the passive patient circuit 170, the passive patient circuit 440, and the like) that includes a suitable passive leak valve (e.g., the leak valve 177, the valve assembly 448, the valve assembly 1448, and the like) is used, gas flows to the patient 102 through the passive patient circuit during the insufflation phase. Some of the flow leaks out through the passive leak valve, and the rest travels into the patient's lung(s) 142 (see FIG. 1). If the ventilation assembly 190 includes the cough assist valve 204 (see FIGS. 5A-5D and 17A-18B), at the end of the insufflation phase, the control system 220 transitions the cough assist valve 204 to the second configuration (see FIGS. 5B, 5D, and 18B), and increases the speed of the blower 222 to achieve a desired exsufflation pressure. On the other hand, if the ventilation assembly 190 includes the cough assist valve 2000 (see FIGS. 34A and 34B), at the end of the insufflation phase, the control system 220 transitions the cough assist valve 2000 to the second configuration (see FIG. 34B), and increases the speed of the blower 222 to achieve a desired exsufflation pressure. A check valve component (e.g., the flap 179, the leaf 470, the leaf 1470, and the like) of the passive leak valve prevents external flow from entering the passive patient circuit.

Alternatively, the active patient circuit 600 illustrated in FIG. 3A may be used during a cough assist maneuver. When the active patient circuit 600 is used, the active exhalation valve assembly 604 is closed during both the insufflation and exsufflation phases. During the insufflation phase, the control system 220 closes the active exhalation valve assembly 604 by energizing or activates the solenoid valve SV6 (using the control signal 286), which connects the pressure of the gases 252 (via the port 275B) to the pilot port 111C. During the exsufflation phase, the control system 220 de-energizes or deactivates the solenoid valve SV6 (using the control signal 286), which connects the internal pressure of the accumulator A2 (or the pilot pressure) to the active exhalation valve assembly 604. This causes the active exhalation valve assembly 604 to remain closed. The active exhalation valve assembly 604 remains closed because the pilot pressure is higher than patient pressure, and (as explained above) the area of the double bellows member 644 exposed to a pressure provided by the patient 102 (see FIG. 1) via the patient connection 106 is less than an area exposed to the pressure of the pressure signal 1090. Thus, even if the two pressures are equal, the closed end 666 of the double bellows member 644 will move to or remain in the closed position against the seat 680. It is noted that in the cough assist mode, the pressure in Accumulator A2 is set to zero. At the beginning of exsufflation, the patient pressure is higher than pressure signal 109C, so the exhalation valve opens. This is beneficial since it drops the pressure faster, and creates greater exsufflation flow. When the patient pressure drops below ambient, the active exhalation valve assembly 604 closes, preventing ambient gas from entering into the patient circuit.

Section Trap

During a conventional cough assist maneuver, the patient connection 106 (e.g., a tracheostomy tube) is pneumatically connected by cough assist tubing (e.g., tubing having an inner diameter of about 22 mm) to a cough assist device. By way of a non-limiting example, the patient connection 106 (e.g., a tracheostomy tube) may have an outer diameter of about 15 mm and an inner diameter of about 8 mm. Current practice is to connect the cough assist tubing to the patient connection 106 utilizing a connector, such as a connector or adapter having an outer diameter of 22 mm and an inner diameter of 15 mm. The connector may be straight, right angled, flexible, or outfitted with a swivel connector. The connector functions as an adaptor that transitions from the outside diameter (e.g., about 15 mm) of the patient connection 106 (e.g., a tracheostomy tube) to the inside diameter (e.g., about 22 mm) of the cough assist tubing. Thus, the flow pathway from the patient connection 106 to the cough assist tubing includes an abrupt transition (e.g., from an inner diameter of about 15 mm to an inner diameter of about 22 mm).

Unfortunately, currently available connectors used to connect the patient connection 106 to the cough assist tubing (which is connected to a cough assist device) are not designed to trap secretions generated by a cough assist maneuver. It is common for patient secretions to exit the patient connection 106 (e.g., a tracheostomy tube) during the exsufflation phase, collect in the connector, and travel back toward and/or into the patient connection 106 during the insufflation phase, which is not desired. This process is typically repeated several times until the secretions eventually migrate into the cough assist tubing. Then, the cough assist tubing is removed and disposed of or cleaned.

Figure 27:
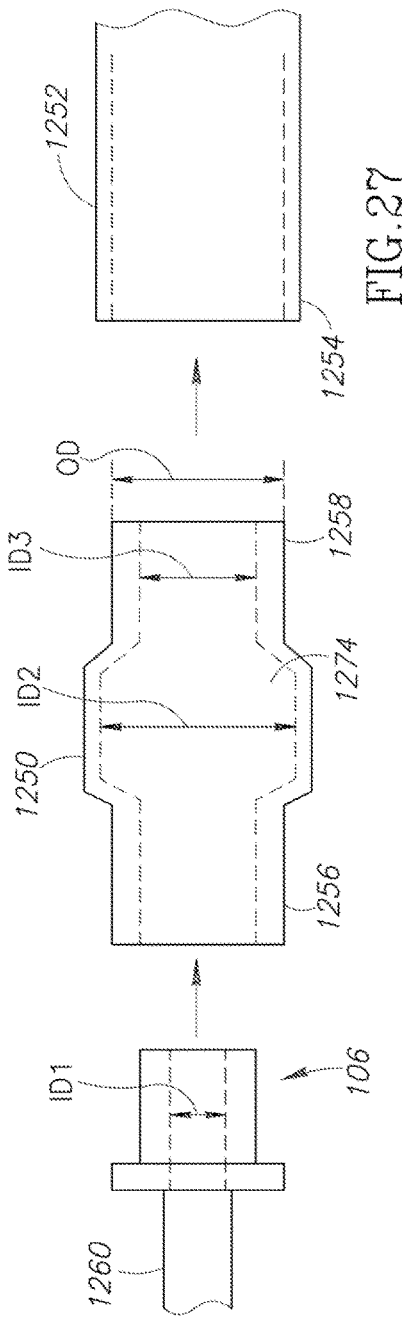
FIG. 27 is a side view of a secretion trap.
Figure 28:
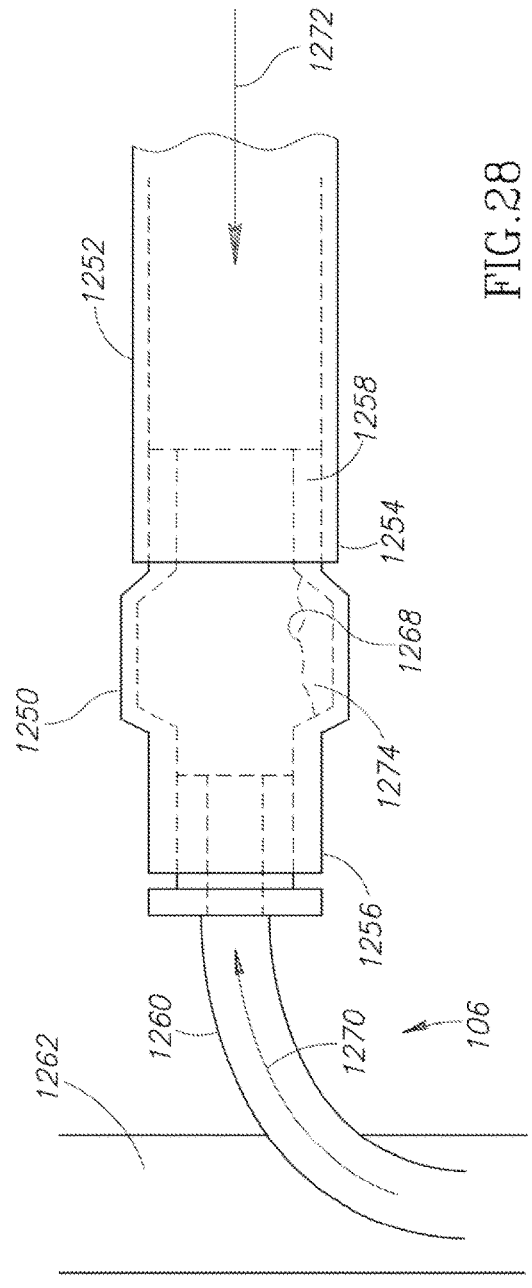
FIG. 28 is a side view of the secretion trap of FIG. 27 connected to both a patient connection and a patient circuit connection.

FIG. 27 illustrates a secretion trap 1250 that may be used instead of a conventional connector to connect the patient connection 106 to a cough assist tube 1252 serving as or as part of the patient circuit 110. Alternatively, the secretion trap 1250 may be formed in an end 1254 of the cough assist tube 1252. In FIGS. 27 and 28, the patient connection 106 has been illustrated as a tracheostomy tube 1260 connected to a patient airway 1262 (see FIG. 28). The cough assist tube 1252 may be connected to a conventional cough assist device (not shown).

Alternatively, the secretion trap 1250 may be used to connect the patient connection 106 to the patient circuit 110 (e.g., the passive patient circuit 440, the active patient circuit 600, and the like) directly or using a hose, flow line, conduit, or tube. In such embodiments, the patient circuit 110 is connected to the main ventilator connection 104 (and optionally to the patient oxygen outlet 105). Alternatively, the secretion trap 1250 may be implemented as a component of the patient circuit 110.

In the embodiment illustrated, the secretion trap 1250 has a first end portion 1256 opposite a second end portion 1258. The first end portion 1256 is couplable to the patient connection 106, and the second end portion 1258 is couplable to the cough assist tube 1252 or the patient circuit 110 (see FIG. 1).

Referring to FIG. 28, unlike conventional connectors (that may be used to connect the patient connection 106 to the cough assist tube 1252), the secretion trap 1250 is configured to trap patient secretions 1268 during a cough assist maneuver. Referring to FIG. 27, internal geometry of the secretion trap 1250 is configured to create first and second inner diameter steps. The first step transitions from an inner diameter "ID1" of the patient connection 106 (e.g., about 8 mm) to a significantly larger inner diameter "ID2" (e.g., greater than about 22 mm) of the secretion trap 1250. The second step transitions from the inner diameter "ID2" to a smaller inner diameter "IDS" (e.g., about 15 mm). The second end portion 1258 of the secretion trap 1250 has an outer diameter "OD" (e.g., about 22 mm) configured to mate with the cough assist tube 1252.

The small inner diameter "ID1" causes exsufflation flows (identified by an arrow 1270 in FIG. 28) to have a high first velocity that mobilizes secretions. The first (rapid) step to the larger inner diameter "ID2" causes the velocity of the exsufflation flows to reduce to a slower second velocity. This reduction in velocity causes the secretions 1268 (see FIG. 28) to settle or collect in a well 1274 created by the larger inner diameter "ID2." The well 1274 protects the secretions 1268 (see FIG. 28) from re-mobilization during inspiratory flows (identified by an arrow 1272 in FIG. 28). Further, patient secretions typically have a high surface tension that helps retain them in the well 1274 until they can be removed, which helps prevent contamination of the cough assist tube 1252 or the patient circuit 110 (see FIG. 1).

As mentioned above, because a cough assist maneuver may move secretions during both the exsufflation and insufflation phases, some secretions may remain within the patient connection 106 after the cough assist maneuver. For this reason, the patient connection 106 is often suctioned to remove these remaining secretions after the cough assist maneuver.

Figure 29:
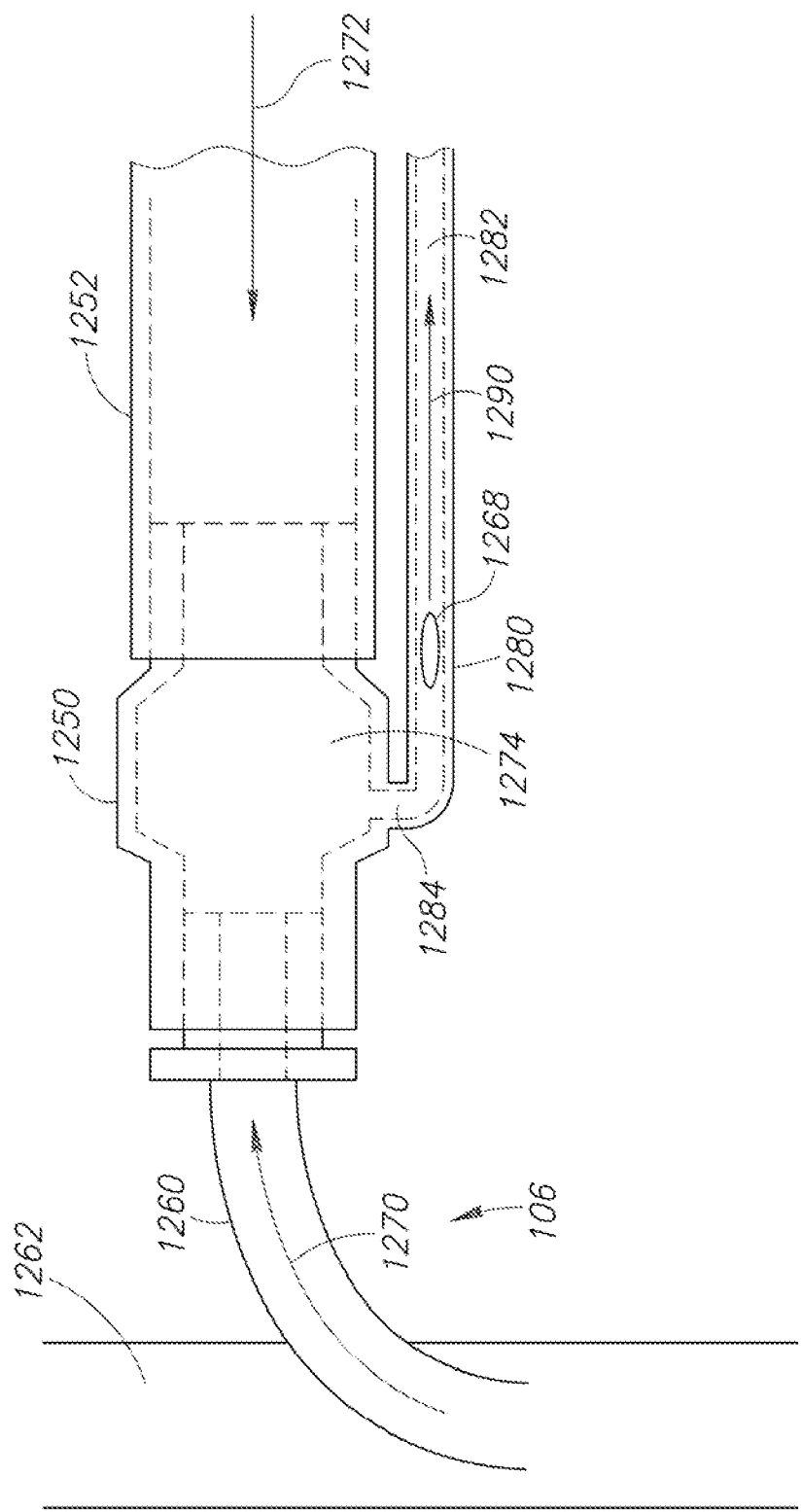
FIG. 29 is a side view of an embodiment of the secretion trap of FIG. 28 including a drain.

FIG. 29 illustrates the secretion trap 1250 connected to a drain 1280 configured to provide suction during a cough assist maneuver. Thus, the secretion trap 1250 may be used to provide an improved therapy in which the secretions 1268 are suctioned as they exit the patient connection 106 during a cough assist maneuver. The drain 1280 includes an open-ended tube section 1282 having a first end portion 1284 in fluid communication with the well 1274, and a second end portion (not shown) in fluid communication with a suction device (e.g., the suction assembly 152 illustrated in FIGS. 1 and 16). The first end portion 1284 may be positioned nearer the patient connection 106 than the cough assist tube 1252 or the patient circuit 110 (see FIG. 1). The suction device provides negative pressure (depicted as an arrow 1290) to the drain 1280 during a cough assist maneuver that suctions the secretions 1268 from the well 1274. The negative pressure draws the secretions 1268 into the open-ended tube section 1282 (via its first end portion 1284) as the secretions exit the patient connection 106, thereby keeping the ventilation airway (e.g., the patient circuit 110) clear of secretions that may impede ventilation.

While the drain 1280 has been described and illustrated as being connected to the secretion trap 1250, in alternate embodiments, the drain 1280 may be connected to other structures at or near the patient connection 106. For example, the drain 1280 may be connected directly to the patient connection 106. Alternatively, the drain 1280 may be connected to the patient circuit 110.

The drain 1280 may provide one or more of the following features:
1. improved clearance of the ventilation airway,
2. reduced contamination, and
3. reduced need to disconnect the patient connection 106 from mechanical ventilation (e.g., provided by the ventilator 100).

Because the drain 1280 provides secretion clearance without disconnecting the patient circuit 110 from the patient 102, the drain 1280 may be particularly useful with the ventilator 100, which is configured to provide both mechanical ventilation and cough assist.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. An active exhalation valve for use with a patient connection and a ventilator having a pressure source usable to control operation of the valve, comprising:
   a valve body having an internal body chamber with gasses therein having a body chamber pressure;
   a first body port in fluid communication with the body chamber and configured for fluid communication with the patient connection;
   a second body port in fluid communication with the body chamber and configured for fluid communication with the ventilator;
   a passageway in fluid communication with the body chamber and with ambient air exterior of the valve body; and
   a valve seal movable between a closed position sealing the passageway and an open position opening the passageway, the valve seal having:
   (a) an outer member,
   (b) an inner member positioned within the outer member,
   (c) an internal seal chamber located between the outer and inner members and in fluid communication with the pressure source, and (d) a seal member extending between the inner and outer members and movable therewith, the seal member having a first surface portion inside the seal chamber configured for movement of the valve seal toward the closed position in response to pressure applied thereto by the pressure source and a second surface portion outside the seal chamber configured for movement of the valve seal toward the open position in response to pressure applied thereto by the body chamber pressure, with amount and direction of movement of the valve seal being responsive to a resultant force generated by the pressure source and the body chamber pressure on the first and second surface portions.

2. The exhalation valve of claim 1, wherein the inner member has an inner member fluid passageway extending therethrough in fluid communication with the body chamber and having a first end in fluid communication with the first body port and a second end in fluid communication with the second body port.

3. The exhalation valve of claim 2, wherein the inner member fluid passageway is in continuous fluid communication with the first and second body ports during operation of the exhalation valve, and out of fluid communication with the seal chamber between the inner and outer members.

4. The exhalation valve of claim 1, wherein the inner member has an inner member fluid passageway extending therethrough with a first opening in continuous fluid communication with the first body port and a second opening in continuous fluid communication with the second body port.

5. The exhalation valve of claim 1, wherein the body has a wall portion positioned outward of the valve seal and defining another chamber positioned outward of the valve seal with the passageway being in the wall portion.

6. The exhalation valve of claim 1, wherein the body has a perimeter wall portion extending circumferentially about the body chamber and positioned outward of the valve seal, and defining an elongated perimeter chamber extending at least partially about the body chamber, with the passageway being in the perimeter wall portion.

7. The exhalation valve of claim 1, wherein the passageway comprises a plurality of apertures in an external wall of the body in fluid communication with the body chamber and with ambient air exterior of the valve body.

8. An active exhalation valve for use with a patient connection and a ventilator having a pressure source usable to control operation of the valve, comprising:
a valve body having an internal body chamber with gasses therein having a body chamber pressure and a body wall portion with a channel therein for fluid communication with the pressure source and an aperture in fluid communication with the channel;
a first body port in fluid communication with the body chamber and configured for fluid communication with the patient connection;
a second body port in fluid communication with the body chamber and configured for fluid communication with the ventilator;
a passageway in fluid communication with the body chamber and with ambient air exterior of the valve body; and
a valve seal movable between a closed position sealing the passageway and an open position opening the passageway, the valve seal having:
(a) an outer longitudinally extending and longitudinally compressible wall,
(b) an inner longitudinally extending and longitudinally compressible wall positioned within the outer wall, each of the outer and inner walls having a first end and a second end,
(c) a seal end wall closing a space between the first ends of the outer and inner walls and being longitudinally movable with the first ends of the outer and inner walls,
(d) the body wall portion closing a space between the second ends of the outer and inner walls, and
(e) an internal seal chamber located between the outer and inner walls and extending between the seal end wall and the body wall portion, the aperture of the body wall portion being in fluid communication with the seal chamber to provide fluid communication with the pressure source, the seal end wall being longitudinally movable within the valve body between the closed position with the outer and inner walls being in an extended configuration and the open position with the outer and inner walls being compressed into at least a partially longitudinally compressed position, the seal end wall having a first surface portion inside the seal chamber configured for movement of the valve seal toward the closed position in response to pressure applied thereto by the pressure source and a second surface portion outside the seal chamber configured for movement of the valve seal toward the open position in response to pressure applied thereto by the body chamber pressure, with amount and direction of movement of the valve seal being responsive to a resultant force generated by the pressure source and the body chamber pressure on the first and second surface portions of the seal end wall.

9. The exhalation valve of claim 8, wherein the inner wall has an inner wall fluid passageway extending therethrough in fluid communication with the body chamber and having a first end in fluid communication with the first body port and a second end in fluid communication with the second body port.

10. The exhalation valve of claim 9, wherein the inner wall fluid passageway is in continuous fluid communication with the first and second body ports during operation of the exhalation valve, and out of fluid communication with the seal chamber between the inner and outer walls.

11. The exhalation valve of claim 8, wherein the inner wall has an inner wall fluid passageway extending therethrough with a first opening in continuous fluid communication with the first body port and a second opening in continuous fluid communication with the second body port.

12. The exhalation valve of claim 8, wherein the longitudinally compressible outer and inner walls are corrugated with a plurality of corrugations, and when in the at least partially longitudinally compressed position more than one of the corrugations is longitudinally compressed.

13. An active exhalation valve for use with a patient connection and a ventilator having a pressure source usable to control operation of the valve, comprising:
a valve body having an internal body chamber with gasses therein having a body chamber pressure and a channel therein for fluid communication with the pressure source and an aperture in fluid communication with the channel;
a first body port in fluid communication with the body chamber and configured for fluid communication with the patient connection;

a second body port in fluid communication with the body chamber and configured for fluid communication with the ventilator;

a passageway in fluid communication with the body chamber and with ambient air exterior of the valve body; and a valve seal movable between a closed position sealing the passageway and an open position opening the passageway, the valve seal having a seal chamber defined by first and second longitudinally spaced apart ends, and by an outer longitudinally extendable wall and an inner longitudinally extendable wall positioned within the outer wall, the aperture of the valve body being in fluid communication with the seal chamber to provide fluid communication with the pressure source, the first end of the seal chamber being longitudinally movable within the valve body between the closed position of the valve seal whereat the outer and inner walls are in a longitudinally extended configuration and the open position of the valve seal whereat the outer and inner walls are in a longitudinally retracted configuration, the valve seal being moved toward the closed position in response to pressure applied by the pressure source and toward the open position in response to pressure applied by the body chamber pressure, with amount and direction of movement of the valve seal being responsive to a resultant force generated by the pressure source and the body chamber pressure.

14. The exhalation valve of claim 13, wherein the inner wall has an inner wall fluid passageway extending therethrough in fluid communication with the body chamber and having a first end in fluid communication with the first body port and a second end in fluid communication with the second body port.

15. The exhalation valve of claim 14, wherein the inner wall fluid passageway is in continuous fluid communication with the first and second body ports during operation of the exhalation valve, and out of fluid communication with the seal chamber between the inner and outer walls.

16. The exhalation valve of claim 13, wherein the inner wall has an inner wall fluid passageway extending therethrough with a first opening in continuous fluid communication with the first body port and a second opening in continuous fluid communication with the second body port.

* * * * *

UNITED STATES PATENT AND TRADEMARK OFFICE
CERTIFICATE OF CORRECTION

PATENT NO. : 10,576,237 B2
APPLICATION NO. : 16/167414
DATED : March 3, 2020
INVENTOR(S) : Douglas F. DeVries et al.

It is certified that error appears in the above-identified patent and that said Letters Patent is hereby corrected as shown below:

In the Drawings

On sheet 18 of 61, in Figure 6, reference numeral 246, Line 1, delete "FI02" and insert -- FIO2 --, therefor.

On sheet 19 of 61, in Figure 7A, reference numeral 116, Line 1, delete "PATENT" and insert -- PATIENT --, therefor.

In the Specification

In Column 1, Line 13, delete "Apr. 25," and insert -- Apr. 24, --, therefor.

In Column 6, Line 33, delete "or" and insert -- for --, therefor.

In Column 7, Line 43, delete "80" and insert -- 8C --, therefor.

In Column 13, Line 67, delete "20)" and insert -- 2C) --, therefor.

In Column 14, Line 4, delete "20," and insert -- 2C, --, therefor.

In Column 14, Line 22, delete "patent" and insert -- patient --, therefor.

In Column 14, Line 66, delete "phases," and insert -- phases. --, therefor.

In Column 15, Line 3, delete "("cmH20")." and insert -- ("cmH2O"). --, therefor.

In Column 16, Line 53, delete "31A-310," and insert -- 31A-31C, --, therefor.

In Column 16, Line 55, delete "20-2E)." and insert -- 2C-2E). --, therefor.

Signed and Sealed this
Second Day of June, 2020

Andrei Iancu
*Director of the United States Patent and Trademark Office*

CERTIFICATE OF CORRECTION (continued)
U.S. Pat. No. 10,576,237 B2

In Column 16, Line 62, delete "310," and insert -- 31C, --, therefor.

In Column 17, Line 13, delete "patent" and insert -- patient --, therefor.

In Column 17, Line 48, delete "cmH20." and insert -- cmH2O. --, therefor.

In Column 18, Line 13, delete "28)," and insert -- 2B), --, therefor.

In Column 18, Line 45, delete "1110" and insert -- 111C --, therefor.

In Column 19, Line 17, delete "1110" and insert -- 111C --, therefor.

In Column 24, Line 23, delete "0-ring)," and insert -- O-ring), --, therefor.

In Column 25, Line 37, delete "190," and insert -- 19C, --, therefor.

In Column 26, Line 1, delete "valve¬to-blower" and insert -- valve-to-blower --, therefor.

In Column 27, Line 3, delete "valve-to¬blower" and insert -- valve-to-blower --, therefor.

In Column 27, Line 62, delete "0-ring)," and insert -- O-ring), --, therefor.

In Column 27, Line 64, delete "0-ring)," and insert -- O-ring), --, therefor.

In Column 28, Line 19, delete "51" and insert -- S1 --, therefor.

In Column 30, Line 11, delete "2750" and insert -- 275C --, therefor.

In Column 30, Line 56, delete ""S1" to "S4"" and insert -- "S1'" to "S4'" --, therefor.

In Column 31, Line 8, delete "0-ring)," and insert -- O-ring), --, therefor.

In Column 31, Line 62, delete ""511"" and insert -- "S1" --, therefor.

In Column 31, Line 65, delete ""S21"" and insert -- "S2" --, therefor.

In Column 31, Line 67, delete ""S21"" and insert -- "S2" --, therefor.

In Column 32, Line 1, delete ""S1"" and insert -- "S1'" --, therefor.

In Column 32, Line 1, delete ""S2"" and insert -- "S2'" --, therefor.

In Column 32, Line 16, delete ""S3"" and insert -- "S3" --, therefor.

In Column 32, Line 20, delete ""S3"" and insert -- "S3'" --, therefor.

CERTIFICATE OF CORRECTION (continued)
U.S. Pat. No. 10,576,237 B2

In Column 32, Line 20, delete ““S4”” and insert -- “S4” --, therefor.

In Column 32, Line 27, delete ““Si”” and insert -- “S1” --, therefor.

In Column 32, Line 29, delete ““S3”” and insert -- “S3” --, therefor.

In Column 32, Line 37, delete ““S1”” and insert -- “S1” --, therefor.

In Column 32, Line 41, delete ““Si',”” and insert -- “S1',” --, therefor.

In Column 34, Line 17, delete ““Si”” and insert -- “S1” --, therefor.

In Column 34, Line 27, delete ““S3”” and insert -- “S3” --, therefor.

In Column 34, Line 27, delete ““S4°.”” and insert -- “S4'.” --, therefor.

In Column 34, Line 31, delete ““S2”” and insert -- “S2” --, therefor.

In Column 35, Line 11, delete ““ST,”” and insert -- “S3',” --, therefor.

In Column 35, Line 41, delete "51'-S4°" and insert -- S1'-S4' --, therefor.

In Column 35, Line 48, delete "51" and insert -- S1 --, therefor.

In Column 35, Line 53, delete "51'" and insert -- S1' --, therefor.

In Column 41, Line 16, delete "(“F102”)" and insert -- (“FIO2”) --, therefor.

In Column 41, Line 19, delete "activing" and insert -- activating --, therefor.

In Column 41, Line 20, delete "activing" and insert -- activating --, therefor.

In Column 41, Line 33, delete "If" and insert -- if --, therefor.

In Column 41, Line 43, delete "T," and insert -- $T_i$ --, therefor.

In Column 41, Line 46, delete "T,)" and insert -- $T_i$) --, therefor.

In Column 41, Line 49, delete "T,)" and insert -- $T_i$) --, therefor.

In Column 41, Line 66, delete "F102" and insert -- FIO2 --, therefor.

In Column 42, Line 26, delete "standalone" and insert -- stand-alone --, therefor.

In Column 46, Line 20, delete "100)." and insert -- 10C). --, therefor.

CERTIFICATE OF CORRECTION (continued)
U.S. Pat. No. 10,576,237 B2

In Column 47, Line 8, delete "0-ring" and insert -- O-ring --, therefor.

In Column 47, Line 26, delete "832" and insert -- 832. --, therefor.

In Column 50, Line 54, delete "process," and insert -- process. --, therefor.

In Column 51, Line 47, delete ""DI")" and insert -- "D1") --, therefor.

In Column 52, Line 40, delete "CV5¬CV8" and insert -- CV5-CV8 --, therefor.

In Column 57, Line 51, delete "F102" and insert -- FIO2 --, therefor.

In Column 57, Line 52, delete "F102" and insert -- FIO2 --, therefor.

In Column 57, Line 52, delete "F102" and insert -- FIO2 --, therefor.

In Column 58, Line 63, delete "50," and insert -- 5C, --, therefor.

In Column 59, Line 42, delete "to¬valve" and insert -- to-valve --, therefor.

In Column 61, Line 40, delete "1090." and insert -- 109C. --, therefor.

In Column 62, Line 54, delete ""IDS"" and insert -- "ID3" --, therefor.